(12) United States Patent
Ramløv et al.

(10) Patent No.: US 9,241,511 B2
(45) Date of Patent: Jan. 26, 2016

(54) POLYPEPTIDES COMPRISING AN ICE-BINDING ACTIVITY

(71) Applicant: Roskilde Universitet, Roskilde (DK)

(72) Inventors: Hans Ramløv, Vanløse (DK); Casper Wilkens, Copenhagen (DK); Anders Løbner-Olesen, Virum (DK)

(73) Assignee: Roskilde Universitet, Roskilde (DK)

( * ) Notice: Subject to any disclaimer, the term of this patent is extended or adjusted under 35 U.S.C. 154(b) by 0 days.

(21) Appl. No.: 14/481,056

(22) Filed: Sep. 9, 2014

(65) Prior Publication Data

US 2015/0079254 A1 Mar. 19, 2015

Related U.S. Application Data

(63) Continuation of application No. 12/744,050, filed as application No. PCT/DK2008/050278 on Nov. 21, 2008, now Pat. No. 8,859,230.

(60) Provisional application No. 61/003,979, filed on Nov. 21, 2007.

(30) Foreign Application Priority Data

Nov. 21, 2007 (DK) .................................. 2007 01656

(51) Int. Cl.
| | | |
|---|---|---|
| *A23C 1/08* | (2006.01) | |
| *A23L 3/375* | (2006.01) | |
| *A01N 1/02* | (2006.01) | |
| *A23G 9/38* | (2006.01) | |
| *C07K 14/435* | (2006.01) | |
| *A23L 3/3526* | (2006.01) | |

(52) U.S. Cl.
CPC . *A23L 3/375* (2013.01); *A01N 1/02* (2013.01); *A01N 1/0221* (2013.01); *A23G 9/38* (2013.01); *A23L 3/3526* (2013.01); *C07K 14/43563* (2013.01); *A23V 2002/00* (2013.01)

(58) Field of Classification Search
CPC ....................................................... A23C 1/08
See application file for complete search history.

(56) References Cited

U.S. PATENT DOCUMENTS

| | | | |
|---|---|---|---|
| 5,118,792 A | 6/1992 | Warren et al. | |
| 5,358,931 A | 10/1994 | Rubinsky et al. | |
| 5,676,985 A | 10/1997 | Fletcher et al. | |
| 6,090,917 A | 7/2000 | Lillford et al. | |
| 6,156,880 A | 12/2000 | Lill ford et al. | |
| 6,200,622 B1 | 3/2001 | Darling et al. | |
| 6,312,733 B1 | 11/2001 | Jann et al. | |
| 6,436,460 B1 | 8/2002 | Daniel et al. | |
| 6,447,829 B1 | 9/2002 | Daniel et al. | |
| 6,491,960 B1 | 12/2002 | Daniel et al. | |
| 6,503,548 B1 | 1/2003 | Daniel et al. | |
| 6,565,908 B1 | 5/2003 | Daniel et al. | |
| 6,774,210 B1 | 8/2004 | Sidebottom et al. | |
| 6,793,952 B2 | 9/2004 | Fenn et al. | |
| 6,797,690 B1 | 9/2004 | Byass et al. | |
| 6,852,841 B1 | 2/2005 | Jarman et al. | |
| 6,887,984 B2 | 5/2005 | Berry et al. | |
| 6,914,043 B1 | 7/2005 | Chapman et al. | |
| 7,132,263 B2 | 11/2006 | Demmer et al. | |
| 7,297,516 B2 | 11/2007 | Chapman et al. | |
| 2001/0048962 A1 | 12/2001 | Fenn et al. | |
| 2002/0072108 A1 | 6/2002 | Berry et al. | |
| 2003/0022371 A1 | 1/2003 | Griffith | |
| 2004/0146884 A1 | 7/2004 | Demmer et al. | |
| 2005/0129810 A1 | 6/2005 | Lindner et al. | |
| 2005/0163902 A1 | 7/2005 | Barfod et al. | |
| 2005/0205833 A1 | 9/2005 | Chapman et al. | |
| 2006/0008440 A1 | 1/2006 | Blatt et al. | |
| 2006/0292281 A1 | 12/2006 | Kragh et al. | |
| 2007/0113304 A1 | 5/2007 | Demmer et al. | |
| 2007/0141206 A1 | 6/2007 | Bramley et al. | |
| 2007/0286936 A1 | 12/2007 | Bramley et al. | |
| 2008/0026127 A1 | 1/2008 | Lindner et al. | |
| 2008/0032017 A1 | 2/2008 | Bramley et al. | |
| 2008/0131936 A1 | 6/2008 | Miasnikov et al. | |
| 2008/0213453 A1 | 9/2008 | Burmester et al. | |

FOREIGN PATENT DOCUMENTS

| | | |
|---|---|---|
| CN | WO2005/095586 | 10/2005 |
| WO | 97/02343 | 1/1997 |
| WO | WO2003/008540 | 1/2003 |
| WO | WO2006/032707 | 3/2006 |
| WO | 2008/059220 | 5/2008 |
| WO | 2008/064675 | 6/2008 |
| WO | 2009/065415 | 5/2009 |
| WO | WO2009/094401 | 7/2009 |

OTHER PUBLICATIONS

Li, et al. "Enhancement of insect antifreeze protein activity by solutes of low molecular mass". Journal of Experimental Biology, 1998, 201, pp. 2243-2251.

Li, et al. "Further discussion on the thermal hysteresis of the ice growth inhibitor". Chemical Physics Letters, 1994, 223, pp. 181-184.

Li, et al. "Solution structure of an antifreeze protein CfAFP-501 from *Choristoneura fumiferana*". Journal of Biomolecular NMR, 2005, 32, pp. 251-256.

Li, et al. "Structure of an Antifreeze Polypeptide and Its Precursor from the Ocean Pout, *Macroxoarces americanus*". Journal of Biological Chemistry, 1985, 260, pp. 12904-12909.

Li, et al. "The kinetic theory of thermal hysteresis of macromolecule solution". Chemical Physics Letters, 1993, 216, pp. 453-457.

(Continued)

*Primary Examiner* — Maryam Monshipouri
(74) *Attorney, Agent, or Firm* — Postemak Blankstein & Lund LLP

(57) ABSTRACT

The present invention relates to novel polypeptides comprising an ice-binding capability resulting in an ice crystal formation and/or growth reducing or inhibiting activity. The present invention also relates to an edible product and to a solid support comprising the novel polypeptide. Furthermore, the present invention also relates to a method for producing the novel polypeptide and to different uses of the novel polypeptide.

14 Claims, 16 Drawing Sheets

(56) References Cited

OTHER PUBLICATIONS

Li, et al. "The role of Ca2+-coordinating residues of herring antifreeze protein in antifreeze activity". Biochemistry, 2004 ,43, pp. 14547-14554.

Liepinsh, et al., "Solution structure of a hydrophobic analogue of the winter flounder antifreeze protein", European Journal of Biochemistry, 2002, 269, pp. 1259-1266.

Liou, et al. "Folding and structural characterization of a highly disulfide-bonded beetle antifreeze protein produced in bacteria". Protein Expression and Purification, 2000, 19, pp. 148-157.

Liou, et al. "Mimicry of ice structure by surface hydroxyls and water of a b-helix antifreeze protein". Nature, 2000, 406, pp. 322-324.

Liu, et al. "Structure and evolutionary origin of Ca2+-dependent herring type II antifreeze protein". PloS One, 2007, 2, e548.

Liu, et al. "Systematic size study of an insect antifreeze protein and its interaction with ice". Biophysical Journal, 2005, 88, pp. 953-958.

Loewen, et al. "Alternative roles for putative ice-binding residues in type I antifreeze protein". Biochemistry, 1999, 38, pp. 4743-4749.

Low, et al. "Isolation and characterization of skin-type, type I antifreeze polypeptides from the longhorn *Ocephalus octodecemspinosus*". Journal of Biological Chemistry, 2001, 276, pp. 11582-11589.

Low, et al. "The role of N and c termini in the antifreeze activity of winter flounder (*Pleuronectes americanus*) antifreeze proteins". Journal of Biological Chemistry, 2003, 278, pp. 10334-10343.

Madura, et al. "Molecular recognition and binding of thermal hysteresis proteins to ice". Journal of Molecular Recognition, 2000, 13, pp. 101-113.

Marshall, et al. "Enhancing the activity of a β-helical antifreeze protein by the engineered addition of coils". Biochemistry, 2004, 43, pp. 11637-11646.

Marshall, et al. "Hyperactive antifreeze protein from winter flounder is a very long. Rod-like dimer of alpha-helices". Journal of Biological Chemistry, 2005, 280, pp. 17920-17929.

Marshall, et al. "Hyperactive antifreeze protein in a fish". Nature, 2004, 429, pp. 153.

Marshall, et al. "Identification of the ice-binding face of antifreeze protein from *Tenebrio molitor*". FEBS Letters, 2002, 529, pp. 261-267.

Marshall, et al. "Partitioning of fish and insect antifreeze proteins into ice suggests they bind with comparable affinity". Biochemistry, 2004, 43, pp. 148-154.

Mirendorf, et al. "Newsletter from Novagen Inc.—advanced products and protocols for molecular biology research". Innovations, 1994, vol. 1—No. 1.

Miura, et al. "NMR analysis of type III antifreeze protein intramolecular dimer". Journal of Biological Chemistry, 2001, 276, pp. 1304-1310.

Murray, et al. "Localization of cells from the winter flounder gill expressing a skin type antifreeze protein gene". Canadian Journal of Zoology, 2002, 80, pp. 110-119.

Nada, et al. "Anisotropic growth kinetics of ice crystals from water studied by molecular dynamics simulation". Journal of Crystal Growth, 1996, 169, pp. 587-597.

Nada, et al. "Anisotropic properties of ice/water interface: A molecular dynamics study". Japanese Journal of Applied Physics, 1995, 34, pp. 583-588.

Nada, et al. "Anisotropy in molecular-scaled growth kinetics at ice-water interfaces". Journal of Physical Chemistry B, 1997, 101, pp. 6163-6166.

Nada, et al. "Anisotropy in structural transitions between basal and prismatic faces of ice studied by molecular dynamics simulations". Surface Science, 2000, 446, pp. 1-16.

Nagashima, et al. "Solute distribution in front of an ice/water interface during directional growth of ice crystals and its relationship to interfacial patterns". Journal of Physical Chemistry, 1997, 101, pp. 6174-6176.

Nguyen, et al. "The dynamics, structure, and conformational free energy of praline-containing antifreeze glycoprotein". Biophysical Journal, 2002, 82, pp. 2892-2905.

Nishimiya, et al. "Co-operative effect the isoforms of type III antifreeze protein expressed in the notched-fin eelpout, *Zoarces elonaatus* Kner". FEBS Journal , 2005, 272, pp. 482-492.

Nishimiya, et al. "Crystal structure and mutational analysis of Ca2+-independent type II antifreeze protein from Longsnout poacher, *Brachyopsis rostratus*". Journal of Molecular Biology, 2008, 382, pp. 734-746.

Nishimiya, et al. "Crystallization and preliminary X-ray crystallographic analysis of Ca2+- independent and Ca2+-dependent species of the type II antifreeze protein". Acta Crystalloaraphica F, 2006, 62, pp. 538-541.

O'Grady, et al. "Comparison of antifreeze glycopeptides from Arctic and Antarctic fishes". Journal of Experimental Zoology, 1982, 224, pp. 177-185.

Olsen, et al. "Factors contributing to seasonal increases in inoculative freezing resistance in overwintering fire-colored beetle larvae *Dendroides canadensis* (Pyrochroidae")". Journal of Experimental Biology, 1998, 201, pp. 1585-1594.

Olsen, et al. "Maintenance of the supercooled state in the gut fluid of overwintering pyrochroid beetle larvae, *Dendroides canadensis*: role of ice nucleators and antifreeze proteins". Journal of Comparative Physiology B, 1997a, 167, pp. 114-122.

Pertaya, et al. "Fluorescence microscopy evidence for quasi-permanent attachment of antifreeze proteins to ice surfaces". Biophysical Journal, 2007, 92, pp. 3663-3673.

Pertaya, et al. "Growth-melt asymmetry in ice crystals under the influence of pruce budworm antifreeze protein". Journal of Physics: Condensed Matter, 2007, 19, pp. 412101.

Qiu, et al. "Expression of biologically active antifreeze protein His-MpAfp149 from the desert beetle (*Microdera punctipennis dzungarica*) in *Escherichia coli*". Molecular Biology Reports, 2009, Epub ahead of print.

Ramlov, "Aspects of natural cold tolerance in ectothermic animals". Human Reproduction, 2000, 15, pp. 26-46.

Ramsay. "The rectal complex of the mealworm *Tenebrio molitor*, L. (Coleoptera, Tenebrionidae)". Philosophical Transactions of the Royal Society of London, 1964, 248, pp. 279-314.

Rao, et al. "Comparison by 1H-NMR spectroscopy of the conformation of the 2600 Dalton antifreeze glycopeptide of polar cod with that of the high molecular weight antifreeze glycoprotein". Biopolymers, 1987, 26, pp. 1227-1244.

Raymond, et al. "Inhibition of growth of nonbasal planes in ice by fish anti-antifreezes". Proc. Natl. Acad. Sci. USA, 1989, 89, pp. 881-885.

Raymond, et al."Adsorption-inhibition as a mechanism of freezing resistance in polar fishes". Proceedings of National Academy Science of USA, 1977, 74, pp. 2589-2593.

Reiss. "The replacement free energy in nucleation theory". Advances in colloid and interface science, 1977, 7, pp. 1-66.

Schrag, et al. "Primary and secondary structure of antifreeze peptides from arctic and antiarctic zoarcid fishes". Biochimica et Biophysica Acta, 1987, 915, pp. 357-370.

Schrag, et al. "Relationship of amino acid composition and molecular weight of antifreeze glycopeptides to non-colligative freezing point depression". Biochimica at Biophysica Acta, 1982, 717, pp. 322-326.

Scott, et al. "Wolffish antifreeze protein genes are primarily organized as tandem repeats that each contain two genes in inverted orientation". Molecular and Cellular Biology, 1988, 8, pp. 3670-3675.

Scotter, et al. "The basis for hyperactivity antifreeze proteins". Cryobiology, 2006, 53, pp. 229-239.

Shimada, et al."Pattern formation of ice crystals during free growth in supercooled water". Journal of Physical Chemistry B, 1997, 101, pp. 6171-6173.

Sicheri, et al. "Ice-binding structure and mechanism of an antifreeze protein from winter flounder". Nature, 1995, 375, pp. 427-431.

Ewart, et al. "Structural and Fuctional Similarity between Fish Antifreeze Proteins and Calcium-Dependent Lectins". Biochemical and Biophysical Research Communication, 1992, 185, pp. 335-341.

Beaglehole et al., "Extrinsic premelting at the ice-glass interface", J. Phys. Chem., vol. 98, No. 33, 1994, pp. 8096-8100.

(56) References Cited

OTHER PUBLICATIONS

Franks, "Biophysics and Biochemistry of Low Temperatures and Freezing". Effects of low temperatures on biological membranes, 1981, pp. 3-19.
Heneghan et al., "Heterogeneous nucleation of supercooled water, and the effect of an added catalyst", Proc. Natl. Acad. Sci., 2002, 99, No. 15, pp. 9631-9634.
Heneghan et al., "Liquid-to-crystal nucleation: Automated lag-time apparatus to study supercooled liquids", J. Chem. Phys., 2001, vol. 115, No. 16., pp. 7599-7607.
Payne et al., "Comparison of the freeze/thaw characteristics of antarctic cod (*Dissostichus mawsoni*) and black cod (*Paranotothenia augustata*)—possible effects of antifreeze glycoproteins", J. Muscle Foods, 5, 1994, pp. 233-244.
Wilson et al., "Antifreeze glycopeptide adsorption on single crystal ice surfaces using ellipsonnetry", Biophys. J., 64, 1993, pp. 1878-1884.
Wilson et al., Hemolymph ice nucleating proteins from the New Zealand alpine weta *Hemideina maul* (Orthoptera: Stenopelmatidae), Comp. Biochem. Physiol., 1995, vol. 112B, No. 3, pp. 535-542.
Wilson et al., "Hydrodynamic diameter of fish antifreeze molecules by quasi-elastic light scattering", Cryo-Letters 15, 1994, pp. 127-130.
Wilson et al., "Ice premelting during differential scanning calorimetry", Biophys. J., 1999, 77, pp. 2850-2855.
Wilson, "A model for thermal hysteresis utilizing the anisotropic interfacial energy of ice crystals", Cryobiology 31, 1994, pp. 406-412.
Wilson, "A simple technique for measuring freeze-concentration effects", Cryo-Letters 13, 1992, pp. 389-394.
Wilson, "Physical basis of action of biological ice nucleating agents", Cryo-Letters 15, 1994, pp. 119-125.
Wilson, "The role of ice in the mechanism of action of antifreeze proteins", Doctoral thesis, Roskilde University, 2005.
Zepeda, et al. "Diffusion, incorporation, and, segregation of antifreeze glycoproteins at the ice/solution interface". Physics and Chemistry of Ice, 2007, 669-676.
Zachariassen, "Physiology of cold tolerance in insects", The American Physiological Society, vol. 64, No. 4, 1985, pp. 799-832.
Andorfer et al., "Isolation and characterization of cDNA clones encoding antifreeze proteins of the pyrochroid beetle *Dendroides canadensis*," Journal of Insect Physiology, 46:365-372, 2000.
DeLuca et al., "Antifreeze Proteins Bind Independently to Ice," Biophysical Journal, 74:1502-1508, 1998.
DeVries, "Antifreeze Peptides and Glycopeptides in Cold-Water Fishes," Ann. Rev. Physiol., 45:245-260, 1983.
Doucet et al., "Structure-function relationships in spruce budworm antifreeze protein revealed by isoform diversity," Eur. J. Biochem., 267:6082-6088, 2000.
Duman et al., "Molecular characterization and sequencing of antifreeze proteins from larvae of the beetle *Dendroides canadensis*," J. Comp. Physiol. B, 168:225-232, 1998.
Duman et al., "Site-specific forms of antifreeze protein in the beetle *Dendroides canadensis*," J. Comp. Physiol. B, 172:547-552, 2002.
Gauthier et al., "Disulfide bond mapping and structural characterization of spruce budworm antifreeze protein," Eur. J. Biochem., 258:445-453, 1998.
Graether et al., "Spruce Budworm Antifreeze Protein: Changes in Structure and Dynamics at Low Temperature," J. Mal. Biol., 327:1155-1168, 2003.
Graether et al., "β-Helix structure and ice-binding properties of a hyperactive antifreeze protein from an insect," Nature, 406:325-328, 2000.
Hew et al., "Structures of shorthorn sculpin antifreeze polypeptides," Eur. J. Biochem., 151: 167-172, 1985.
Huang et al., "Expression of an insect (*Dendroides canadensis*) antifreeze protein in *Arabidopsis thaliana* results in a decrease in plant freezing temperature," Plant Molecular Biology, 50:333-344, 2002.

Huang et al., "Cloning and characterization of a thermal hysteresis (antifreeze) protein with DNA-binding activity from winter bittersweet nightshade, *Solanum dulcamara*," Plant Molecular Biology, 48:339-350, 2002.
Knight et al., "Fish antifreeze protein and the freezing and recrystallization of ice," Nature, 308:295-296, 1984.
Knight et al., "Inhibition of Recrystallization of Ice by Insect Thermal Hysteresis Proteins: A Possible Cryoprotective Role," Cryobiology, 23:256-262, 1986.
Knight et al., "Adsorption of a-helical antifreeze peptides on specific ice crystal surface planes", Biophysical Journal, 59:409-418, 1991.
Knight et al., "Nonequilibrium Antifreeze Peptides and the Recrystallization of Ice," Cryobiology, 32:23-34, 1995.
Kristiansen et al., "Antifreeze activity in the cerambycid beetle *Rhagium inquisitor*," J. Comp. Physiol. B, 169:55-60, 1999.
Kristiansen et al., "The mechanism by which fish antifreeze proteins cause thermal hysteresis," Cryobiology, 51:262-280, 2005.
Kristiansen et al., "Isolation and characterization of hemolymph antifreeze proteins from larvae of the longhorn beetle *Rhagium inquisitor* (L.)," Comparative Biochemistry and Physiology, Part B, 142:90-97, 2005.
Leinala et al., "A β-Helical Antifreeze Protein Isoform with Increased Activity," The Journal of Bioloical Chemistry, 277 (36):33349-33352, 2002.
Leinala et al., "Crystal Structure of β-Helical Antifreeze Protein Points to a General Ice Binding Model," Structure, 10:619-627, 2002.
Leinala et al., "Elevated temperature and tyrosine iodination aid in the crystallization and structure determination of an antifreeze protein," Acta Cryst., D58: 1081-1083, 2002.
Li et al., "Secondary Structure of Antifreeze Proteins from Overwintering Larvae of the Beetle *Dendroides canadensis*," Archives of Biochemistry and Biophysics, 360(1 ):25-32, 1998.
Li et al., "Mapping of Disulfide Bridges in Antifreeze Proteins from Overwintering Larvae of the Beetle *Dendroides canadensis*," Biochemistry, 37:6343-6350, 1998.
Liou et al., "A Complex Family of Highly Heterogeneous and Internally Repetitive Hyperactive Antifreeze Proteins from the Beetle *Tenebrio molitor*," Biochemistry, 38:11415-11424, 1999.
Marshall et al., "Partitioning of Fish and Insect Antifreeze Proteins into Ice Suggests They Bind with Comparable Affinity," Biochemistry, 43: 148-154, 2004.
Ramlov et al., "Recrystallization in a Freezing Tolerant Antarctic Nematode, *Panagrolaimus davidi*, and an Alpine Weta, *Hemideina maori* (Orthoptera; stenopelmatidae)," Cryobiology, 33:607-613, 1996.
Raymond et al., "Adsorption inhibition as a mechanism of freezing resistance in polar fishes", Proc. Natl. Acad. Sci. USA, 74(6):2589-2593, 1977.
Schrag et al., "Fluorescence Depolarization of Glycopeptide Antifreezes," Abstracts, 19th Annual Meeting, 26:658, 1982.
Qiang et al., "New advances on insect antifreeze proteins: Regular structure suitable for function," Acta Entomologica Sinica, 49(3):491-496, 2006.
Wikipedia, "In vitro fertilisation," URL=http://en.wikipedia.org/wiki/In_vitro_fertilisation, download date Mar. 14, 2011, 19 pages.
Wilson, "Explaining Thermal Hysteresis by the Kelvin Effect," Cryo-Letters, 14:31-36, 1993.
Wilson, "A Model for Thermal Hysteresis Utilizing the Anisotropic Interfacial Energy of Ice Crystals," Cryobiology, 31:406-412, 1994.
Wilson et al., "Heterogeneous nucleation of clathrates from supercooled tetrahydrofuran (THF)/water mixtures, and the effect of an added catalyst," Chemical Engineering Science, 60:2937-2941, 2005.
Wu et al., "Antifreeze glycoproteins: relationship between molecular weight, thermal hysteresis and the inhibition of leakage from liposomes during thermotropic phase transition," Comparative Biochemistry and Physiology Part B, 128:265-273, 2001.
Zachariassen et al., "Effect of ice fraction and dilution factor on the antifreeze activity in the hemolymph of the cerambycid beetle *Rhagium inquisitor*," Cryobiology, 44: 132-141, 2002.
Zachariassen, "The Role of Polyols and Nucleating Agents in Cold-Hardy Beetles," J. Comp. Physiol., 40:227-234, 1980.

(56) References Cited

OTHER PUBLICATIONS

Achenbach, et al. "Structural and Functional Characterization of a C-Type Lectin-like Antifreeze Protein from Rainbow Smelt (*Osmerus mordax*)". European Journal of Biochemistry, 2002, 269, pp. 1219-1226.
Ahlgren, et al. "Comparison of Antifreeze Glycopeptides from Several Antarctic Fishes". Polar Bioloav, 1984, 3, pp. 93-97.
Albers, et al. "Purification and Structural Analysis of a Type III Antifreeze Protein from the European Eel Pout *Zoarces* Vivioarous". CrvoLetters, 2007, 28, pp. 51-60.
Ananthanarayanan, et al. "Antifreeze Proteins from the Ocean Pout, *Macrozoarces americanus*: Circular Dichroism Spectral Studies on the Native and Denatured States". Biochimica et Biophysica, 1986 Acta, 870, pp. 154-159.
Angell, "Supercooled Water". Water, 1982, 7, pp. 1-81.
Anklam, et al. "An Interfacial Energy Mechanism for the Complete Inhibition of Crystal Growth bv Inhibitor Adsorption". Journal of Chemical Physics, 2005, 123, p. 144708.
Anston, et al. "Understanding the Mechanism of Ice Binding by Type III Antifreeze Proteins". Journal of Molecular Biolo_qy, 2001, 305, pp. 875-889.
Beaglehole, et al. "Thickness and Anisotropy of the Ice-Water Interface". Journal of Physical Chemistry, 1993, 97, pp. 11053-11055.
Burcham, et al. "A Kinetic Description of Antifreeze Glycoprotein Activity". Journal of Bioloaical Chemistry, 1986b, 261, pp. 6390-6397.
Burcham, et al. "Purification and Primary Sequences of the Major Arginine-Containing Antifreeze Glycopeptides from the Fish *Eleginus gracilis*". Journal of Biological Chemistry, 1986a, 261, pp. 6384-6389.
Bush, et al. "Antifreeze Glycoprotein". International Journal of Peptide Protein Research, 1981, 17, 00. 125-129.
Bush, et al. "Conformation of the Antifreeze Glycoprotein of Polar Fish". Archives of Biochemistry and Biophysics, 1984, 232, pp. 624-631.
Bush, et al. "Conformation of the Glycotripeptide Repeating Unit of Antifreeze Glycoprotein of Polar Fish as Determined from the Fully Assigned Proton n.m.r. Spectrum". International Journal of Peptide Protein Research, 1986, 28, pp. 386-397.
Baardsnes et al. "Antifreeze Protein from Shorthorn Sculpin: Identification of the Ice-Bindinq Surface". Protein Science, 2001, 10, pp. 2566-2576.
Baardsnes et al. New Ice-Binding Face for Type I Antifreeze Protein. FEBS Letters, 1999, 463, pp. 87-91.
Baardsnes, et al. "Contribution of Hydrophobic Residues to Ice Binding by Fish Type III Antifreeze Protein". Biochimica et Biophysica, 2002, Acta 1601, pp. 49-54.
Chakrabartty, et al. "The Effect of Enhanced Alfa-Helicity on the Activity of a Winter Flounder Antifreeze Polypeptide". European Journal of Biochemsitry, 1991, 202, pp. 1057-1063.
Chao, et al. "A Diminished Role for Hydrogen Bonds in Antifreeze Protein Binding to Ice", Biochemistry, 1997, 36, pp. 14652-14660.
Chao, et al. "A Natural Variant of Type I Antifreeze Protein with Four Ice-Binding Repeats is a Particular Potent Antifreeze". Protein Science, 1996, 5, pp. 1150-1156.
Chao, et al. "Structure-Function Relationship in the Globular Type III Antifreeze Protein: Identification of a Cluster of Surface Residues Required for Binding to Ice". Protein Science, 1994, 3, pp. 1760-1769.
Chao, et al. "Use of Praline Mutants to Help Solve the NMR Solution Structure of Type III Antifreeze Protein". Protein Science, 1993, 2, pp. 1411-1428.
Cheng, et al "The Role of Antifreeze Glycopeptides in the Freezing Avoidance of Cold-Water Fish". Ute under extreme conditions, 1992, pp. 1-14.
Cheng, et al. "Structure of Antifreeze Peptides from the Antarctic Eel Pout, *Austrolycicthys brachvceohalus* ". Biochimica et Biophysica Acta, 1989, 997, pp. 55-64.
Cheng, et al."Ice-Binding Mechanism of Winter Flounder Antifreeze Proteins". Biophysical Journal, 1993, 73, pp. 2851-2873.

Chou(1992). "Energy-Optimized Structure of Antifreeze Protein and its Binding Mechanism". Journal of Molecular Biolology, 1992, 223, pp. 509-517.
D'Arcy, et al. "Using Natural Seeding Material to Generate Nucleation in Protein Crystallization Experiments". Acta Crystallography D, 2003, 59, pp. 1343-1346.
Dalal, et al. "Source of the Ice-Binding Specificity of Antifreeze Protein Type I". Journal of Informative Comouter Science, 2000, 40, pp. 1276-1284.
Daley, et al. "Characterization of Threonine Side Chain Dynamics in an Antifreeze Protein Using Natural Abundance 13C NMR Spectroscopy". Journal of Biomolecular NMR, 2004, 29, pp. 139-150.
Daley, et al. "Structure and Dynamics of a 13-Helical Antifreeze Protein" Biochemistry, 2002, 41 , pp. 5515-5525.
Daley, et al. "The Role of Side Chain Conformational Flexibility in Surface Recognition by *Tenebrio molitor* Antifreeze Protein". Protein Science, 2003, 12, pp. 1323-1331.
DeLuca, et al. "Effect of Type III Antifreeze Protein Dilution and Mutation on the Growth Inhibition of Ice". Biophysical Journal, 1996, 71, pp. 2346-2355.
Deng et al. "Amino Acid Sequence of a New Type of Antifreeze Protein: From the Longhorn Sculpin *Myoxocephalus octodecimspinosis*". FEBS Letters, 1997, 402,pp. 17-20.
Deng, et al. "Isolation and characterization of an antifreeze protein from the longhorn sculpin, *Myoxocephalus octodecimspinosis*". Biochimica et Biophysica Acta-Protein Structure and Molecular Enzymology, 1998 1388, 305-314.
Devries et al. "Freezing Resistance in Some Antarctic Fishes". Science, 1969, 163, pp. 1073-1075.
Devries, et al. "Chemical and Physical Properties of Freezing Point-Depressing Glycoproteins from Antarctic Fishes". Journal of Biological Chemistry, 1970, 245, pp. 2901-2908.
Devries, et al. "Structure of a Peptide Antifreeze and Mechanism of Adsorption to Ice". Biochimica et Biophysica Acta, 1977, 495, pp. 388-392.
Diederichs, et al."Improved R-factors for Difraction Data Analysis in Macromolecular Crystallography". Nature Structure Biology, 1997, 4, pp. 269-275.
Doucet, et al. "A Family of Extressed Antifreeze Protein Genes from the Moth, *Choristoneura fumiferna*", European Journal of Biochemistry, 2002, 269, pp. 38-46.
Drewes, et al. "Evidence for a y-turn Motif in Antifreeze Glycopeptides". Biophysical Journal, 1993, 65, pp. 985-991.
Duman, et al. "Antifreeze Agents of Terrestrial Arthropods". Comparative Biochemistry and Physiology, 1982, 73A, pp. 545-555.
Duman. "Antifreeze and Ice Nucleator Proteins in Terrestrial Arthropods". Annual Review of Physiology, 2001, 63, pp. 327-357.
Evans et al. Isolation and Characterization of Type I Antifreeze Proteins from Atlantic Snailfish (*Uparis atlanticus*) and Dusky Snailfish (*Uparis gibbus*). Biochimica et Biophysica Acta, 2005, 1547, pp. 235-244.
Evans, et al. Isolation and Characterization of Type I Antifreeze Proteins from Atlantic Snailfish (*Uparis atlanticus*) and Dusky Snailfish (*Uparis gibbus*). Biochemica et Biophysica Acta, 2001, 1547, pp. 235-244.
Evans, et al. "The Importance of Dissolved Salts to the in Vivo Efficacy of Antifreeze Proteins". Comparative Biochemistry Physiology A, 2007, 148, pp. 556-561.
Ewart, et al. "Ca2+-dependent Antifreeze Proteins". Journal of Biological Chemistry, 1996, 271, pp. 16627-16632.
Ewart, et al. Isolation and Characterization of Antifreeze Proteins from Smelt (*Osmerus mordax*) and Atlantic Herring (*Clupea harengus* harengus). Canadian Journal of Zoology, 1990, 68, 00. 1652-1658.
Ewart, et al. "Structural and Functional Similarity between Fish Antifreeze Proteins and Calcium-Dependent Lectins". Biochemical and Biophysical Research Communication, 1992, 185, pp. 335-341.
Fairley, et al. "Type I Shorthorn Sculpin Antifreeze Protein". Journal of Biological Chemistry, 2002, 277, pp. 24073-24080.
Fletcher, et al. "Antifreeze Proteins of Teleost Fishes". Annual Review of Physiology, 2001, pp. 359-390.

(56) References Cited

OTHER PUBLICATIONS

Fourney, et al. "Accumulation of Wither Flounder Antifreeze Messenger RNA after Hypophysectomy". General and Comparative Endocrinology, 1984, 54, pp. 392-401.
Slaughter, et al. "Antifreeze proteins from the sea raven, *Hemitripterus americanus*". Journal of Biological Chemistry, 1981, 256, pp. 2022-2026.
Strom, et al. "Why does insect antifreeze protein from *Tenebrio molitor* produce pyramidal ice crystallites?". Biophysical Journal, 2005, 89, pp. 2618-2627.
Somme. "Supercooling and winter survival in terrestrial arthropods". Comparative Biochemistry and Physiology, 1982, 73A, pp. 519-543.
Sonnichsen, et al. "Comparative modeling of the three-dimensional structure of type II antifreeze protein". Protein Science, 1995, 4, pp. 460-471.
Sonnichsen, et al. "NMR structural studies on antifreeze proteins". Biochemistry and Cell Biology, 1998, 76, pp. 284-293.
Sonnichsen, et al. "Refined solution structure of type III antifreeze protein: hydrophobic groups may be involved in the energetics of the protein-ice interaction". Structure, 1996, 4, pp. 1325-1337.
Sonnichsen, et al. "The nonhelical structure of antifreeze protein type III". Science, 1993, 259, pp. 1154-1157.
Sorensen, et al. "Isolation and some characterization of antifreeze protein from the European eelpout *Zoarces viviparous*". Cryo Letters, 2006, 27, pp. 387-399.
Sorensen, et al. "Variations in antifreeze activity and serum inorgani ions in the eelpout *Zoarces viviparus*: antifreeze activity in the embryonic state". Comparative Biochemistry and Physiology A, 2001, 130, pp. 123-132.
Takamichi, et al. "Fully active QAE isoform confers thermal hysteresis activity on a defective SP isoform of type III antifreeze protein". FEBS Journal, 2009, 276, pp. 1471-1479.
Taylor. "Physico-chemical principles in low temperature biology". The effects of low temperatures on biological systems, 1987, pp. 3-71.
Teraoka, et al. "Ice crystal growth in supercooled solution". International Journal of Refrigeration, 2002, 25, pp. 218-225.
Tsvetkova, et al. "Dynamics of antifreeze glycoproteins in the presence of ice". Biophysical Journal, 2002, 82, pp. 464-473.
Tyshenko, et al. "The antifreeze potential of the spruce budworm thermal hysteresis protein". Nature Biotechnology, 1997, 15, pp. 887-890.
Uda, et al. "Adsorption-induced conformational changes of antifreeze glycoproteins at the ice/water interface". Journal of Physical Chemistry, 2007, 111, pp. 14355-14361.
Vali, "Principies of ice nucleation". Book: "Biological ice nucleation and its applications", 1995, pp. 1-28.
Wang, et al. "A thaumatin-like protein from larvae of the beetle *Dendroides canadensis* enhances the activity of antifreeze proteins". Biochemistry, 2006, 45, pp. 1278-1284.
Wang, et al. "Antifreeze peptide heterogeneity in an antarctic eel pout includes an unusually large major variant comprised of two 7 kDa type III AFPs linked in tandem". Biochemica et Biophysica Acta, 1995, 1247, pp. 163-172.
Wang, et al. "Antifreeze proteins of the beetle *Dendroides canadensis* enhance one another's activities". Biochemistry, 2005, 44, pp. 10305-10312.
Wang, et al. "Arginine, a key residue for the enhancing ability of an antifreeze protein of the beetle *Dendroides canadensis*". Biochemistry, 2009, 48, pp. 9696-9703.
Wathen, et al. "New simulation model of multicomponent crystal growth and inhibition". Chemical European Journal, 2004, 10, pp. 1-8.
Wen, et al. "Structure-function relationships in a antifreeze polypeptide". Journal of Biological Chemistry, 1993, 268, pp. 16396-16400.
Wen, et al. "Structure-function relationships in an antifreeze polypeptide". Journal of Biological Chemistry, 1993, 268, pp. 16401-16405.
Westh, et al. "Vapour pressure of aqueous antifreeze glycopeptide solutions". Cryo-letters, 1997, 18, pp. 277-282.
Wierzbicki, et al. "Analysis of shorthorn sculpin antifreeze protein stereospecific binding to (2-10) faces of ice". Biophysical Journal, 1996, 71, pp. 8-18.
Wierzbicki, et al. "Modeling studies of binding of sea raven type II antifreeze protein to ice". Journal of Chemical Information and Computer Science, 1997, 37, pp. 1006-1010.
Wilson, et al. "Heterogeneous Nucleation of Clathrates from Supercooled Tetrahydrofuran (THF)/Water Mixtures, and the Effect of an Added Catalyst", Chemical Engineering Science, 2005, 60, pp. 2937-2941.
Wilson, et al. "Ice nucleation in nature: supercooling point (SCP) measurements and the role of heterogeneous nucleation". Cryobiology, 2003, 46, pp. 88-98.
Wilson, et al. "Stabilization of supercooled fluids by thermal hysteresis proteins". Biophysical Journal, 1995, 68, pp. 2098-2107.
Wilson, et al. "Hexagonal shaped ice spicules in frozen antifreeze protein solutions". Cryobiology, 2002, 44, pp. 240-250.
Wilson. "Explaining thermal hysteresis by the Kelvin effect". Cryo-Letters, 1993, 14, pp. 31-36.
Wu, et al. "Enchancement of insect antifreeze protein activity by antibodies". Biochemistry Biophysics et Acta, 1991, 1076, pp. 416-420.
Wohrmann. "Antifreeze glycopeptides and peptides in Antarctic fish species from the Weddell Sea and the Lazarev Sea". Marine Ecology Progress Series, 1996, 130, pp. 47-59.
Yamashita; et al., Type II antifreeze protein from a mid-latitude freshwater fish, Japanese smelt (*Hypomesus nipponensis*). Bioscience, Biotechnology, and Biochemistry, 2003, 67, pp. 461-466.
Yang, et al., "Crystal structure of an antifreeze polypeptide and its mechanistic implications". Nature, 1988, 333, pp. 232-237.
Yang, et al. "Hydrophobic tendency of polar group hydration as a major force in type I antifreeze protein recognition". Proteins, 2005, 59, pp. 266-274.
Yang, et al. "Identification of the ice-binding surface on a type III antifreeze protein with a "flatness function" algorithm". Biophysical Journal, 1998, 74, pp. 2142-2151.
Yang, et al. "The mechanism of the type III antifreeze protein action: a computational study". Biophysical Chemistry, 2004, 109, pp. 137-148.
Yeh, et al. "Antifreeze proteins: Structures and mechanisms of function". Chemical Reviews, 1996, 96, pp. 601-618.
Zachariassen, et al. "Antifreeze effect of thermal hysteresis agents protects highly supercooled insects". Nature, 1982, 298, pp. 865-867.
Zachariassen, et al. "Nucleating agents in the haemolymph of insects tolerant to freezing". Nature, 1976, 262, pp. 285-287.
Zachariassen. "Nucleating agents in cold-hardy insects". Comparative Biochemistry and Physiology, 1982, 73A, pp. 557-562.
Zepeda, et al. "In situ observation of antifreeze glycoprotein kinetics at the ice interface reveals a two-step reversible mechanism". Crystal Growth and Design, 2008, 8, pp. 3666-3672.
Zhang, et al. "Structure-function relationships in a type I antifreeze polypeptide". Journal of Biological Chemistry, 1998, 273, pp. 34806-24812.
Zhao, et al. "Cloning and sequencing of cDNA encoding the LS-12 antifreeze protein in the longhorn sculpin, *Myoxocephalus octodecimspinosis*". Biochimica et Biophysica Acta, 1998, 1382, pp. 177-180.
Franks, et al. "Blood Glycoprotein from Antarctic Fish", Biochimica et Biophysica Acta, 1978, 540, pp. 346-356.
Franks, "Biophysics and biochemistry at low temperatures", Cambridge, 1985, Cambridge University Press.
Franks, "The properties of aqueous solutions at subzero temperatures", Water, 1982, vol. 7, pp. 215-338.
Franks, "Physiological water stress", Biophysics of water, 1982, pp. 279-294.
Franks, "The Nucleation of Ice in Undercooled Aqueous Solutions", CryoLetters, 1981, 2, pp. 27-31.
Furukawa, et al. "Ellipsometric study of the transition layer on the surface of an ice crystal" Journal of Crystal Growth, 1987, 82, pp. 665-677.

(56) References Cited

OTHER PUBLICATIONS

Furukawa, et al. "Anisotropic surface melting of an ice crystal and its relationship to growth forms", Journal of Physical Chemistry B, 1997, 101, pp. 6167-6170.
Gallagher, et al. "Analysis of thermal hysteresis protein hydration using the random network model", Biophysical Chemistry, 2003, 105, pp. 195-209.
Gauthier, et al. "A re-evaluation of the role of type IV antifreeze protein", Cryobiology, 2008, 57, 00. 292-296.
Gauthier, et al. "Hyperactive antifreeze protein in flounder species. The sole protectant in American plaice", FEBS Journal, 2005, 275, pp. 4439-4449.
Gehrken. "Inoculative freezing and thermal hysteresis in the adult beetles fbs acuminatus and *Rhagium inquisitor*", Journal of Insect Physiology, 1992, 38, pp. 519-524.
Gilbert, et al. "Demonstration of antifreeze protein activity in Antarctic lake bacteria", Microbiology, 2004, 150, pp. 171-180.
Gong, et al. "Skin antifreeze protein genes of the winter flounder, *Pleuronectes americanus*,encode distinct and active polypeptides without the secretory signal and prosequences", Journal of Biological Chemistry, 1996, 271, pp. 4601-411.
Graether, et al. "Cold survival in freeze-intolerant insects", European journal of Biochemistry, 2004, 271, pp. 3285-3296.
Graether, et al "Quantitative and qualitative analysis of type III antifreeze protein structure and function", Journal of Biological Chemistry, 1999, 174, pp. 11842-11847.
Graether, et al. "Structure of type I antifreeze protein and mutants in supercooled water", Biophysical Journal, 2001, 81, pp. 1677-1683.
Graham, et al. "Hyperactive antifreeze protein from fish contains multiple ice-binding sites", Biochemistry, 2008, 47, pp. 2051-2063.
Graham, et al., "Hyperactive antifreeze protein from beetles", Nature, 388, pp. 727-728.
Griffith, et al. "Antifreeze proteins in overwintering plants: a tale of two activities", TRENDS in Plant Science, 2001, 9, pp. 399-405.
Grisshammer, et al. "Purification of over-produced proteins from *E. coli* cells", DNA cloning 2: A Practical Approach: Expression Systems, 1995, pp. 59-92.
Gronwald, et al. "The solution structure of type II antifreeze protein reveals a new member of the lectin family", Biochemistry, 1998, 37, pp. 4712-4721.
Hall, et al., "Phenomenology and mechanism of antifreeze peptide activity", Langmuir, 1995, 15, pp. 1905-1912.
Harding, et al. "'Antifreeze' glycoproteins from polar fish", European Journal of Biochemistry, 2003, 270, pp. 1381-1392.
Haymet, et al. "Hydrophobic analogues of the winter flounder 'antifreeze' protein", FEBS Letters, 2001, 491, pp. 285-288.
Haymet, et al. "Valine substituted winter flounder 'antifreeze': preservation of ice growth hysteresis", FEBS Letters, 1998, 430, pp. 301-306.
Haymet, et al. "Winter flounder "antifreeze" proteins: Synthesis and ice growth inhibition of analogues that probe the relative importance of hydrophobic and hydrogen-bonding interactions", Journal of the American Chemical Society, 1999, 121, pp. 941-948.
Hayward, et al. "The ice/water interface: molecular dynamics simulations of the basal, prism, {20-21}, and {2-1-10} interfaces of ice lh", Journal of Chemical Physics, 2001, 114, pp. 3713-3726.
Hew, et al. "Antifreeze polypeptides from the newfoundland ocean pout, *Macrozoarces americanus*: presence of multiple and compositionally diverse components". Journal of Comparative Physiology B, 1984, 155, pp. 81-88.
Hew, et al. "Multiple genes provide the basis for antifreeze protein diversity and dosage in the ocean pout, *Macrozoarces americanus*", Journal of Biological Chemistry, 1988, 263, pp. 12049-12055.
Holland, et al. "Activity of a two-domain antifreeze protein is not dependent on linker sequence", Biophysical Journal, 2007, 92, pp. 541.546.
Houston, et al., "Binding of n oligopeptide to a specific plane of ice", Journal of Biological Chemistry, 1998, vol. 273, No. 19, issue of May 8, pp. 11714-11718.
Jia, et al. "Crystallization and preliminary x-ray crystallographic studies on type III antifreeze protein", Protein Science, 1995, 4, pp. 1236-1238.
Jorov, et al. "Theoretical study of interaction of winter flounder antifreeze protein with ice", Protein Science, 2004, 13, pp. 1524-1537.
Jorgensen, et al. "Molecular dynamics simulation of winter flounder antifreeze protein variants in solution: correlation between side chain spacing and ice lattice", Protein Engineering, 1993, 6, pp. 19-27.
Kao, et al. "The relationship between molecular weight and antifreeze polypeptide activity in marine fish", Canadian Journal of Zoology, 1985, 64, pp. 578-582.
Karim, et al. "The ice/water interface", Chemical Physics Letters, 1987, 138, pp. 531-534.
Karim, et al. "The ice/water interface: a molecular dynamics simulation study", Journal of Chemical Physics, 1988, 89, pp. 6889-6896.
Karim, et al. "The ice/water interface: a molecular dynamics simulation using the simple point charge model", Journal of Chemical Physics, 1990, 92, pp. 4634-4635.
Knight, et al. "Adsorption of biomolecules to ice and their effects upon ice growth. 2. A discussion of the basic mechanism of "antifreeze" phenomena", Crystal Growth and Design, 2001, 1, 00. 439-446.
Knight. "Curved growth of ice on surfaces", Journal of Applied Physics, 1962, 33, pp. 1808-1815.
Knight. "The freezing of supercooled liquids", D. Van Nostrand company, Inc, 1967.
Ko, et al. "The refined crystal structure of an eel pout type III antifreeze protein RD1 at 0.62-A resolution reveals structural microheterogeneity of protein and salvation", Biochemical Journal, 2003, 84, 00. 1228-1237.
Kristiansen, et al. "Salt-induced enhancement of antifreeze protein activity: a salting-out effect", Cryobiology, 2008, 57, pp. 122-129.
Kristiansen. "Studies on antifreeze proteins", Doctoral thesis, Norwegian University of Science and Technology, 2005.
Kuiper, et al. "Purification of antifreeze proteins by adsorptions to ice", Biochemical and Biophysical Research Communication, 2003, 300, pp. 645-648.
Kwan, et al. "Solution structure of a recombinant type I sculpin antifreeze protein", Biochemistry, 2005,44, pp. 1980-1988.
Lal, et al. "Inhibition of ice crystal growth by preferential peptide adsorption: A molecular modelling study", Faraday Discussions of the Chemical Society, 1993, 95, pp. 299-306.
Lane, et al. "Conformational and dynamic properties of a 14 residue antifreeze glycopeptide from Antarctic cod", Protein Science, 1998, 7, pp. 1555-1563.
Lee. "Principles of insect low temperature tolerance", Insect at low temperature, 1991, pp. 17-46.
Li, et al. "Adsorption kinetics in the solution of a thermal hysteresis protein", Chemical Physics Letters, 2000, 320, pp. 335-338.

Figure 2

```
                       1                                                50
AFP1-complete    (1)   ------------------------------------------------AT
AFP2 complete    (1)   ------------------------------------------------AT
AFP3-complete    (1)   ATGTCAATGAAAATGATTCAAACGTTTGCTTTCGCGTGTTTAGTGATAAC
AFP4-complete    (1)   --------------------------------------------------
AFP5-complete    (1)   ATGTCAATGAAAATGATTCAAAGGTTTGCTTTCGCGTGTTTAGTGATAAC
AFP6-complete    (1)   ---------------------------------------------ATGAT
AFP7-complete    (1)   ---------------------------------------------ATGAT
AFP8-complete    (1)   -----------ATGATTCAAGCGTTTGCTTTCGCGTGTTTAGTGATGAT 51                                               100
AFP1-complete    (3)   GCTCACGAGTCCTGCCATAGCACATGCATATTCT-TGCAGAGCTGTTGGA
AFP2 complete    (3)   GCTCACGAGTCCTGCCATAGCACATGCATATTCT-TGCAGAGCTGTTGGA
AFP3-complete   (51)   GCTCACGAGTCCTGCCATAGCACATGCATATTCT-TGCAGAGCTGTTGGA
AFP4-complete    (1)   ----------------------ATGCATACTCCCTGCAGAGCTGTTGGA
AFP5-complete   (51)   GCTCACGAGTCCTGCCATAGCACATGCATACTCC-TGCAGAGCTGTTGGA
AFP6-complete    (6)   GCTCACGAGTCCTGCCATAGCACATGCATACTCC-TGCAGAGCTGTTGGA
AFP7-complete    (6)   GCTCACGAGTCCTGCCATAGCACATGCATATTCT-TGCAGAGCTGTTGGA
AFP8-complete   (39)   GCTCACGAGTCCTGCCATAGCACATGCATATTCT-TGCAGAGCTGTTGGA 101                                              150
AFP1-complete   (52)   GTGGATGCATCCACGGTTACCGATGTCCAAGGCACTTGTCATGCGAAAGC
AFP2 complete   (52)   GTGGATGCATCCACGGTTACCGATGTCCAAGGCACTTGTCATGCGAAAGC
AFP3-complete  (100)   GTAGATGGGCCAGCGGTTACCGATATCCAAGGCACTTGTAATGCGAAAGC
AFP4-complete   (28)   GTAGATGGGCCAGTGGTTACCGATGTTCAAGGCACTTGTACTGCGAAAGC
AFP5-complete  (100)   GTAGATGGGCCAGTGGTTACCGATGTTCAAGGCACTTGTACTGCGAAAGC
AFP6-complete   (55)   GTAGATGGGCAAGCGGTTACCGATATCCACGGCACTTGTAATGCGAAAGC
AFP7-complete   (55)   GTGGATGCATCCACGGTTACCGATGTCCAAGGCACTTGTCATGCGAAAGC
AFP8-complete   (88)   GTGGATGCATCCACGGTTACCGATGTCCAAGGCACTTGTCATGCGAAAGC
```

Figure 2 continued

```
AFP1-complete  (102)  GACTGGTCCCGGAGCAGTCGCTTCCGGCACGTCTGTAGATGGATCAACAT
AFP2 complete  (102)  GACTGGTCCCGGAGCAGTCGCTTCCGGCACGTCTGTAGATGGATCAACAT
AFP3-complete  (150)  GACTGGTTACGGAGCAGTTGCTTCCGGCACGTCTGAAGATGGATCAACAT
AFP4-complete   (78)  GACTGGTGTCGGAGCAGTTGCTTCCGGCACGTCTGTAGATGGATCAACAT
AFP5-complete  (150)  GACTGGTGTCGGAGCAGTTGCTTCCGGCACGTCTGTAGATGGATCAACAT
AFP6-complete  (105)  GACTGGTAGCGGAGCGGTTGCTTCCGGCACGTCTGAAGATGGATCAAGAT
AFP7-complete  (105)  GACTGGTCCCGGAGCAGTCGCTTCCGGCACGTCTGTAGATGGATCAACAT
AFP8-complete  (138)  GACTGGTCCCGGAGCAGTCGCTTCCGGCACGTCTGTAGATGGATCAACAT 201                                              250
AFP1-complete  (152)  CAACAGCCACAGCGACAGGGAGTGGGGCCACTGCAACATCAACTTCGACA
AFP2 complete  (152)  CAACAGCCACAGCGACAGGGAGTGGGGCCACTGCAACATCAACTTCGACA
AFP3-complete  (200)  CGACAGCCACAGCAACAGGAAGTGGAGCCGTTGCAACATCAACTTCGACA
AFP4-complete  (128)  CAACAGCCACAGCAACAGGAAGTGGGGCCTCTGCAACATCAACTTCGACA
AFP5-complete  (200)  CAACAGCCACAGCAACAGGAAGTGGGGCCTCTGCAACATCAACTTCGACA
AFP6-complete  (155)  CAACAGCCACAGCAACAGGAAGTGGGGCCATTGCAACATCAACTTCGTCA
AFP7-complete  (155)  CAACAGCCACAGCGACAGGGAGTGGGGCCACTGCAACATCAACTTCGACA
AFP8-complete  (188)  CAACAGCCACAGCGACAGGGAGTGGGGCCACTGCAACATCAACTTCGACA 251                                              300
AFP1-complete  (202)  GGAACTGGAACGGCCACTACGACAGCCACGAGTAACGCAGCGGCCACTTC
AFP2 complete  (202)  GGAACTGGAACGGCCACTACGACAGCCACGAGTAACGCAGCGGCCACTTC
AFP3-complete  (250)  GGAAGAGGAACGGCCACTACGACAGCCACGAGTAACGCAGAGGCCACTTC
AFP4-complete  (178)  GGAAGTGGAACGGCCACTACGACAGCCACAAGTAACGCATCGGCCACTTC
AFP5-complete  (250)  GGAAGTGGAACGGCCACTACGACAGCCACAAGTAACGCATCGGCCACTTC
AFP6-complete  (205)  GGAAGTGGAACGGCCACTACGACAGCCACGGGTAACGCAGCGGCCACTTC
AFP7-complete  (205)  GGAACTGGAACGGCCACTACGACAGCCACGAGTAACGCAGCGGCCACTTC
AFP8-complete  (238)  GGAACTGGAACGGCCACTACGACAGCCACGAGTAACGCAGCGGCCACTTC
```

Figure 2 continued

```
AFP1-complete  (252)  TAATGCCATTGGTCAGGGGACAGCAACGTCAACAGCCACTGGAACCGCTG
AFP2 complete  (252)  TAATGCCATTGGTCAGGGGACAGCAACGTCAACAGCCACTGGAACCGCTG
AFP3-complete  (300)  TAATGCCATTGGTCAGGGGACAGCAACAACAACAGCCACTGGAAACGGTG
AFP4-complete  (228)  TAATGCCATTGATCAGGGCACAGCAACATCAACAGCCACTGGAACCGCTG
AFP5-complete  (300)  TAATGCCATTGATCAGGGCACAGCAACATCAACAGCCACTGGAACCGCTG
AFP6-complete  (255)  TAATGCCATTGGTCGAGGGACAGCAACAACAACAGCCACTGGAACCGGCG
AFP7-complete  (255)  TAATGCCATTGGTCAGGGGACAGCAACGTCAACAGCCACTGGAACCGCTG
AFP8-complete  (288)  TAATGCCATTGGTCAGGGGACAGCAACGTCAACAGCCACTGGAACCGCTG 351                                              400
AFP1-complete  (302)  CTGCAAGGGCAATAGGATCGTCGACTACATCAGCCAGTGCAACGGAGCCA
AFP2 complete  (302)  CTGCAAGGGCAATAGGATCGTCGACTACATCAGCCAGTGCAACGGAGCCA
AFP3-complete  (350)  GTGCAAGGGCAATAGGAGCGTCAACTACATCAGCCAGTGCATCCGAGCCA
AFP4-complete  (278)  CTGCAAGGGCAATAGGAGCGTCAACTACATCAGCCAGTGCATCCGAGCCA
AFP5-complete  (350)  CTGCAAGGGCAATAGGAGCGTCAACTACATCAGCCAGTGCATCCGAGCCA
AFP6-complete  (305)  G---AAGGGCAACAGGAACGTCAACTATATCAGCCAGTGCATCCGAGCCA
AFP7-complete  (305)  CTGCAAGGGCAATAGGATCGTCGACTACATCAGCCAGTGCAACGGAGCCA
AFP8-complete  (338)  CTGCAAGGGCAATAGGATCGTCGACTACATCAGCCAGTGCAACGGAGCCA 401                                              450
AFP1-complete  (352)  ACACAAACTAAAACCGTCAGCGGACCGGGCGCTCAAACAGCGACCGCAAT
AFP2 complete  (352)  ACACAAACTAAAACCGTCAGCGGACCGGGCGCTCAAACAGCGACCGCAAT
AFP3-complete  (400)  ACACAAACTAGAACCATCACCGGACCGGGCTCCCAAACAGCGACCGCATT
AFP4-complete  (328)  ACACAAACTCAGACCATCAGCGGAGTGGGCACTCAAACAGCGACCGCATT
AFP5-complete  (400)  ACACAAACTCAGACCATCAGCGGAGTGGGCACTCAAACAGCGACCGCATT
AFP6-complete  (352)  ACACAAACTAGTACCGTCACCGGACCGGGCTCTCAAACAGGGACCGCATT
AFP7-complete  (355)  ACACAAACTAAAACCGTCAGCGGACCGGGCGCTCAAACAGCGACCGCAAT
AFP8-complete  (388)  ACACAAACTAAAACCGTCAGCGGACCGGGCGCTCAAACAGCGACCGCAAT
```

Figure 2 continued

```
AFP1-complete    (402)  CGCCATAGACACTGCCACAACCACTGTGACGGCATCCTAGACATAACCTA

AFP2 complete    (402)  CGCCATAGACACTGCCACAACCACTGTGACGGCATCCTAGACATAACCNA

AFP3-complete    (450)  CGCCAGAGACACTGCCACAACCACTGTGACGGCATCCTAGACATAATCTA

AFP4-complete    (378)  CGCCACAGACACTGCCACAACCACTGTGACGGCATCCTAGGCATAACCTA

AFP5-complete    (450)  CGCCACAGACACTGCCACAACCACTGTGACGGCATCCTAGGCATAACCTA

AFP6-complete    (402)  CGCCAGAGACACTGCCACAACCACTGTGACTTCATCCTAGACATAACCTA

AFP7-complete    (405)  CGCCATAGACACTGCCACAACCACTGTGACGGCATCCTAGACATAACCTA

AFP8-complete    (438)  CGCCATAGACACTGCCACAACCACTGTGACGGCATCCTAGACATAACCTA 501                                              550

AFP1-complete    (452)  TAGATATAATTGTTAATTA-CATC---AGTT-ATTTATTAACAATAAAGA

AFP2 complete    (452)  TANANATAATTGTTAATTA-CATC---AGTT-ATTTATTANCAATAAAGA

AFP3-complete    (500)  TAGAAACAATTGGTAATTA-CATC---AGTTATTTATTAACAATAAAGA

AFP4-complete    (428)  TGGATAAAATTGTTATTAATTATTGATATTTAATTGTTTCATTTTTTAAA

AFP5-complete    (500)  TGGATAAAATTGTTATTAATTATTGATATTTAATTGTTTCATTTTTTAAA

AFP6-complete    (452)  TAGATACAGTTG--------CATC---AGTTTATTTATTAACAATAAAAA

AFP7-complete    (455)  TAGATATAATTGTTAATTA-CATC---AGTT-ATTTATTAACAATAAAGA

AFP8-complete    (488)  TAGATATAATTGTTAATTA-CATC---AGTT-ATTTATTAACAATAAAGA 551                                              600

AFP1-complete    (497)  GACTT-ATTAATTATTGATAAAAAAAAAAAAAAAA-------------T

AFP2 complete    (497)  GACTT-ATTAATTAAAAAAAAAAAAAAAAAAAAAAAAAAAAAAAAAAAAT

AFP3-complete    (546)  CACTTTATTAATTAATGATAAAAAAAAAAAAAAAA---------------

AFP4-complete    (478)  TAAAT-TTTACTACTTAAAAAAAAAAAAAAAAAAT---------------

AFP5-complete    (550)  TAAAT-TTTACTACTTAAAAAAAAAAAAAAAAAAT---------------

AFP6-complete    (491)  GACTT-ATTAATTAATAA-AAAAAAAAAAAAAAAT---------------

AFP7-complete    (500)  GACTT-ATTAATTAAAAAAAAAAAAAAAAAAAAAAA--------AAAAAT

AFP8-complete    (533)  GACTT-ATTAATTATTGATAAAAAAAAAAAAAAAAAA------------T
```

Figure 2 continued

```
AFP1-complete   (532)  CG-ATGGATCCGACTCGAGTC
AFP2 complete   (546)  CGGATGGATCCGACTCGAGTC
AFP3-complete   (581)  TCGATGGATCCGACTCGAGTC
AFP4-complete   (512)  CG-ATGGATCCGACTCGAGTC
AFP5-complete   (584)  CGGATGGATCCGACTCGAGTC
AFP6-complete   (524)  CGGATGGATCCGACTCGAGTC
AFP7-complete   (540)  CGGATGGATCCGACTCGAGTC
AFP8-complete   (569)  CGGATGGATCCGACTCGAGTC
```

Figure 3

```
                       1                                                50
AFP1    (1)   ---------------MLTSPAIAHAYSCRAVGVDASTVTDVQG TCHAKA
AFP2    (1)   ---------------MLTSPAIAHAYSCRAVGVDASTVTDVQG TCHAKA
AFP3    (1)   MSMKMIQTFAFACLVITLTSPAIAHAYSCRAVGVDGPAVTDIQG TCNAKA
AFP6    (1)   --------------MMLTSPAIAHAYSCRAVGVDGQAVTDIHG TCNAKA
AFP4    (1)   ----------------------MHTPCRAVGVDGPVVTDVQG TCTAKA
AFP5    (1)   MSMKMIQRFAFACLVITLTSPAIAHAYSCRAVGVDGPVVTDVQG TCTAKA
AFP7    (1)   --------------MMLTSPAIAHAYSCRAVGVDASTVTDVQG TCHAKA
AFP8    (1)   ----MIQAFAFACLVMMLTSPAIAHAYSCRAVGVDASTVTDVQG TCHAKA 51                                               100
AFP1    (35)  T GPGAVASGTSVDGS TSTATAT GSGA TATSTST GTG TATTTAT SNAAATS
AFP2    (27)  T GPGAVASGTSVDGS TSTATAT GSGA TATSTST GTG TATTTAT SNAAATS
AFP3    (51)  T GYGAVASGTSEDGS TSTATAT GSGA VATSTST GRG TATTTAT SNAEATS
AFP6    (36)  T GSGAVASGTSEDGS RSTATAT GSGA IATSTSS GSG TATTTAT GNAAATS
AFP4    (27)  T GVGAVASGTSVDGS TSTATAT GSGA SATSTST GSG TATTTAT SNASATS
AFP5    (51)  T GVGAVASGTSVDGS TSTATAT GSGA SATSTST GSG TATTTAT SNASATS
AFP7    (36)  T GPGAVASGTSVDGS TSTATAT GSGA TATSTST GTG TATTTAT SNAAATS
AFP8    (47)  T GPGAVASGTSVDGS TSTATAT GSGA TATSTST GTG TATTTAT SNAAATS 101                                               150
AFP1    (85)  NAIGQG TATSTAT GTAAARAIG SSTTSAS ATEP TQTKTVS GPGAQTATAI
AFP2    (77)  NAIGQG TATSTAT GTAAARAIG SSTTSAS ATEP TQTKTVS GPGAQTATAI
AFP3   (101)  NAIGQG TATTTAT GNGGARAIG ASTTSAS ASEP TQTRTIT GPGSQTATAF
AFP6    (86)  NAIGRG TATTTAT GTG-GRATG TSTISAS ASEP TQTSTVT GPGSQTGTAF
AFP4    (77)  NAIDQG TATSTAT GTAAARAIG ASTTSAS ASEP TQTQTIS GVGTQTATAF
AFP5   (101)  NAIDQG TATSTAT GTAAARAIG ASTTSAS ASEP TQTQTIS GVGTQTATAF
AFP7    (86)  NAIGQG TATSTAT GTAAARAIG SSTTSAS ATEP TQTKTVS GPGAQTATAI
AFP8    (97)  NAIGQG TATSTAT GTAAARAIG SSTTSAS ATEP TQTKTVS GPGAQTATAI
```

Figure 3 continued

```
              151        162
AFP1  (135)  AID TATTTVT AS    (SEQ ID NO:5)

AFP2  (127)  AID TATTTVT AS    (SEQ ID NO:6)

AFP3  (151)  ARD TATTTVT AS    (SEQ ID NO:7)

AFP6  (135)  ARD TATTTVT SS    (SEQ ID NO:8)

AFP4  (127)  ATD TATTTVT AS    (SEQ ID NO:9)

AFP5  (151)  ATD TATTTVT AS    (SEQ ID NO:10)

AFP7  (136)  AID TATTTVT AS    (SEQ ID NO:11)

AFP8  (147)  AID TATTTVT AS    (SEQ ID NO:12)
```

A

B

SEQUENCE LISTING

```
<160> NUMBER OF SEQ ID NOS: 91

<210> SEQ ID NO 1
<211> LENGTH: 146
<212> TYPE: PRT
<213> ORGANISM: Rhagium mordax

<400> SEQUENCE: 1

Met Leu Thr Ser Pro Ala Ile Ala His Ala Tyr Ser Cys Arg Ala Val
1               5                   10                  15

Gly Val Asp Ala Ser Thr Val Thr Asp Val Gln Gly Thr Cys His Ala
            20                  25                  30

Lys Ala Thr Gly Pro Gly Ala Val Ala Ser Gly Thr Ser Val Asp Gly
        35                  40                  45

Ser Thr Ser Thr Ala Thr Ala Thr Gly Ser Gly Ala Thr Ala Thr Ser
    50                  55                  60

Thr Ser Thr Gly Thr Gly Thr Ala Thr Thr Thr Ala Thr Ser Asn Ala
65                  70                  75                  80

Ala Ala Thr Ser Asn Ala Ile Gly Gln Gly Thr Ala Thr Ser Thr Ala
                85                  90                  95

Thr Gly Thr Ala Ala Ala Arg Ala Ile Gly Ser Ser Thr Thr Ser Ala
            100                 105                 110

Ser Ala Thr Glu Pro Thr Gln Thr Lys Thr Val Ser Gly Pro Gly Ala
        115                 120                 125

Gln Thr Ala Thr Ala Ile Ala Ile Asp Thr Ala Thr Thr Thr Val Thr
    130                 135                 140

Ala Ser
145

<210> SEQ ID NO 2
<211> LENGTH: 146
<212> TYPE: PRT
<213> ORGANISM: Rhagium mordax

<400> SEQUENCE: 2

Met Leu Thr Ser Pro Ala Ile Ala His Ala Tyr Ser Cys Arg Ala Val
1               5                   10                  15

Gly Val Asp Ala Ser Thr Val Thr Asp Val Gln Gly Thr Cys His Ala
            20                  25                  30

Lys Ala Thr Gly Pro Gly Ala Val Ala Ser Gly Thr Ser Val Asp Gly
        35                  40                  45

Ser Thr Ser Thr Ala Thr Ala Thr Gly Ser Gly Ala Thr Ala Thr Ser
    50                  55                  60

Thr Ser Thr Gly Thr Gly Thr Ala Thr Thr Thr Ala Thr Ser Asn Ala
65                  70                  75                  80
```

```
Ala Ala Thr Ser Asn Ala Ile Gly Gln Gly Thr Ala Thr Ser Thr Ala
                85                  90                  95

Thr Gly Thr Ala Ala Ala Arg Ala Ile Gly Ser Ser Thr Thr Ser Ala
            100                 105                 110

Ser Ala Thr Glu Pro Thr Gln Thr Lys Thr Val Ser Gly Pro Gly Ala
        115                 120                 125

Gln Thr Ala Thr Ala Ile Ala Ile Asp Thr Ala Thr Thr Thr Val Thr
    130                 135                 140

Ala Ser
145

<210> SEQ ID NO 3
<211> LENGTH: 162
<212> TYPE: PRT
<213> ORGANISM: Rhagium mordax

<400> SEQUENCE: 3

Met Ser Met Lys Met Ile Gln Thr Phe Ala Phe Ala Cys Leu Val Ile
1               5                   10                  15

Thr Leu Thr Ser Pro Ala Ile Ala His Ala Tyr Ser Cys Arg Ala Val
            20                  25                  30

Gly Val Asp Gly Pro Ala Val Thr Asp Ile Gln Gly Thr Cys Asn Ala
        35                  40                  45

Lys Ala Thr Gly Tyr Gly Ala Val Ala Ser Gly Thr Ser Glu Asp Gly
    50                  55                  60

Ser Thr Ser Thr Ala Thr Ala Thr Gly Ser Gly Ala Val Ala Thr Ser
65                  70                  75                  80

Thr Ser Thr Gly Arg Gly Thr Ala Thr Thr Thr Ala Thr Ser Asn Ala
                85                  90                  95

Glu Ala Thr Ser Asn Ala Ile Gly Gln Gly Thr Ala Thr Thr Thr Ala
            100                 105                 110

Thr Gly Asn Gly Gly Ala Arg Ala Ile Gly Ala Ser Thr Thr Ser Ala
        115                 120                 125

Ser Ala Ser Glu Pro Thr Gln Thr Arg Thr Ile Thr Gly Pro Gly Ser
    130                 135                 140

Gln Thr Ala Thr Ala Phe Ala Arg Asp Thr Ala Thr Thr Thr Val Thr
145                 150                 155                 160

Ala Ser

<210> SEQ ID NO 4
<211> LENGTH: 138
<212> TYPE: PRT
<213> ORGANISM: Rhagium mordax

<400> SEQUENCE: 4

Met His Thr Pro Cys Arg Ala Val Gly Val Asp Gly Pro Val Val Thr
1               5                   10                  15

Asp Val Gln Gly Thr Cys Thr Ala Lys Ala Thr Gly Val Gly Ala Val
            20                  25                  30

Ala Ser Gly Thr Ser Val Asp Gly Ser Thr Ser Thr Ala Thr Ala Thr
        35                  40                  45

Gly Ser Gly Ala Ser Ala Thr Ser Thr Ser Thr Gly Ser Gly Thr Ala
    50                  55                  60

Thr Thr Thr Ala Thr Ser Asn Ala Ser Ala Thr Ser Asn Ala Ile Asp
65                  70                  75                  80
```

-continued

```
Gln Gly Thr Ala Thr Ser Thr Ala Thr Gly Thr Ala Ala Ala Arg Ala
                85                  90                  95
Ile Gly Ala Ser Thr Thr Ser Ala Ser Ala Ser Glu Pro Thr Gln Thr
            100                 105                 110
Gln Thr Ile Ser Gly Val Gly Thr Gln Thr Ala Thr Ala Phe Ala Thr
        115                 120                 125
Asp Thr Ala Thr Thr Thr Val Thr Ala Ser
    130                 135

<210> SEQ ID NO 5
<211> LENGTH: 162
<212> TYPE: PRT
<213> ORGANISM: Rhagium mordax

<400> SEQUENCE: 5

Met Ser Met Lys Met Ile Gln Arg Phe Ala Phe Ala Cys Leu Val Ile
1               5                   10                  15
Thr Leu Thr Ser Pro Ala Ile Ala His Ala Tyr Ser Cys Arg Ala Val
            20                  25                  30
Gly Val Asp Gly Pro Val Val Thr Asp Val Gln Gly Thr Cys Thr Ala
        35                  40                  45
Lys Ala Thr Gly Val Gly Ala Val Ala Ser Gly Thr Ser Val Asp Gly
    50                  55                  60
Ser Thr Ser Thr Ala Thr Ala Thr Gly Ser Gly Ala Ser Ala Thr Ser
65                  70                  75                  80
Thr Ser Thr Gly Ser Gly Thr Ala Thr Thr Thr Ala Thr Ser Asn Ala
                85                  90                  95
Ser Ala Thr Ser Asn Ala Ile Asp Gln Gly Thr Ala Thr Ser Thr Ala
            100                 105                 110
Thr Gly Thr Ala Ala Ala Arg Ala Ile Gly Ala Ser Thr Thr Ser Ala
        115                 120                 125
Ser Ala Ser Glu Pro Thr Gln Thr Gln Thr Ile Ser Gly Val Gly Thr
    130                 135                 140
Gln Thr Ala Thr Ala Phe Ala Thr Asp Thr Ala Thr Thr Thr Val Thr
145                 150                 155                 160
Ala Ser

<210> SEQ ID NO 6
<211> LENGTH: 146
<212> TYPE: PRT
<213> ORGANISM: Rhagium mordax

<400> SEQUENCE: 6

Met Met Leu Thr Ser Pro Ala Ile Ala His Ala Tyr Ser Cys Arg Ala
1               5                   10                  15

Val Gly Val Asp Gly Gln Ala Val Thr Asp Ile His Gly Thr Cys Asn
            20                  25                  30

Ala Lys Ala Thr Gly Ser Gly Ala Val Ala Ser Gly Thr Ser Glu Asp
        35                  40                  45

Gly Ser Arg Ser Thr Ala Thr Ala Thr Gly Ser Gly Ala Ile Ala Thr
    50                  55                  60

Ser Thr Ser Ser Gly Ser Gly Thr Ala Thr Thr Thr Ala Thr Gly Asn
65                  70                  75                  80

Ala Ala Ala Thr Ser Asn Ala Ile Gly Arg Gly Thr Ala Thr Thr Thr
                85                  90                  95
```

```
Ala Thr Gly Thr Gly Gly Arg Ala Thr Gly Thr Ser Thr Ile Ser Ala
            100                 105                 110

Ser Ala Ser Glu Pro Thr Gln Thr Ser Thr Val Thr Gly Pro Gly Ser
        115                 120                 125

Gln Thr Gly Thr Ala Phe Ala Arg Asp Thr Ala Thr Thr Thr Val Thr
    130                 135                 140

Ser Ser
145

<210> SEQ ID NO 7
<211> LENGTH: 147
<212> TYPE: PRT
<213> ORGANISM: Rhagium mordax

<400> SEQUENCE: 7

Met Met Leu Thr Ser Pro Ala Ile Ala His Ala Tyr Ser Cys Arg Ala
1               5                   10                  15

Val Gly Val Asp Ala Ser Thr Val Thr Asp Val Gln Gly Thr Cys His
            20                  25                  30

Ala Lys Ala Thr Gly Pro Gly Ala Val Ala Ser Gly Thr Ser Val Asp
        35                  40                  45

Gly Ser Thr Ser Thr Ala Thr Ala Thr Gly Ser Gly Ala Thr Ala Thr
    50                  55                  60

Ser Thr Ser Thr Gly Thr Gly Thr Ala Thr Thr Thr Ala Thr Ser Asn
65                  70                  75                  80

Ala Ala Ala Thr Ser Asn Ala Ile Gly Gln Gly Thr Ala Thr Ser Thr
                85                  90                  95

Ala Thr Gly Thr Ala Ala Ala Arg Ala Ile Gly Ser Ser Thr Thr Ser
            100                 105                 110

Ala Ser Ala Thr Glu Pro Thr Gln Thr Lys Thr Val Ser Gly Pro Gly
        115                 120                 125

Ala Gln Thr Ala Thr Ala Ile Ala Ile Asp Thr Ala Thr Thr Thr Val
    130                 135                 140

Thr Ala Ser
145

<210> SEQ ID NO 8
<211> LENGTH: 158
<212> TYPE: PRT
<213> ORGANISM: Rhagium mordax

<400> SEQUENCE: 8

Met Ile Gln Ala Phe Ala Phe Ala Cys Leu Val Met Met Leu Thr Ser
1               5                   10                  15

Pro Ala Ile Ala His Ala Tyr Ser Cys Arg Ala Val Gly Val Asp Ala
            20                  25                  30

Ser Thr Val Thr Asp Val Gln Gly Thr Cys His Ala Lys Ala Thr Gly
        35                  40                  45

Pro Gly Ala Val Ala Ser Gly Thr Ser Val Asp Gly Ser Thr Ser Thr
    50                  55                  60

Ala Thr Ala Thr Gly Ser Gly Ala Thr Ala Thr Ser Thr Ser Thr Gly
65                  70                  75                  80

Thr Gly Thr Ala Thr Thr Thr Ala Thr Ser Asn Ala Ala Ala Thr Ser
                85                  90                  95

Asn Ala Ile Gly Gln Gly Thr Ala Thr Ser Thr Ala Thr Gly Thr Ala
            100                 105                 110
```

-continued

Ala Ala Arg Ala Ile Gly Ser Ser Thr Thr Ser Ala Ser Ala Thr Glu
        115                 120                 125

Pro Thr Gln Thr Lys Thr Val Ser Gly Pro Gly Ala Gln Thr Ala Thr
        130                 135                 140

Ala Ile Ala Ile Asp Thr Ala Thr Thr Val Thr Ala Ser
145                 150                 155

<210> SEQ ID NO 9
<211> LENGTH: 7
<212> TYPE: PRT
<213> ORGANISM: Rhagium mordax

<400> SEQUENCE: 9

Thr Cys His Ala Lys Ala Thr
1               5

<210> SEQ ID NO 10
<211> LENGTH: 7
<212> TYPE: PRT
<213> ORGANISM: Rhagium mordax

<400> SEQUENCE: 10

Thr Ser Thr Ala Thr Ala Thr
1               5

<210> SEQ ID NO 11
<211> LENGTH: 7
<212> TYPE: PRT
<213> ORGANISM: Rhagium mordax

<400> SEQUENCE: 11

Thr Ala Thr Ser Thr Ser Thr
1               5

<210> SEQ ID NO 12
<211> LENGTH: 7
<212> TYPE: PRT
<213> ORGANISM: Rhagium mordax

<400> SEQUENCE: 12

Thr Ala Thr Thr Thr Ala Thr
1               5

<210> SEQ ID NO 13
<211> LENGTH: 7
<212> TYPE: PRT
<213> ORGANISM: Rhagium mordax

<400> SEQUENCE: 13

Thr Ala Thr Ser Thr Ala Thr
1               5

<210> SEQ ID NO 14
<211> LENGTH: 7
<212> TYPE: PRT
<213> ORGANISM: Rhagium mordax

<400> SEQUENCE: 14

Ser Ser Thr Thr Ser Ala Ser
1               5

```
<210> SEQ ID NO 15
<211> LENGTH: 7
<212> TYPE: PRT
<213> ORGANISM: Rhagium mordax

<400> SEQUENCE: 15

Thr Gln Thr Lys Thr Val Ser
1               5

<210> SEQ ID NO 16
<211> LENGTH: 7
<212> TYPE: PRT
<213> ORGANISM: Rhagium mordax

<400> SEQUENCE: 16

Thr Ala Thr Thr Thr Val Thr
1               5

<210> SEQ ID NO 17
<211> LENGTH: 7
<212> TYPE: PRT
<213> ORGANISM: Rhagium mordax

<400> SEQUENCE: 17

Thr Cys His Ala Lys Ala Thr
1               5

<210> SEQ ID NO 18
<211> LENGTH: 7
<212> TYPE: PRT
<213> ORGANISM: Rhagium mordax

<400> SEQUENCE: 18

Thr Ser Thr Ala Thr Ala Thr
1               5

<210> SEQ ID NO 19
<211> LENGTH: 7
<212> TYPE: PRT
<213> ORGANISM: Rhagium mordax

<400> SEQUENCE: 19

Thr Ala Thr Ser Thr Ser Thr
1               5

<210> SEQ ID NO 20
<211> LENGTH: 7
<212> TYPE: PRT
<213> ORGANISM: Rhagium mordax

<400> SEQUENCE: 20

Thr Ala Thr Thr Thr Ala Thr
1               5

<210> SEQ ID NO 21
<211> LENGTH: 7
<212> TYPE: PRT
<213> ORGANISM: Rhagium mordax

<400> SEQUENCE: 21

Thr Ala Thr Ser Thr Ala Thr
1               5
```

```
<210> SEQ ID NO 22
<211> LENGTH: 7
<212> TYPE: PRT
<213> ORGANISM: Rhagium mordax

<400> SEQUENCE: 22

Ser Ser Thr Thr Ser Ala Ser
1               5

<210> SEQ ID NO 23
<211> LENGTH: 7
<212> TYPE: PRT
<213> ORGANISM: Rhagium mordax

<400> SEQUENCE: 23

Thr Gln Thr Lys Thr Val Ser
1               5

<210> SEQ ID NO 24
<211> LENGTH: 7
<212> TYPE: PRT
<213> ORGANISM: Rhagium mordax

<400> SEQUENCE: 24

Thr Ala Thr Thr Thr Val Thr
1               5

<210> SEQ ID NO 25
<211> LENGTH: 7
<212> TYPE: PRT
<213> ORGANISM: Rhagium mordax

<400> SEQUENCE: 25

Thr Cys Asn Ala Lys Ala Thr
1               5

<210> SEQ ID NO 26
<211> LENGTH: 7
<212> TYPE: PRT
<213> ORGANISM: Rhagium mordax

<400> SEQUENCE: 26

Thr Ser Thr Ala Thr Ala Thr
1               5

<210> SEQ ID NO 27
<211> LENGTH: 7
<212> TYPE: PRT
<213> ORGANISM: Rhagium mordax

<400> SEQUENCE: 27

Val Ala Thr Ser Thr Ser Thr
1               5

<210> SEQ ID NO 28
<211> LENGTH: 7
<212> TYPE: PRT
<213> ORGANISM: Rhagium mordax

<400> SEQUENCE: 28

Thr Ala Thr Thr Thr Ala Thr
1               5
```

```
<210> SEQ ID NO 29
<211> LENGTH: 7
<212> TYPE: PRT
<213> ORGANISM: Rhagium mordax

<400> SEQUENCE: 29

Thr Ala Thr Thr Thr Ala Thr
1               5

<210> SEQ ID NO 30
<211> LENGTH: 7
<212> TYPE: PRT
<213> ORGANISM: Rhagium mordax

<400> SEQUENCE: 30

Ala Ser Thr Thr Ser Ala Ser
1               5

<210> SEQ ID NO 31
<211> LENGTH: 7
<212> TYPE: PRT
<213> ORGANISM: Rhagium mordax

<400> SEQUENCE: 31

Thr Gln Thr Arg Thr Ile Thr
1               5

<210> SEQ ID NO 32
<211> LENGTH: 7
<212> TYPE: PRT
<213> ORGANISM: Rhagium mordax

<400> SEQUENCE: 32

Thr Ala Thr Thr Thr Val Thr
1               5

<210> SEQ ID NO 33
<211> LENGTH: 7
<212> TYPE: PRT
<213> ORGANISM: Rhagium mordax

<400> SEQUENCE: 33

Thr Cys Thr Ala Lys Ala Thr
1               5

<210> SEQ ID NO 34
<211> LENGTH: 7
<212> TYPE: PRT
<213> ORGANISM: Rhagium mordax

<400> SEQUENCE: 34

Thr Ser Thr Ala Thr Ala Thr
1               5

<210> SEQ ID NO 35
<211> LENGTH: 7
<212> TYPE: PRT
<213> ORGANISM: Rhagium mordax

<400> SEQUENCE: 35

Ser Ala Thr Ser Thr Ser Thr
1               5
```

```
<210> SEQ ID NO 36
<211> LENGTH: 7
<212> TYPE: PRT
<213> ORGANISM: Rhagium mordax

<400> SEQUENCE: 36

Thr Ala Thr Thr Thr Ala Thr
1               5

<210> SEQ ID NO 37
<211> LENGTH: 7
<212> TYPE: PRT
<213> ORGANISM: Rhagium mordax

<400> SEQUENCE: 37

Thr Ala Thr Ser Thr Ala Thr
1               5

<210> SEQ ID NO 38
<211> LENGTH: 7
<212> TYPE: PRT
<213> ORGANISM: Rhagium mordax

<400> SEQUENCE: 38

Ala Ser Thr Thr Ser Ala Ser
1               5

<210> SEQ ID NO 39
<211> LENGTH: 7
<212> TYPE: PRT
<213> ORGANISM: Rhagium mordax

<400> SEQUENCE: 39

Thr Gln Thr Gln Thr Ile Ser
1               5

<210> SEQ ID NO 40
<211> LENGTH: 7
<212> TYPE: PRT
<213> ORGANISM: Rhagium mordax

<400> SEQUENCE: 40

Thr Ala Thr Thr Thr Val Thr
1               5

<210> SEQ ID NO 41
<211> LENGTH: 7
<212> TYPE: PRT
<213> ORGANISM: Rhagium mordax

<400> SEQUENCE: 41

Thr Cys Thr Ala Lys Ala Thr
1               5

<210> SEQ ID NO 42
<211> LENGTH: 7
<212> TYPE: PRT
<213> ORGANISM: Rhagium mordax

<400> SEQUENCE: 42

Thr Ser Thr Ala Thr Ala Thr
1               5
```

```
<210> SEQ ID NO 43
<211> LENGTH: 7
<212> TYPE: PRT
<213> ORGANISM: Rhagium mordax

<400> SEQUENCE: 43

Ser Ala Thr Ser Thr Ser Thr
1               5

<210> SEQ ID NO 44
<211> LENGTH: 7
<212> TYPE: PRT
<213> ORGANISM: Rhagium mordax

<400> SEQUENCE: 44

Thr Ala Thr Thr Thr Ala Thr
1               5

<210> SEQ ID NO 45
<211> LENGTH: 7
<212> TYPE: PRT
<213> ORGANISM: Rhagium mordax

<400> SEQUENCE: 45

Thr Ala Thr Ser Thr Ala Thr
1               5

<210> SEQ ID NO 46
<211> LENGTH: 7
<212> TYPE: PRT
<213> ORGANISM: Rhagium mordax

<400> SEQUENCE: 46

Ala Ser Thr Thr Ser Ala Ser
1               5

<210> SEQ ID NO 47
<211> LENGTH: 7
<212> TYPE: PRT
<213> ORGANISM: Rhagium mordax

<400> SEQUENCE: 47

Thr Gln Thr Gln Thr Ile Ser
1               5

<210> SEQ ID NO 48
<211> LENGTH: 7
<212> TYPE: PRT
<213> ORGANISM: Rhagium mordax

<400> SEQUENCE: 48

Thr Ala Thr Thr Thr Val Thr
1               5

<210> SEQ ID NO 49
<211> LENGTH: 7
<212> TYPE: PRT
<213> ORGANISM: Rhagium mordax

<400> SEQUENCE: 49

Thr Cys Asn Ala Lys Ala Thr
1               5
```

```
<210> SEQ ID NO 50
<211> LENGTH: 7
<212> TYPE: PRT
<213> ORGANISM: Rhagium mordax

<400> SEQUENCE: 50

Arg Ser Thr Ala Thr Ala Thr
1               5

<210> SEQ ID NO 51
<211> LENGTH: 7
<212> TYPE: PRT
<213> ORGANISM: Rhagium mordax

<400> SEQUENCE: 51

Ile Ala Thr Ser Thr Ser Ser
1               5

<210> SEQ ID NO 52
<211> LENGTH: 7
<212> TYPE: PRT
<213> ORGANISM: Rhagium mordax

<400> SEQUENCE: 52

Thr Ala Thr Thr Thr Ala Thr
1               5

<210> SEQ ID NO 53
<211> LENGTH: 7
<212> TYPE: PRT
<213> ORGANISM: Rhagium mordax

<400> SEQUENCE: 53

Thr Ala Thr Thr Thr Ala Thr
1               5

<210> SEQ ID NO 54
<211> LENGTH: 7
<212> TYPE: PRT
<213> ORGANISM: Rhagium mordax

<400> SEQUENCE: 54

Thr Ser Thr Ile Ser Ala Ser
1               5

<210> SEQ ID NO 55
<211> LENGTH: 7
<212> TYPE: PRT
<213> ORGANISM: Rhagium mordax

<400> SEQUENCE: 55

Thr Gln Thr Ser Thr Val Thr
1               5

<210> SEQ ID NO 56
<211> LENGTH: 7
<212> TYPE: PRT
<213> ORGANISM: Rhagium mordax

<400> SEQUENCE: 56

Thr Ala Thr Thr Thr Val Thr
1               5
```

```
<210> SEQ ID NO 57
<211> LENGTH: 7
<212> TYPE: PRT
<213> ORGANISM: Rhagium mordax

<400> SEQUENCE: 57

Thr Cys His Ala Lys Ala Thr
1               5

<210> SEQ ID NO 58
<211> LENGTH: 7
<212> TYPE: PRT
<213> ORGANISM: Rhagium mordax

<400> SEQUENCE: 58

Thr Ser Thr Ala Thr Ala Thr
1               5

<210> SEQ ID NO 59
<211> LENGTH: 7
<212> TYPE: PRT
<213> ORGANISM: Rhagium mordax

<400> SEQUENCE: 59

Thr Ala Thr Ser Thr Ser Thr
1               5

<210> SEQ ID NO 60
<211> LENGTH: 7
<212> TYPE: PRT
<213> ORGANISM: Rhagium mordax

<400> SEQUENCE: 60

Thr Ala Thr Thr Thr Ala Thr
1               5

<210> SEQ ID NO 61
<211> LENGTH: 7
<212> TYPE: PRT
<213> ORGANISM: Rhagium mordax

<400> SEQUENCE: 61

Thr Ala Thr Ser Thr Ala Thr
1               5

<210> SEQ ID NO 62
<211> LENGTH: 7
<212> TYPE: PRT
<213> ORGANISM: Rhagium mordax

<400> SEQUENCE: 62

Ser Ser Thr Thr Ser Ala Ser
1               5

<210> SEQ ID NO 63
<211> LENGTH: 7
<212> TYPE: PRT
<213> ORGANISM: Rhagium mordax

<400> SEQUENCE: 63

Thr Gln Thr Lys Thr Val Ser
1               5
```

```
<210> SEQ ID NO 64
<211> LENGTH: 7
<212> TYPE: PRT
<213> ORGANISM: Rhagium mordax

<400> SEQUENCE: 64

Thr Ala Thr Thr Thr Val Thr
1               5

<210> SEQ ID NO 65
<211> LENGTH: 7
<212> TYPE: PRT
<213> ORGANISM: Rhagium mordax

<400> SEQUENCE: 65

Thr Cys His Ala Lys Ala Thr
1               5

<210> SEQ ID NO 66
<211> LENGTH: 7
<212> TYPE: PRT
<213> ORGANISM: Rhagium mordax

<400> SEQUENCE: 66

Thr Ser Thr Ala Thr Ala Thr
1               5

<210> SEQ ID NO 67
<211> LENGTH: 7
<212> TYPE: PRT
<213> ORGANISM: Rhagium mordax

<400> SEQUENCE: 67

Thr Ala Thr Ser Thr Ser Thr
1               5

<210> SEQ ID NO 68
<211> LENGTH: 7
<212> TYPE: PRT
<213> ORGANISM: Rhagium mordax

<400> SEQUENCE: 68

Thr Ala Thr Thr Thr Ala Thr
1               5

<210> SEQ ID NO 69
<211> LENGTH: 7
<212> TYPE: PRT
<213> ORGANISM: Rhagium mordax

<400> SEQUENCE: 69

Thr Ala Thr Ser Thr Ala Thr
1               5

<210> SEQ ID NO 70
<211> LENGTH: 7
<212> TYPE: PRT
<213> ORGANISM: Rhagium mordax

<400> SEQUENCE: 70

Ser Ser Thr Thr Ser Ala Ser
1               5
```

```
<210> SEQ ID NO 71
<211> LENGTH: 7
<212> TYPE: PRT
<213> ORGANISM: Rhagium mordax

<400> SEQUENCE: 71

Thr Gln Thr Lys Thr Val Ser
1               5

<210> SEQ ID NO 72
<211> LENGTH: 7
<212> TYPE: PRT
<213> ORGANISM: Rhagium mordax

<400> SEQUENCE: 72

Thr Ala Thr Thr Thr Val Thr
1               5

<210> SEQ ID NO 73
<211> LENGTH: 7
<212> TYPE: PRT
<213> ORGANISM: Rhagium mordax
<220> FEATURE:
<221> NAME/KEY: MISC_FEATURE
<222> LOCATION: (3)..(3)
<223> OTHER INFORMATION: X could be any of the amino acids H, N or T.

<400> SEQUENCE: 73

Thr Cys Xaa Ala Lys Ala Thr
1               5

<210> SEQ ID NO 74
<211> LENGTH: 7
<212> TYPE: PRT
<213> ORGANISM: Rhagium mordax
<220> FEATURE:
<221> NAME/KEY: MISC_FEATURE
<222> LOCATION: (1)..(1)
<223> OTHER INFORMATION: X could be any of the amino acids R or T.

<400> SEQUENCE: 74

Xaa Ser Thr Ala Thr Ala Thr
1               5

<210> SEQ ID NO 75
<211> LENGTH: 7
<212> TYPE: PRT
<213> ORGANISM: Rhagium mordax
<220> FEATURE:
<221> NAME/KEY: MISC_FEATURE
<222> LOCATION: (1)..(1)
<223> OTHER INFORMATION: X could be any of the amino acids I, S, T or V.
<220> FEATURE:
<221> NAME/KEY: MISC_FEATURE
<222> LOCATION: (7)..(7)
<223> OTHER INFORMATION: X could be any of the amino acids S or T.

<400> SEQUENCE: 75

Xaa Ala Thr Ser Thr Ser Xaa
1               5

<210> SEQ ID NO 76
<211> LENGTH: 7
<212> TYPE: PRT
<213> ORGANISM: Rhagium mordax
```

```
<400> SEQUENCE: 76

Thr Ala Thr Thr Thr Ala Thr
1               5

<210> SEQ ID NO 77
<211> LENGTH: 7
<212> TYPE: PRT
<213> ORGANISM: Rhagium mordax
<220> FEATURE:
<221> NAME/KEY: MISC_FEATURE
<222> LOCATION: (4)..(4)
<223> OTHER INFORMATION: X could be any of the amino acids S or T.

<400> SEQUENCE: 77

Thr Ala Thr Xaa Thr Ala Thr
1               5

<210> SEQ ID NO 78
<211> LENGTH: 7
<212> TYPE: PRT
<213> ORGANISM: Rhagium mordax
<220> FEATURE:
<221> NAME/KEY: MISC_FEATURE
<222> LOCATION: (1)..(1)
<223> OTHER INFORMATION: X could be any of the amino acids A, S or T.
<220> FEATURE:
<221> NAME/KEY: MISC_FEATURE
<222> LOCATION: (4)..(4)
<223> OTHER INFORMATION: X could be any of the amino acids I or T.

<400> SEQUENCE: 78

Xaa Ser Thr Xaa Ser Ala Ser
1               5

<210> SEQ ID NO 79
<211> LENGTH: 7
<212> TYPE: PRT
<213> ORGANISM: Rhagium mordax
<220> FEATURE:
<221> NAME/KEY: MISC_FEATURE
<222> LOCATION: (4)..(4)
<223> OTHER INFORMATION: X could be any of the amino acids K, R, Q or S.
<220> FEATURE:
<221> NAME/KEY: MISC_FEATURE
<222> LOCATION: (6)..(6)
<223> OTHER INFORMATION: X could be any of the amino acids I or V.
<220> FEATURE:
<221> NAME/KEY: MISC_FEATURE
<222> LOCATION: (7)..(7)
<223> OTHER INFORMATION: X could be any of the amino acids S or T.

<400> SEQUENCE: 79

Thr Gln Thr Xaa Thr Xaa Xaa
1               5

<210> SEQ ID NO 80
<211> LENGTH: 7
<212> TYPE: PRT
<213> ORGANISM: Rhagium mordax

<400> SEQUENCE: 80

Thr Ala Thr Thr Thr Val Thr
1               5

<210> SEQ ID NO 81
<211> LENGTH: 8
<212> TYPE: PRT
<213> ORGANISM: Rhagium mordax
```

```
<220> FEATURE:
<221> NAME/KEY: MISC_FEATURE
<222> LOCATION: (8)..(8)
<223> OTHER INFORMATION: X could be any of the amino acids A or G.

<400> SEQUENCE: 81

Cys Arg Ala Val Gly Val Asp Xaa
1               5

<210> SEQ ID NO 82
<211> LENGTH: 8
<212> TYPE: PRT
<213> ORGANISM: Rhagium mordax
<220> FEATURE:
<221> NAME/KEY: MISC_FEATURE
<222> LOCATION: (4)..(4)
<223> OTHER INFORMATION: X could be any of the amino acids V, I or L.
<220> FEATURE:
<221> NAME/KEY: MISC_FEATURE
<222> LOCATION: (5)..(5)
<223> OTHER INFORMATION: X could be any of the amino acids H or Q.

<400> SEQUENCE: 82

Val Thr Asp Xaa Xaa Gly Thr Cys
1               5

<210> SEQ ID NO 83
<211> LENGTH: 8
<212> TYPE: PRT
<213> ORGANISM: Rhagium mordax

<400> SEQUENCE: 83

Gly Ala Val Ala Ser Gly Thr Ser
1               5

<210> SEQ ID NO 84
<211> LENGTH: 14
<212> TYPE: PRT
<213> ORGANISM: Rhagium mordax
<220> FEATURE:
<221> NAME/KEY: MISC_FEATURE
<222> LOCATION: (4)..(4)
<223> OTHER INFORMATION: X could be any of the amino acids T, S, K, R or
      H.

<400> SEQUENCE: 84

Asp Gly Ser Xaa Ser Thr Ala Thr Ala Thr Gly Ser Gly Ala
1               5                   10

<210> SEQ ID NO 85
<211> LENGTH: 11
<212> TYPE: PRT
<213> ORGANISM: Rhagium mordax
<220> FEATURE:
<221> NAME/KEY: MISC_FEATURE
<222> LOCATION: (9)..(9)
<223> OTHER INFORMATION: X could be any of the amino acids S or G.

<400> SEQUENCE: 85

Gly Thr Ala Thr Thr Thr Ala Thr Xaa Asn Ala
1               5                   10

<210> SEQ ID NO 86
<211> LENGTH: 17
<212> TYPE: PRT
<213> ORGANISM: Rhagium mordax
```

```
<220> FEATURE:
<221> NAME/KEY: MISC_FEATURE
<222> LOCATION: (7)..(7)
<223> OTHER INFORMATION: X could be any of the amino acids A, G, D or E.
<220> FEATURE:
<221> NAME/KEY: MISC_FEATURE
<222> LOCATION: (8)..(8)
<223> OTHER INFORMATION: X could be any of the amino acids N, Q, R, K or
      H.
<220> FEATURE:
<221> NAME/KEY: MISC_FEATURE
<222> LOCATION: (13)..(13)
<223> OTHER INFORMATION: X could be any of the amino acids S or T.

<400> SEQUENCE: 86

Ala Thr Ser Asn Ala Ile Xaa Xaa Gly Thr Ala Thr Xaa Thr Ala Thr
1               5                   10                  15

Gly

<210> SEQ ID NO 87
<211> LENGTH: 10
<212> TYPE: PRT
<213> ORGANISM: Rhagium mordax
<220> FEATURE:
<221> NAME/KEY: MISC_FEATURE
<222> LOCATION: (5)..(5)
<223> OTHER INFORMATION: X could be any of the amino acids S or T.

<400> SEQUENCE: 87

Ser Ala Ser Ala Xaa Glu Pro Thr Gln Thr
1               5                   10

<210> SEQ ID NO 88
<211> LENGTH: 9
<212> TYPE: PRT
<213> ORGANISM: Rhagium mordax
<220> FEATURE:
<221> NAME/KEY: MISC_FEATURE
<222> LOCATION: (2)..(2)
<223> OTHER INFORMATION: X could be any of the amino acids S or T.
<220> FEATURE:
<221> NAME/KEY: MISC_FEATURE
<222> LOCATION: (5)..(5)
<223> OTHER INFORMATION: X could be any of the amino acids A or G.
<220> FEATURE:
<221> NAME/KEY: MISC_FEATURE
<222> LOCATION: (8)..(8)
<223> OTHER INFORMATION: X could be any of the amino acids I, V or F.

<400> SEQUENCE: 88

Gly Xaa Gln Thr Xaa Thr Ala Xaa Ala
1               5

<210> SEQ ID NO 89
<211> LENGTH: 10
<212> TYPE: PRT
<213> ORGANISM: Rhagium mordax
<220> FEATURE:
<221> NAME/KEY: MISC_FEATURE
<222> LOCATION: (9)..(9)
<223> OTHER INFORMATION: X could be any of the amino acids A, G, S or T.

<400> SEQUENCE: 89

Asp Thr Ala Thr Thr Thr Val Thr Xaa Ser
1               5                   10

<210> SEQ ID NO 90
<211> LENGTH: 9
<212> TYPE: PRT
<213> ORGANISM: Rhagium mordax
```

```
<220> FEATURE:
<221> NAME/KEY: MISC_FEATURE
<222> LOCATION: (1)..(1)
<223> OTHER INFORMATION: X could be any of the amino acids A, D, G or S.
<220> FEATURE:
<221> NAME/KEY: MISC_FEATURE
<222> LOCATION: (2)..(2)
<223> OTHER INFORMATION: X could be any of the amino acids A, V, I, T or
      S.
<220> FEATURE:
<221> NAME/KEY: MISC_FEATURE
<222> LOCATION: (3)..(3)
<223> OTHER INFORMATION: X could be any of the amino acids A, G or S.
<220> FEATURE:
<221> NAME/KEY: MISC_FEATURE
<222> LOCATION: (4)..(4)
<223> OTHER INFORMATION: X could be any of the amino acids I, T, V or S.
<220> FEATURE:
<221> NAME/KEY: MISC_FEATURE
<222> LOCATION: (5)..(5)
<223> OTHER INFORMATION: X could be any of the amino acids I, T, A or S.
<220> FEATURE:
<221> NAME/KEY: MISC_FEATURE
<222> LOCATION: (6)..(6)
<223> OTHER INFORMATION: X could be any of the amino acids T, V or S.
<220> FEATURE:
<221> NAME/KEY: MISC_FEATURE
<222> LOCATION: (7)..(7)
<223> OTHER INFORMATION: X could be any of the amino acids A, G or S.
<220> FEATURE:
<221> NAME/KEY: MISC_FEATURE
<222> LOCATION: (8)..(8)
<223> OTHER INFORMATION: X could be any of the amino acids T, V or S.
<220> FEATURE:
<221> NAME/KEY: MISC_FEATURE
<222> LOCATION: (9)..(9)
<223> OTHER INFORMATION: X could be any of the amino acids A, G or S.

<400> SEQUENCE: 90

Xaa Xaa Xaa Xaa Xaa Xaa Xaa Xaa Xaa
1               5

<210> SEQ ID NO 91
<211> LENGTH: 16
<212> TYPE: PRT
<213> ORGANISM: Synthetic peptide

<400> SEQUENCE: 91

Gly Gly Ser Gly Gly Ser Gly Gly Gly Ser Gly Gly Gly Gly Ser
1               5                   10                  15
```

POLYPEPTIDES COMPRISING AN ICE-BINDING ACTIVITY

This application is a continuation application of U.S. application Ser. No. 12/744,050, filed on Aug. 23, 2010, which is a U.S. national phase application of PCT/DK2008/050278, filed on Nov. 21, 2008, which claims benefit of U.S. provisional application Ser. No. 61/003,979 filed on Nov. 21, 2007 and Danish application PA 2007 01656 filed on Nov. 21, 2007, all of which are hereby incorporated by reference in their entirety. All patent and non-patent references cited in the aforementioned provisional application, or in the present application, are hereby incorporated by reference in their entirety.

FIELD OF INVENTION

The present invention relates to novel polypeptides comprising an ice-binding capability resulting in an ice crystal formation and/or growth reducing or inhibiting activity. Methods for producing and using such polypeptides are also disclosed.

BACKGROUND OF INVENTION

The body temperature of marine teleosts living in polar waters is in temperature equilibrium with the surrounding sea, and is thus at a temperature of approximately −1.8° C. during winter or year round in for example Antarctic waters. The blood of marine teleosts is hypoosmotic to the seawater and its melting point is predicted to be approximately −0.7° C. The polar teleosts are thus supercooled and lethal freezing would be expected in the absence of an adaptation to such harsh climatic conditions.

Similar observations are applicable for a variety of cold-adapted terrestrial organisms, including arthropods, plants, fungi and bacteria although many of these organisms are subjected to much lower temperatures than marine fish. Psychrophilic (cold-loving) organisms have successfully adapted to all the permanently cold regions on earth: They can be found in the deep sea, on freezing mountain tops and in the Polar regions even at temperatures as low as −60° C. Despite the lethal conditions, these organisms have overcome key barriers inherent to permanently cold environments. These barriers include: reduced enzyme activity, decreased membrane fluidity, altered transport of nutrients and waste products, decreased rates of transcription, translation and cell division, polypeptide cold-denaturation, inappropriate polypeptide folding and intracellular ice formation. Research on the mechanisms that allow certain organisms to exist at subzero temperatures has revealed that they rely on at least two strategies: Lowering of the freezing point of water (colligatively by synthesis of low molecular weight substances and non-colligatively via synthesis of unique polypeptides) by either inhibiting ice growth or by giving rise to controlled ice crystal formation. Anti-freeze polypeptides (AFPs) and low molecular weight substances, such as polyalcohols, free amino acids and sugars are believed to be responsible for the former process, while Ice Nucleating polypeptides (INPs) are responsible for the latter.

Anti-freeze polypeptides (AFP—in some publications also known as thermal hysteresis polypeptides, THP, or ice structuring polypeptides, ISP) lower the freezing point of a solution substantially while the predicted melting point is only moderately depressed. This means that whereas the freezing point is lowered dramatically, the melting point of the solution is predicted by the colligative melting point depression. This is true for solutions where ice is present—the question as to whether anti-freeze polypeptides can lower the supercooling point of an ice-free solution is largely unsolved.

The displacement of the freezing temperature is limited and rapid ice growth will take place at a sufficiently low temperature. The separation of the melting and freezing temperature is usually referred to as thermal hysteresis (TH) (Knight et al. 1991, Raymond and DeVries 1977, Wilson 1993), and the temperature of ice growth is referred to as the hysteresis freezing point. The difference between the melting point and the hysteresis freezing point is called the hystersis or the anti-freeze activity. A second functionality of the AFPs is in the frozen state, where they show ice recrystallization inhibition (RI). The AFPs inhibit the formation of large crystals at the expense of small crystals at temperatures above the temperature of recrystrallisation. (Knight et 1.1984, 1995, Knight and Duman 1986, Ramløv et al. 1996).

Mechanism of Inhibition of Ice Formation

The mechanism by which anti-freeze polypeptides inhibit ice growth is still under investigation. AFPs seem all to be amphiphilic. This means that they have one part which is more hydrophobic than the rest of the molecule. Hitherto the explanation for their activity is that their hydrophilic side binds to the ice crystal. However, this view has during the last decade been challenged as when looking at ice/water one can with good reason ask which is per definition most hydrophilic—ice or water. Various evidence for the binding of the AFPs to the ice via their hydrophobic side/domains is emerging, but as the exact mechanism for the binding is not known all evidence so far has been circumstantial.

However, consensus at this point in time is that the anti-freeze polypeptides recognize and bind to various ice surface planes, depending on the type (and isoform) of anti-freeze polypeptide. Ice growth stops where the anti-freeze polypeptides are bound, but continues to a certain extent between the anti-freeze molecules (Raymond and DeVries 1977, DeLuca et al. 1998, Marshall et al. 2004). When the curvature of the ice growing between the anti-freeze polypeptide molecules becomes sufficiently large (or curved), ice growth stops due to the increased surface tension of the curved surfaces (known as the Kelvin effect (Atkins and De Paula 2002, Wilson 1994, 2005, Kristiansen 2005)). It is now not energetically favourable for the water molecules to bind to the curved ice surfaces.

The hysteresis freezing point is thus the temperature where it again becomes energetically favourable for the water molecules to bind to the ice and ice growth continues explosively (Knight et al. 1991, Raymond and DeVries 1977, Wilson 1993).

In most fish anti-freeze solutions, spicular ice growth is seen at the hysteresis freezing point. It is assumed that this is due to the fact that the fish anti-freeze polypeptides bind to the prismplanes on the ice crystals but not to the basal planes. Growth at the hysteresis freezing point is in this case due to binding (addition) of water molecules to the basal planes where growth at the prism planes is still inhibited, thus the ice crystals grow like long spears (spicules).

In solutions containing anti-freeze polypeptides from insects the growth pattern at the hysteresis freezing point is more random and it is suggested that the reason for this is that insect anti-freeze polypeptides also bind to the basal planes (also giving rise to the much higher anti-freeze activity observed in solutions from these animals) and growth thus occurs at spots at any place on the ice crystals once the temperature is low enough (the hysteresis freezing point).

When ice growth is occurring at the hysteresis freezing point in the presence of insect anti-freeze polypeptides the ice growth pattern is cauliflower like in stead of spicular. The thermal hysteresis is thus dependent on at least 2 parameters: 1) the type of anti-freeze polypeptide (dependent on organism, isoform) and 2) the concentration, albeit that the concentration dependency shows saturation (DeVries 1983, Kao et al. 1985, Schrag et al. 1982).

Apparently, there is also a positive correlation between the size of the anti-freeze polypeptide molecules and the amount of hysteresis observed (Kao et al. 1985, Schrag et al. 1982, Wu et al. 2001). Apart from the above mentioned parameters determining the anti-freeze effect it is also substantiated that there is a reciprocal relationship between anti-freeze activity and ice crystal fraction (when the ice crystal is within the hysteresis gap). This effect is most noticeable in the case of insect anti-freeze polypeptides (Zachariassen et al. 2002).

Insect-Derived Anti-Freeze Polypeptides

Several AFPs have been found in insects. This is presumably due to the exposure of insects to much lower temperatures than those which fish may encounter (the freezing point of sea water is approximately −1.8° C.).

To date, the structure of insect AFPs has been elucidated for 3 species: *Tenebrio molitor*, *Choristoneura fumiferana* and *Dendroides canadensis*. Two of the three characterized AFPs from insects (from *T. molitor* and *D. canadensis*) have many structures in common, presumably because they both come from beetles, whereas *C. fumiferana* is a moth.

An example of an insect AFP that is very well characterized is the AFP from the beetle *Tenebrio molitor*. This polypeptide is found in a least 9 isoforms which are all very much alike, but with lengths from 84, 96 to 120 amino acids (Liou et al. 1999). In all the 9 known isoforms a repetitive sequence of 12 amino acids is found: T/A-C-T-X-S-X-X-C-X-X-A-X. This sequence is repeated 6 to 9 times in these AFPs. TmAFP is a right handed beta-helix structure of repetitive amino acid sequences. A highly regular array of threonine residues on the flat beta sheet is thought to interact with water/ice, as the distances between the threonine residues is predicted to fit exactly with the oxygen atom positions in the water molecules of the ice lattice structure. This AFP has an extremely regular structure and a predicted high structural stability provided by a high number for cysteine-cysteine sulphur bridges; every sixth amino acid is a cysteine.

From *D. canadensis* 13 isoforms with varying length and weight (7.3-12.3 kDa) have been isolated (Andorfer and Duman 2000, Duman et al. 2002). In these AFPs the repeating sequence is the same as is found in *T. molitor* albeit a 13eth amino acid is sometimes present in some of the repeating sequences ((Duman 1998, Li et al 1998a, 1998b). The cysteines are placed exactly in the same positions as in the AFPs from *T. molitor* (Li et al. 1998a, 1998b).

The amino acid sequences of the AFPs from *C. fumiferana* are not homologous to the two other known AFP amino acid sequences from insects. However, a sequence T-X-T is found at every 15th amino acid but only the last threonine is conserved; the first Threonine are in many cases substituted with valine (V), arginine (R) or isoleucine (I). The AFPs from *C. fumiferana* also contain fewer cysteines than the other two insect AFPs (Doucet et al. 2000). However, all cysteines participate in disulfide bindings (Gauthier et al. 1998). Apparently the AFPs from *C. fumiferana* contains a hydrophobic core and the polypeptides are stabilized by a network of hydrogen bonds and the disulfide bridges, which all together stabilises the structure (Graether et al. 2000, 2003, Leinala et al 2002).

SUMMARY OF THE INVENTION

The present invention is directed in one aspect to anti-freeze polypeptides and fragments thereof, including anti-freeze polypeptides produced by certain Cerambycid bark beetles and comprising a plurality of ice-binding sites. Methods for making and using such polypeptides, as disclosed herein below in more detail, are also within the scope of the present invention.

The Cerambycid bark beetles *Rhagium inquisitor* and *Rhagium mordax*, both in their adult and larval stages, can be subjected to temperatures as low as −30° C. and still overwinter under bark on tree stumps in northern Scandinavia. Both of these species belong to the group of cold tolerant animals called freeze avoiders, which means that they survive the extremely low temperatures without ice formation in their tissues. They can be regarded to adopt a supercooled (or undercooled) conditions for long time periods.

The supercooled state is potentially lethal to the Cerambycid bark beetles as ice formation in a metastable, supercooled liquid can in principle occur due to random nucleation or as a consequence of inoculation of ice from the surroundings. The Cerambycid bark beetles cannot survive such an ice formation.

Accordingly, both *R. inquisitor* and *R. mordax* have adapted to the climatic conditions and they are able to survive at low temperatures for extended time periods. This makes the Cerambycid bark beetles interesting as a source for anti-freeze polypeptides (AFPs).

In *R. inquisitor*, adaptation to low temperatures has involved accumulation of cryoprotective glycerol in the haemolymph regions, elimination of potential ice nucleating agents from body fluids (giving a much higher probability of supercooling) and synthesis of a number of anti-freeze polypeptides prior to the onset of winter. So far, the anti-freeze activity (7° C.) of the anti-freeze polypeptides found in *R. inquisitor* has been considered the highest known.

Larvae of *R. mordax* are capable of surviving almost as cold temperatures as *R. inquisitor*—in spite of having a very limited accumulation of cryoprotective compounds. According to one presently preferred hypothesis, the ability of *Rhagium mordax* to withstand low temperatures can almost exclusively be ascribed to the synthesis and accumulation of one or more anti-freeze polypeptides (AFP's) prior to the onset of winter.

Anti-freeze polypeptides according to the present invention are surprisingly found to have a significantly lower number of cysteine residues than other insect AFPs presently known. This feature, together with the fact that the polypeptides according to the present invention have fewer repeated sequences than many state-of-the-art insect anti-freeze polypeptides, make them better candidates for expression in heterologous host organisms.

In presently preferred embodiments, the anti-freeze polypeptides according to the present invention, and functional fragments thereof exhibiting anti-freeze activity, preferably have less than 4 cysteine residues, such as less than 3 cysteine residues, for example 2 cysteine residues.

The anti-freeze polypeptides according to the present invention have a variety of utilities and industrial applications as will be clear from the below disclosure. The polypeptides, or genes encoding the polypeptides, can be used in various ways to suppress ice crystal growth. The polypeptides may be introduced directly, or they may be introduced as a gene which is expressed in a host cell under the control of a suitable expression signal to produce the polypeptide(s).

Suitable concentrations of anti-freeze polypeptides will vary depending on the use, but will typically be in the range of from about one part per billion to about one part per thousand (i.e., from about 1 µg/l to about 1 mg/l).

In some aspects of the present invention, the polypeptides are introduced into edible products, or brought into contact with edible products, so as to reduce or inhibit ice crystal growth and/or formation e.g. during production and/or storage of the edible products in their frozen condition.

It has surprisingly been found that the polypeptides according to the present invention provides ice crystallisation that are markedly different than crystals obtained in the presence of other known anti-freeze polypeptides. In particular it has been found that in the presence of the polypeptides according to the present invention crystals with a small spheric structure are obtained while known anti-freeze polypeptides such as e.g. anti-freeze protein type III HPLC 12 mentioned in U.S. Pat. No. 6,914,043 or the ice crystal growth inhibiting agent as mentioned in U.S. Pat. No. 6,312,733 provides ice crystals with a spicular structure.

Hence, one major advantage of the present invention is that when the polypeptides according to the present invention are incorporated into e.g. ice cream an improved mouth feel is obtained due to the fact that the crystals formed in the ice cream during production and storage will have an essentially small spheric structure compared to the rough spicular crystals obtained when using known anti-freeze polypeptides of type III of herein above.

The texture, taste, and useful storage life of frozen edible products, including vegetables, will be greatly improved as a result of the action of the polypeptides according to the present invention. For example, the texture, taste, and useful storage life of frozen vegetables, such as e.g. celery, potatoes, asparagus, peas, carrots, beans, broccoli, sweet corn, spinach, and the like, will be improved. Similarly, the texture, taste and useful storage life of various frozen fruits will be enhanced, including strawberries, blueberries, raspberries, citrus fruits, bananas, grapes, kiwis, peaches, pineapples, plums, cherries, tomatoes and mangoes.

The introduction into vegetables, and other edible products, can be accomplished e.g. by genetic introduction of appropriate polynucleotides into the target organism. Expression of a polynucleotide, either constitutively or inducibly, before food processing has begun, or after harvesting and processing has begun, results in sufficiently high levels of polypeptides according to the present invention to effectively protect the edible product, including a food product, such as up to about 0.1% of total plant polypeptide by mass. Expression can also be on a tissue specific basis. For example, linkage to ripening genes in fruits may result in expression even after harvesting from the producing plant.

The polypeptides, in one important aspect of the invention, are added to foods which are expected to be or remain frozen until, or even during, consumption—and in particular edible products which are consumed in a frozen or cold state.

Many frozen food products are intended to be consumed in the frozen or cold state, for example, ice cream, frozen yogurt, ice milk, sherbet, popsicles, frozen whipped cream, frozen cream pies, frozen puddings and the like. In particular, texture and flavour are adversely affected by the formation of large ice crystals throughout a freeze-thaw cycle that occurs in most home frost-free freezers, or upon sustained storage in the frozen state. This ice crystal growth process may be reduced or even prevented entirely, or at least minimized, by using the anti-freeze polypeptides according to the present invention. The anti-freeze polypeptides according to the present invention may be either incorporated throughout the edible product, and/or they may, i.e. such as alternatively, be applied to the surface of the edible product, where condensation and ice crystal formation is expected to occur most readily. Another important aspect of the present invention relates to yeasts, including bakers yeast, comprising polynucleotides encoding the polypeptides according to the present invention. Methods related to this aspect include methods for transform dough yeast with polynucleotides encoding these polypeptides. Upon incorporation and expression of the polynucleotides into the yeasts, and use of these yeasts e.g. in frozen dough, the dough will naturally leaven upon thawing because the yeast viability will remain high upon thawing. Because less damage accumulates from storage in the presence of these anti-freeze polypeptides and because thawed samples will have preserved a high viability of the yeast cells, either longer storage times in a frozen state will be possible, or smaller samples of dough will need to be stored.

An alternative way of incorporating anti-freeze polypeptides into frozen, fermented edible products is to have the organism responsible for the fermentation process produce the anti-freeze polypeptides while fermenting the food. Hence, the present invention also embraces methods for preparing a frozen fermented food product. This method comprises the steps of (a) contacting a food product with a microorganism that is capable of secreting a polypeptide according to the present invention, wherein the microorganism is capable of fermenting the food product to produce the fermented food product, (b) incubating the food product with the microorganism under conditions in which fermentation takes place so that a fermented food product is produced having anti-freeze polypeptides according to the present invention present in an amount effective for inhibiting ice crystal growth and/or formation in the product or on the surface of the product; and (c) freezing the fermented food product at a temperature of preferably below $-5°$ C., so as to produce a frozen, fermented food product.

Yet another aspect of the present invention is directed to the introduction of anti-freeze polypeptides according to the present invention present into biological cells, or extracts thereof destined for frozen storage. For example, bacterial cells, yeast cells, plant cells and animal cells comprising the anti-freeze polypeptides according to the present invention present have an increased cell or tissue viability with minimal or no loss of inherent characteristics due to the freeze-thaw process. Sub-cellular samples or cellular extracts may have similar sensitivities to freezing, especially on prolonged storage. Typical examples will be in vitro polypeptide translation systems, enzyme preparations, and particularly samples which contain sensitive membrane components, such as chloroplast or mitochondrial membrane preparations.

In particular, samples containing organelles may display increased resistance to freezing damage upon addition of the anti-freeze polypeptides according to the present invention present. Soft animal tissues will exhibit less damage upon freezing in the presence of the subject polypeptides, and addition of the polypeptides according to the present invention present will be useful in situations, when cellular integrity upon freezing and subsequent thawing is important or desired, such as for tissue culture deposits. Thus, samples destined for frozen storage, such as for cell or tissue depositories, might routinely have the polypeptides according to the present invention present added to them. Among the biological cell types often stored are genetic variants of bacteria, fungi (including yeast), and, particularly, higher eucaryote cells (such as hybridoma strains and tissue culture cell lines).

The present invention in other aspects are directed to applications which are not specific to the food area. One non-food application of the polypeptides according to the present invention present is the protection of crops and plants from climatic freezing conditions. The anti-freeze polypeptides according to the present invention present may be either internally incorporated into the cytoplasm by expression of an introduced gene, or the polypeptides may be externally applied to the plants—e.g. by spraying or otherwise. External application may thus be achieved either by direct application of the polypeptides to the plant, or by the external deposit onto the plant of an organism which secretes the polypeptide. These same alternatives for introduction apply to other uses as well.

Another embodiment is the introduction of an anti-freeze polypeptide into a liquid surrounding an organ, tissue or other biological sample. One particular use would be during transportation to a hospital for a transplantation operation or for storage purposes. The anti-freeze polypeptide according to the present invention present should allow short- or long-term storage at a subfreezing temperature, thereby minimizing inherent metabolism or degradation, but with substantially diminished cellular damage from ice crystal growth. Other medically important temperature sensitive biological samples are blood and blood products, therapeutic agents, polypeptide drugs, bioassay reagents and vaccines.

The present invention also provides a cosmetic or dermatological preparation which comprises the polypeptides according to the present invention. The use of the polypeptides according to the present invention in cosmetic or topical dermatological preparations renders possible an effective treatment, but also a prophylaxis of structural and cellular damage in the skin due to cold, which damage with distinct climate- and weather-induced drops in temperature cause changes in the cell physiology in the cell and in the extracellular space through loss of the temperature optima of cellular enzymes, skin damage, skin redness and tight feeling of the skin and increased sensory sensitivities, induced, e.g., by cold, wind and/or UV light, temperature-sensitive skin, negative changes in the skin, the lips and the mucous membranes in the nose and mouth area and the integumentary appendage caused by environmental stress (caused by temperature changes and UV light, smoking, smog, reactive oxygen species, free radicals).

Also included in the present invention are compositions and uses based on the mixture of anti-freeze polypeptides according to the present invention with state-of-the-art stabilizers, emulsifiers and surfactants well known to those skilled in the art and other additives. These compounds may be present to inhibit decay, inhibit oxidation, prevent discoloration, inhibit microbial growth, stabilize emulsions and so forth.

As will be clear from the above, the present invention is directed in one aspect to polypeptides capable of inhibiting and/or reducing ice crystal formation associated with the freezing or supercooling of an object or substance, including an edible product. Supercooling conditions are conditions allowing the cooling of a substance below the temperature at which a change of state would ordinarily take place (i.e. from a water phase to ice) without such a change of state occurring. Accordingly, the cooling of a liquid below its freezing point without freezing taking place constitutes supercooling and results in a metastable state.

The polypeptides according to the present invention will interchangeably be denoted anti-freeze polypeptides and, for short, polypeptides, throughout the present description.

In one aspect there is provided a polypeptide selected from the group consisting of SEQ ID NO:1 to SEQ ID NO:8. The annotation SEQ ID NO:1 to SEQ ID NO:8, and other similar annotations indicating a starting number and an end number of a range of sequence identity numbers, shall, when used herein, denote each and every one of said sequence identity numbers, such as, in the above cited example, the sequence identity numbers SEQ ID NO:1, SEQ ID NO:2, SEQ ID NO:3, SEQ ID NO:4, SEQ ID NO:5, SEQ ID NO:6, SEQ ID NO:7 and SEQ ID NO:8, unless otherwise noted.

Polypeptides comprising or consisting of any of SEQ ID NO:1 to SEQ ID NO:8, fragments thereof having anti-freeze activity, and variants thereof being at least about 75% identical to any of SEQ ID NO:1 to SEQ ID NO:8, or a fragment thereof, also fall within the scope of the present invention. In particular, a fragment of the polypeptide comprising or consisting of any of SEQ ID NO:1 to SEQ ID NO:8 having at least 20 amino acids and an ice binding and anti-freeze activity are also disclosed. The fragment preferably has less than 200 amino acids, such as preferably less than 150 amino acids, for example preferably less than 100 amino acids, such as 80 amino acids, for example 60 amino acids.

The invention is also directed to polypeptides comprising one or more "ice binding sites" (IBSs) according to the present invention, such as polypeptides comprising one or more of any of SEQ ID NO:9 to SEQ ID NO: 72—a total of 64 specific "ice binding sites", IBSs, as indicated in FIG. 3.

In particular, the present invention is directed towards the following polypeptides:

A polypeptide comprising 4 or more sequences, such as 5 or more sequences, for example 6 or more sequences, such as 7 or all of the sequences selected from the group consisting of SEQ ID NO: 9 to SEQ ID NO:16.

A polypeptide comprising 4 or more sequences, such as 5 or more sequences, for example 6 or more sequences, such as 7 or all of the sequences selected from the group consisting of SEQ ID NO: 17 to SEQ ID NO:24.

A polypeptide comprising 4 or more sequences, such as 5 or more sequences, for example 6 or more sequences, such as 7 or all of the sequences selected from the group consisting of SEQ ID NO: 25 to SEQ ID NO:32.

A polypeptide comprising 4 or more sequences, such as 5 or more sequences, for example 6 or more sequences, such as 7 or all of the sequences selected from the group consisting of SEQ ID NO: 33 to SEQ ID NO:40.

A polypeptide comprising 4 or more sequences, such as 5 or more sequences, for example 6 or more sequences, such as 7 or all of the sequences selected from the group consisting of SEQ ID NO: 41 to SEQ ID NO:48.

A polypeptide comprising 4 or more sequences, such as 5 or more sequences, for example 6 or more sequences, such as 7 or all of the sequences selected from the group consisting of SEQ ID NO: 49 to SEQ ID NO:56.

A polypeptide comprising 4 or more sequences, such as 5 or more sequences, for example 6 or more sequences, such as 7 or all of the sequences selected from the group consisting of SEQ ID NO: 57 to SEQ ID NO:64.

A polypeptide comprising 4 or more sequences, such as 5 or more sequences, for example 6 or more sequences, such as 7 or all of the sequences selected from the group consisting of SEQ ID NO: 65 to SEQ ID NO:72.

There is also provided polypeptides comprising one or more of the sequences SEQ ID NO: 73 to 80, such as 4 or more sequences, such as 5 or more sequences, for example 6 or more sequences, such as 7 or all of the sequences of SEQ ID NO: 73 to 80—in the form of conserved "ice binding domains", IBDs.

SEQ ID NO: 81 to 89 relate to further conserved domains which may also be present, singly, or in any combination, in the polypeptides according to the present invention.

The present invention is also directed to SEQ ID NO: 90, in the form of a general ice binding domain, general IBD, which can be present a number of times, such as 2 times, 3 times, 4 times, 5 times, 6 times, 7 times, 8 times, more than 8 times and preferably less than 30 times in the polypeptides according to the present invention. Identical sequences can be present a plurality of times, or variants of SEQ ID NO:90 can be present a plurality of times, as disclosed herein below in the section citing items of the present invention.

Polypeptides comprising pair-wise combinations of ice binding domains are listed in Table 1 herein below. A total of 64 different combinations are listed—in the form of each and every pair-wise and independent combination of any of the 8 ice binding domains (IBDs) disclosed herein as SEQ ID NO: 73 to SEQ ID NO:80.

The present invention is also directed to a polypeptide comprising 4 or more sequences, such as 5 or more sequences, for example 6 or more sequences, such as 7 or all of the sequences selected from the group consisting of SEQ ID NO: 73 to SEQ ID NO:80

In a further aspect, there is provided a polypeptide comprising 4 or more copies, such as 5 or more copies, for example 6 or more copies, such as 7 or more copies, for example 8 or more copies, and preferably less than 20 copies, of the sequence SEQ ID NO: 90.

As stated herein above, the present invention in one aspect is directed to a polypeptide comprising a combination of different ice binding domains (IBDs), said combination comprising as least 1 combination, such as at least 2 combinations, of any of the combinations of 2 IBDs selected from the group of 64 pair-wise ice binding domain sequence combinations presented in Table 1, herein immediately below, said polypeptide preferably having less than 20 general ice binding domains, such as less than 15 general ice binding domains, for example less than 12 general ice binding domains, such as less than 10 general ice binding domains defined by SEQ ID NO:90.

TABLE 1

|  | IBD I | IBD II | IBD III | IBD IV | IBD V | IBD VI | IBD VII | IBD VIII |
|---|---|---|---|---|---|---|---|---|
| IBD I | A1 | A2 | A3 | A4 | A5 | A6 | A7 | A8 |
| IBD II | B1 | B2 | B3 | B4 | B5 | B6 | B7 | B8 |
| IBD III | C1 | C2 | C3 | C4 | C5 | C6 | C7 | C8 |
| IBD IV | D1 | D2 | D3 | D4 | D5 | D6 | D7 | D8 |
| IBD V | E1 | E2 | E3 | E4 | E5 | E6 | E7 | E8 |
| IBD VI | F1 | F2 | F3 | F4 | F5 | F6 | F7 | F8 |
| IBD VII | G1 | G2 | G3 | G4 | G5 | G6 | G7 | G8 |
| IBD VIII | H1 | H2 | H3 | H4 | H5 | H6 | H7 | H8 |

IBD: Ice Binding Domain

Each of the sequences SEQ ID NO:1 to SEQ ID NO:8 contains a total of 8 IBDs, denoted I, II, III, IV, V, VI, VII and VIII, herein above in Table 1. In Table 1 IBD I represents SEQ ID NO 73, IBD II represents SEQ ID NO 74, IBD III represents SEQ ID NO 75, IBD IV represents SEQ ID NO 76, IBD V represents SEQ ID NO 77, IBD VI represents SEQ ID NO 78, IBD VII represents SEQ ID NO 79 and IBD VIII represents SEQ ID NO 80.

Each of the separate letter/number combinations presented in the matrix denoted Table 1 herein above is cross-combined with each other to produce the combinations listed herein below in Table 2. To exemplify, the combination A1A1 originates from the combination of two IBD I domains with another two IBD I domains whereas the combination B3A6 originates from the combination of one IBD II and one IBD III with one IBD I and one IBD VI. The resulting polypeptide thus comprises the following polypeptide ice binding domains: IBD I, IBD II, IBD III and IBD VI.

The present invention thus further provides a polypeptide comprising a combination of different ice binding domains (IBDs), said combination comprising as least 1 combination, such as at least 2 combinations, for example 3 combinations of any of the combination of 4 IBDs selected from the group of 4096 combinations of any 4 ice-binding domain sequences presented in Table 2, herein immediately below, said polypeptide preferably having less than 20 general ice binding domains, such as less than 15 general ice binding domains, for example less than 12 general ice binding domains, such as less than 10 general ice binding domains defined by SEQ ID NO:90.

To further exemplify Table 2, the combinations originates from a 64×64 matrix and A1A1 is the combination of two IBD I domains with another two IBD I domains whereas the combination B3A6 is originated from the combination of one IBD II and one IBD III domains with one IBD I and one IBD VI domain. The later thereby consisting of the following polypeptide domains: IBD I, IBD II, IBD III and IBD VI.

TABLE 2

| A1A1 | A7A4 | B5A7 | C4A2 | D2A5 | D8A8 |
|---|---|---|---|---|---|
| A1A2 | A7A5 | B5A8 | C4A3 | D2A6 | E1A1 |
| A1A3 | A7A6 | B6A1 | C4A4 | D2A7 | E1A2 |
| A1A4 | A7A7 | B6A2 | C4A5 | D2A8 | E1A3 |
| A1A5 | A7A8 | B6A3 | C4A6 | D3A1 | E1A4 |
| A1A6 | A8A1 | B6A4 | C4A7 | D3A2 | E1A5 |
| A1A7 | A8A2 | B6A5 | C4A8 | D3A3 | E1A6 |
| A1A8 | A8A3 | B6A6 | C5A1 | D3A4 | E1A7 |
| A2A1 | A8A4 | B6A7 | C5A2 | D3A5 | E1A8 |
| A2A2 | A8A5 | B6A8 | C5A3 | D3A6 | E2A1 |
| A2A3 | A8A6 | B7A1 | C5A4 | D3A7 | E2A2 |
| A2A4 | A8A7 | B7A2 | C5A5 | D3A8 | E2A3 |
| A2A5 | A8A8 | B7A3 | C5A6 | D4A1 | E2A4 |
| A2A6 | B1A1 | B7A4 | C5A7 | D4A2 | E2A5 |
| A2A7 | B1A2 | B7A5 | C5A8 | D4A3 | E2A6 |
| A2A8 | B1A3 | B7A6 | C6A1 | D4A4 | E2A7 |

TABLE 2-continued

| A3A1 | B1A4 | B7A7 | C6A2 | D4A5 | E2A8 |
|---|---|---|---|---|---|
| A3A2 | B1A5 | B7A8 | C6A3 | D4A6 | E3A1 |
| A3A3 | B1A6 | B8A1 | C6A4 | D4A7 | E3A2 |
| A3A4 | B1A7 | B8A2 | C6A5 | D4A8 | E3A3 |
| A3A5 | B1A8 | B8A3 | C6A6 | D5A1 | E3A4 |
| A3A6 | B2A1 | B8A4 | C6A7 | D5A2 | E3A5 |
| A3A7 | B2A2 | B8A5 | C6A8 | D5A3 | E3A6 |
| A3A8 | B2A3 | B8A6 | C7A1 | D5A4 | E3A7 |
| A4A1 | B2A4 | B8A7 | C7A2 | D5A5 | E3A8 |
| A4A2 | B2A5 | B8A8 | C7A3 | D5A6 | E4A1 |
| A4A3 | B2A6 | C1A1 | C7A4 | D5A7 | E4A2 |
| A4A4 | B2A7 | C1A2 | C7A5 | D5A8 | E4A3 |
| A4A5 | B2A8 | C1A3 | C7A6 | D6A1 | E4A4 |
| A4A6 | B3A1 | C1A4 | C7A7 | D6A2 | E4A5 |
| A4A7 | B3A2 | C1A5 | C7A8 | D6A3 | E4A6 |
| A4A8 | B3A3 | C1A6 | C8A1 | D6A4 | E4A7 |
| A5A1 | B3A4 | C1A7 | C8A2 | D6A5 | E4A8 |
| A5A2 | B3A5 | C1A8 | C8A3 | D6A6 | E5A1 |
| A5A3 | B3A6 | C2A1 | C8A4 | D6A7 | E5A2 |
| A5A4 | B3A7 | C2A2 | C8A5 | D6A8 | E5A3 |

TABLE 2-continued

| | | | | | |
|---|---|---|---|---|---|
| A5A5 | B3A8 | C2A3 | C8A6 | D7A1 | E5A4 |
| A5A6 | B4A1 | C2A4 | C8A7 | D7A2 | E5A5 |
| A5A7 | B4A2 | C2A5 | C8A8 | D7A3 | E5A6 |
| A5A8 | B4A3 | C2A6 | D1A1 | D7A4 | E5A7 |
| A6A1 | B4A4 | C2A7 | D1A2 | D7A5 | E5A8 |
| A6A2 | B4A5 | C2A8 | D1A3 | D7A6 | E6A1 |
| A6A3 | B4A6 | C3A1 | D1A4 | D7A7 | E6A2 |
| A6A4 | B4A7 | C3A2 | D1A5 | D7A8 | E6A3 |
| A6A5 | B4A8 | C3A3 | D1A6 | D8A1 | E6A4 |
| A6A6 | B5A1 | C3A4 | D1A7 | D8A2 | E6A5 |
| A6A7 | B5A2 | C3A5 | D1A8 | D8A3 | E6A6 |
| A6A8 | B5A3 | C3A6 | D2A1 | D8A4 | E6A7 |
| A7A1 | B5A4 | C3A7 | D2A2 | D8A5 | E6A8 |
| A7A2 | B5A5 | C3A8 | D2A3 | D8A6 | E7A1 |
| A7A3 | B5A6 | C4A1 | D2A4 | D8A7 | E7A2 |
| E7A3 | F5A8 | G4A5 | H3A2 | A1B7 | A8B4 |
| E7A4 | F6A1 | G4A6 | H3A3 | A1B8 | A8B5 |
| E7A5 | F6A2 | G4A7 | H3A4 | A2B1 | A8B6 |
| E7A6 | F6A3 | G4A8 | H3A5 | A2B2 | A8B7 |
| E7A7 | F6A4 | G5A1 | H3A6 | A2B3 | A8B8 |
| E7A8 | F6A5 | G5A2 | H3A7 | A2B4 | B1B1 |
| E8A1 | F6A6 | G5A3 | H3A8 | A2B5 | B1B2 |
| E8A2 | F6A7 | G5A4 | H4A1 | A2B6 | B1B3 |
| E8A3 | F6A8 | G5A5 | H4A2 | A2B7 | B1B4 |
| E8A4 | F7A1 | G5A6 | H4A3 | A2B8 | B1B5 |
| E8A5 | F7A2 | G5A7 | H4A4 | A3B1 | B1B6 |
| E8A6 | F7A3 | G5A8 | H4A5 | A3B2 | B1B7 |
| E8A7 | F7A4 | G6A1 | H4A6 | A3B3 | B1B8 |
| E8A8 | F7A5 | G6A2 | H4A7 | A3B4 | B2B1 |
| F1A1 | F7A6 | G6A3 | H4A8 | A3B5 | B2B2 |
| F1A2 | F7A7 | G6A4 | H5A1 | A3B6 | B2B3 |
| F1A3 | F7A8 | G6A5 | H5A2 | A3B7 | B2B4 |
| F1A4 | F8A1 | G6A6 | H5A3 | A3B8 | B2B5 |
| F1A5 | F8A2 | G6A7 | H5A4 | A4B1 | B2B6 |
| F1A6 | F8A3 | G6A8 | H5A5 | A4B2 | B2B7 |
| F1A7 | F8A4 | G7A1 | H5A6 | A4B3 | B2B8 |
| F1A8 | F8A5 | G7A2 | H5A7 | A4B4 | B3B1 |
| F2A1 | F8A6 | G7A3 | H5A8 | A4B5 | B3B2 |
| F2A2 | F8A7 | G7A4 | H6A1 | A4B6 | B3B3 |
| F2A3 | F8A8 | G7A5 | H6A2 | A4B7 | B3B4 |
| F2A4 | G1A1 | G7A6 | H6A3 | A4B8 | B3B5 |
| F2A5 | G1A2 | G7A7 | H6A4 | A5B1 | B3B6 |
| F2A6 | G1A3 | G7A8 | H6A5 | A5B2 | B3B7 |
| F2A7 | G1A4 | G8A1 | H6A6 | A5B3 | B3B8 |
| F2A8 | G1A5 | G8A2 | H6A7 | A5B4 | B4B1 |
| F3A1 | G1A6 | G8A3 | H6A8 | A5B5 | B4B2 |
| F3A2 | G1A7 | G8A4 | H7A1 | A5B6 | B4B3 |
| F3A3 | G1A8 | G8A5 | H7A2 | A5B7 | B4B4 |
| F3A4 | G2A1 | G8A6 | H7A3 | A5B8 | B4B5 |
| F3A5 | G2A2 | G8A7 | H7A4 | A6B1 | B4B6 |
| F3A6 | G2A3 | G8A8 | H7A5 | A6B2 | B4B7 |
| F3A7 | G2A4 | H1A1 | H7A6 | A6B3 | B4B8 |
| F3A8 | G2A5 | H1A2 | H7A7 | A6B4 | B5B1 |
| F4A1 | G2A6 | H1A3 | H7A8 | A6B5 | B5B2 |
| F4A2 | G2A7 | H1A4 | H8A1 | A6B6 | B5B3 |
| F4A3 | G2A8 | H1A5 | H8A2 | A6B7 | B5B4 |
| F4A4 | G3A1 | H1A6 | H8A3 | A6B8 | B5B5 |
| F4A5 | G3A2 | H1A7 | H8A4 | A7B1 | B5B6 |
| F4A6 | G3A3 | H1A8 | H8A5 | A7B2 | B5B7 |
| F4A7 | G3A4 | H2A1 | H8A6 | A7B3 | B5B8 |
| F4A8 | G3A5 | H2A2 | H8A7 | A7B4 | B6B1 |
| F5A1 | G3A6 | H2A3 | H8A8 | A7B5 | B6B2 |
| F5A2 | G3A7 | H2A4 | A1B1 | A7B6 | B6B3 |
| F5A3 | G3A8 | H2A5 | A1B2 | A7B7 | B6B4 |
| F5A4 | G4A1 | H2A6 | A1B3 | A7B8 | B6B5 |
| F5A5 | G4A2 | H2A7 | A1B4 | A8B1 | B6B6 |
| F5A6 | G4A3 | H2A8 | A1B5 | A8B2 | B6B7 |
| F5A7 | G4A4 | H3A1 | A1B6 | A8B3 | B6B8 |
| B7B1 | C5B6 | D4B3 | E2B8 | F1B5 | F8B2 |
| B7B2 | C5B7 | D4B4 | E3B1 | F1B6 | F8B3 |
| B7B3 | C5B8 | D4B5 | E3B2 | F1B7 | F8B4 |
| B7B4 | C6B1 | D4B6 | E3B3 | F1B8 | F8B5 |
| B7B5 | C6B2 | D4B7 | E3B4 | F2B1 | F8B6 |
| B7B6 | C6B3 | D4B8 | E3B5 | F2B2 | F8B7 |
| B7B7 | C6B4 | D5B1 | E3B6 | F2B3 | F8B8 |
| B7B8 | C6B5 | D5B2 | E3B7 | F2B4 | G1B1 |
| B8B1 | C6B6 | D5B3 | E3B8 | F2B5 | G1B2 |
| B8B2 | C6B7 | D5B4 | E4B1 | F2B6 | G1B3 |
| B8B3 | C6B8 | D5B5 | E4B2 | F2B7 | G1B4 |
| B8B4 | C7B1 | D5B6 | E4B3 | F2B8 | G1B5 |

TABLE 2-continued

| | | | | | |
|---|---|---|---|---|---|
| B8B5 | C7B2 | D5B7 | E4B4 | F3B1 | G1B6 |
| B8B6 | C7B3 | D5B8 | E4B5 | F3B2 | G1B7 |
| B8B7 | C7B4 | D6B1 | E4B6 | F3B3 | G1B8 |
| B8B8 | C7B5 | D6B2 | E4B7 | F3B4 | G2B1 |
| C1B1 | C7B6 | D6B3 | E4B8 | F3B5 | G2B2 |
| C1B2 | C7B7 | D6B4 | E5B1 | F3B6 | G2B3 |
| C1B3 | C7B8 | D6B5 | E5B2 | F3B7 | G2B4 |
| C1B4 | C8B1 | D6B6 | E5B3 | F3B8 | G2B5 |
| C1B5 | C8B2 | D6B7 | E5B4 | F4B1 | G2B6 |
| C1B6 | C8B3 | D6B8 | E5B5 | F4B2 | G2B7 |
| C1B7 | C8B4 | D7B1 | E5B6 | F4B3 | G2B8 |
| C1B8 | C8B5 | D7B2 | E5B7 | F4B4 | G3B1 |
| C2B1 | C8B6 | D7B3 | E5B8 | F4B5 | G3B2 |
| C2B2 | C8B7 | D7B4 | E6B1 | F4B6 | G3B3 |
| C2B3 | C8B8 | D7B5 | E6B2 | F4B7 | G3B4 |
| C2B4 | D1B1 | D7B6 | E6B3 | F4B8 | G3B5 |
| C2B5 | D1B2 | D7B7 | E6B4 | F5B1 | G3B6 |
| C2B6 | D1B3 | D7B8 | E6B5 | F5B2 | G3B7 |
| C2B7 | D1B4 | D8B1 | E6B6 | F5B3 | G3B8 |
| C2B8 | D1B5 | D8B2 | E6B7 | F5B4 | G4B1 |
| C3B1 | D1B6 | D8B3 | E6B8 | F5B5 | G4B2 |
| C3B2 | D1B7 | D8B4 | E7B1 | F5B6 | G4B3 |
| C3B3 | D1B8 | D8B5 | E7B2 | F5B7 | G4B4 |
| C3B4 | D2B1 | D8B6 | E7B3 | F5B8 | G4B5 |
| C3B5 | D2B2 | D8B7 | E7B4 | F6B1 | G4B6 |
| C3B6 | D2B3 | D8B8 | E7B5 | F6B2 | G4B7 |
| C3B7 | D2B4 | E1B1 | E7B6 | F6B3 | G4B8 |
| C3B8 | D2B5 | E1B2 | E7B7 | F6B4 | G5B1 |
| C4B1 | D2B6 | E1B3 | E7B8 | F6B5 | G5B2 |
| C4B2 | D2B7 | E1B4 | E8B1 | F6B6 | G5B3 |
| C4B3 | D2B8 | E1B5 | E8B2 | F6B7 | G5B4 |
| C4B4 | D3B1 | E1B6 | E8B3 | F6B8 | G5B5 |
| C4B5 | D3B2 | E1B7 | E8B4 | F7B1 | G5B6 |
| C4B6 | D3B3 | E1B8 | E8B5 | F7B2 | G5B7 |
| C4B7 | D3B4 | E2B1 | E8B6 | F7B3 | G5B8 |
| C4B8 | D3B5 | E2B2 | E8B7 | F7B4 | G6B1 |
| C5B1 | D3B6 | E2B3 | E8B8 | F7B5 | G6B2 |
| C5B2 | D3B7 | E2B4 | F1B1 | F7B6 | G6B3 |
| C5B3 | D3B8 | E2B5 | F1B2 | F7B7 | G6B4 |
| C5B4 | D4B1 | E2B6 | F1B3 | F7B8 | G6B5 |
| C5B5 | D4B2 | E2B7 | F1B4 | F8B1 | G6B6 |
| G6B7 | H5B4 | A4C1 | B2C6 | C1C3 | C7C8 |
| G6B8 | H5B5 | A4C2 | B2C7 | C1C4 | C8C1 |
| G7B1 | H5B6 | A4C3 | B2C8 | C1C5 | C8C2 |
| G7B2 | H5B7 | A4C4 | B3C1 | C1C6 | C8C3 |
| G7B3 | H5B8 | A4C5 | B3C2 | C1C7 | C8C4 |
| G7B4 | H6B1 | A4C6 | B3C3 | C1C8 | C8C5 |
| G7B5 | H6B2 | A4C7 | B3C4 | C2C1 | C8C6 |
| G7B6 | H6B3 | A4C8 | B3C5 | C2C2 | C8C7 |
| G7B7 | H6B4 | A5C1 | B3C6 | C2C3 | C8C8 |
| G7B8 | H6B5 | A5C2 | B3C7 | C2C4 | D1C1 |
| G8B1 | H6B6 | A5C3 | B3C8 | C2C5 | D1C2 |
| G8B2 | H6B7 | A5C4 | B4C1 | C2C6 | D1C3 |
| G8B3 | H6B8 | A5C5 | B4C2 | C2C7 | D1C4 |
| G8B4 | H7B1 | A5C6 | B4C3 | C2C8 | D1C5 |
| G8B5 | H7B2 | A5C7 | B4C4 | C3C1 | D1C6 |
| G8B6 | H7B3 | A5C8 | B4C5 | C3C2 | D1C7 |
| G8B7 | H7B4 | A6C1 | B4C6 | C3C3 | D1C8 |
| G8B8 | H7B5 | A6C2 | B4C7 | C3C4 | D2C1 |
| H1B1 | H7B6 | A6C3 | B4C8 | C3C5 | D2C2 |
| H1B2 | H7B7 | A6C4 | B5C1 | C3C6 | D2C3 |
| H1B3 | H7B8 | A6C5 | B5C2 | C3C7 | D2C4 |
| H1B4 | H8B1 | A6C6 | B5C3 | C3C8 | D2C5 |
| H1B5 | H8B2 | A6C7 | B5C4 | C4C1 | D2C6 |
| H1B6 | H8B3 | A6C8 | B5C5 | C4C2 | D2C7 |
| H1B7 | H8B4 | A7C1 | B5C6 | C4C3 | D2C8 |
| H1B8 | H8B5 | A7C2 | B5C7 | C4C4 | D3C1 |
| H2B1 | H8B6 | A7C3 | B5C8 | C4C5 | D3C2 |
| H2B2 | H8B7 | A7C4 | B6C1 | C4C6 | D3C3 |
| H2B3 | H8B8 | A7C5 | B6C2 | C4C7 | D3C4 |
| H2B4 | A1C1 | A7C6 | B6C3 | C4C8 | D3C5 |
| H2B5 | A1C2 | A7C7 | B6C4 | C5C1 | D3C6 |
| H2B6 | A1C3 | A7C8 | B6C5 | C5C2 | D3C7 |
| H2B7 | A1C4 | A8C1 | B6C6 | C5C3 | D3C8 |
| H2B8 | A1C5 | A8C2 | B6C7 | C5C4 | D4C1 |
| H3B1 | A1C6 | A8C3 | B6C8 | C5C5 | D4C2 |
| H3B2 | A1C7 | A8C4 | B7C1 | C5C6 | D4C3 |
| H3B3 | A1C8 | A8C5 | B7C2 | C5C7 | D4C4 |
| H3B4 | A2C1 | A8C6 | B7C3 | C5C8 | D4C5 |
| H3B5 | A2C2 | A8C7 | B7C4 | C6C1 | D4C6 |

TABLE 2-continued

| | | | | | |
|---|---|---|---|---|---|
| H3B6 | A2C3 | A8C8 | B7C5 | C6C2 | D4C7 |
| H3B7 | A2C4 | B1C1 | B7C6 | C6C3 | D4C8 |
| H3B8 | A2C5 | B1C2 | B7C7 | C6C4 | D5C1 |
| H4B1 | A2C6 | B1C3 | B7C8 | C6C5 | D5C2 |
| H4B2 | A2C7 | B1C4 | B8C1 | C6C6 | D5C3 |
| H4B3 | A2C8 | B1C5 | B8C2 | C6C7 | D5C4 |
| H4B4 | A3C1 | B1C6 | B8C3 | C6C8 | D5C5 |
| H4B5 | A3C2 | B1C7 | B8C4 | C7C1 | D5C6 |
| H4B6 | A3C3 | B1C8 | B8C5 | C7C2 | D5C7 |
| H4B7 | A3C4 | B2C1 | B8C6 | C7C3 | D5C8 |
| H4B8 | A3C5 | B2C2 | B8C7 | C7C4 | D6C1 |
| H5B1 | A3C6 | B2C3 | B8C8 | C7C5 | D6C2 |
| H5B2 | A3C7 | B2C4 | C1C1 | C7C6 | D6C3 |
| H5B3 | A3C8 | B2C5 | C1C2 | C7C7 | D6C4 |
| D6C5 | E5C2 | F3C7 | G2C4 | H1C1 | H7C6 |
| D6C6 | E5C3 | F3C8 | G2C5 | H1C2 | H7C7 |
| D6C7 | E5C4 | F4C1 | G2C6 | H1C3 | H7C8 |
| D6C8 | E5C5 | F4C2 | G2C7 | H1C4 | H8C1 |
| D7C1 | E5C6 | F4C3 | G2C8 | H1C5 | H8C2 |
| D7C2 | E5C7 | F4C4 | G3C1 | H1C6 | H8C3 |
| D7C3 | E5C8 | F4C5 | G3C2 | H1C7 | H8C4 |
| D7C4 | E6C1 | F4C6 | G3C3 | H1C8 | H8C5 |
| D7C5 | E6C2 | F4C7 | G3C4 | H2C1 | H8C6 |
| D7C6 | E6C3 | F4C8 | G3C5 | H2C2 | H8C7 |
| D7C7 | E6C4 | F5C1 | G3C6 | H2C3 | H8C8 |
| D7C8 | E6C5 | F5C2 | G3C7 | H2C4 | A1D1 |
| D8C1 | E6C6 | F5C3 | G3C8 | H2C5 | A1D2 |
| D8C2 | E6C7 | F5C4 | G4C1 | H2C6 | A1D3 |
| D8C3 | E6C8 | F5C5 | G4C2 | H2C7 | A1D4 |
| D8C4 | E7C1 | F5C6 | G4C3 | H2C8 | A1D5 |
| D8C5 | E7C2 | F5C7 | G4C4 | H3C1 | A1D6 |
| D8C6 | E7C3 | F5C8 | G4C5 | H3C2 | A1D7 |
| D8C7 | E7C4 | F6C1 | G4C6 | H3C3 | A1D8 |
| D8C8 | E7C5 | F6C2 | G4C7 | H3C4 | A2D1 |
| E1C1 | E7C6 | F6C3 | G4C8 | H3C5 | A2D2 |
| E1C2 | E7C7 | F6C4 | G5C1 | H3C6 | A2D3 |
| E1C3 | E7C8 | F6C5 | G5C2 | H3C7 | A2D4 |
| E1C4 | E8C1 | F6C6 | G5C3 | H3C8 | A2D5 |
| E1C5 | E8C2 | F6C7 | G5C4 | H4C1 | A2D6 |
| E1C6 | E8C3 | F6C8 | G5C5 | H4C2 | A2D7 |
| E1C7 | E8C4 | F7C1 | G5C6 | H4C3 | A2D8 |
| E1C8 | E8C5 | F7C2 | G5C7 | H4C4 | A3D1 |
| E2C1 | E8C6 | F7C3 | G5C8 | H4C5 | A3D2 |
| E2C2 | E8C7 | F7C4 | G6C1 | H4C6 | A3D3 |
| E2C3 | E8C8 | F7C5 | G6C2 | H4C7 | A3D4 |
| E2C4 | F1C1 | F7C6 | G6C3 | H4C8 | A3D5 |
| E2C5 | F1C2 | F7C7 | G6C4 | H5C1 | A3D6 |
| E2C6 | F1C3 | F7C8 | G6C5 | H5C2 | A3D7 |
| E2C7 | F1C4 | F8C1 | G6C6 | H5C3 | A3D8 |
| E2C8 | F1C5 | F8C2 | G6C7 | H5C4 | A4D1 |
| E3C1 | F1C6 | F8C3 | G6C8 | H5C5 | A4D2 |
| E3C2 | F1C7 | F8C4 | G7C1 | H5C6 | A4D3 |
| E3C3 | F1C8 | F8C5 | G7C2 | H5C7 | A4D4 |
| E3C4 | F2C1 | F8C6 | G7C3 | H5C8 | A4D5 |
| E3C5 | F2C2 | F8C7 | G7C4 | H6C1 | A4D6 |
| E3C6 | F2C3 | F8C8 | G7C5 | H6C2 | A4D7 |
| E3C7 | F2C4 | G1C1 | G7C6 | H6C3 | A4D8 |
| E3C8 | F2C5 | G1C2 | G7C7 | H6C4 | A5D1 |
| E4C1 | F2C6 | G1C3 | G7C8 | H6C5 | A5D2 |
| E4C2 | F2C7 | G1C4 | G8C1 | H6C6 | A5D3 |
| E4C3 | F2C8 | G1C5 | G8C2 | H6C7 | A5D4 |
| E4C4 | F3C1 | G1C6 | G8C3 | H6C8 | A5D5 |
| E4C5 | F3C2 | G1C7 | G8C4 | H7C1 | A5D6 |
| E4C6 | F3C3 | G1C8 | G8C5 | H7C2 | A5D7 |
| E4C7 | F3C4 | G2C1 | G8C6 | H7C3 | A5D8 |
| E4C8 | F3C5 | G2C2 | G8C7 | H7C4 | A6D1 |
| E5C1 | F3C6 | G2C3 | G8C8 | H7C5 | A6D2 |
| A6D3 | B4D8 | C3D5 | D2D2 | D8D7 | E7D4 |
| A6D4 | B5D1 | C3D6 | D2D3 | D8D8 | E7D5 |
| A6D5 | B5D2 | C3D7 | D2D4 | E1D1 | E7D6 |
| A6D6 | B5D3 | C3D8 | D2D5 | E1D2 | E7D7 |
| A6D7 | B5D4 | C4D1 | D2D6 | E1D3 | E7D8 |
| A6D8 | B5D5 | C4D2 | D2D7 | E1D4 | E8D1 |
| A7D1 | B5D6 | C4D3 | D2D8 | E1D5 | E8D2 |
| A7D2 | B5D7 | C4D4 | D3D1 | E1D6 | E8D3 |
| A7D3 | B5D8 | C4D5 | D3D2 | E1D7 | E8D4 |
| A7D4 | B6D1 | C4D6 | D3D3 | E1D8 | E8D5 |
| A7D5 | B6D2 | C4D7 | D3D4 | E2D1 | E8D6 |
| A7D6 | B6D3 | C4D8 | D3D5 | E2D2 | E8D7 |
| A7D7 | B6D4 | C5D1 | D3D6 | E2D3 | E8D8 |
| A7D8 | B6D5 | C5D2 | D3D7 | E2D4 | F1D1 |
| A8D1 | B6D6 | C5D3 | D3D8 | E2D5 | F1D2 |
| A8D2 | B6D7 | C5D4 | D4D1 | E2D6 | F1D3 |
| A8D3 | B6D8 | C5D5 | D4D2 | E2D7 | F1D4 |
| A8D4 | B7D1 | C5D6 | D4D3 | E2D8 | F1D5 |
| A8D5 | B7D2 | C5D7 | D4D4 | E3D1 | F1D6 |
| A8D6 | B7D3 | C5D8 | D4D5 | E3D2 | F1D7 |
| A8D7 | B7D4 | C6D1 | D4D6 | E3D3 | F1D8 |
| A8D8 | B7D5 | C6D2 | D4D7 | E3D4 | F2D1 |
| B1D1 | B7D6 | C6D3 | D4D8 | E3D5 | F2D2 |
| B1D2 | B7D7 | C6D4 | D5D1 | E3D6 | F2D3 |
| B1D3 | B7D8 | C6D5 | D5D2 | E3D7 | F2D4 |
| B1D4 | B8D1 | C6D6 | D5D3 | E3D8 | F2D5 |
| B1D5 | B8D2 | C6D7 | D5D4 | E4D1 | F2D6 |
| B1D6 | B8D3 | C6D8 | D5D5 | E4D2 | F2D7 |
| B1D7 | B8D4 | C7D1 | D5D6 | E4D3 | F2D8 |
| B1D8 | B8D5 | C7D2 | D5D7 | E4D4 | F3D1 |
| B2D1 | B8D6 | C7D3 | D5D8 | E4D5 | F3D2 |
| B2D2 | B8D7 | C7D4 | D6D1 | E4D6 | F3D3 |
| B2D3 | B8D8 | C7D5 | D6D2 | E4D7 | F3D4 |
| B2D4 | C1D1 | C7D6 | D6D3 | E4D8 | F3D5 |
| B2D5 | C1D2 | C7D7 | D6D4 | E5D1 | F3D6 |
| B2D6 | C1D3 | C7D8 | D6D5 | E5D2 | F3D7 |
| B2D7 | C1D4 | C8D1 | D6D6 | E5D3 | F3D8 |
| B2D8 | C1D5 | C8D2 | D6D7 | E5D4 | F4D1 |
| B3D1 | C1D6 | C8D3 | D6D8 | E5D5 | F4D2 |
| B3D2 | C1D7 | C8D4 | D7D1 | E5D6 | F4D3 |
| B3D3 | C1D8 | C8D5 | D7D2 | E5D7 | F4D4 |
| B3D4 | C2D1 | C8D6 | D7D3 | E5D8 | F4D5 |
| B3D5 | C2D2 | C8D7 | D7D4 | E6D1 | F4D6 |
| B3D6 | C2D3 | C8D8 | D7D5 | E6D2 | F4D7 |
| B3D7 | C2D4 | D1D1 | D7D6 | E6D3 | F4D8 |
| B3D8 | C2D5 | D1D2 | D7D7 | E6D4 | F5D1 |
| B4D1 | C2D6 | D1D3 | D7D8 | E6D5 | F5D2 |
| B4D2 | C2D7 | D1D4 | D8D1 | E6D6 | F5D3 |
| B4D3 | C2D8 | D1D5 | D8D2 | E6D7 | F5D4 |
| B4D4 | C3D1 | D1D6 | D8D3 | E6D8 | F5D5 |
| B4D5 | C3D2 | D1D7 | D8D4 | E7D1 | F5D6 |
| B4D6 | C3D3 | D1D8 | D8D5 | E7D2 | F5D7 |
| B4D7 | C3D4 | D2D1 | D8D6 | E7D3 | F5D8 |
| F6D1 | G4D6 | H3D3 | A1E8 | A8E5 | B7E2 |
| F6D2 | G4D7 | H3D4 | A2E1 | A8E6 | B7E3 |
| F6D3 | G4D8 | H3D5 | A2E2 | A8E7 | B7E4 |
| F6D4 | G5D1 | H3D6 | A2E3 | A8E8 | B7E5 |
| F6D5 | G5D2 | H3D7 | A2E4 | B1E1 | B7E6 |
| F6D6 | G5D3 | H3D8 | A2E5 | B1E2 | B7E7 |
| F6D7 | G5D4 | H4D1 | A2E6 | B1E3 | B7E8 |
| F6D8 | G5D5 | H4D2 | A2E7 | B1E4 | B8E1 |
| F7D1 | G5D6 | H4D3 | A2E8 | B1E5 | B8E2 |
| F7D2 | G5D7 | H4D4 | A3E1 | B1E6 | B8E3 |
| F7D3 | G5D8 | H4D5 | A3E2 | B1E7 | B8E4 |
| F7D4 | G6D1 | H4D6 | A3E3 | B1E8 | B8E5 |
| F7D5 | G6D2 | H4D7 | A3E4 | B2E1 | B8E6 |
| F7D6 | G6D3 | H4D8 | A3E5 | B2E2 | B8E7 |
| F7D7 | G6D4 | H5D1 | A3E6 | B2E3 | B8E8 |
| F7D8 | G6D5 | H5D2 | A3E7 | B2E4 | C1E1 |
| F8D1 | G6D6 | H5D3 | A3E8 | B2E5 | C1E2 |
| F8D2 | G6D7 | H5D4 | A4E1 | B2E6 | C1E3 |
| F8D3 | G6D8 | H5D5 | A4E2 | B2E7 | C1E4 |
| F8D4 | G7D1 | H5D6 | A4E3 | B2E8 | C1E5 |
| F8D5 | G7D2 | H5D7 | A4E4 | B3E1 | C1E6 |
| F8D6 | G7D3 | H5D8 | A4E5 | B3E2 | C1E7 |
| F8D7 | G7D4 | H6D1 | A4E6 | B3E3 | C1E8 |
| F8D8 | G7D5 | H6D2 | A4E7 | B3E4 | C2E1 |
| G1D1 | G7D6 | H6D3 | A4E8 | B3E5 | C2E2 |
| G1D2 | G7D7 | H6D4 | A5E1 | B3E6 | C2E3 |
| G1D3 | G7D8 | H6D5 | A5E2 | B3E7 | C2E4 |
| G1D4 | G8D1 | H6D6 | A5E3 | B3E8 | C2E5 |
| G1D5 | G8D2 | H6D7 | A5E4 | B4E1 | C2E6 |
| G1D6 | G8D3 | H6D8 | A5E5 | B4E2 | C2E7 |
| G1D7 | G8D4 | H7D1 | A5E6 | B4E3 | C2E8 |
| G1D8 | G8D5 | H7D2 | A5E7 | B4E4 | C3E1 |
| G2D1 | G8D6 | H7D3 | A5E8 | B4E5 | C3E2 |
| G2D2 | G8D7 | H7D4 | A6E1 | B4E6 | C3E3 |
| G2D3 | G8D8 | H7D5 | A6E2 | B4E7 | C3E4 |
| G2D4 | H1D1 | H7D6 | A6E3 | B4E8 | C3E5 |
| G2D5 | H1D2 | H7D7 | A6E4 | B5E1 | C3E6 |
| G2D6 | H1D3 | H7D8 | A6E5 | B5E2 | C3E7 |
| G2D7 | H1D4 | H8D1 | A6E6 | B5E3 | C3E8 |
| G2D8 | H1D5 | H8D2 | A6E7 | B5E4 | C4E1 |

TABLE 2-continued

| | | | | | |
|---|---|---|---|---|---|
| G3D1 | H1D6 | H8D3 | A6E8 | B5E5 | C4E2 |
| G3D2 | H1D7 | H8D4 | A7E1 | B5E6 | C4E3 |
| G3D3 | H1D8 | H8D5 | A7E2 | B5E7 | C4E4 |
| G3D4 | H2D1 | H8D6 | A7E3 | B5E8 | C4E5 |
| G3D5 | H2D2 | H8D7 | A7E4 | B6E1 | C4E6 |
| G3D6 | H2D3 | H8D8 | A7E5 | B6E2 | C4E7 |
| G3D7 | H2D4 | A1E1 | A7E6 | B6E3 | C4E8 |
| G3D8 | H2D5 | A1E2 | A7E7 | B6E4 | C5E1 |
| G4D1 | H2D6 | A1E3 | A7E8 | B6E5 | C5E2 |
| G4D2 | H2D7 | A1E4 | A8E1 | B6E6 | C5E3 |
| G4D3 | H2D8 | A1E5 | A8E2 | B6E7 | C5E4 |
| G4D4 | H3D1 | A1E6 | A8E3 | B6E8 | C5E5 |
| G4D5 | H3D2 | A1E7 | A8E4 | B7E1 | C5E6 |
| C5E7 | D4E4 | E3E1 | F1E6 | F8E3 | G6E8 |
| C5E8 | D4E5 | E3E2 | F1E7 | F8E4 | G7E1 |
| C6E1 | D4E6 | E3E3 | F1E8 | F8E5 | G7E2 |
| C6E2 | D4E7 | E3E4 | F2E1 | F8E6 | G7E3 |
| C6E3 | D4E8 | E3E5 | F2E2 | F8E7 | G7E4 |
| C6E4 | D5E1 | E3E6 | F2E3 | F8E8 | G7E5 |
| C6E5 | D5E2 | E3E7 | F2E4 | G1E1 | G7E6 |
| C6E6 | D5E3 | E3E8 | F2E5 | G1E2 | G7E7 |
| C6E7 | D5E4 | E4E1 | F2E6 | G1E3 | G7E8 |
| C6E8 | D5E5 | E4E2 | F2E7 | G1E4 | G8E1 |
| C7E1 | D5E6 | E4E3 | F2E8 | G1E5 | G8E2 |
| C7E2 | D5E7 | E4E4 | F3E1 | G1E6 | G8E3 |
| C7E3 | D5E8 | E4E5 | F3E2 | G1E7 | G8E4 |
| C7E4 | D6E1 | E4E6 | F3E3 | G1E8 | G8E5 |
| C7E5 | D6E2 | E4E7 | F3E4 | G2E1 | G8E6 |
| C7E6 | D6E3 | E4E8 | F3E5 | G2E2 | G8E7 |
| C7E7 | D6E4 | E5E1 | F3E6 | G2E3 | G8E8 |
| C7E8 | D6E5 | E5E2 | F3E7 | G2E4 | H1E1 |
| C8E1 | D6E6 | E5E3 | F3E8 | G2E5 | H1E2 |
| C8E2 | D6E7 | E5E4 | F4E1 | G2E6 | H1E3 |
| C8E3 | D6E8 | E5E5 | F4E2 | G2E7 | H1E4 |
| C8E4 | D7E1 | E5E6 | F4E3 | G2E8 | H1E5 |
| C8E5 | D7E2 | E5E7 | F4E4 | G3E1 | H1E6 |
| C8E6 | D7E3 | E5E8 | F4E5 | G3E2 | H1E7 |
| C8E7 | D7E4 | E6E1 | F4E6 | G3E3 | H1E8 |
| C8E8 | D7E5 | E6E2 | F4E7 | G3E4 | H2E1 |
| D1E1 | D7E6 | E6E3 | F4E8 | G3E5 | H2E2 |
| D1E2 | D7E7 | E6E4 | F5E1 | G3E6 | H2E3 |
| D1E3 | D7E8 | E6E5 | F5E2 | G3E7 | H2E4 |
| D1E4 | D8E1 | E6E6 | F5E3 | G3E8 | H2E5 |
| D1E5 | D8E2 | E6E7 | F5E4 | G4E1 | H2E6 |
| D1E6 | D8E3 | E6E8 | F5E5 | G4E2 | H2E7 |
| D1E7 | D8E4 | E7E1 | F5E6 | G4E3 | H2E8 |
| D1E8 | D8E5 | E7E2 | F5E7 | G4E4 | H3E1 |
| D2E1 | D8E6 | E7E3 | F5E8 | G4E5 | H3E2 |
| D2E2 | D8E7 | E7E4 | F6E1 | G4E6 | H3E3 |
| D2E3 | D8E8 | E7E5 | F6E2 | G4E7 | H3E4 |
| D2E4 | E1E1 | E7E6 | F6E3 | G4E8 | H3E5 |
| D2E5 | E1E2 | E7E7 | F6E4 | G5E1 | H3E6 |
| D2E6 | E1E3 | E7E8 | F6E5 | G5E2 | H3E7 |
| D2E7 | E1E4 | E8E1 | F6E6 | G5E3 | H3E8 |
| D2E8 | E1E5 | E8E2 | F6E7 | G5E4 | H4E1 |
| D3E1 | E1E6 | E8E3 | F6E8 | G5E5 | H4E2 |
| D3E2 | E1E7 | E8E4 | F7E1 | G5E6 | H4E3 |
| D3E3 | E1E8 | E8E5 | F7E2 | G5E7 | H4E4 |
| D3E4 | E2E1 | E8E6 | F7E3 | G5E8 | H4E5 |
| D3E5 | E2E2 | E8E7 | F7E4 | G6E1 | H4E6 |
| D3E6 | E2E3 | E8E8 | F7E5 | G6E2 | H4E7 |
| D3E7 | E2E4 | F1E1 | F7E6 | G6E3 | H4E8 |
| D3E8 | E2E5 | F1E2 | F7E7 | G6E4 | H5E1 |
| D4E1 | E2E6 | F1E3 | F7E8 | G6E5 | H5E2 |
| D4E2 | E2E7 | F1E4 | F8E1 | G6E6 | H5E3 |
| D4E3 | E2E8 | F1E5 | F8E2 | G6E7 | H5E4 |
| H5E5 | A4F2 | B2F7 | C1F4 | C8F1 | D6F6 |
| H5E6 | A4F3 | B2F8 | C1F5 | C8F2 | D6F7 |
| H5E7 | A4F4 | B3F1 | C1F6 | C8F3 | D6F8 |
| H5E8 | A4F5 | B3F2 | C1F7 | C8F4 | D7F1 |
| H6E1 | A4F6 | B3F3 | C1F8 | C8F5 | D7F2 |
| H6E2 | A4F7 | B3F4 | C2F1 | C8F6 | D7F3 |
| H6E3 | A4F8 | B3F5 | C2F2 | C8F7 | D7F4 |
| H6E4 | A5F1 | B3F6 | C2F3 | C8F8 | D7F5 |
| H6E5 | A5F2 | B3F7 | C2F4 | D1F1 | D7F6 |
| H6E6 | A5F3 | B3F8 | C2F5 | D1F2 | D7F7 |
| H6E7 | A5F4 | B4F1 | C2F6 | D1F3 | D7F8 |
| H6E8 | A5F5 | B4F2 | C2F7 | D1F4 | D8F1 |
| H7E1 | A5F6 | B4F3 | C2F8 | D1F5 | D8F2 |
| H7E2 | A5F7 | B4F4 | C3F1 | D1F6 | D8F3 |
| H7E3 | A5F8 | B4F5 | C3F2 | D1F7 | D8F4 |
| H7E4 | A6F1 | B4F6 | C3F3 | D1F8 | D8F5 |
| H7E5 | A6F2 | B4F7 | C3F4 | D2F1 | D8F6 |
| H7E6 | A6F3 | B4F8 | C3F5 | D2F2 | D8F7 |
| H7E7 | A6F4 | B5F1 | C3F6 | D2F3 | D8F8 |
| H7E8 | A6F5 | B5F2 | C3F7 | D2F4 | E1F1 |
| H8E1 | A6F6 | B5F3 | C3F8 | D2F5 | E1F2 |
| H8E2 | A6F7 | B5F4 | C4F1 | D2F6 | E1F3 |
| H8E3 | A6F8 | B5F5 | C4F2 | D2F7 | E1F4 |
| H8E4 | A7F1 | B5F6 | C4F3 | D2F8 | E1F5 |
| H8E5 | A7F2 | B5F7 | C4F4 | D3F1 | E1F6 |
| H8E6 | A7F3 | B5F8 | C4F5 | D3F2 | E1F7 |
| H8E7 | A7F4 | B6F1 | C4F6 | D3F3 | E1F8 |
| H8E8 | A7F5 | B6F2 | C4F7 | D3F4 | E2F1 |
| A1F1 | A7F6 | B6F3 | C4F8 | D3F5 | E2F2 |
| A1F2 | A7F7 | B6F4 | C5F1 | D3F6 | E2F3 |
| A1F3 | A7F8 | B6F5 | C5F2 | D3F7 | E2F4 |
| A1F4 | A8F1 | B6F6 | C5F3 | D3F8 | E2F5 |
| A1F5 | A8F2 | B6F7 | C5F4 | D4F1 | E2F6 |
| A1F6 | A8F3 | B6F8 | C5F5 | D4F2 | E2F7 |
| A1F7 | A8F4 | B7F1 | C5F6 | D4F3 | E2F8 |
| A1F8 | A8F5 | B7F2 | C5F7 | D4F4 | E3F1 |
| A2F1 | A8F6 | B7F3 | C5F8 | D4F5 | E3F2 |
| A2F2 | A8F7 | B7F4 | C6F1 | D4F6 | E3F3 |
| A2F3 | A8F8 | B7F5 | C6F2 | D4F7 | E3F4 |
| A2F4 | B1F1 | B7F6 | C6F3 | D4F8 | E3F5 |
| A2F5 | B1F2 | B7F7 | C6F4 | D5F1 | E3F6 |
| A2F6 | B1F3 | B7F8 | C6F5 | D5F2 | E3F7 |
| A2F7 | B1F4 | B8F1 | C6F6 | D5F3 | E3F8 |
| A2F8 | B1F5 | B8F2 | C6F7 | D5F4 | E4F1 |
| A3F1 | B1F6 | B8F3 | C6F8 | D5F5 | E4F2 |
| A3F2 | B1F7 | B8F4 | C7F1 | D5F6 | E4F3 |
| A3F3 | B1F8 | B8F5 | C7F2 | D5F7 | E4F4 |
| A3F4 | B2F1 | B8F6 | C7F3 | D5F8 | E4F5 |
| A3F5 | B2F2 | B8F7 | C7F4 | D6F1 | E4F6 |
| A3F6 | B2F3 | B8F8 | C7F5 | D6F2 | E4F7 |
| A3F7 | B2F4 | C1F1 | C7F6 | D6F3 | E4F8 |
| A3F8 | B2F5 | C1F2 | C7F7 | D6F4 | E5F1 |
| A4F1 | B2F6 | C1F3 | C7F8 | D6F5 | E5F2 |
| E5F3 | F3F8 | G2F5 | H1F2 | H7F7 | A6G4 |
| E5F4 | F4F1 | G2F6 | H1F3 | H7F8 | A6G5 |
| E5F5 | F4F2 | G2F7 | H1F4 | H8F1 | A6G6 |
| E5F6 | F4F3 | G2F8 | H1F5 | H8F2 | A6G7 |
| E5F7 | F4F4 | G3F1 | H1F6 | H8F3 | A6G8 |
| E5F8 | F4F5 | G3F2 | H1F7 | H8F4 | A7G1 |
| E6F1 | F4F6 | G3F3 | H1F8 | H8F5 | A7G2 |
| E6F2 | F4F7 | G3F4 | H2F1 | H8F6 | A7G3 |
| E6F3 | F4F8 | G3F5 | H2F2 | H8F7 | A7G4 |
| E6F4 | F5F1 | G3F6 | H2F3 | H8F8 | A7G5 |
| E6F5 | F5F2 | G3F7 | H2F4 | A1G1 | A7G6 |
| E6F6 | F5F3 | G3F8 | H2F5 | A1G2 | A7G7 |
| E6F7 | F5F4 | G4F1 | H2F6 | A1G3 | A7G8 |
| E6F8 | F5F5 | G4F2 | H2F7 | A1G4 | A8G1 |
| E7F1 | F5F6 | G4F3 | H2F8 | A1G5 | A8G2 |
| E7F2 | F5F7 | G4F4 | H3F1 | A1G6 | A8G3 |
| E7F3 | F5F8 | G4F5 | H3F2 | A1G7 | A8G4 |
| E7F4 | F6F1 | G4F6 | H3F3 | A1G8 | A8G5 |
| E7F5 | F6F2 | G4F7 | H3F4 | A2G1 | A8G6 |
| E7F6 | F6F3 | G4F8 | H3F5 | A2G2 | A8G7 |
| E7F7 | F6F4 | G5F1 | H3F6 | A2G3 | A8G8 |
| E7F8 | F6F5 | G5F2 | H3F7 | A2G4 | B1G1 |
| E8F1 | F6F6 | G5F3 | H3F8 | A2G5 | B1G2 |
| E8F2 | F6F7 | G5F4 | H4F1 | A2G6 | B1G3 |
| E8F3 | F6F8 | G5F5 | H4F2 | A2G7 | B1G4 |
| E8F4 | F7F1 | G5F6 | H4F3 | A2G8 | B1G5 |
| E8F5 | F7F2 | G5F7 | H4F4 | A3G1 | B1G6 |
| E8F6 | F7F3 | G5F8 | H4F5 | A3G2 | B1G7 |
| E8F7 | F7F4 | G6F1 | H4F6 | A3G3 | B1G8 |
| E8F8 | F7F5 | G6F2 | H4F7 | A3G4 | B2G1 |
| F1F1 | F7F6 | G6F3 | H4F8 | A3G5 | B2G2 |
| F1F2 | F7F7 | G6F4 | H5F1 | A3G6 | B2G3 |
| F1F3 | F7F8 | G6F5 | H5F2 | A3G7 | B2G4 |
| F1F4 | F8F1 | G6F6 | H5F3 | A3G8 | B2G5 |
| F1F5 | F8F2 | G6F7 | H5F4 | A4G1 | B2G6 |
| F1F6 | F8F3 | G6F8 | H5F5 | A4G2 | B2G7 |
| F1F7 | F8F4 | G7F1 | H5F6 | A4G3 | B2G8 |
| F1F8 | F8F5 | G7F2 | H5F7 | A4G4 | B3G1 |
| F2F1 | F8F6 | G7F3 | H5F8 | A4G5 | B3G2 |
| F2F2 | F8F7 | G7F4 | H6F1 | A4G6 | B3G3 |
| F2F3 | F8F8 | G7F5 | H6F2 | A4G7 | B3G4 |

TABLE 2-continued

| | | | | | |
|---|---|---|---|---|---|
| F2F4 | G1F1 | G7F6 | H6F3 | A4G8 | B3G5 |
| F2F5 | G1F2 | G7F7 | H6F4 | A5G1 | B3G6 |
| F2F6 | G1F3 | G7F8 | H6F5 | A5G2 | B3G7 |
| F2F7 | G1F4 | G8F1 | H6F6 | A5G3 | B3G8 |
| F2F8 | G1F5 | G8F2 | H6F7 | A5G4 | B4G1 |
| F3F1 | G1F6 | G8F3 | H6F8 | A5G5 | B4G2 |
| F3F2 | G1F7 | G8F4 | H7F1 | A5G6 | B4G3 |
| F3F3 | G1F8 | G8F5 | H7F2 | A5G7 | B4G4 |
| F3F4 | G2F1 | G8F6 | H7F3 | A5G8 | B4G5 |
| F3F5 | G2F2 | G8F7 | H7F4 | A6G1 | B4G6 |
| F3F6 | G2F3 | G8F8 | H7F5 | A6G2 | B4G7 |
| F3F7 | G2F4 | H1F1 | H7F6 | | B4G8 |
| B5G1 | C3G6 | D2G3 | D8G8 | E7G5 | F6G2 |
| B5G2 | C3G7 | D2G4 | E1G1 | E7G6 | F6G3 |
| B5G3 | C3G8 | D2G5 | E1G2 | E7G7 | F6G4 |
| B5G4 | C4G1 | D2G6 | E1G3 | E7G8 | F6G5 |
| B5G5 | C4G2 | D2G7 | E1G4 | E8G1 | F6G6 |
| B5G6 | C4G3 | D2G8 | E1G5 | E8G2 | F6G7 |
| B5G7 | C4G4 | D3G1 | E1G6 | E8G3 | F6G8 |
| B5G8 | C4G5 | D3G2 | E1G7 | E8G4 | F7G1 |
| B6G1 | C4G6 | D3G3 | E1G8 | E8G5 | F7G2 |
| B6G2 | C4G7 | D3G4 | E2G1 | E8G6 | F7G3 |
| B6G3 | C4G8 | D3G5 | E2G2 | E8G7 | F7G4 |
| B6G4 | C5G1 | D3G6 | E2G3 | E8G8 | F7G5 |
| B6G5 | C5G2 | D3G7 | E2G4 | F1G1 | F7G6 |
| B6G6 | C5G3 | D3G8 | E2G5 | F1G2 | F7G7 |
| B6G7 | C5G4 | D4G1 | E2G6 | F1G3 | F7G8 |
| B6G8 | C5G5 | D4G2 | E2G7 | F1G4 | F8G1 |
| B7G1 | C5G6 | D4G3 | E2G8 | F1G5 | F8G2 |
| B7G2 | C5G7 | D4G4 | E3G1 | F1G6 | F8G3 |
| B7G3 | C5G8 | D4G5 | E3G2 | F1G7 | F8G4 |
| B7G4 | C6G1 | D4G6 | E3G3 | F1G8 | F8G5 |
| B7G5 | C6G2 | D4G7 | E3G4 | F2G1 | F8G6 |
| B7G6 | C6G3 | D4G8 | E3G5 | F2G2 | F8G7 |
| B7G7 | C6G4 | D5G1 | E3G6 | F2G3 | F8G8 |
| B7G8 | C6G5 | D5G2 | E3G7 | F2G4 | G1G1 |
| B8G1 | C6G6 | D5G3 | E3G8 | F2G5 | G1G2 |
| B8G2 | C6G7 | D5G4 | E4G1 | F2G6 | G1G3 |
| B8G3 | C6G8 | D5G5 | E4G2 | F2G7 | G1G4 |
| B8G4 | C7G1 | D5G6 | E4G3 | F2G8 | G1G5 |
| B8G5 | C7G2 | D5G7 | E4G4 | F3G1 | G1G6 |
| B8G6 | C7G3 | D5G8 | E4G5 | F3G2 | G1G7 |
| B8G7 | C7G4 | D6G1 | E4G6 | F3G3 | G1G8 |
| B8G8 | C7G5 | D6G2 | E4G7 | F3G4 | G2G1 |
| C1G1 | C7G6 | D6G3 | E4G8 | F3G5 | G2G2 |
| C1G2 | C7G7 | D6G4 | E5G1 | F3G6 | G2G3 |
| C1G3 | C7G8 | D6G5 | E5G2 | F3G7 | G2G4 |
| C1G4 | C8G1 | D6G6 | E5G3 | F3G8 | G2G5 |
| C1G5 | C8G2 | D6G7 | E5G4 | F4G1 | G2G6 |
| C1G6 | C8G3 | D6G8 | E5G5 | F4G2 | G2G7 |
| C1G7 | C8G4 | D7G1 | E5G6 | F4G3 | G2G8 |
| C1G8 | C8G5 | D7G2 | E5G7 | F4G4 | G3G1 |
| C2G1 | C8G6 | D7G3 | E5G8 | F4G5 | G3G2 |
| C2G2 | C8G7 | D7G4 | E6G1 | F4G6 | G3G3 |
| C2G3 | C8G8 | D7G5 | E6G2 | F4G7 | G3G4 |
| C2G4 | D1G1 | D7G6 | E6G3 | F4G8 | G3G5 |
| C2G5 | D1G2 | D7G7 | E6G4 | F5G1 | G3G6 |
| C2G6 | D1G3 | D7G8 | E6G5 | F5G2 | G3G7 |
| C2G7 | D1G4 | D8G1 | E6G6 | F5G3 | G3G8 |
| C2G8 | D1G5 | D8G2 | E6G7 | F5G4 | G4G1 |
| C3G1 | D1G6 | D8G3 | E6G8 | F5G5 | G4G2 |
| C3G2 | D1G7 | D8G4 | E7G1 | F5G6 | G4G3 |
| C3G3 | D1G8 | D8G5 | E7G2 | F5G7 | G4G4 |
| C3G4 | D2G1 | D8G6 | E7G3 | F5G8 | G4G5 |
| C3G5 | D2G2 | D8G7 | E7G4 | F6G1 | G4G6 |
| G4G7 | H3G4 | A2H1 | A8H6 | B7H3 | C5H8 |
| G4G8 | H3G5 | A2H2 | A8H7 | B7H4 | C6H1 |
| G5G1 | H3G6 | A2H3 | A8H8 | B7H5 | C6H2 |
| G5G2 | H3G7 | A2H4 | B1H1 | B7H6 | C6H3 |
| G5G3 | H3G8 | A2H5 | B1H2 | B7H7 | C6H4 |
| G5G4 | H4G1 | A2H6 | B1H3 | B7H8 | C6H5 |
| G5G5 | H4G2 | A2H7 | B1H4 | B8H1 | C6H6 |
| G5G6 | H4G3 | A2H8 | B1H5 | B8H2 | C6H7 |
| G5G7 | H4G4 | A3H1 | B1H6 | B8H3 | C6H8 |
| G5G8 | H4G5 | A3H2 | B1H7 | B8H4 | C7H1 |
| G6G1 | H4G6 | A3H3 | B1H8 | B8H5 | C7H2 |
| G6G2 | H4G7 | A3H4 | B2H1 | B8H6 | C7H3 |
| G6G3 | H4G8 | A3H5 | B2H2 | B8H7 | C7H4 |
| G6G4 | H5G1 | A3H6 | B2H3 | B8H8 | C7H5 |
| G6G5 | H5G2 | A3H7 | B2H4 | C1H1 | C7H6 |
| G6G6 | H5G3 | A3H8 | B2H5 | C1H2 | C7H7 |
| G6G7 | H5G4 | A4H1 | B2H6 | C1H3 | C7H8 |
| G6G8 | H5G5 | A4H2 | B2H7 | C1H4 | C8H1 |
| G7G1 | H5G6 | A4H3 | B2H8 | C1H5 | C8H2 |
| G7G2 | H5G7 | A4H4 | B3H1 | C1H6 | C8H3 |
| G7G3 | H5G8 | A4H5 | B3H2 | C1H7 | C8H4 |
| G7G4 | H6G1 | A4H6 | B3H3 | C1H8 | C8H5 |
| G7G5 | H6G2 | A4H7 | B3H4 | C2H1 | C8H6 |
| G7G6 | H6G3 | A4H8 | B3H5 | C2H2 | C8H7 |
| G7G7 | H6G4 | A5H1 | B3H6 | C2H3 | C8H8 |
| G7G8 | H6G5 | A5H2 | B3H7 | C2H4 | D1H1 |
| G8G1 | H6G6 | A5H3 | B3H8 | C2H5 | D1H2 |
| G8G2 | H6G7 | A5H4 | B4H1 | C2H6 | D1H3 |
| G8G3 | H6G8 | A5H5 | B4H2 | C2H7 | D1H4 |
| G8G4 | H7G1 | A5H6 | B4H3 | C2H8 | D1H5 |
| G8G5 | H7G2 | A5H7 | B4H4 | C3H1 | D1H6 |
| G8G6 | H7G3 | A5H8 | B4H5 | C3H2 | D1H7 |
| G8G7 | H7G4 | A6H1 | B4H6 | C3H3 | D1H8 |
| G8G8 | H7G5 | A6H2 | B4H7 | C3H4 | D2H1 |
| H1G1 | H7G6 | A6H3 | B4H8 | C3H5 | D2H2 |
| H1G2 | H7G7 | A6H4 | B5H1 | C3H6 | D2H3 |
| H1G3 | H7G8 | A6H5 | B5H2 | C3H7 | D2H4 |
| H1G4 | H8G1 | A6H6 | B5H3 | C3H8 | D2H5 |
| H1G5 | H8G2 | A6H7 | B5H4 | C4H1 | D2H6 |
| H1G6 | H8G3 | A6H8 | B5H5 | C4H2 | D2H7 |
| H1G7 | H8G4 | A7H1 | B5H6 | C4H3 | D2H8 |
| H1G8 | H8G5 | A7H2 | B5H7 | C4H4 | D3H1 |
| H2G1 | H8G6 | A7H3 | B5H8 | C4H5 | D3H2 |
| H2G2 | H8G7 | A7H4 | B6H1 | C4H6 | D3H3 |
| H2G3 | H8G8 | A7H5 | B6H2 | C4H7 | D3H4 |
| H2G4 | A1H1 | A7H6 | B6H3 | C4H8 | D3H5 |
| H2G5 | A1H2 | A7H7 | B6H4 | C5H1 | D3H6 |
| H2G6 | A1H3 | A7H8 | B6H5 | C5H2 | D3H7 |
| H2G7 | A1H4 | A8H1 | B6H6 | C5H3 | D3H8 |
| H2G8 | A1H5 | A8H2 | B6H7 | C5H4 | D4H1 |
| H3G1 | A1H6 | A8H3 | B6H8 | C5H5 | D4H2 |
| H3G2 | A1H7 | A8H4 | B7H1 | C5H6 | D4H3 |
| H3G3 | A1H8 | A8H5 | B7H2 | C5H7 | D4H4 |
| D4H5 | E2H6 | E8H7 | F6H8 | G5H1 | H3H2 |
| D4H6 | E2H7 | E8H8 | F7H1 | G5H2 | H3H3 |
| D4H7 | E2H8 | F1H1 | F7H2 | G5H3 | H3H4 |
| D4H8 | E3H1 | F1H2 | F7H3 | G5H4 | H3H5 |
| D5H1 | E3H2 | F1H3 | F7H4 | G5H5 | H3H6 |
| D5H2 | E3H3 | F1H4 | F7H5 | G5H6 | H3H7 |
| D5H3 | E3H4 | F1H5 | F7H6 | G5H7 | H3H8 |
| D5H4 | E3H5 | F1H6 | F7H7 | G5H8 | H4H1 |
| D5H5 | E3H6 | F1H7 | F7H8 | G6H1 | H4H2 |
| D5H6 | E3H7 | F1H8 | F8H1 | G6H2 | H4H3 |
| D5H7 | E3H8 | F2H1 | F8H2 | G6H3 | H4H4 |
| D5H8 | E4H1 | F2H2 | F8H3 | G6H4 | H4H5 |
| D6H1 | E4H2 | F2H3 | F8H4 | G6H5 | H4H6 |
| D6H2 | E4H3 | F2H4 | F8H5 | G6H6 | H4H7 |
| D6H3 | E4H4 | F2H5 | F8H6 | G6H7 | H4H8 |
| D6H4 | E4H5 | F2H6 | F8H7 | G6H8 | H5H1 |
| D6H5 | E4H6 | F2H7 | F8H8 | G7H1 | H5H2 |
| D6H6 | E4H7 | F2H8 | G1H1 | G7H2 | H5H3 |
| D6H7 | E4H8 | F3H1 | G1H2 | G7H3 | H5H4 |
| D6H8 | E5H1 | F3H2 | G1H3 | G7H4 | H5H5 |
| D7H1 | E5H2 | F3H3 | G1H4 | G7H5 | H5H6 |
| D7H2 | E5H3 | F3H4 | G1H5 | G7H6 | H5H7 |
| D7H3 | E5H4 | F3H5 | G1H6 | G7H7 | H5H8 |
| D7H4 | E5H5 | F3H6 | G1H7 | G7H8 | H6H1 |
| D7H5 | E5H6 | F3H7 | G1H8 | G8H1 | H6H2 |
| D7H6 | E5H7 | F3H8 | G2H1 | G8H2 | H6H3 |
| D7H7 | E5H8 | F4H1 | G2H2 | G8H3 | H6H4 |
| D7H8 | E6H1 | F4H2 | G2H3 | G8H4 | H6H5 |
| D8H1 | E6H2 | F4H3 | G2H4 | G8H5 | H6H6 |
| D8H2 | E6H3 | F4H4 | G2H5 | G8H6 | H6H7 |
| D8H3 | E6H4 | F4H5 | G2H6 | G8H7 | H6H8 |
| D8H4 | E6H5 | F4H6 | G2H7 | G8H8 | H7H1 |
| D8H5 | E6H6 | F4H7 | G2H8 | H1H1 | H7H2 |
| D8H6 | E6H7 | F4H8 | G3H1 | H1H2 | H7H3 |
| D8H7 | E6H8 | F5H1 | G3H2 | H1H3 | H7H4 |
| D8H8 | E7H1 | F5H2 | G3H3 | H1H4 | H7H5 |
| E1H1 | E7H2 | F5H3 | G3H4 | H1H5 | H7H6 |
| E1H2 | E7H3 | F5H4 | G3H5 | H1H6 | H7H7 |
| E1H3 | E7H4 | F5H5 | G3H6 | H1H7 | H7H8 |
| E1H4 | E7H5 | F5H6 | G3H7 | H1H8 | H8H1 |
| E1H5 | E7H6 | F5H7 | G3H8 | H2H1 | H8H2 |
| E1H6 | E7H7 | F5H8 | G4H1 | H2H2 | H8H3 |

TABLE 2-continued

| E1H7 | E7H8 | F6H1 | G4H2 | H2H3 | H8H4 |
|------|------|------|------|------|------|
| E1H8 | E8H1 | F6H2 | G4H3 | H2H4 | H8H5 |
| E2H1 | E8H2 | F6H3 | G4H4 | H2H5 | H8H6 |
| E2H2 | E8H3 | F6H4 | G4H5 | H2H6 | H8H7 |
| E2H3 | E8H4 | F6H5 | G4H6 | H2H7 | H8H8 |
| E2H4 | E8H5 | F6H6 | G4H7 | H2H8 |      |
| E2H5 | E8H6 | F6H7 | G4H8 | H3H1 |      |

The above-cited polypeptides can further comprise one or more sequences selected from the group consisting of SEQ ID NO: 81 to 89.

There is also provided a composition comprising a plurality of identical or different polypeptides as defined herein above and a physiologically acceptable carrier. The composition can be a dried composition and the dried composition can be in freeze dried form or spray dried form.

In an even further aspect the present invention is directed to a polypeptide having an ice-binding activity and being capable of reducing or inhibiting the growth and/or formation of ice-crystals, wherein the polypeptide comprises the sequence $X_1$-$X_2$-$X_3$-$X_4$-$X_5$-$X_6$-$X_7$-$X_8$-$X_9$ (SEQ ID NO:90), wherein $X_1$ is selected from the group of amino acid residues consisting of S, A, G and D;

$X_2$ is selected from the group of amino acid residues consisting of A, V, I, T and S;

$X_3$ is selected from the group of amino acid residues consisting of non-bulky amino acid residues;

$X_4$ is selected from the group of amino acid residues consisting of S, I, T and V;

$X_5$ is selected from the group of amino acid residues consisting of S, A, I and T;

$X_6$ is selected from the group of amino acid residues consisting of S, T and V;

$X_7$ is selected from the group of amino acid residues consisting of non-bulky amino acid residues;

$X_8$ is selected from the group of amino acid residues consisting of S, T and V;

$X_9$ is selected from the group of amino acid residues consisting of S, A and G; and wherein at least one of the residues $X_2$, $X_4$, $X_6$ and $X_8$ of SEQ ID NO:1 is T or V; and wherein the total number of amino acid residues of the polypeptide is less than 250.

The sequence $X_1$-$X_2$-$X_3$-$X_4$-$X_5$-$X_6$-$X_7$-$X_8$-$X_9$ (SEQ ID NO:90) will be referred to herein as a general "ice-binding domain". Whether or not said domain is directly involved in ice-binding or only indirectly involved in ice-binding (i.e. is required in order for the polypeptide to have an ice-binding activity) is immaterial to this definition.

The invention further relates to polypeptides comprising a plurality of general "ice-binding domains", such as sequences having a substantial homology/identity to SEQ ID NO:90. A substantial homology to SEQ ID NO:90 shall in this respect encompass any sequence, which differs from the sequence of SEQ ID NO:90 in only one or at the most two of the positions $X_1$, $X_2$, $X_3$, $X_4$, $X_5$, $X_6$, $X_7$, $X_8$ and $X_9$.

Plurality as used in this respect shall encompass the integers 2, 3, 4, 5, 6, 7, 8, 8, 9, such as less than 10, 11, 12, 13, 14, 15, 16, 17, 18, 19, 20, for example less than 25, wherein any of said plurality of general "ice-binding domains" can be identical to or substantially identical to or substantially homologous to SEQ ID NO:90.

The invention also relates to modifications and derivatives of the polypeptide according to the present invention comprising one or more copies of SEQ ID NO:90 and optionally further comprising one or more copies of SEQ ID NO:90, or sequences substantially identical or substantially homologous thereto.

The term "isolated polypeptide" clarifies that the polypeptide according to the present invention is at least essentially free from contaminating cellular components natively associated with the polypeptide.

The polypeptides according to the present invention can be expressed as fusion polypeptides. Such fusion polypeptides can serve many functions, such as aiding in purification and/or production of the polypeptide in an active conformation. One example of a fusion polypeptide is a polypeptide according to the present invention fused to an affinity tag. The fusion polypeptides can also form part of a complement/anti-complement pair as defined herein, although this term is not limited exclusively to polypeptides. Modifications of the polypeptides, such as splice variants, allelic variants, orthologs and paralogs as defined herein are also within the scope of the present invention. Examples of fusions polypeptides are disclosed herein below in more detail.

The polypeptides according to the present invention can be labelled with a detactable label, for example a fluorescently detactable label. This can help the practitioner in isolating or identifying the polypeptides according to the present invention.

Also provided are polynucleotides encoding the polypeptides according to the present invention, polynucleotide constructs, such as vectors comprising said nucleotides in linear or circular form, host cells transformed with said polynucleotides or vectors comprising said nucleotides, and transgenic organisms comprising said host cells.

Polynucleotide is used interchangeably with "nucleic acid" and "nucleic acid molecule" unless otherwise indicated. In principle the invention can make use of such a polynucleotide or a complement of such a polynucleotide, for example in the form of a cDNA or an "anti-sense oligonucleotide". The polynucleotide can be a degenerated sequence of individual nucleotides as long as the polynucleotide encodes a polypeptide according to the present invention.

The polynucleotide need not comprise all of the individual nucleotides of a native gene as isolated from a natural host organism. Any truncation of such as native gene, including sequences which are at least 75% homologous or identical, such as at least 80% homologous or identical, for example at least 85% homologous or identical, such as at least 90% homologous or identical, for example at least 91% homologous or identical, such as at least 92% homologous or identical, for example at least 93% homologous or identical, such as at least 94% homologous or identical, for example at least 95% homologous or identical, such as at least 96% homologous or identical, for example at least 97% homologous or identical, such as at least 98% homologous or identical, for example at least 99% homologous or identical, such as at least 99.5% homologous or identical to the native gene shall be encompassed by the present invention. Any such functional truncation of a native gene, including any derivative or modification thereof capable of being expressed in a suitable host organism, shall be denoted a "structural gene".

Expression can be obtained e.g. when a polynucleotide sequence cloned in a cloning vector or expression vector is introduced into a host organism and expressed. The expression is suitably directed by a regulatory sequence typically comprising a promoter which may again comprising elements such as a core promoter and one or more regulatory elements, including an enhancer of expression.

The host organism will typically be a recombinant host, i.e. a host not natively harbouring the polynucleotide sequence to be expressed, or not natively comprising the polynucleotide sequence to be expressed operably linked to the native expression signal. When preceded by a secretory signal sequence the polypeptide according to the present invention is destined for secretion—irrespective of whether such a secretion takes place or not.

For the sake of clarity a polynucleotide according to the present invention will be referred to as an "isolated" polynucleotide in order to distinguish the polynucleotide from the same or a related sequence in its native environment. Likewise, the term "heterologous polynucleotide" as defined herein signifies a polynucleotide or polynucleotide construct which differs from the native form of the polypeptide according to the present invention. The polynucleotides according to the present invention can be chromosomally integrated or episomal.

The invention also provides antibodies, or binding fragments thereof, specific for the polypeptides according to the invention. The antibodies can be produced by any state-of-the-art method and the antibodies can be e.g. a naked antibody, a binding fragment of an antibody, an antibody component, an anti-idiotype antibody, a chimeric antibody and a humanized antibody.

Also provided with the scope of the present invention are methods for producing and using both a) polynucleotides according to the present invention, b) polypeptides according to the present invention, and c) antibodies according to the present invention specific for said polypeptides. The antibodies according to the present invention can be used for identifying or partitioning from a population of polypeptides a "target polypeptide" or "target peptide" as defined herein. The "target peptide" can be an antigenic peptide as defined herein.

In a further aspect there is provided a solid support comprising the polypeptides and/or the antibodies according to the present invention as well as methods for making and using such a solid support.

BRIEF DESCRIPTION OF THE DRAWINGS

FIG. 2 illustrates the full-length cDNA sequences of AFPs 1-8 from R. mordax. Coding sequences for putative signal peptides are underlined. The AFP's corresponding to these cDNAs (AFP 1-8) mainly differed in their N-terminal part, where AFP4 would appear to be without a signal sequence. The AFPs each contained 8 repeats of an amino acid sequence with the core consensus sequence T-A-T-T-T-A-T. This matches part of the putative IB-motif also observed for R. inquisitor (FIG. 1), and it is conceivable that this represents the IB motif of R. mordax or at least part of it.

FIG. 3. Full length amino acid sequences of AFPs 1-8 from Rhagium mordax. These sequences are denoted SEQ ID NO:1 to SEQ ID NO:8, respectively. Putative signal sequences are indicated in underscore and putative ice binding motives are indicated in boxes.

DEFINITIONS

Figure 1:
FIG. 1 illustrates the amino acid sequence of a fragment of a R. Inquisitor AFP. Putative ice binding motifs are indicated by black boxes. The forward (F) and reverse (R) primers are given by sequence, and the parts of the polypeptide they are derived from is also indicated. The amino acid sequence has a domain which represents or harbours an ice-binding (IB) motif (consensus A/G-Q/R-G-T-A-T-T-T-A-T-G-X-A/G) repeated X times and separated by 1-8 amino acid residues.
Figure 4:
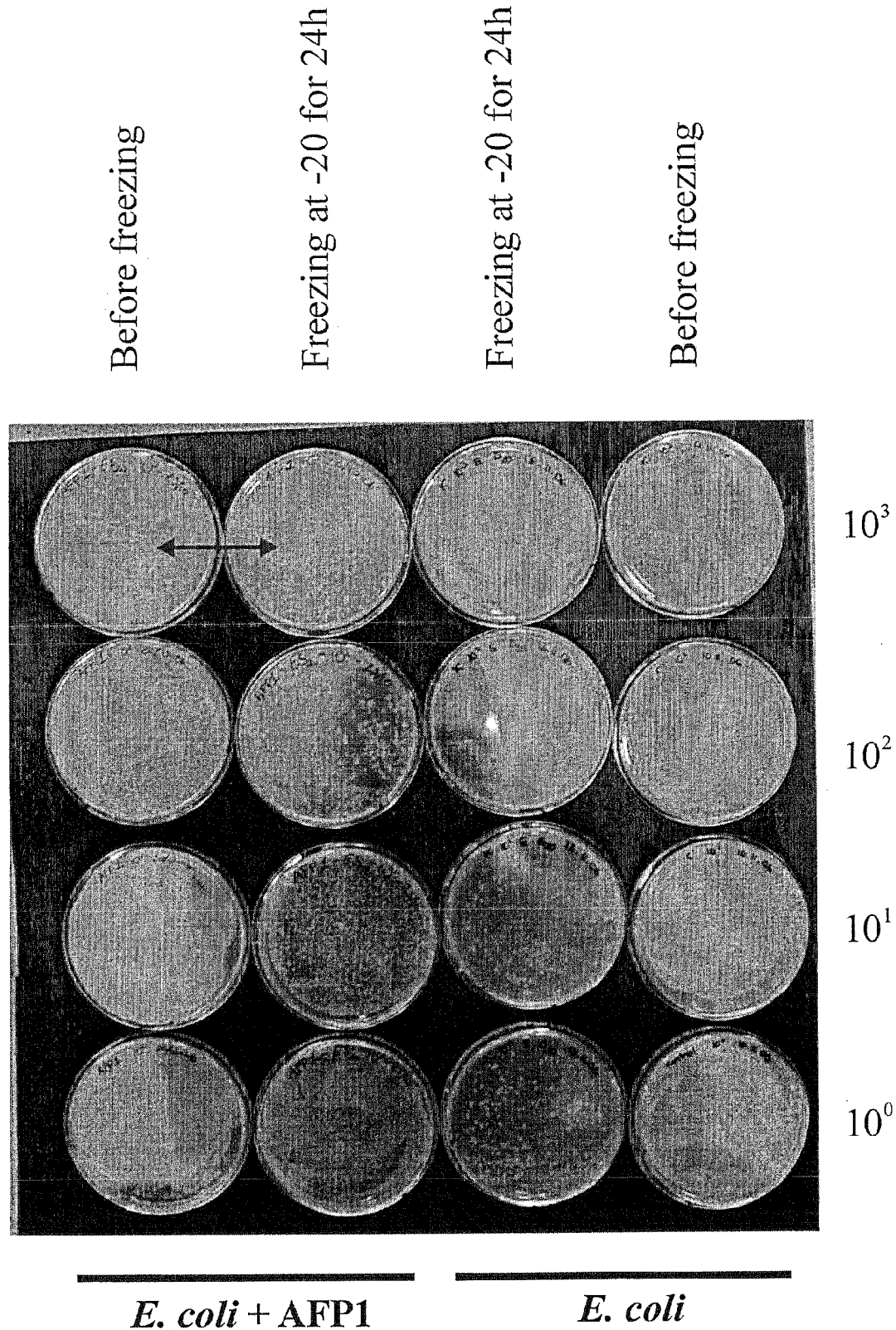
FIG. 4. Illustration of E. coli cells harbouring full length cDNA's cloned into the expression vector pET26B(+). IPTG can be used to induce synthesis of the pertinent AFP. Initially we have induced synthesis of AFP1 in E. coli. The results demonstrate that AFP1 produced in E. coli confer on the E. coli cells the ability to withstand freezing.

Antifreeze proteins lower the freezing temperature of a solution noncolligatively by binding to ice crystals and inhibiting crystal growth, but the proteins alter the melting temperature of the solution only by colligative effects. This thermal hysteresis (the difference between freezing and melting temperatures) is determined by observing the effect of temperature on the growth of a single ice crystal. Melting occurs when faces of the ice crystal become round; freezing occurs when the ice crystal elongates along its c-axis.

Hence, the term "anti-freeze activity" refers to the separation of the melting and freezing temperature. It also refers to the difference between melting point and the freezing point. It further refers to the inhibition of formation of large crystals at the expense of small crystals at temperatures above the temperature of recrystallisation. The term anti-freeze activity can be used interchangeably with thermal hysteresis.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. polynucleotide molecules can be composed of monomers that are naturally-occurring nucleotides (such as DNA and RNA), or analogs of naturally-occurring nucleotides (e.g., (alpha-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. polynucleotide monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide polynucleotides," which comprise naturally-occurring or modified polynucleotide bases attached to a polyamide backbone. polynucleotides can be either single stranded or double stranded.

The term "complement of a polynucleotide molecule" refers to a polynucleotide molecule having a complementary nucleotide sequence and reverse orientation as compared to a reference nucleotide sequence. For example, the sequence 5' ATGCACGGG 3' is complementary to 5' CCCGTGCAT 3'.

The term "degenerate nucleotide sequence" denotes a sequence of nucleotides that includes one or more degenerate codons as compared to a reference polynucleotide molecule that encodes a polypeptide. Degenerate codons contain different triplets of nucleotides, but encode the same amino acid residue (i.e., GAU and GAC triplets each encode Asp).

The term "structural gene" refers to a polynucleotide molecule that is transcribed into messenger RNA (mRNA), which is then translated into a sequence of amino acids characteristic of a specific polypeptide.

An "isolated polynucleotide molecule" is a polynucleotide molecule that is not integrated in the genomic DNA of an organism. For example, a DNA molecule that encodes a growth factor that has been separated from the genomic DNA of a cell is an isolated DNA molecule. Another example of an isolated polynucleotide molecule is a chemically-synthesized polynucleotide molecule that is not integrated in the genome of an organism. A polynucleotide molecule that has been isolated from a particular species is smaller than the complete DNA molecule of a chromosome from that species.

A "nucleic acid molecule construct" is a polynucleotide molecule, either single- or double-stranded, that has been modified through human intervention to contain segments of polynucleotide combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., Mol. Endocrinol. 7:551 (1993)), cyclic AMP response elements (CREs), serum response elements (SREs; Treisman, Seminars in Cancer Biol. 1:47 (1990)), glucocorticoid response elements (GREs), and binding sites for other transcription factors, such as CRE/ATF (O'Reilly et al., J. Biol. Chem. 267:19938 (1992)), AP2 (Ye et al., J. Biol. Chem. 269:25728 (1994)), SP1, cAMP response element binding polypeptide (CREB; Loeken, Gene Expr. 3:253 (1993)) and octamer factors (see, in general, Watson et al., eds., Molecular Biology of the Gene, 4th ed. (The Benjamin/Cummings Publishing Company, Inc. 1987), and Lemaigre and Rousseau, Biochem. J. 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues preferably joined exclusively by peptide bonds, whether produced naturally or synthetically. A polypeptide produced by expression of a non-host DNA molecule is a "heterologous" peptide or polypeptide. An "amino acid residue" can be a natural or non-natural amino acid residue linked peptide bonds or bonds different from peptide bonds. The amino acid residues can be in D-configuration or L-configuration.

A "homopolymer" is a polypeptide which is built up by adding several similar polypeptides to an original polypeptide thereby creating multiple copies of the same polypeptide as one larger polypeptide.

A "heteropolymer" is a polypeptide which is built up by adding several different polypeptides to an original polypeptide thereby creating multiple copies of the different polypeptide as one larger polypeptide.

A "non-bulky amino acid residue" is preferably a natural amino acid excluding amino acids having either a cyclic (aliphatic or aromatic) side chain, such as e.g. Pro, Phe, Trp, Tyr and His, or a long or branched aliphatic side chain, such as e.g. Arg, Lys, Leu, Ile, Met and Val, or more generally, a bulky amino acid has a side chain having at least 3 carbons, which are linked and form a branched or unbranched side chain. Presently preferred examples of "non-bulky amino acids" comprise Gly, Ala and Ser.

A "polypeptide according to the present invention" is any polypeptide cited in the claims of the present patent application or the patent granted on the basis of claims of this patent application.

A "polynucleotide according to the present invention" or a "nucleic acid according to the present invention" is any polynucleotide encoding a "polypeptide according to the present invention", including any polypeptide cited in the claims of the present patent application or the patent granted on the basis of claims of this patent application.

An "integrated genetic element" is a segment of DNA that has been incorporated into a chromosome of a host cell after that element is introduced into the cell through human manipulation. Within the present invention, integrated genetic elements are most commonly derived from linearized plasmids that are introduced into the cells by electroporation or other techniques. Integrated genetic elements are passed from the original host cell to its progeny.

A "cloning vector" is a polynucleotide molecule, such as a plasmid, cosmid, or bacteriophage, that has the capability of replicating autonomously in a host cell. Cloning vectors typically contain one or a small number of restriction endonuclease recognition sites that allow insertion of a polynucleotide molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a polynucleotide molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous polynucleotide molecule, such as a cloning vector or expression vector.

"Integrative transformants" are recombinant host cells, in which heterologous DNA has become integrated into the genomic DNA of the cells.

A "fusion polypeptide" is a hybrid polypeptide expressed by a polynucleotide molecule comprising nucleotide sequences of at least two genes. For example, a fusion polypeptide can comprise at least part of a polypeptide according to the present invention fused with a polypeptide that binds an affinity matrix. Such a fusion polypeptide provides a means to isolate large quantities of a polypeptide according to the present invention using affinity chromatography.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other polypeptideaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular polypeptide preparation contains an isolated polypeptide is by the appearance of a single band following sodium dodecyl sulfate (SDS)-polyacrylamide gel electrophoresis of the polypeptide preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9$ M$^{-1}$.

An "anti-idiotype antibody" is an antibody that binds with the variable region domain of an immunoglobulin. In the present context, an anti-idiotype antibody binds with the variable region of an anti-antibody, and thus, an anti-idiotype antibody mimics an epitope of a polypeptide according to the present invention.

An "antibody fragment" is a portion of an antibody such as F(ab')$_2$, F(ab)$_2$, Fab', Fab, and the like. Regardless of structure, an antibody fragment binds with the same antigen that is recognized by the intact antibody. For example, an anti-(polypeptide according to the present invention) monoclonal antibody fragment binds an epitope of a polypeptide according to the present invention.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv polypeptides"), and minimal recognition units consisting of the amino acid residues that mimic the hypervariable region.

A "chimeric antibody" is a recombinant polypeptide that contains the variable domains and complementary determining regions derived from a rodent antibody, while the remainder of the antibody molecule is derived from a human antibody.

"Humanized antibodies" are recombinant polypeptides in which murine complementarity determining regions of a monoclonal antibody have been transferred from heavy and light variable chains of the murine immunoglobulin into a human variable domain.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or polypeptide for which an antibody or other specific binding agent is available can be used as an affinity tag. Affinity tags include a polyhistidine tract, polypeptide A (Nilsson et al., EMBO J. 4:1075 (1985); Nilsson et al., Methods Enzymol. 198:3 (1991)), glutathione S transferase (Smith and Johnson, Gene 67:31 (1988)), Glu-Glu affinity tag (Grussenmeyer et al., Proc. Natl. Acad. Sci. USA 82:7952 (1985)), substance P, FLAG peptide (Hopp et al., Biotechnology 6:1204 (1988)), streptavidin binding peptide, or other antigenic epitope or binding domain. See, in general, Ford et al., polypeptide Expression and Purification 2:95 (1991). DNAs encoding affinity tags are available from commercial suppliers (e.g., Pharmacia Biotech, Piscataway, N.J.).

A "naked antibody" is an entire antibody, as opposed to an antibody fragment, which is not conjugated with a therapeutic agent. Naked antibodies include both polyclonal and monoclonal antibodies, as well as certain recombinant antibodies, such as chimeric and humanized antibodies.

As used herein, the term "antibody component" includes both an entire antibody and an antibody fragment.

A "target polypeptide" or a "target peptide" is an amino acid sequence that comprises at least one epitope, and that is expressed on a target cell, such as a tumor cell, or a cell that carries an infectious agent antigen. T cells recognize peptide epitopes presented by a major histocompatibility complex molecule to a target polypeptide or target peptide and typically lyse the target cell or recruit other immune cells to the site of the target cell, thereby killing the target cell.

An "antigenic peptide" is a peptide, which will bind a major histocompatibility complex molecule to form an MHC-peptide complex which is recognized by a T cell, thereby inducing a cytotoxic lymphocyte response upon presentation to the T cell. Thus, antigenic peptides are capable of binding to an appropriate major histocompatibility complex molecule and inducing a cytotoxic T cells response, such as cell lysis or specific cytokine release against the target cell which binds or expresses the antigen. The antigenic peptide can be bound in the context of a class I or class II major histocompatibility complex molecule, on an antigen presenting cell or on a target cell.

In eukaryotes, RNA polymerase II catalyzes the transcription of a structural gene to produce mRNA. A polynucleotide molecule can be designed to contain an RNA polymerase II template in which the RNA transcript has a sequence that is complementary to that of a specific mRNA. The RNA transcript is termed an "anti-sense RNA" and a polynucleotide molecule that encodes the anti-sense RNA is termed an "anti-sense gene." Anti-sense RNA molecules are capable of binding to mRNA molecules, resulting in an inhibition of mRNA translation.

An "anti-sense oligonucleotide specific for a polynucletide encoding a polypeptide according to the present invention" is an oligonucleotide having a sequence (a) capable of forming a stable triplex with a portion of a gene encoding a polypeptide according to the present invention, or (b) capable of forming a stable duplex with a portion of an mRNA transcript of such a gene.

The term "variant gene" refers to polynucleotide molecules that encode a polypeptide having an amino acid sequence that is a modification of a polypeptide according to the present invention. Such variants include naturally-occurring polymorphisms of genes according to the present invention, as well as synthetic genes that contain conservative amino acid substitutions of the amino acid sequence of a polypeptide according to the present invention. Additional variant forms of genes are polynucleotide molecules that contain insertions or deletions of the nucleotide sequences described herein. A variant gene according to the present invention can be identified by determining whether the gene hybridizes with a polynucleotide molecule having the nucleotide sequence of a polypeptide according to the present invention, or its complement, under stringent conditions.

Alternatively, variant genes can be identified by sequence comparison. Two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art (see, for example, Peruski and Peruski, The Internet and the New Biology: Tools for Genomic and Molecular Research (ASM Press, Inc. 1997), Wu et al. (eds.), "Information Superhighway and Computer Databases of polynucleotides and polypeptides," in Methods in Gene Biotechnology, pages 123 151 (CRC Press, Inc. 1997), and Bishop (ed.), Guide to Human Genome Computing, 2nd Edition (Academic Press, Inc. 1998)). Particular methods for determining sequence identity are described below.

Regardless of the particular method used to identify a variant gene, a variant gene encodes a polypeptide which can be characterized by its ability to bind specifically to an anti-(polypeptide according to the invention) antibody.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a polypeptide encoded by an allelic variant of a gene.

The term "ortholog" denotes a polypeptide or polypeptide obtained from one species that is the functional counterpart of a polypeptide or polypeptide from a different species. Sequence differences among orthologs are the result of speciation.

"Paralogs" are distinct but structurally related polypeptides made by an organism. Paralogs are believed to arise through gene duplication. For example, alpha-globin, beta-globin, and myoglobin are paralogs of each other.

Due to the imprecision of standard analytical methods, molecular weights and lengths of polymers are understood to be approximate values. When such a value is expressed as "about" X or "approximately" X, the stated value of X will be understood to be accurate to +/−20%, such as +/−10%, for example +/−5%.

DETAILED DESCRIPTION OF THE INVENTION

The present invention provides in one embodiment an isolated polypeptide comprising or consisting of a sequence of amino acid residues selected from the group consisting of SEQ ID NO:1; SEQ ID NO:2; SEQ ID NO:3; SEQ ID NO:4; SEQ ID NO:5; SEQ ID NO:6; SEQ ID NO:7 and SEQ ID NO:8, wherein said polypeptide is capable of reducing or inhibiting the formation and/or growth of ice crystals, or a fragment thereof capable of reducing or inhibiting the formation and/or growth of ice crystals, or a sequence which is at least 75% identical to any of said sequences.

There is also provided an isolated polynucleotide comprising a sequence of nucleotides encoding a polypeptide according to the present invention, wherein said polynucleotide can further comprise an expression signal capable of directing the expression, in a suitable host cell, of the sequence of nucleotides encoding a polypeptide according to the present invention. There is also provided a vector comprising a polynucleotide according to the present invention capable of expressing a polypeptide according to the present invention. An isolated, recombinant cell can comprise the polynucleotide according to the present invention or the vector according to the present invention or the polypeptide according to the present invention.

There is also provided an edible product comprising the polypeptide according to the present invention, wherein the edible product can be frozen, or in the form of a frozen confectionary product, such as ice cream product, or bread.

As an example of a non-food application there is provided a solid support material comprising the polypeptide according to the present invention The present invention also pertains to methods for making or using the polypeptides according to the present invention, including, in one embodiment, a method for producing the polypeptide according to the present invention, said method comprising the steps of
  i) providing the polynucleotide according to the present invention or the vector according to the present invention,
  ii) providing a host cell suitable for the production of a polypeptide according to the present invention by recombinant expression of the polynucleotide provided in step i),
  iii) producing the polypeptide according to the present invention, and optionally
  iv) purifying and/or isolating said polypeptide.

When being directed to in situ production of a polypeptide according to the present invention, there is provided a method comprising the steps of
  i) providing a fermentable starting material
  ii) providing a microorganism capable of fermenting said fermentable food starting material and capable of producing a polypeptide according to the present invention under suitable conditions when fermenting said fermentable food starting material,
  iii) fermenting said food starting material in the presence of said microorganism, thereby producing a fermented, edible product,
    wherein said fermented, edible product comprises the polypeptide according to the present invention In further embodiments there is provided the following methods:

A method for reducing or inhibiting ice crystal formation in a frozen, edible product, said method comprising the steps of
  i) providing a frozen edible product, or one or more ingredients required for the production thereof, and
  ii) contacting said product and/or said ingredients, prior to, during, or after, the production of the product, as the case may be, with a polypeptide according to the present invention,
    thereby reducing or inhibiting ice crystal formation in the frozen, edible product.

A method for reducing or inhibiting ice crystal growth in a frozen, edible product, said method comprising the steps of
  i) providing a frozen edible product, or one or more ingredients required for the production thereof, and
  ii) contacting said product and/or said ingredients, prior to, during, or after, the production of the product, as the case may be, with a polypeptide according to the present invention,
    thereby reducing or inhibiting ice crystal growth in the frozen, edible product.

A method for structuring ice crystals in a frozen, edible product, said method comprising the steps of
  i) providing a frozen edible product, or one or more ingredients required for the production thereof, and
  ii) contacting said product and/or said ingredients, prior to, during, or after, the production of the product, as the case may be, with a polypeptide according to the present invention,
  thereby structuring ice crystals in the frozen, edible product.

A method for modulating the texture or organoleptic qualities of a frozen, edible product, said method comprising the steps of
i) providing a frozen edible product, or one or more ingredients required for the production thereof, and
ii) contacting said product and/or said ingredients, prior to, during, or after, the production of the product, as the case may be, with a polypeptide according to the present invention,
thereby modulating the texture or organoleptic qualities of the frozen, edible product.

A method for monitoring ice crystal formation during the manufacture or storage of a frozen, edible product, said method comprising the steps of
i) providing a frozen edible product, or one or more ingredients required for the production thereof, and
ii) contacting said product and/or said ingredients, prior to, during, or after, the production of the product, as the case may be, with a polypeptide according to the present invention, and
iii) monitoring ice crystal formation at different time points during the manufacture or storage of the frozen, edible product.

A method for performing an in vitro fertilisation (IVF) treatment in a female individual, said method comprising the steps of removing one or more oocyte(s) from a female individual, optionally together with a biological sample comprising follicular fluid; freezing the one or more oocyte(s), optionally together with the biological sample, in the presence of a polypeptide according to the present invention; fertilising one or more of the removed oocytes in vitro; and implanting one or more of the fertilized oocytes into the female individual.

A method for increasing the likelihood or probability of pregnancy in a female individual, said method comprising the steps of removing one or more oocyte(s) from a female individual, optionally together with a biological sample comprising follicular fluid; freezing the one or more oocyte(s), optionally together with the biological sample, in the presence of a polypeptide according to the present invention; fertilising one or more of the removed oocytes in vitro; and implanting one or more fertilized oocytes into the female individual, wherein the freezing of the one or more oocyte(s) in the presence of the polypeptide according to the present invention reduces ice crystal growth and/or formation on the oocyte(s), or in an environment, wherein the oocyte(s) are present, thereby increasing the likelihood or probability of pregnancy.

The sample can further comprise granulosa-lutein cells or follicular cells and optionally also other ovarian cells recovered from the ovarian follicles of the female individual. In one embodiment, the sample further comprises frozen cells from the environment of an oocyte.

The present invention is in a further embodiment directed to a polypeptide having an ice-binding activity and comprising one or more copies of the sequence $X_1-X_2-X_3-X_4-X_5-X_6-X_7-X_8-X_9$ (SEQ ID NO:90), such as, for example, 2, 3, 4, 5, 6, 7, 8, 9 or 10 individually selected copies of the general ice binding domain SEQ ID NO:90,
wherein $X_1$ is selected from the group of amino acid residues consisting of S, A, G and D;
$X_2$ is selected from the group of amino acid residues consisting of A, V, I, T and S;
$X_3$ is selected from the group of amino acid residues consisting of non-bulky amino acid residues;
$X_4$ is selected from the group of amino acid residues consisting of S, I, T and V;
$X_5$ is selected from the group of amino acid residues consisting of S, A, I and T;
$X_6$ is selected from the group of amino acid residues consisting of S, T and V;
$X_7$ is selected from the group of amino acid residues consisting of non-bulky amino acid residues;
$X_8$ is selected from the group of amino acid residues consisting of S, T and V;
$X_9$ is selected from the group of amino acid residues consisting of S, A and G; and
wherein at least one of the residues $X_2$, $X_4$, $X_6$ and $X_8$ of SEQ ID NO:90 is T or V; and
wherein the maximum number of amino acid residues of the polypeptide is less than 1000.

The maximum number of amino acid residues of a polypeptide according to the invention is preferably less than 500, such as less than 400, for example less than 300, such as less than 250, for example less than 240, such as less than 230, for example less than 220, such as less than 210, for example less than 200, such as less than 190, for example less than 180, such as less than 150, for example less than 140, such as less than 130, for example less than 120, such as less than 110, for example less than 100, such as less than 95, for example less than 90, such as less than 85, for example less than 80, such as less than 75, for example less than 70, such as less than 65, for example less than 60, such as less than 55, for example less than 50, such as less than 45, for example less than 40, such as less than 30, for example less than 20, such as less than 15.

In functional conjunction with the above-cited limitation of the size of the polypeptide, the minimum number of amino acid residues of the polypeptide according to the invention may be 10 or more, such as 12 or more, for example 14 or more, such as 16 or more, for example 18 or more, such as 20 or more, for example 22 or more, such as 24 or more, for example 26 or more, such as 28 or more, for example 30 or more, such as 32 or more, for example 34 or more, such as 36 or more, for example 38 or more, such as 40 or more, for example 42 or more, such as 44 or more, for example 46 or more, such as 48 or more, for example 50 or more, such as 55 or more, for example 60 or more, such as 65 or more, for example 70 or more, such as 75 or more, for example 80 or more, such as 85 or more, for example 90 or more, such as 95 or more, for example 100 or more, wherein, when any maximum number and minimum number is paired, the maximum number is larger than the minimum number.

In one embodiment, the polypeptide according to the invention comprises a plurality of general ice-binding domains each comprising the sequence of SEQ ID NO:90, or a variant or derivative or modification thereof, as described herein elsewhere, and preferably having 250 amino acid residues at most.

In one embodiment the invention relates to a polypeptide sequence that comprises a second sequence, in the form of a further independently selected copy of SEQ ID NO:90, wherein the further copy of SEQ ID NO:90 does not overlap with the first copy of SEQ ID NO:90. The invention in a another embodiment relates to a polypeptide which further comprises a third copy of SEQ ID NO: 90 (i.e. the polypeptide comprises three independently selected copies of SEQ ID NO:90), and in a still further embodiment the polypeptide further comprises a fourth copy of SEQ ID NO:90 (i.e. the polypeptide comprises three independently selected copies of SEQ ID NO:90). The independently selected copies of SEQ ID NO:90 can be identical or different as disclosed herein elsewhere.

The copies of SEQ ID NO:90 can be present in any order relative to each other, and any two sequences can be separated by at least 2 amino acid residues, such as at least 3 amino acid residues, for example at least 4 amino acid residues, such as at least 5 amino acid residues, for example at least 6 amino acid residues, such as at least 7 amino acid residues, for example at least 8 amino acid residues, such as at least 9 amino acid residues, for example at least 10 amino acid residues, such as at least 11 amino acid residues, for example at least 12 amino acid residues, such as at least 13 amino acid residues, for example at least 14 amino acid residues, such as at least 15 amino acid residues, for example at least 16 amino acid residues, such as at least 17 amino acid residues, for example at least 18 amino acid residues, such as at least 19 amino acid residues, for example at least 20 amino acid residues, such as at least 21 amino acid residues, for example at least 22 amino acid residues, such as at least 23 amino acid residues, for example at least 24 amino acid residues, such as at least 25 amino acid residues, for example at least 26 amino acid residues, such as at least 27 amino acid residues, for example at least 28 amino acid residues, such as at least 29 amino acid residues, for example at least 30 amino acid residues.

The polypeptide according to the invention can be linked to a carrier, such as a solid support or semi-solid support. The polypeptide can be covalently or non-covalently linked to any such carrier, for example a surface of a material desirably displaying the polypeptides according to the invention.

The invention further relates to a polypeptide according to the present invention fused to an affinity tag. Examples of such affinity tags are known from the literature and can be selected from the group comprising for example: His-tag, polypeptide A tag, Avidin/streptavidin, polypeptide G, GluthationeS-tranferase, dihyfrofolate reductase (DHFR), Green fluorescent polypeptide (GFP), polyarginine, polycysteine, c-myc, calmodulin binding polypeptide, influenzavirus hemagglutinin; maltos binding protein (MBP) (HA).

The invention also encompasses polypeptides wherein one or more amino acid residues are modified, wherein said one or more modification(s) are preferably selected from the group consisting of in vivo or in vitro chemical derivatization, such as acetylation or carboxylation, glycosylation, such as glycosylation resulting from exposing the polypeptide to enzymes which affect glycosylation, for example mammalian glycosylating or deglycosylating enzymes, phosphorylation, such as modification of amino acid residues which results in phosphorylated amino acid residues, for example phosphotyrosine, phosphoserine and phosphothreonine. The polypeptide according to the invention can comprise one or more amino acids independently selected from the group consisting of naturally occurring L-amino acids, naturally occurring D-amino acids as well as non-naturally occurring, synthetic amino acids.

The invention also relates to polypeptides of the invention where blocking groups are introduced in order to protect and/or stabilize the N- and/or C-termini of the polypeptide from undesirable degradation. Such blocking groups may be selected from the group comprising branched or non-branched alkyl groups and acyl groups, such as formyl and acetly groups, as well substituted froms thereof, such as the acetamidomethyl.

The invention further relates to modifications and derivatives of the polypeptide according to the invention, nucleotides encoding said polypeptides, vectors comprising said nucleotides, host cells transformed with said vectors and transgenic organisms comprising said cells.

Patent Despositions Under the Budapest Treaty

The following bacterial strains have been deposited on 4 Jun. 2007 with the DSMZ under the provisions of the Budapest Treaty:

*Escherichia coli* ALO3231
DSM 19401: *E. coli* strain JM109 containing plasmid pGEM-T-Easy-RmAFP1
*Escherichia coli* ALO3232
DSM 19402: *E. coli* strain JM109 containing plasmid pGEM-T-Easy-RmAFP2
*Escherichia coli* ALO3233
DSM 19403: *E. coli* strain JM109 containing plasmid pGEM-T-Easy-RmAFP3
*Escherichia coli* ALO3234
DSM 19404: *E. coli* strain JM109 containing plasmid pGEM-T-Easy-RmAFP4
*Escherichia coli* ALO3235
DSM 19405: *E. coli* strain JM109 containing plasmid pGEM-T-Easy-RmAFP5
*Escherichia coli* ALO3236
DSM 19406: *E. coli* strain JM109 containing plasmid pGEM-T-Easy-RmAFP6
*Escherichia coli* ALO3237
DSM 19407: *E. coli* strain JM109 containing plasmid pGEM-T-Easy-RmAFP7
*Escherichia coli* ALO3238
DSM 19408: *E. coli* strain JM109 containing plasmid pGEM-T-Easy-RmAFP8

The following statement is made for the below cited regional areas and national states in relation to the above-cited DSMZ deposition numbers.

EPO: The applicant hereby requests that until the publication of the mention of the grant of a European Patent or for 20 years from the date of filing if the application is refused or withdrawn or deemed to be withdrawn, the biological material shall be made available as provided in Rule 28(3) EPC only by the issue of a sample to an expert nominated by the requester (Rule 28 (4) EPC).

AUSTRALIA: The applicant hereby gives notice that the furnishing of a sample of a microorganism shall only be effected prior to the grant of a patent, or to the lapsing, refusal or withdrawal of an application, to a person who is a skilled addressee without an interest in the invention (Regulation 3.25(3) of the Australian Patents Regulation).

CANADA: The applicant requests that, until either a Canadian patent has been issued on the basis of the present application or the application has been refused, or is abandoned and no longer subject to reinstatement, or is withdrawn, the Commissioner of Patents only authorizes the furnishing of a sample of the deposited biological material referred to in the application to an independent expert nominated by the Commissioner.

CROATIA: The applicant hereby requests that, samples shall be, upon request, made available between the publication of the application and the granting of the patent only to an independent expert.

DENMARK: The applicant hereby requests that, until the present application has been laid open to public inspection (by the Danish Patent Office), or has been finally decided upon by the Danish Patent office without having been laid open to public inspection, the furnishing of a sample of the deposited biological material referred to in the application shall only be effected to an expert in the art.

FINLAND: The applicant hereby requests that, until the present application has been laid open to public inspection (by the National Board of Patents and Regulations), or has been finally decided upon by the National Board of Patents and Registration without having been laid open to public inspection, the furnishing of a sample of the deposited biological material referred to in the application shall only be effected to an expert in the art.

GERMANY: The applicant hereby requests that, until the grant of a patent or from 20 years from the date of filing if the application is refused or withdrawn, a sample shall only be issued to an independent expert nominated by the applicant.

ICELAND: The applicant hereby requests that until a patent has been granted or a final decision taken by the Icelandic Patent Office concerning the present application, which decision has not resulted in a patent, the furnishing of a sample of the deposited biological material referred to in the application shall only be effected to an expert in the art.

NORWAY: The applicant hereby requests that until the present application has been laid open to public inspection (by the Norwegian Patent Office), or has been finally decided upon by the Norwegian Patent Office without having been laid open inspection, the furnishing of a sample of the deposited biological material referred to in the application shall only be effected to an expert in the art.

SINGAPORE: The applicant hereby requests that the furnishing of a sample of the deposited biological material referred to in the application shall only be made available to an expert.

SPAIN: The applicant hereby requests that until the publication of the mention of the grant of a Spanish patent or for 20 years from the date of filing if the present application is refused or withdrawn, the biological material shall be made available as provided in Article 45 SPL only by the issue of a sample of the deposited biological material referred to in the application to an independent expert.

SWEDEN: The applicant hereby requests that, until the present application has been laid open to public inspection (by the Swedish Patent Office), or has been finally decided upon by the Swedish Patent Office without having been laid open to public inspection, the furnishing of a sample of the deposited biological material referred to in the application shall only be effected to an expert in the art.

UNITED KINGDOM: The applicant hereby requests that the furnishing of a sample of the deposited biological material referred to in the application shall only be made available to an expert.

Determination of Sequence Homologies and Identities

In one aspect the present invention also provides isolated polypeptides that have a substantially similar sequence identity to the polypeptides according to the present invention, such as any of SEQ ID NO:1 to SEQ ID NO:8, or their orthologs.

The term "substantially similar sequence identity" is used herein to denote polypeptides having at least 70%, such as at least 72%, for example at least 74%, such as at least 76%, for example at least 78%, such as at least 80%, for example at least 82%, such as at least 84%, for example at least 86%, such as at least 88%, for example at least 90%, such as at least 91%, for example at least 92%, such as at least 93%, for example at least 94%, such as at least 95%, for example at least 96%, such as at least 97%, for example at least 98%, such as at least 99%, or greater than 99% sequence identity to any of the sequences SEQ ID NO:1 to SEQ ID NO:8, or their orthologs.

The present invention also contemplates variant polynucleotide molecules that can be identified using two criteria: a) a determination of the identity or similarity between a polypeptide having the amino acid sequence of any of the sequences SEQ ID NO:1 to SEQ ID NO:8, cf above, and b) a hybridization assay carried out under stringent conditions. For example, certain gene variants comprise polynucleotides that remain hybridized with a polynucleotide encoding a polypeptide according to the present invention, such as any of the sequences SEQ ID NO:1 to SEQ ID NO:8, or a complement of such a polynucleotide, following washing under stringent washing conditions, in which the wash stringency is equivalent to 0.5× to 2×SSC with 0.1% SDS at 55° C. to 65° C. Alternatively, variant genes can be characterized as polynucleotide molecules that remain hybridized with a polynucleotide encoding a polypeptide according to the present invention, such as any of the sequences SEQ ID NO:1 to SEQ ID NO:8, or a complement of such a polynucleotide, following washing under stringent washing conditions, in which the wash stringency is equivalent to 0.1× to 0.2×SSC with 0.1% SDS at 55° C. to 65° C.

Percent sequence identity is determined by conventional methods. See, for example, Altschul et al., Bull. Math. Bio. 48:603 (1986), and Henikoff and Henikoff, Proc. Natl. Acad. Sci. USA 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.). The percent identity is then calculated as: ([Total number of identical matches]/[length of the longer sequence plus the number of gaps introduced into the longer sequence in order to align the two sequences])×(100).

Those skilled in the art appreciate that there are many established algorithms available to align two amino acid sequences. The "FASTA" similarity search algorithm of Pearson and Lipman is a suitable polypeptide alignment method for examining the level of identity shared by an amino acid sequence disclosed herein and the amino acid sequence of a putative or variant. The FASTA algorithm is described by Pearson and Lipman, Proc. Nat'l Acad. Sci. USA 85:2444 (1988), and by Pearson, Meth. Enzymol. 183:63 (1990).

Briefly, FASTA first characterizes sequence similarity by identifying regions shared by the query sequence (e.g., any of the sequences SEQ ID NO:1 to SEQ ID NO:8) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, J. Mol. Biol. 48:444 (1970); Sellers, SIAM J. Appl. Math. 26:787 (1974)), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, Meth. Enzymol. 183:63 (1990).

FASTA can also be used to determine the sequence identity of polynucleotide molecules using a ratio as disclosed above. For nucleotide sequence comparisons, the ktup value can range between one to six, preferably from three to six, and most preferably, three. The other parameters can be set as: gap opening penalty=10, and gap extension penalty=1.

Substitution of Amino Acid Residues in Polypeptides According to the Present Invention The present invention is also directed to polypeptides having one or more conservative amino acid substitution(s) and polynucleotides encoding polypeptides having one or more conservative amino acid substitution(s), as compared with the amino acid sequence of any of the sequences SEQ ID NO:1 to SEQ ID NO:8. That is, variants can be obtained that contain one or more amino acid substitutions of any of the sequences SEQ ID NO:1 to SEQ ID NO:8. Variants include sequences wherein an alkyl amino acid is substituted for an alkyl amino acid, wherein an aromatic amino acid is substituted for an aromatic amino acid, wherein a sulfur-containing amino acid is substituted for a sulfur-containing amino acid in, wherein a hydroxy-containing amino acid is substituted for a hydroxy-containing amino acid, wherein an acidic amino acid is substituted for an acidic amino acid, wherein a basic amino acid is substituted for a basic amino acid, or wherein a dibasic monocarboxylic amino acid is substituted for a dibasic monocarboxylic amino acid.

Among the common amino acids, for example, a "conservative amino acid substitution" can also be illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

The BLOSUM62 table is an amino acid substitution matrix derived from about 2,000 local multiple alignments of polypeptide sequence segments, representing highly conserved regions of more than 500 groups of related polypeptides (Henikoff and Henikoff, Proc. Nat'l Acad. Sci. USA 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Particular variants of polypeptides are characterized by having at least 70%, at least 80%, at least 85%, at least 90%, at least 95% or greater than 95% sequence identity to a corresponding amino acid sequence disclosed herein (i.e., any of the sequences SEQ ID NO:1 to SEQ ID NO:8), e.g. when the variation in amino acid sequence is due to one or more conservative amino acid substitutions.

Variants of amino acid sequences, such as "conservative amino acid" variants, can be obtained, for example, by oligonucleotide-directed mutagenesis, linker-scanning mutagenesis, mutagenesis using the polymerase chain reaction, and the like (see Ausubel (1995) at pages 810 to 822; and McPherson (ed.), Directed Mutagenesis: A Practical Approach (IRL Press 1991)).

The polypeptides according to the present invention can also comprise non-naturally occurring amino acid residues. Non-naturally occurring amino acids include e.g., without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine.

Several methods are known in the art for incorporating non-naturally occurring amino acid residues into polypeptides. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an E. coli S30 extract and commercially available enzymes and other reagents. polypeptides are purified by chromatography. See, for example, Robertson et al., J. Am. Chem. Soc. 113:2722 (1991), Ellman et al., Methods Enzymol. 202:301 (1991), Chung et al., Science 259:806 (1993), and Chung et al., Proc. Nat'l Acad. Sci. USA 90:10145 (1993).

Multiple amino acid substitutions can be made and tested using known methods of mutagenesis and screening, such as those disclosed by Reidhaar-Olson and Sauer (Science 241: 53 (1988)) or Bowie and Sauer (Proc. Nat'l Acad. Sci. USA 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832 (1991), Ladner et al., U.S. Pat. No. 5,223,409, Huse, international publication No. WO 92/06204, and region-directed mutagenesis (Derbyshire et al., Gene 46:145 (1986), and Ner et al., DNA 7:127, (1988)).

Variants of the disclosed nucleotide and polypeptide sequences according to the present invention can also be generated through DNA shuffling as disclosed by Stemmer, Nature 370:389 (1994), Stemmer, Proc. Nat'l Acad. Sci. USA 91:10747 (1994), and international publication No. WO 97/20078. Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind specific antibodies, can be recovered from the host cells and rapidly sequenced using modern equipment. These methods allow the rapid determination of the importance of individual amino acid residues in a polypeptide of interest, and can be applied to polypeptides of unknown structure.

Fragments of Polypeptides According to the Present Invention

The present invention also includes "functional fragments" of polypeptides and polynucleotide molecules according to the present invention encoding such functional fragments. Routine deletion analyses of polynucleotide molecules can be performed to obtain functional fragments of a polynucleotide molecule that encodes a polypeptide according to the present invention. As an illustration, DNA molecules encoding any of the sequences SEQ ID NO:1 to SEQ ID NO:8 can be digested with Bal31 nuclease to obtain a series of nested deletions. The fragments are then inserted into expression vectors in proper reading frame, and the expressed polypeptides are isolated and tested for the ability to bind specifically to anti-antibodies. One alternative to exonuclease digestion is to use oligonucleotide-directed mutagenesis to introduce deletions or stop codons to specify production of a desired fragment. Alternatively, particular fragments of a gene according to the present invention can be synthesized using the polymerase chain reaction.

Fragments of SEQ ID NO:1 to SEQ ID NO:8 preferably comprises one or more of the ice binding sites denoted SEQ ID NO:9 to SEQ ID NO:72, as described herein elsewhere. Chimeric polypeptides and polypeptide fragments are also provided.

The following fragment:
GSYSCRAVGVDASTVTDVQGTCHAKATG-PGAVASGTSVDGSTSTATATGSC originates from the full length sequences SEQ ID NO 1, SEQ ID NO 2, SEQ NO 7 and SEQ ID NO 8 and contains the alternative residues C in the C-terminal end and GS in the N-terminal end.

Methods for identifying functional domains are well-known to those of skill in the art. For example, studies on the truncation at either or both termini of interferons have been summarized by Horisberger and Di Marco, Pharmac. Ther. 66:507 (1995). Moreover, standard techniques for functional analysis of polypeptides are described by, for example, Treuter et al., Molec. Gen. Genet. 240:113 (1993), Content et al., "Expression and preliminary deletion analysis of the 42 kDa 2 5A synthetase induced by human interferon," in Biological Interferon Systems, Proceedings of ISIR-TNO Meeting on Interferon Systems, Cantell (ed.), pages 65 72 (Nijhoff 1987), Herschman, "The EGF Receptor," in Control of Animal Cell Proliferation, Vol. 1, Boynton et al., (eds.) pages 169 199 (Academic Press 1985), Coumailleau et al., J. Biol. Chem. 270:29270 (1995); Fukunaga et al., J. Biol. Chem. 270:25291 (1995); Yamaguchi et al., Biochem. Pharmacol. 50:1295 (1995), and Meisel et al., Plant Molec. Biol. 30:1 (1996).

The present invention also contemplates functional fragments of a polypeptide according to the present invention that have amino acid changes, compared with the amino acid sequence of any of the sequences SEQ ID NO:1 to SEQ ID NO:8. A variant polypeptide can be identified on the basis of structure by determining the level of identity with a particular amino acid sequence disclosed herein. An alternative approach to identifying a variant polypeptide on the basis of structure is to determine whether a polynucleotide molecule encoding a potential variant polypeptide can hybridize to a polynucleotide molecule having the nucleotide sequence of any of the sequences SEQ ID NO:1 to SEQ ID NO:8, as discussed above.

The present invention also provides polypeptide fragments or peptides comprising an epitope-bearing portion of a polypeptide according to the present invention as described herein. Such fragments or peptides may comprise an "immunogenic epitope," which is a part of a polypeptide that elicits an antibody response when the entire polypeptide is used as an immunogen. Immunogenic epitope-bearing peptides can be identified using standard methods (see, for example, Geysen et al., Proc. Nat'l Acad. Sci. USA 81:3998 (1983)).

In contrast, polypeptide fragments or peptides may comprise an "antigenic epitope," which is a region of a polypeptide molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a polypeptide can be used to stimulate the production of antibodies against the polypeptide (see, for example, Sutcliffe et al., Science 219:660 (1983)). Accordingly, antigenic epitope-bearing peptides and polypeptides of the present invention are useful to raise antibodies that bind with the polypeptides described herein.

Antigenic epitope-bearing peptides and polypeptides can contain at least four to ten amino acids, such as at least ten to fifteen amino acids, for example about 15 to about 30 amino acids of any of the sequences SEQ ID NO:1 to SEQ ID NO:8. Such epitope-bearing peptides and polypeptides can be produced by fragmenting a polypeptide according to the present invention, or by chemical peptide synthesis, as described herein. Moreover, epitopes can be selected by phage display of random peptide libraries (see, for example, Lane and Stephen, Curr. Opin. Immunol. 5:268 (1993), and Cortese et al., Curr. Opin. Biotechnol. 7:616 (1996)). Standard methods for identifying epitopes and producing antibodies from small peptides that comprise an epitope are described, for example, by Mole, "Epitope Mapping," in Methods in Molecular Biology, Vol. 10, Manson (ed.), pages 105 116 (The Humana Press, Inc. 1992), Price, "Production and Characterization of Synthetic Peptide-Derived Antibodies," in Monoclonal Antibodies: Production, Engineering, and Clinical Application, Ritter and Ladyman (eds.), pages 60 84 (Cambridge University Press 1995), and Coligan et al. (eds.), Current Protocols in Immunology, pages 9.3.1 9.3.5 and pages 9.4.1 9.4.11 (John Wiley & Sons 1997).

Regardless of the particular nucleotide sequence of a variant gene according to the present invention, the gene encodes a polypeptide that may be characterized by its ability to bind specifically to an antibody capable of specifically binding to any of the sequences SEQ ID NO:1 to SEQ ID NO:8.

Fusion Polypeptides Comprising Anti-Freeze Polypeptides or Ice Binding Sites or Ice Binding Domains According to the Invention The present invention also includes anti-freeze fusion polypeptides. Anti-freeze fusion polypeptides of the present invention may be targeted to a particular cellular compartment or to the extracellular space, to a particular cell or to particular cell types. By attachment of polypeptide segments which specify or determine targeting to cellular compartments, the anti-freeze segments may be targeted to a particular cellular organelle. Not only will the peptide be directed to the organelle, but the anti-freeze function may remain functional even when surrounded by other polypeptide segments. By fusion to antibodies or other molecules having cell specificity in binding, the resistance to cellular damage upon freezing can be conferred to those cell types. This technique will also find use in organs. Examples of polypeptides to which the polypeptide according to the present invention can be bound are listed below:

| Fussion to (protein) | Advantages of fusion |
|---|---|
| Protein A | Detectability, secretion from GRAM-positive bacteria, purification, readily cleaved to yield free peptide |

-continued

| Fussion to (protein) | Advantages of fusion |
|---|---|
| Beta-Galactosidase | Measurement by enzyme assay, detectability on Western Blots |
| Beta-lactamase | Detectability on Western Blots, secretion to periplasm in GRAM-negative bacteria |
| Chlortamphenicol acetyltransferase | Detectability on Western blots, measurement by enzyme assay in plant extracts |
| Pathogenesis-related polypeptide prib | Secretion from dicotyledonous plants |
| Alpha-amylase | Secretion from monocotyledonous plants |
| Phytohemagglutinin | Vacuole targeting in plants |
| RuBPCASE small subunit | Chloroplast targeting in plants |
| Phaseolin | Accumulation in seeds |
| Alcohol dehydrogenase | Expression in yeast |
| Alpha mating factor | Secretion from yeast |
| Luciferase | Detectability by light emmision |

Fusion polypeptides comprising polypeptides according to the present invention can thus be used to express a polypeptide according to the present invention in a recombinant host, and to isolate expressed polypeptides. One type of fusion polypeptide comprises a peptide that guides a polypeptide according to the present invention from a recombinant host cell. To direct a polypeptide according to the present invention into the secretory pathway of a eukaryotic host cell, a secretory signal sequence (also known as a signal peptide, a leader sequence, prepro sequence or pre sequence) is provided in a suitable expression vector. While the secretory signal sequence may be derived from a polypeptide according to the present invention, a suitable signal sequence may also be derived from another secreted polypeptide or synthesized de novo. The secretory signal sequence is operably linked to a gene encoding sequence according to the present invention such that the two sequences are joined in the correct reading frame and positioned to direct the newly synthesized polypeptide into the secretory pathway of the host cell. Secretory signal sequences are commonly positioned 5' to the nucleotide sequence encoding the polypeptide of interest, although certain secretory signal sequences may be positioned elsewhere in the nucleotide sequence of interest (see, e.g., Welch et al., U.S. Pat. No. 5,037,743; Holland et al., U.S. Pat. No. 5,143,830).

Although the secretory signal sequence of a gene according to the present invention, or another polypeptide produced by mammalian cells (e.g., tissue-type plasminogen activator signal sequence, as described, for example, in U.S. Pat. No. 5,641,655) is useful for expression of a gene according to the present invention in recombinant mammalian hosts, a yeast signal sequence is preferred for expression in yeast cells. Examples of suitable yeast signal sequences are those derived from yeast mating phermone alpha-factor (encoded by the MF-alpha1 gene), invertase (encoded by the SUC2 gene), or acid phosphatase (encoded by the PHO5 gene). See, for example, Romanos et al., "Expression of Cloned Genes in Yeast," in DNA Cloning 2: A Practical Approach, 2.sup.nd Edition, Glover and Hames (eds.), pages 123 167 (Oxford University Press 1995).

In bacterial cells, it is often desirable to express a heterologous polypeptide as a fusion polypeptide to decrease toxicity, increase stability, and to enhance recovery of the expressed polypeptide. For example, a gene according to the present invention can be expressed as a fusion polypeptide comprising a glutathione S-transferase polypeptide. Glutathione S-transferease fusion polypeptides are typically soluble, and easily purifiable from E. coli lysates on immobilized glutathione columns. In similar approaches, a fusion polypeptide according to the present invention comprising a maltose binding polypeptide polypeptide can be isolated with an amylose resin column, while a fusion polypeptide comprising the C-terminal end of a truncated polypeptide A gene can be purified using IgG-Sepharose. Established techniques for expressing a heterologous polypeptide as a fusion polypeptide in a bacterial cell are described, for example, by Williams et al., "Expression of Foreign polypeptides in E. coli Using Plasmid Vectors and Purification of Specific Polyclonal Antibodies," in DNA Cloning 2: A Practical Approach, 2.sup.nd Edition, Glover and Hames (Eds.), pages 15 58 (Oxford University Press 1995). In addition, commercially available expression systems are available. For example, the PIN-POINT Xa polypeptide purification system (Promega Corporation; Madison, Wis.) provides a method for isolating a fusion polypeptide comprising a polypeptide that becomes biotinylated during expression with a resin that comprises avidin.

Peptide tags that are useful for isolating heterologous polypeptides expressed by either prokaryotic or eukaryotic cells include polyHistidine tags (which have an affinity for nickel-chelating resin), c-myc tags, calmodulin binding polypeptide (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., Arch. Biochem. Biophys. 329:215 (1996), Morganti et al., Biotechnol. Appl. Biochem. 23:67 (1996), and Zheng et al., Gene 186:55 (1997). polynucleotide molecules encoding such peptide tags are available, for example, from Sigma-Aldrich Corporation (St. Louis, Mo.).

Another form of fusion polypeptide comprises a polypeptide according to the present invention and an immunoglobulin heavy chain constant region, typically an $F_c$ fragment, which contains two constant region domains and a hinge region but lacks the variable region. As an illustration, Chang et al., U.S. Pat. No. 5,723,125, describe a fusion polypeptide comprising a human interferon and a human immunoglobulin Fc fragment. The C-terminal of the interferon is linked to the N-terminal of the Fc fragment by a peptide linker moiety. An example of a peptide linker is a peptide comprising primarily a T cell inert sequence, which is immunologically inert. An exemplary peptide linker has the amino acid sequence: GGSGG SGGGG SGGGG S (SEQ ID NO:91). In this fusion polypeptide, a preferred $F_c$ moiety is a human gamma4 chain, which is stable in solution and has little or no complement activating activity. Accordingly, the present invention contemplates a fusion polypeptide that comprises a polypeptide according to the present invention, or a fragment thereof, and a human $F_c$ fragment, wherein the C-terminus of the polypeptide according to the present invention, or a fragment thereof, is attached to the N-terminus of the $F_c$ fragment via a peptide linker.

In another variation, a fusion polypeptide comprising a polypeptide according to the present invention further comprises an IgG sequence. The polypeptide moiety according to the present invention is covalently joined to the amino terminal end of the IgG sequence, and a signal peptide that is covalently joined to the amino terminal of the polypeptide moiety according to the present invention, wherein the IgG sequence comprises or consists of the following elements in the following order: a hinge region, a $CH_2$ domain, and a $CH_3$ domain. Accordingly, the IgG sequence lacks a $CH_1$ domain. The polypeptide moiety according to the present invention displays an ice-binding activity. The above, general approaches for producing fusion polypeptides that comprise both antibody and nonantibody portions has been described by LaRochelle et al., EP 742830 (WO 95/21258).

Fusion polypeptides can be prepared by methods known to those skilled in the art by preparing each component of the fusion polypeptide and chemically conjugating them. Alternatively, a polynucleotide encoding both components of the fusion polypeptide in the proper reading frame can be generated using known techniques and expressed by the methods described herein. General methods for enzymatic and chemical cleavage of fusion polypeptides are described, for example, by Ausubel (1995) at pages 16 19 to 16 25.

General Methods for the Production of Polypeptides and Fragments Thereof According to the Present Invention Synthesis of anti-freeze polypeptides according to the present invention may be pursued in two forms, either biological or synthetic. The biological method is by expression of polypeptide coding sequence or gene; the synthetic method is by chemical synthesis of a polypeptide.

A preferred synthetic method utilizes solid phase peptide synthesis, such as that developed by Merrifield (J. Am. Chem. Soc., (1963) 85:2149-2156). This method will be particularly useful in testing particular compositions or formulations for anti-freeze activity.

For large scale production, the biological expression would typically be preferred. The encoding polynucleotide or gene can be a natural gene with recombinant modifications or a totally synthetic sequence that will be expressed in an appropriate expression system. The methods utilized for insertion of a natural sequence segment into an appropriate vector are well known to persons of ordinary skill in the art, see Maniatis or Wu, et al. (1987) Methods in Enzymology, Vol. 153, Academic Press, New York, N.Y.

Synthetic sequences can be synthesized by the phosphoramidite chemistry to make particular sections of the sequence (Beaucage and Carruthers, (1981) Tet. Letters, 22:1859-1862). Overlapping segments can be synthesized and then ligated together to produce a larger gene.

Finally, by selecting particular sequences for the antifreeze segments, restriction enzyme cutting sites may be introduced which will provide convenient segments which may be easily linked together or inserted to generate tandem repeats, as will be obvious to one of ordinary skill in the art.

Purification of the anti-freeze polypeptides will be by methods known to a person of ordinary skill in the art of polypeptide purification. Standard purification techniques may be from either cell lysates or culture medium if the polypeptides are secreted. Typical methods are column chromatography, ammonium sulfate salt precipitations, antibody affinity column chromatography and others. With naturally occurring polypeptides (e.g., produced in fish), a preferred method of purification is as described by DeVries et al. (1977) Biochem Biophys. Acta 495:388-392.

Preferably, the anti-freeze polypeptides will be purified to substantial homogeneity, usually at least about 70% to 80% pure, preferably about 90-95% pure, most preferably 99% or more pure. Typically, the polypeptides will be substantially free of contaminating, naturally associated fish compounds.

It is clear from the above that the polypeptides of the present invention, including full-length polypeptides, functional fragments, and fusion polypeptides, can advantageously be produced in recombinant host cells following conventional techniques.

To express a gene according to the present invention, a polynucleotide molecule encoding the polypeptide must be operably linked to regulatory sequences that control transcriptional expression in an expression vector and then, introduced into a host cell. In addition to transcriptional regulatory sequences, such as promoters and enhancers, expression vectors can include translational regulatory sequences and a marker gene, which is suitable for selection of cells that carry the expression vector.

Expression vectors that are suitable for production of a foreign polypeptide in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence.

As discussed above, expression vectors can also include nucleotide sequences encoding a secretory sequence that directs the heterologous polypeptide into the secretory pathway of a host cell. For example, an expression vector may comprise a gene according to the present invention and a secretory sequence derived from said gene or another secreted gene.

Examples of vectors commonly used with bacteria include the pET series (Novagen), pGEX series (Ge Healthcare), pBAD-series (Invitrogen). Examples of vectors in yeasts are the pPic series for *Pichia* (Invitrogen), the pKlac system from *Kluyveromyces lactis* (New England biolabs), *S. cerevisiae* vectors (Patel, O., Fearnley, R., and Macreadie, I. 3002. *Saccharomyces cerevisiae* expression vectors with thrombin-cleavable N- and C-terminal 6×(His) tags. Biotechnol Lett. 2003 25(4):331-334) and the pYes system for *S. cerevisiae* (Invitrogen).

Examples of vectors for use in funghi are the pBAR series (described in Pall, M. L. and J. Brunelli. 1993. A series of six compact fungal transformation vectors containing polylinkers with unique restrictions sites. Fungal Genetics Newsletter 40:59-61). The plEx plasmid based system (Merck) or the baculovirus based system (Merck) are two examples of systems useful for insect cells. Similar products are available from other companies.

Examples of vectors for use in insect cells include the tetracycline regulated systems pTet and pTre, the adenovirus-based system Adeno-X, the retrovirus-based system Rethro-X (all Clontech) and the pcDNA vectors (Invitrogen). Again, many more examples exist and are on the market.

Polypeptides according to the present invention may be expressed in mammalian cells. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 [Chasin et al., Som. Cell. Molec. Genet. 12:555 1986]), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., J. Molec. Appl. Genet. 1:273 (1982)), the TK promoter of Herpes virus (McKnight, Cell 31:355 (1982)), the SV40 early promoter (Benoist et al., Nature 290:304 (1981)), the Rous sarcoma virus promoter (Gorman et al., Proc. Nat'l Acad. Sci. USA 79:6777 (1982)), the cytomegalovirus promoter (Foecking et al., Gene 45:101 (1980)), and the mouse mammary tumor virus promoter (see, generally, Etcheverry, "Expression of Engineered polypeptides in Mammalian Cell Culture," in polypeptide Engineering: Principles and Practice, Cleland et al. (eds.), pages 163 181 (John Wiley & Sons, Inc. 1996)).

Alternatively, a prokaryotic promoter, such as the bacteriophage T3 RNA polymerase promoter, can be used to control gene expression in mammalian cells if the prokaryotic promoter is regulated by a eukaryotic promoter (Zhou et al., Mol. Cell. Biol. 10:4529 (1990), and Kaufman et al., Nucl. Acids Res. 19:4485 (1991)).

An expression vector can be introduced into host cells using a variety of standard techniques including calcium phosphate transfection, liposome-mediated transfection, microprojectile-mediated delivery, electroporation, and the like. The transfected cells can be selected and propagated to provide recombinant host cells that comprise the expression vector stably integrated in the host cell genome.

Techniques for introducing vectors into eukaryotic cells and techniques for selecting such stable transformants using a dominant selectable marker are described, for example, by Ausubel (1995) and by Murray (ed.), Gene Transfer and Expression Protocols (Humana Press 1991). A gene according to the present invention may thus be expressed in higher eukaryots, such as avian, fungal, insect, yeast, and plant cells.

For example, one suitable selectable marker is a gene that provides resistance to the antibiotic neomycin. In this case, selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes.

A suitable amplifiable selectable marker is dihydrofolate reductase, which confers resistance to methotrexate. Other drug resistance genes (e.g., hygromycin resistance, multidrug resistance, puromycin acetyltransferase) can also be used. Alternatively, markers that introduce an altered phenotype, such as green fluorescent polypeptide, or cell surface polypeptides such as CD4, CD8, Class I MHC, placental alkaline phosphatase may be used to sort transfected cells from untransfected cells by such means as FACS sorting or magnetic bead separation technology.

Polypeptides according to the present invention can also be produced by cultured mammalian cells using a viral delivery system. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous polynucleotide (for a review, see Becker et al., Meth. Cell Biol. 43:161 (1994), and Douglas and Curiel, Science & Medicine 4:44 (1997)). Advantages of the adenovirus system include the accommodation of relatively large DNA inserts, the ability to grow to high-titer, the ability to infect a broad range of mammalian cell types, and flexibility that allows use with a large number of available vectors containing different promoters.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. An option is to delete the essential E1 gene from the viral vector, which results in the inability to replicate unless the E1 gene is provided by the host cell. Adenovirus vector-infected human 293 cells (ATCC Nos. CRL-1573, 45504, 45505), for example, can be grown as adherent cells or in suspension culture at relatively high cell density to produce significant amounts of polypeptide (see Garnier et al., Cytotechnol. 15:145 (1994)).

Methods for generating transgenic organisms are known in the art, cf Table 3:

| | |
|---|---|
| Bacteria, Yeasts and Fungi | The transgenic organisms are obtained simply by introducing the relevant expression plasmids. Methods for this are listed herein elsewhere |
| Insects: | Li W, Jin L, An L. 2003. Construction of targeting vector and expression of green fluorescent polypeptide in the silkworm, *Antheraea pernyi*. DNA Cell Biol. 22: 441-6. Yamao M, Katayama N, Nakazawa H, Yamakawa M, Hayashi Y, Hara S, Kamei K, Mori H. 1999. Gene targeting in the silkworm by use of a baculovirus. Genes Dev. 13: 511-6. Allen M L, Scholl P J. 2005. Quality of transgenic laboratory strains of *Cochliomyia hominivorax* (Diptera: Calliphoridae). J Econ Entomol. 98:2301-6. |
| Plants | See p. 47 of the patent (Horsch et al., Science 227: 1229 (1985), Klein et al., Biotechnology 10: 268 (1992), and Miki et al., "Procedures for Introducing Foreign DNA into Plants," in Methods in Plant Molecular Biology and Biotechnology, Glick et al. (eds.), pages 67 88 (CRC Press, 1993). |
| Fish | Rembold M, Lahiri K, Foulkes N S, Wittbrodt J. 2006. Transgenesis in fish: efficient selection of transgenic fish by co-injection with a fluorescent reporter construct. Nature Protocols 1: 1133-9 Rahman M A, Mak R, Ayad H, Smith A, Maclean N. 1998. Expression of a novel piscine growth hormone gene results in growth enhancement in transgenic tilapia (*Oreochromis niloticus*). Transgenic Res. 7: 357-69. Uzbekova S, Chyb J, Ferriere F, Bailhache T, Prunet P, Alestrom P, Breton B. 2000. Transgenic rainbow trout expressed sGnRH-antisense RNA under the control of sGnRH promoter of Atlantic salmon. J Mol Endocrinol. 25: 337-50. |
| Animals | Nagashima H, Fujimura T, Takahagi Y, Kurome M, Wako N, Ochiai T, Esaki R, Kano K, Saito S, Okabe M, Murakami H. 2003. Development of efficient strategies for the production of genetically modified pigs. Theriogenology. 59: 95-106 Lai L, Prather R S. 2003. Creating genetically modified pigs by using nuclear transfer. Reprod Biol Endocrinol. 1: 82 Hofmann A, Kessler B, Ewerling S, Weppert M, Vogg B, Ludwig H, Stojkovic M, Boelhauve M, Brem G, Wolf E, Pfeifer A. 2003. Efficient transgenesis in farm animals by lentiviral vectors. EMBO Rep. 4: 1054-60. |

| | |
|---|---|
| DNA microinjection | (Gordon, J. W. and Ruddle, F. H. 1981. Integration and stable germ line transformation of genes injected into mouse pronuclei. Science 214: 1244-1246), |
| Embryonic stem cell-mediated gene transfer | Transgenesis by means of blastocyst-derived embryonic stem cell line. Proc. Natl. Acad. Sci. 83: 9065-9069) |
| Retrovirus-mediated gene transfer | Jaenisch, R. 1976. Germ line integration and Mendelian transmission of the exogenous Moloney leukemia virus. Proc. Natl. Acad. Sci. 73: 1260-1264) |

The baculovirus system provides an efficient means to introduce cloned genes according to the present invention into insect cells. Suitable expression vectors are based upon the *Autographa californica* multiple nuclear polyhedrosis virus (AcMNPV), and contain well-known promoters such as *Drosophila* heat shock polypeptide (hsp) 70 promoter, *Autographa californica* nuclear polyhedrosis virus immediate-early gene promoter (ie-1) and the delayed early 39K promoter, baculovirus p10 promoter, and the *Drosophila* metallothionein promoter.

A second method of making recombinant baculovirus utilizes a transposon-based system described by Luckow (Luckow, et al., J. Virol. 67:4566 (1993)). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the DNA encoding the polypeptide according to the present invention into a baculovirus genome maintained in *E. coli* as a large plasmid called a "bacmid." See, Hill-Perkins and Possee, J. Gen. Virol. 71:971 (1990), Bonning, et al., J. Gen. Virol. 75:1551 (1994), and Chazenbalk, and Rapoport, J. Biol. Chem. 270:1543 (1995).

In addition, transfer vectors can include an in-frame fusion with DNA encoding an epitope tag at the C- or N-terminus of the expressed polypeptide according to the present invention, for example, a Glu-Glu epitope tag (Grussenmeyer et al., Proc. Nat'l Acad. Sci. 82:7952 (1985)). Using a technique known in the art, a transfer vector containing a gene according to the present invention is transformed into *E. coli*, and screened for bacmids, which contain an interrupted lacZ gene indicative of recombinant baculovirus. The bacmid DNA containing the recombinant baculovirus genome is then isolated using common techniques.

The illustrative PFASTBAC vector can be modified to a considerable degree. For example, the polyhedrin promoter can be removed and substituted with the baculovirus basic polypeptide promoter (also known as Pcor, p6.9 or MP promoter) which is expressed earlier in the baculovirus infection, and has been shown to be advantageous for expressing secreted polypeptides (see, for example, Hill-Perkins and Possee, J. Gen. Virol. 71:971 (1990), Bonning, et al., J. Gen. Virol. 75:1551 (1994), and Chazenbalk and Rapoport, J. Biol. Chem. 270:1543 (1995). In such transfer vector constructs, a short or long version of the basic polypeptide promoter can be used. Moreover, transfer vectors can be constructed which replace the native secretory signal sequences of polypeptides according to the present invention with secretory signal sequences derived from insect polypeptides. For example, a secretory signal sequence from Ecdysteroid Glucosyltransferase (EGT), honey bee Melittin (Invitrogen Corporation; Carlsbad, Calif.), or baculovirus gp67 (PharMingen: San Diego, Calif.) can be used in constructs to replace native secretory signal sequences.

The recombinant virus or bacmid is used to transfect host cells. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as *Drosophila* Schneider-2 cells, and the HIGH FIVEO cell line (Invitrogen) derived from *Trichoplusia ni* (U.S. Pat. No. 5,300,435). Commercially available serum-free media can be used to grow and to maintain the cells. Suitable media are Sf900 II™ (Life Technologies) or ESF 921 ™ (Expression Systems) for Sf9 cells; and Ex-cellO405™ (JRH Biosciences, Lenexa, Kans.) or Express FiveO™ (Life Technologies) for *T. ni* cells. When recombinant virus is used, the cells are typically grown up from an inoculation density of approximately 2 to $5 \times 10^5$ cells to a density of 1 to $2 \times 10^6$ cells at which time a recombinant viral stock is added at a multiplicity of infection (MOI) of 0.1 to 10, more typically near 3.

Established techniques for producing recombinant polypeptides in baculovirus systems are provided by Bailey et al., "Manipulation of Baculovirus Vectors," in Methods in Molecular Biology, Volume 7: Gene Transfer and Expression Protocols, Murray (ed.), pages 147 168 (The Humana Press, Inc. 1991), by Patel et al., "The baculovirus expression system," in DNA Cloning 2: Expression Systems, 2nd Edition, Glover et al. (eds.), pages 205 244 (Oxford University Press 1995), by Ausubel (1995) at pages 16 37 to 16 57, by Richardson (ed.), Baculovirus Expression Protocols (The Humana Press, Inc. 1995), and by Lucknow, "Insect Cell Expression Technology," in polypeptide Engineering: Principles and Practice, Cleland et al. (eds.), pages 183 218 (John Wiley & Sons, Inc. 1996).

Fungal cells, including yeast cells, can also be used to express the genes described herein. Yeast species of particular interest in this regard include *Saccharomyces cerevisiae, Pichia pastoris*, and *Pichia methanolica*. Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include YIp-based vectors, such as YIp5, YRp vectors, such as YRp17, YEp vectors such as YEp13 and YCp vectors, such as YCp19. Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat. No. 4,931,373, Brake, U.S. Pat. No. 4,870,008, Welch et al., U.S. Pat. No. 5,037,743, and Murray et al., U.S. Pat. No. 4,845,075. Transformed cells are selected by phenotype determined by the selectable marker, commonly drug resistance or the ability to grow in the absence of a particular nutrient (e.g., leucine). A suitable vector system for use in *Saccharomyces cerevisiae* is the POT1 vector system disclosed by Kawasaki et al. (U.S. Pat. No. 4,931,373), which allows transformed cells to be selected by growth in glucose-containing media. Additional suitable promoters and terminators for use in yeast include those from glycolytic enzyme genes (see, e.g., Kawasaki, U.S. Pat. No. 4,599,311, Kingsman et al., U.S. Pat. No. 4,615,974, and Bitter, U.S. Pat. No. 4,977,092) and alcohol dehydrogenase genes. See also U.S. Pat. Nos. 4,990,446, 5,063,154, 5,139,936, and 4,661,454. Other examples of commonly used and/or commercially available vectors suitable for use in yeast are the pPic series (Invitrogen), the pKlac system from *Kluyveromyces lactis* (New England Biolabs) and *S. cerevisae* vectors (Patel et al., Biotechnology letters 2003 vol 25(4): 331-334) as well as the pYes system for *S. cerevisae* (Invitrogen). In fungi, the pBAR series is useful (Pall et al., 1993 vol. 40:59-61, Functional Genetics Newsletter).

Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., J. Gen. Microbiol. 132:3459 (1986), and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

For example, the use of *Pichia methanolica* as host for the production of recombinant polypeptides is disclosed by Raymond, U.S. Pat. No. 5,716,808, Raymond, U.S. Pat. No. 5,736,383, Raymond et al., Yeast 14:11 23 (1998), and in international publication Nos. WO 97/17450, WO 97/17451, WO 98/02536, and WO 98/02565. DNA molecules for use in transforming *P. methanolica* will commonly be prepared as double-stranded, circular plasmids, which can be linearized prior to transformation. For polypeptide production in *P. methanolica*, the promoter and terminator in the plasmid can be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A suitable selectable marker for use in *Pichia methanolica* is a *P. methanolica* ADE2 gene, which encodes phosphoribosyl-5-aminoimidazole carboxylase (AIRC; EC 4.1.1.21), and which allows ade2 host cells to grow in the absence of adenine. For large-scale, industrial processes where it is desirable to minimize the use of methanol, it is possible to use host cells in which both methanol utilization genes (AUG1 and AUG2) are deleted. For production of secreted polypeptides, host cells can be used that are deficient in vacuolar pro tease genes (PEP4 and PRB1). Electroporation is used to facilitate the introduction of a plasmid containing DNA encoding a polypeptide of interest into *P. methanolica* cells. *P. methanolica* cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Expression vectors can also be introduced into plant protoplasts, intact plant tissues, or isolated plant cells. Methods for introducing expression vectors into plant tissue include the direct infection or co-cultivation of plant tissue with *Agrobacterium tumefaciens*, microprojectile-mediated delivery, DNA injection, electroporation, and the like. See, for example, Horsch et al., Science 227:1229 (1985), Klein et al., Biotechnology 10:268 (1992), and Miki et al., "Procedures for Introducing Foreign DNA into Plants," in Methods in Plant Molecular Biology and Biotechnology, Glick et al. (eds.), pages 67 88 (CRC Press, 1993).

Alternatively, genes according to the present invention can be expressed in prokaryotic host cells. Suitable promoters that can be used to express polypeptides according to the present invention in a prokaryotic host are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, Ipp-lacSpr, phoA, and lacZ promoters of *E. coli*, promoters of *B. subtilis*, the promoters of the bacteriophages of *Bacillus, Streptomyces* promoters, the int promoter of bacteriophage lambda, the bla promoter of pBR322, and the CAT promoter of the chloramphenicol acetyl transferase gene. Prokaryotic promoters have been reviewed by Glick, J. Ind. Microbiol. 1:277 (1987), Watson et al., Molecular Biology of the Gene, 4th Ed. (Benjamin Cummins 1987), and by Ausubel et al. (1995).

Suitable prokaryotic hosts include *E. coli* and *Bacillus subtilus*. Suitable strains of *E. coli* include BL21(DE3), BL21 (DE3)pLysS, BL21(DE3)pLysE, DH1, DH41, DH5, DH51, DH51F, DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), Molecular Biology Labfax (Academic Press 1991)). Suitable strains of *Bacillus subtilus* include BR151, YB886, MI119, MI120, and B170 (see, for example, Hardy, "*Bacillus* Cloning Methods," in DNA Cloning: A Practical Approach, Glover (ed.) (IRL Press 1985)).

When expressing a polypeptide according to the present invention in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the polypeptide, thereby obviating the need for denaturation and refolding.

Methods for expressing polypeptides in prokaryotic hosts are well-known to those of skill in the art (see, for example, Williams et al., "Expression of foreign polypeptides in *E. coli* using plasmid vectors and purification of specific polyclonal antibodies," in DNA Cloning 2: Expression Systems, 2nd Edition, Glover et al. (eds.), page 15 (Oxford University Press 1995), Ward et al., "Genetic Manipulation and Expression of Antibodies," in Monoclonal Antibodies: Principles and Applications, page 137 (Wiley-Liss, Inc. 1995), and Georgiou, "Expression of polypeptides in Bacteria," in polypeptide Engineering: Principles and Practice, Cleland et al. (eds.), page 101 (John Wiley & Sons, Inc. 1996)).

Standard methods for introducing expression vectors into bacterial, yeast, insect, and plant cells are provided, for example, by Ausubel (1995).

General methods for expressing and recovering foreign polypeptide produced by a mammalian cell system are provided by, for example, Etcheverry, "Expression of Engineered polypeptides in Mammalian Cell Culture," in polypeptide Engineering: Principles and Practice, Cleland et al. (eds.), pages 163 (Wiley-Liss, Inc. 1996). Standard techniques for recovering polypeptide produced by a bacterial system is provided by, for example, Grisshammer et al., "Purification of over-produced polypeptides from *E. coli* cells," in DNA Cloning 2: Expression Systems, 2nd Edition, Glover et al. (eds.), pages 59 92 (Oxford University Press 1995). Established methods for isolating recombinant polypeptides from a baculovirus system are described by Richardson (ed.), Baculovirus Expression Protocols (The Humana Press, Inc. 1995).

As an alternative, polypeptides of the present invention can be synthesized by exclusive solid phase synthesis, partial solid phase methods, fragment condensation or classical solution synthesis. These synthesis methods are well-known to those of skill in the art (see, for example, Merrifield, J. Am. Chem. Soc. 85:2149 (1963), Stewart et al., "Solid Phase Peptide Synthesis" (2nd Edition), (Pierce Chemical Co. 1984), Bayer and Rapp, Chem. Pept. Prot. 3:3 (1986), Atherton et al., Solid Phase Peptide Synthesis: A Practical Approach (IRL Press 1989), Fields and Colowick, "Solid-Phase Peptide Synthesis," Methods in Enzymology Volume 289 (Academic Press 1997), and Lloyd-Williams et al., Chemical Approaches to the Synthesis of Peptides and polypeptides (CRC Press, Inc. 1997)). Variations in total chemical synthesis strategies, such as "native chemical ligation" and "expressed polypeptide ligation" are also standard (see, for example, Dawson et al., Science 266:776 (1994), Hackeng et al., Proc. Nat'l Acad. Sci. USA 94:7845 (1997), Dawson, Methods Enzymol. 287: 34 (1997), Muir et al, Proc. Nat'l Acad. Sci. USA 95:6705 (1998), and Severinov and Muir, J. Biol. Chem. 273:16205 (1998)).

The present invention contemplates compositions comprising a peptide or polypeptide described herein. Such compositions can further comprise a carrier. The carrier can be a conventional organic or inorganic carrier. Examples of carriers include water, buffer solution, alcohol, propylene glycol, macrogol, sesame oil, corn oil, and the like.

Isolation of Polypeptides According to the Present Invention

The polypeptides of the present invention can be purified to at least about 80% purity, to at least about 90% purity, to at least about 95% purity, or even greater than 95% purity with respect to contaminating macromolecules, particularly other polypeptides and polynucleotides, and free of infectious and pyrogenic agents. The polypeptides of the present invention can also be purified to a pharmaceutically pure state, which is greater than 99.9% pure. In certain preparations, a purified polypeptide is substantially free of other polypeptides, particularly other polypeptides of animal origin.

Fractionation and/or conventional purification methods can be used to obtain preparations of polypeptides according to the present invention purified from natural sources, and recombinant polypeptides according to the present invention and fusion polypeptides according to the present invention purified from recombinant host cells. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of polypeptides by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Selection of a particular method for polypeptide isolation and purification is a matter of routine design and is determined in part by the properties of the chosen support. See, for example, Affinity Chromatography: Principles & Methods (Pharmacia LKB Biotechnology 1988), and Doonan, polypeptide Purification Protocols (The Humana Press 1996).

Additional variations in the isolation and purification of polypeptides according to the present invention can be devised by those of skill in the art. For example, specific antibodies recognising polypeptides according to the present invention and fragments thereof, obtained as described below, can be used to isolate large quantities of polypeptide by immunoaffinity purification.

The polypeptides of the present invention can also be isolated by exploitation of particular properties. For example, immobilized metal ion adsorption (IMAC) chromatography can be used to purify histidine-rich polypeptides, including those comprising polyhistidine tags. Briefly, a gel is first charged with divalent metal ions to form a chelate (Sulkowski, Trends in Biochem. 3:1 (1985)). Histidine-rich polypeptides will be adsorbed to this matrix with differing affinities, depending upon the metal ion used, and will be eluted by competitive elution, lowering the pH, or use of strong chelating agents. Other methods of purification include purification of glycosylated polypeptides by lectin affinity chromatography and ion exchange chromatography (M. Deutscher, (ed.), Meth. Enzymol. 182:529 (1990)). Within additional embodiments of the invention, a fusion of the polypeptide of interest and an affinity tag (e.g., maltose-binding polypeptide, an immunoglobulin domain) may be constructed to facilitate purification.

Polypeptides and fragments thereof according to the present invention may also be prepared through chemical synthesis, as described above. Polypeptides according to the present invention may be monomers or multimers; glycosylated or non-glycosylated; pegylated or non-pegylated; and may or may not include an initial methionine amino acid residue.

Production of Antibodies Specific for Polypeptides According to the Present Invention Antibodies to an ice-binding polypeptide according to the present invention, or a fragment thereof, can be obtained, for example, by using as an antigen the product produced from an expression vector comprising a gene according to the present invention in a suitable host organism, or by using a polypeptide according to the present invention isolated from a natural source or synthesised using any conventional solid phase synthesis strategy. Particularly useful antibodies "bind specifically" with a polypeptide according to the present invention. Antibodies are considered to be specifically binding if the antibodies exhibit at least one of the following two properties: (1) antibodies bind to a polypeptide according to the present invention with a threshold level of binding activity, and (2) antibodies do not significantly cross-react with polypeptides which are related to a polypeptide according to the present invention as defined herein below.

With regard to the first characteristic, antibodies specifically bind if they bind to a polypeptide, peptide or epitope with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, Ann. NY Acad. Sci. 51:660 (1949)). With regard to the second characteristic, antibodies do not significantly cross-react with related polypeptide molecules, for example, if they detect polypeptides according to the present invention, but do not detect known polypeptides applied in similar or identical amounts in a standard Western blot analysis.

Antibodies can be produced using antigenic epitope-bearing peptides or polypeptides according to the present invention. Antigenic epitope-bearing peptides and polypeptides of the present invention preferably contain a sequence of at least four, or between 15 to about 30 amino acids contained within any of SEQ ID NOs:5 to 12. However, peptides or polypeptides comprising a larger portion of an amino acid sequence of the invention, containing from 30 to 50 amino acids, or any length up to and including the entire amino acid sequence of a polypeptide according to the invention, also are useful for inducing antibodies that bind with polypeptides according to the present invention. It is desirable that the amino acid sequence of the epitope-bearing peptide is selected to provide substantial solubility in aqueous solvents (i.e., the sequence includes relatively hydrophilic residues, while hydrophobic residues are preferably avoided). Moreover, amino acid sequences containing proline residues may be also be desirable for antibody production.

As an illustration, potential antigenic sites in polypeptides according to the present invention can be identified using the Jameson-Wolf method, Jameson and Wolf, CABIOS 4:181, (1988), as implemented by the PROTEAN program (version 3.14) of LASERGENE (DNASTAR; Madison, Wis.). Default parameters were used in this analysis.

The Jameson-Wolf method predicts potential antigenic determinants by combining six major subroutines for polypeptide structural prediction. Briefly, the Hopp-Woods method, Hopp et al., Proc. Nat'l Acad. Sci. USA 78:3824 (1981), was first used to identify amino acid sequences representing areas of greatest local hydrophilicity (parameter: seven residues averaged). In the second step, Emini's method, Emini et al., J. Virology 55:836 (1985), was used to calculate surface probabilities (parameter: surface decision threshold (0.6)=1). Third, the Karplus-Schultz method, Karplus and Schultz, Naturwissenschaften 72:212 (1985), was used to predict backbone chain flexibility (parameter: flexibility threshold (0.2)=1). In the fourth and fifth steps of the analysis, secondary structure predictions were applied to the data using the methods of Chou-Fasman, Chou, "Prediction of polypeptide Structural Classes from Amino Acid Composition," in Prediction of polypeptide Structure and the Principles of polypeptide Conformation, Fasman (ed.), pages 549 586 (Plenum Press 1990), and Garnier-Robson, Gamier et al., J. Mol. Biol. 120:97 (1978) (Chou-Fasman parameters: conformation table=64 polypeptides; .alpha. region threshold=103; .beta. region threshold=105; Garnier-Robson parameters: .alpha. and .beta. decision constants=0). In the sixth subroutine, flexibility parameters and hydropathy/solvent accessibility factors were combined to determine a surface contour value, designated as the "antigenic index." Finally, a peak broadening function was applied to the antigenic index, which broadens major surface peaks by adding 20, 40, 60, or 80% of the respective peak value to account for additional free energy derived from the mobility of surface regions relative to interior regions. This calculation was not applied, however, to any major peak that resides in a helical region, since helical regions tend to be less flexible.

Polyclonal antibodies to recombinant polypeptide or to isolated from natural sources can be prepared using methods well-known to those of skill in the art. See, for example, Green et al., "Production of Polyclonal Antisera," in Immunochemical Protocols (Manson, ed.), pages 1 to 5 (Humana Press 1992), and Williams et al., "Expression of foreign polypeptides in E. coli using plasmid vectors and purification of specific polyclonal antibodies," in DNA Cloning 2: Expression Systems, 2nd Edition, Glover et al. (eds.), page 15 (Oxford University Press 1995). The immunogenicity of a polypeptide can be increased through the use of an adjuvant, such as alum (aluminum hydroxide) or Freund's complete or incomplete adjuvant. Polypeptides useful for immunization also include fusion polypeptides, such as fusions of or a portion thereof with an immunoglobulin polypeptide or with maltose binding polypeptide. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immunization.

Although polyclonal antibodies are typically raised in animals such as horses, cows, dogs, chicken, rats, mice, rabbits, guinea pigs, goats, or sheep, an antibody specific for a polypeptides according to the present invention may also be derived from a subhuman primate antibody. General techniques for raising diagnostically and therapeutically useful antibodies in baboons may be found, for example, in Goldenberg et al., international patent publication No. WO 91/11465, and in Losman et al., Int. J. Cancer 46:310 (1990).

Alternatively, monoclonal antibodies specific for a polypeptides according to the present invention can be generated. Rodent monoclonal antibodies to specific antigens may be obtained by methods known to those skilled in the art (see, for example, Kohler et al., Nature 256:495 (1975), Coligan et al. (eds.), Current Protocols in Immunology, Vol. 1, pages 2.5.1 2.6.7 (John Wiley & Sons 1991) ["Coligan"], Picksley et al., "Production of monoclonal antibodies against polypeptides expressed in E. coli," in DNA Cloning 2: Expression Systems, 2nd Edition, Glover et al. (eds.), page 93 (Oxford University Press 1995)).

Briefly, monoclonal antibodies can be obtained by injecting mice with a composition comprising a gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an antibody specific for polypeptides according to the present invention of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., Nature Genet. 7:13 (1994), Lonberg et al., Nature 368:856 (1994), and Taylor et al., Int. Immun. 6:579 (1994).

Monoclonal antibodies can be isolated and purified from hybridoma cultures by a variety of well-established techniques. Such isolation techniques include affinity chromatography with polypeptide-A Sepharose, size-exclusion chromatography, and ion-exchange chromatography (see, for example, Coligan at pages 2.7.1 2.7.12 and pages 2.9.1 2.9.3; Baines et al., "Purification of Immunoglobulin G (IgG)," in Methods in Molecular Biology, Vol. 10, pages 79 104 (The Humana Press, Inc. 1992)).

For particular uses, it may be desirable to prepare fragments of antibodies specific for polypeptides according to the present invention. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an F$_c$ fragment directly. These methods are described, for example, by Goldenberg, U.S. Pat. No. 4,331,647, Nisonoff et al., Arch Biochem. Biophys. 89:230 (1960), Porter, Biochem. J. 73:119 (1959), Edelman et al. and Coligan, both in Methods in Enzymology Vol. 1, (Academic Press 1967).

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., Proc. Nat'l Acad. Sci. USA 69:2659 (1972). Alternatively, the variable chains can be linked by an intermolecular disulfide bond or cross-linked by chemicals such as glutaraldehyde (see, for example, Sandhu, Crit. Rev. Biotech. 12:437 (1992)).

The Fv fragments may comprise $V_H$ and $V_L$ chains, which are connected by a peptide linker. These single-chain antigen binding polypeptides (scFv) are prepared by constructing a structural gene comprising DNA sequences encoding the $V_H$ and $V_L$ domains which are connected by an oligonucleotide. The structural gene is inserted into an expression vector, which is subsequently introduced into a host cell, such as E. coli. The recombinant host cells synthesize a single polypeptide chain with a linker peptide bridging the two V domains. Methods for producing scFvs are described, for example, by Whitlow et al., Methods: A Companion to Methods in Enzymology 2:97 (1991) (also see, Bird et al., Science 242:423 (1988), Ladner et al., U.S. Pat. No. 4,946,778, Pack et al., Bio/Technology 11:1271 (1993), and Sandhu, supra).

As an illustration, a scFV can be obtained by exposing lymphocytes to polypeptide in vitro, and selecting antibody display libraries in phage or similar vectors (for instance, through use of immobilized or labeled polypeptide or peptide). Genes encoding polypeptides having potential polypeptide binding domains can be obtained by screening random peptide libraries displayed on phage (phage display) or on bacteria, such as E. coli. Nucleotide sequences encoding the polypeptides can be obtained in a number of ways, such as through random mutagenesis and random polynucleotide synthesis. These random peptide display libraries can be used to screen for peptides, which interact with a known target which can be a polypeptide or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., Phage Display of Peptides and polypeptides (Academic Press, Inc. 1996)) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the sequences disclosed herein to identify polypeptides which bind to.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., Methods: A Companion to Methods in Enzymology 2:106 (1991), Courtenay-Luck, "Genetic Manipulation of Monoclonal Antibodies," in Monoclonal Antibodies: Production, Engineering and Clinical Application, Ritter et al. (eds.), page 166 (Cambridge University Press 1995), and Ward et al., "Genetic Manipulation and Expression of Antibodies," in Monoclonal Antibodies: Principles and Applications, Birch et al., (eds.), page 137 (Wiley-Liss, Inc. 1995)).

Alternatively, an antibody specific for a polypeptide according to the present invention may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., Proc. Nat'l Acad. Sci. USA 86:3833 (1989). Techniques for producing humanized monoclonal antibodies are described, for example, by Jones et al., Nature 321:522 (1986), Carter et al., Proc. Nat'l Acad. Sci. USA 89:4285 (1992), Sandhu, Crit. Rev. Biotech. 12:437 (1992), Singer et al., J. Immun. 150: 2844 (1993), Sudhir (ed.), Antibody Engineering Protocols (Humana Press, Inc. 1995), Kelley, "Engineering Therapeutic Antibodies," in polypeptide Engineering: Principles and Practice, Cleland et al. (eds.), pages 399 434 (John Wiley & Sons, Inc. 1996), and by Queen et al., U.S. Pat. No. 5,693,762 (1997).

Polyclonal anti-idiotype antibodies can be prepared by immunizing animals with antibodies or antibody fragments specific for a polypeptide according to the present invention, using standard techniques. See, for example, Green et al., "Production of Polyclonal Antisera," in Methods In Molecular Biology: Immunochemical Protocols, Manson (ed.), pages 1 12 (Humana Press 1992). Also, see Coligan at pages 241 to 247. Alternatively, monoclonal anti-idiotype antibodies can be prepared using antibodies or antibody fragments specific for a polypeptide according to the present invention as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, J. Gen. Virol. 77:1875 (1996).

Host Cells and uses Related Thereto

The host cells which may comprise a polypeptide according to the present invention can be exemplified e.g. by animal cells, mammalian host cells, insect cells, fish cells, fungal cells, yeast cells, bacterial cells and plant cells.

The natural or synthetic nucleic fragments coding for an anti-freeze polypeptide according to the invention will be incorporated in polynucleotide constructs capable of introduction to and/or expression in the ultimate target expressing cell. Usually, the polynucleotide constructs will be suitable for replication in a unicellular or multicellular host, such as yeast or bacteria, but may also be intended for introduction and integration within the genome of cultured mammalian or other eukaryotic cell lines, in particular, plants. polynucleotide constructs prepared for introduction into bacteria or yeast will include a replication system recognized by the host, the polynucleotide fragment encoding the desired anti-freeze polypeptide product, transcriptional and translational initiation regulatory sequences joined to the 5'-end of the anti-freeze polypeptide encoding polynucleotide sequence, and transcriptional and translational termination regulatory sequences joined to the 3'-end of the sequence. The transcriptional regulatory sequences will include a heterologous promoter which is recognized by the host. Conveniently, available expression vectors which include the replication system and transcriptional and translational regulatory sequences together with an insertion site for the anti-freeze polypeptide encoding sequence may be employed.

The gene will include any polynucleotide segment which contains a coding sequence for anti-freeze polypeptide. Normally, the gene will include the coding sequence plus the upstream and downstream associated sequences, particularly any enhancer, promoter, ribosome binding site or transcription initiation markers. Downstream segments may also be important for message polyadenylation and processing, and thus are also contemplated in the usual instance.

The introduction of genes into cells or groups of cells for expression is another method for generally introducing the polypeptides into the sample of interest. The end product of the transformation is also included as the product of this invention, and the term "transformed cell" will include the actual cell transformed, and all progeny of that cell. In the typical case, the final organism will contain cells, each of which will contain the gene. Standard transformation procedures exist for bacteria (Maniatis), fungi (Sherman et al. (1986) in Laboratory Course Manual for Methods in Yeast Genetics CSH), plants (van den Elzen et al. (1985) Plant Mol. Biol., 5:149-154) and animals (Hanahan, (1988) Ann. Rev. Genetics, 22:479-519).

Yeast and Fungus Host Cells Non-limiting examples of yeast host cells suitable for use in accordance with the present invention include yeasts from the Family of Saccharomycetaceae, including members of the genera *Saccharomyces* and *Candida*. Preferred examples include, but are not limited to, *Saccharomyces fragilis, Saccharomyces cervisae, Saccharomyces lactis, Candida pseudotropicalis*.

Bacteria

Bacterial cells are useful as host cells according to the present invention for the production of the polypeptides according to the present invention.

Bacteria, e.g. *Lactobacillus* as well as many yeasts and molds, have been used for thousands of years in the preparation of fermented foods, such as e.g. cheese, pickles, soy sauce, sauerkraut, vinegar, wine and yoghurt.

Anti-freeze polypeptides according to the present invention are useful in maintaining the viability of the microorganisms used to prepare such foods, as well as in the preparation of prebiotic and probiotic edible compositions, including animal feed compositions and foods for human consumption.

Examples of preferred bacteria relevant to the present invention and suitable as host cells in accordance with the present invention are, for example, *Escherichia coli, Streptococcus cremoris, Streptococcus lactis, Streptococcus thermophilus, Leuconostoc citrovorum, Leuconostoc mesenteroides, Lactobacillus acidophilus, Lactobacillus lactis, Lactobacillus bulgaricus, Bifidobacterium bifidum, Bifidobacterium breve, Lactobacillus delbrueckii* ssp. *bulgaricus, Streptococcus thermophilus, Lactobacillus acidophilus, Bifidobacteria, Lactobacillus casei, Lactobacillus rhamnosus, Lactobacillus. casei*, and *Bifidobacterium longum*.

Bacteria can also be used as substitutes for pesticides in a biological pest control programme. The invention in one embodiment is particularly well suited for such applications and provide recombinant microrganisms harbouring polynucleotides according to the invention and producing polypeptides according to the invention capable of being used as environmentally friendly, biological pesticides. One example is *Bacillus thuringiensis*, a Gram-positive, soil dwelling bacterium.

Further non-limiting examples of bacterial host cells suitable for use in accordance with the present invention include Gram-positive bacteria and Gram-negative bacteria. Preferred bacterial cells can also be selected from the groups consisting of Gram-positive cocci, Gram-positive bacilli, Gram-negative cocci and Gram-negative bacilli. Examples of bacterial host cells suitable for use in accordance with the present invention include, but is not limited to, bacteria selected from the following genera: *Acaricomes, Acetitomaculum, Acetivibrio, Acetobacter, Acetobacterium, Acetobacteroides, Acetohalobium, Acetomicrobium, Acetomonas, Acetonema, Achromobacter, Acidaminobacter, Acidaminococcus, Acidicaldus, Acidimicrobium, Acidiphilium, Acidithiobacillus, Acidobacterium, Acidocaldus, Acidocella, Acidomonas, Acidovorax, Acinetobacter, Acrocarpospora, Actinacidiphilus, Actinoacidiphilus, Actinoalloteichus, Actinobacillus, Actinobaculum, Actinobifida, Actinobispora, Actinocatenispora, Actinocorallia, Actinokineospora, Actinomadura, Actinomyces, Actinoplanes, Actinopolyspora, Actinopycnidium, Actinospica, Actinosporangium, Actinostreptospora, Actinosynnema, Actinotalea, Actinotelluria, Adhaeribacter, Aequorivita, Aerobacter, Aerococcus, Aerococcus*-like Organism, *Aeromicrobium, Aeromonas, Aestuariibacter, Afipia, Agarbacterium, Aggregatibacter, Agitococcus, Agreia, Agrobacterium, Agrococcus, Agromonas, Agromyces, Ahrensia, Albidovulum, Alcaligenes, Alcanivorax, Algibacter, Algicola, Algoriphagus, Alicycliphilus, Alicyclobacillus, Alishewanella, Alistipes, Alkalibacillus, Alkalibacter, Alkalibacterium, Alkalilimnicola, Alkalispirillum, Alkanindiges, Allisonella, Allobaculum, Allochromatium, Allofustis, Alteromonas, Alysiella, Aminobacter, Aminobacterium, Aminomonas, Ammonifex, Ammoniphilus, Amoebo-* bacter, Amorphosporangium, Amphibacillus, Ampullariella, Amycolata, Amycolatopsis, Anaeroarcus, Anaerobacter, Anaerobaculum, Anaerobiospirillum, Anaerobranca, Anaerocellum, Anaerococcus, Anaerofilum, Anaerofustis, Anaerolinea, Anaeromusa, Anaerophaga, Anaeroplasma, Anaerosinus, Anaerostipes, Anaerotruncus, Anaerovibrio, Anaerovirgula, Anaerovorax, Ancalomicrobium, Ancylobacter, Aneurinibacillus, Angiococcus, Angulomicrobium, Anoxybacillus, Antarctobacter, Aquabacter, Aquabacterium, Aquamicrobium, Aquaspirillum, Aquicella, Aquifex, Aquiflexum, Aquimarina, Aquimonas, Arcanobacterium, Archangium, Arcicella, Arcobacter, Arenibacter, Arhodomonas, Arizona, Arsenicicoccus, Arsenophonus, Arthrobacter, Asanoa, Asiosporangium, Asticcacaulis, Astrosporangium, Atopobium, Atopococcus, Atopostipes, Aurantimonas, Aureobacterium, Avibacterium, Axonoporis, Azoarcus, Azohydromonas, Azomonas, Azorhizobium, Azorhizophilus, Azospira, Azospirillum, Azotobacter Bacillus, Bacteriovorax, Bacterium, Bacteroides, Balnearium, Balneatrix, Barnesiella, Bartonella, Bdellovibrio, Beggiatoa, Beijerinckia, Belliella, Belnapia, Beneckea, Bergeriella, Betabacterium, Beutenbergia, Bifidobacterium, Bilophila, Blastobacter, Blastochloris, Blastococcus, Blastomonas, Blastopirellula, Bogoriella, Bordetella, Borrelia, Bosea, Brachybacterium, Brachymonas, Brachyspira, Brackiella, Bradyrhizobium, Branhamella, Brenneria, Brevibacillus, Brevibacterium, Brevigemma, Brevundimonas, Brochothrix, Brucella, Bryantella, Budvicia, Bulleidia, Burkholderia, Buttiauxella, Butyribacterium, Butyrivibrio, Byssovorax, Caenibacterium, Caldanaerobacter, Caldicellulosiruptor, Caldilinea, Caldithrix, Caldocellum, Caloramator, Caloranaerobacter, Caminibacillus, Caminibacter, Caminicella, Campylobacter, Capnocytophaga, Carbophilus, Carboxydocella, Carboxydothermus, Cardiobacterium, Carnobacterium, Caryophanon, Caseobacter, Castellaniella, Cat Scratch Disease Bacillus, Catellatospora, Catellibacterium, Catellicoccus, Catenibacterium, Catenococcus, Catenulispora, Catenuloplanes, Catenulospora, Caulobacter, Cdc Enteric Group 36/37, Cdc Group Vd, Cedecea, Cellulomonas, Cellulophaga, Cellulosimicrobium, Cellvibrio, Centipeda, Cerasibacillus, Chainia, Chelatobacter, Chelatococcus, Chitinibacter, Chitinimonas, Chitinophaga, Chlorobaculum, Chlorobium, Chloroflexus, Chondrococcus, Chondromyces, Chromatium, Chromobacterium, Chromohalobacter, Chryseobacterium, Chryseomonas, Chrysiogenes, Citreicella, Citricoccus, Citrobacter, Clavibacter, Clavisporangium, Clo Group Type 2, Clostridium, Cobetia, Cohnella, Collimonas, Collinsella, Colwellia, Comamonas, Conchiformibius, Conexibacter, Coprothermobacter, Corallococcus, Coriobacterium, Corynebacterium, Couchioplanes, Crossiella, Cryobacterium, Cryptanaerobacter, Cryptobacterium, Cryptosporangium, Cupriavidus, Curtobacterium, Curvibacter, Cyclobacterium, Cystobacter, Cytophaga, Dactylosporangium, Dechloromonas, Dechlorosoma, Deefgea, Deferribacter, Defluvibacter, Dehalobacter, Dehalospirillum, Deinococcus, Deleya, Delftia, Demetria, Dendrosporobacter, Denitrovibrio, Dermabacter, Dermacoccus, Dermatophilus, Derxia, Desemzia, Desulfacinum, Desulfarculus, Desulfatibacillum, Desulfitobacterium, Desulfoarculus, Desulfobacca, Desulfobacter, Desulfobacterium, Desulfobacula, Desulfobulbus, Desulfocapsa, Desulfocella, Desulfococcus, Desulfofaba, Desulfofrigus, Desulfofustis, Desulfohalobium, Desulfomicrobium, Desulfomonile, Desulfonatronovibrio, Desulfonatronum, Desulfonauticus, Desulfonema, Desulfonispora, Desulfopila, Desulforegula, Desulforhabdus, Desulforhopalus, Desulfosarcina, Desulfospira, Desulfosporosinus, Desulfotalea, Desulfothermus, Desulfotignum, Desulfotomaculum, Desulfovermiculus, Desulfovibrio, Desulfovirga, Desulfovirgula, Desulfurella, Desulfurobacterium, Desulfuromonas, Desulfuromusa, Dethiosulfovibrio, Devosia, Dialister, Diaphorobacter, Dichelobacter, Dichotomicrobium, Dickeya, Dictyoglomus, Dietzia, Diplococcus, Dokdoa, Dokdonella, Dokdonia, Dolosicoccus, Donghaeana, Dorea, Duganella, Dyadobacter, Dyella, Eberthella, Ectothiorhodospira, Edwardsiella, Eggerthella, Eikenella, Elizabethkingia, Elytrosporangium, Empedobacter, Enhygromyxa, Ensifer, Enterobacter, Enterococcus, Enterovibrio, Epilithonimonas, Eremococcus, Erwinia, Erysipelothrix, Erythrobacter, Erythromicrobium, Escherichia, Ethanoligenens, Eubacterium, Ewingella, Excellospora, Exiguobacterium, Faecalibacterium, Faenia, Falcivibrio, Fastidiosipila, Ferribacter, Ferrimonas, Ferrobacillus, Fervidobacterium, Filibacter, Filifactor, Filobacillus, Filomicrobium, Finegoldia, Flammeovirga, Flavimonas, Flavobacterium, Flectobacillus, Flexibacter, Flexistipes, Flexithrix, Fluoribacter, Fluviicola, Formivibrio, Francisella, Frankia, Frateuria, Friedmanniella, Frigoribacterium, Fulvimarina, Fulvimonas, Fusibacter, Fusobacterium, Gaetbulibacter, Gaffkya, Gallibacterium, Gallicola, Garciella, Gardnerella, Gariaella, Gelidibacter, Gemella, Gemmata, Gemmatimonas, Gemmobacter, Geoalkalibacter, Geobacillus, Geobacter, Geodermatophilus, Geopsychrobacter, Georgenia, Geosinus, Geospirillum, Geothermobacter, Geothrix, Geovibrio, Giesbergeria, Gillisia, Glaciecola, Globicatella, Gluconacetobacter, Gluconoacetobacter, Gluconobacter, Glycomyces, Goodfellowia, Gordona, Gordonia, Gracilibacillus, Gracilibacter, Granulicatella, Granulobacter, Grimontia, Group Ii D, Guggenheimella, Gulosibacter, Haemophilus, Hafnia, Hahella, Halanaerobacter, Halanaerobium, Haliangium, Haliscomenobacter, Haloactinomyces, Haloanaerobacter, Haloanaerobium, Halobacillus, Halobacteroides, Halocella, Halochromatium, Halococcus, Halolactibacillus, Halomonas, Halonatronum, Halorhodospira, Halothermothrix, Halothiobacillus, Helcococcus, Helicobacter, Heliobacillus, Heliobacterium, Heliophilum, Heliorestis, Herbaspirillum, Herbidospora, Herminiimonas, Herpetosiphon, Hespellia, Hippea, Hirschia, Hoeflea, Holdemania, Holophaga, Hongiella, Hordeomyces, Hyalangium, Hydrocarboniphaga, Hydrogenivirga, Hydrogenobacter, Hydrogenobaculum, Hydrogenomonas, Hydrogenophaga, Hydrogenophilus, Hydrogenothermophilus, Hydrogenothermus, Hydrogenovibrio, Hylemonella, Hymenobacter, Hyphomicrobium, Hyphomonas, Idiomarina, Ignatzschineria, Ignavigranum, Ilyobacter, Inflabilis, Inquilinus, Intrasporangium, Iodobacter, Isobaculum, Isochromatium, Isoptericola, Jahnia, Janibacter, Jannaschia, Janthinobacterium, Jensenia, Jeotgalibacillus, Jeotgalicoccus, Jiangella, Jonesia, Kangiella, Kerstersia, Kibdellosporangium, Kibdelosporangium, Kineococcus, Kineosphaera, Kineosporia, Kingella, Kitasatoa, Kitasatospora, Kitasatosporia, Klebsiella, Kluyvera, Knoellia, Kocuria, Kofleria, Koserella, Kozakia, Kribbella, Ktedobacter, Ktedonobacter, Kurthia, Kutzneria, Kytococcus, Labrys, Laceyella, Lachnobacterium, Lachnospira, Lactobacillus, Lactobacterium, Lactococcus, Lactonifactor, Lamprocystis, Lampropedia, Laribacter, Lautropia, Leadbetterella, Lebetimonas, Lechevalieria, Leclercia, Leeuwenhoekiella, Legionella, Leifsonia, Leisingera, Leminorella, Lentibacillus, Lentzea, Leptospirillum, Leptothrix, Leptotrichia, Leucobacter, Leuconostoc, Leucothrix, Levilinea, Levinea, Limnobacter, List, Listeria, Listonella, Loktanella, Lonepinella, Longispora, Lophomonas, Luteibacter, Luteimonas, Luteococcus, Lysobacter, Macrococcus, Macromonas, Magnetospirillum, Mahella, Malikia, Malonomonas, Manjusharmella, Mannheimia, Maribacter, Maricaulis, Marichromatium, Marinibacillus, Marinilabilia, Marinilactibacillus, Marinithermus, Marinitoga, Marinobacter, Marinobacterium, Marinococcus, Marinomonas, Marinospirillum, Marinovum, Marmoricola, Massilia, Mechercharimyces, Mechercharomyces, Megamonas, Megasphaera, Meiothermus, Melittangium, Mesonia, Mesophilobacter, Mesorhizobium, Methanomonas, Methylobacillus, Methylobacter, Methylobacterium, Methylocapsa, Methylocella, Methylocystis, Methylomicrobium, Methylomonas, Methylophaga, Methylophilus, Methylopila, Methylosarcina, Methylotenera, Methylovorus, Microbacterium, Microbispora, Microbulbifer, Microcella, Micrococcus, Microcyclus, Microechinospora, Microellobosporia, Microlunatus, Micromonas, Micromonospora, Micropolyspora, Micropruina, Microscilla, Microstreptospora, Microtetraspora, Microvirgula, Millisia, Mima, Mitsuokella, Mobiluncus, Modestobacter, Moellerella, Mogibacterium, Moorella, Moraxella, Moraxella (Branhamella), Moraxella (Moraxella), Morganella, Moritella, Muricauda, Muricoccus, Myceligenerans, Mycetocola, Mycobacterium, Mycoplana, Myroides, Myxobacter, Myxococcus, Nakamurella, Nannocystis, Natroniella, Natronincola, Nautilia, Naxibacter, Neisseria, Nereida, Nesterenkonia, Nevskia, Nicoletella, Nih Group 12, Nitratifractor, Nitratireductor, Nitratiruptor, Nitrobacter, Nocardia, Nocardioides, Nocardiopsis, Nonomuraea, Novosphingobium, Obesumbacterium, Oceanibulbus, Oceanicaulis, Oceanicola, Oceanimonas, Oceanithermus, Oceanobacillus, Oceanobacter, Oceanomonas, Oceanospirillum, Ochrobactrum, Octadecabacter, Odontomyces, Oenococcus, Oerskovia, Oleiphilus, Oleispira, Oligella, Oligotropha, Olsenella, Opitutus, Orenia, Oribacterium, Ornithinicoccus, Ornithinimicrobium, Ornithobacterium, Oryzihumus, Ottowia, Oxalicibacterium, Oxalobacter, Oxalophagus, Oxobacter, Paenibacillus, Paludibacter, Pandoraea, Pannonibacter, Pantoea, Papillibacter, Parabacteroides, Paracoccus, Paracolobactrum, Paralactobacillus, Paraliobacillus, Parascardovia, Parasporobacterium, Parvibaculum, Parvimonas, Parvopolyspora, Pasteurella, Pasteuria, Patulibacter, Paucibacter, Paucimonas, Paucisalibacillus, Pectinatus, Pectobacterium, Pediococcus, Pedobacter, Pelczaria, Pelobacter, Pelodictyon, Pelomonas, Pelosinus, Pelospora, Pelotomaculum, Peptococcus, Peptoniphilus, Peptostreptococcus, Peredibacter, Persephonella, Persicivirga, Persicobacter, Petrimonas, Petrobacter, Petrotoga, Phaeobacter, Phaeospirillum, Phascolarctobacterium, Phenylobacterium, Phocoenobacter, Photobacterium, Photorhabdus, Phyllobacterium, Phytomonas, Pigmentiphaga, Pilimelia, Pimelobacter, Pirellula, Planctomyces, Planifilum, Planobispora, Planococcus, Planomicrobium, Planomonospora, Planosporangium, Planotetraspora, Plantibacter, Pleomorphomonas, Plesiocystis, Plesiomonas, Podangium, Polaribacter, Polaromonas, Polyangium, Polymorphospora, Pontibacillus, Porphyrobacter, Porphyromonas, Pragia, Prauserella, Prevotella, Proactinomyces, Promicromonospora, Promyxobacterium, Propionibacterium, Propionicimonas, Propioniferax, Propionigenium, Propionimicrobium, Propionispira, Propionispora, Propionivibrio, Prosthecobacter, Prosthecochloris, Prosthecomicrobium, Protaminobacter, polypeptideiphilum, Proteus, Providencia, Pseudaminobacter, Pseudoalteromonas, Pseudoamycolata, Pseudobutyrivibrio, Pseudoclavibacter, Pseudomonas, Pseudonocardia, Pseudoramibacter, Pseudorhodobacter, Pseudospirillum, Pseudoxanthomonas, Psychrobacter, Psychroflexus, Psychromonas, Psychroserpens, Pullulanibacillus, Pusillimonas, Pyxicoccus, Quadrisphaera Rahnella, Ralstonia, Ramibacterium, Ramlibacter, Raoultella, Rarobacter, Rathayibacter, Reinekea, Renibacterium, Renobacter, Rhabdochromatium, Rheinheimera, Rhizobacter, Rhizobium, Rhizomonas, Rhodanobacter, Rhodobacter, Rhodobium, Rhodoblastus, Rhodocista, Rhodococcus, Rhodocyclus, Rhodoferax, Rhodomicrobium, Rhodonellum, Rhodopila, Rhodopirellula, Rhodoplanes, Rhodopseudomonas, Rhodospirillum, Rhodothalassium, Rhodothermus, Rhodovibrio, Rhodovulum, Riemerella, Rikenella, Robiginitalea, Roseateles, Roseburia, Roseiflexus, Roseinatronobacter, Roseobacter, Roseococcus, Roseospira, Roseospirillum, Roseovarius, Rothia, Rubritepida, Rubrivivax, Rubrobacter, Ruegeria, Ruminobacter, Ruminococcus, Runella, Saccharibacter, Saccharococcus, Saccharomonospora, Saccharophagus, Saccharopolyspora, Saccharothrix, Sagittula, Salana, Salegentibacter, Salinibacter, Salinibacterium, Salinicoccus, Salinimonas, Salinispora, Salinivibrio, Salinospora, Salipiger, Salmonella, Samsonia, Sanguibacter, Saprospira, Sarcina, Sarraceniospora, Scardovia, Schlegelella, Schwartzia, Sebekia, Sedimentibacter, Sedimenticola, Segniliparus, Seinonella, Sejongia, Selenomonas, Seliberia, Serinicoccus, Serratia, Shewanella, Shigella, Shinella, Shuttleworthia, Silanimonas, Silvimonas, Simonsiella, Simplicispira, Simsoniella, Sinococcus, Sinorhizobium, Skermania, Slackia, Smaragdicoccus, Smithella, Sodalis, Soehngenia, Sorangium, Sphaerobacter, Sphaerophorus, Sphaerosporangium, Sphaerotilus, Sphingobacterium, Sphingobium, Sphingomonas, Sphingopyxis, Sphingosinicella, Spirilliplanes, Spirillospora, Spirillum, Spirochaeta, Spirosoma, Sporacetigenium, Sporanaerobacter, Sporichthya, Sporobacter, Sporobacterium, Sporocytophaga, Sporohalobacter, Sporolactobacillus, Sporomusa, Sporosarcina, Sporotalea, Sporotomaculum, Stackebrandtia, Staleya, Staphylococcus, Stappia, Starkeya, Stella, Stenotrophomonas, Sterolibacterium, Stigmatella, Streptacidiphilus, Streptimonospora, Streptoallomorpha, Streptoalloteichus, Streptobacillus, Streptobacterium, Streptococcus, Streptomonospora, Streptomyces, Streptomycetoides, Streptomycoides, Streptosporangium, Streptoverticillium, Subdoligranulum, Subtercola, Succiniclasticum, Succinimonas, Succinispira, Succinivibrio, Sulfitobacter, Sulfobacillus, Sulfuricurvum, Sulfurihydrogenibium, Sulfurimonas, Sulfurospirillum, Sutterella, Suttonella, Syntrophobacter, Syntrophobotulus, Syntrophococcus, Syntrophomonas, Syntrophothermus, Syntrophus, Tatlockia, Tatumella, Taxeobacter, Taylorella, Teichococcus, Telluria, Tenacibaculum, Tepidanaerobacter, Tepidibacter, Tepidimicrobium, Tepidimonas, Tepidiphilus, Terasakiella, Terrabacter, Terracoccus, Terribacillus, Terrimonas, Tessaracoccus, Tetragenococcus, Tetrasphaera, Tetrathiobacter, Thalassobacillus, Thalassobacter, Thalassobius, Thalassolituus, Thalassomonas, Thalassospira, Thauera, Thaxtera, Thermacetogenium, Thermaerobacter, Thermanaeromonas, Thermanaerovibrio, Thermicanus, Thermincola, Thermithiobacillus, Thermoactinomyces, Thermoanaerobacter, Thermoanaerobacterium, Thermoanaerobium, Thermoanaerolinea, Thermobacterium, Thermobacteroides, Thermobifida, Thermobispora, Thermobrachium, Thermochromatium, Thermocrinis, Thermocrispum, Thermodesulfatator, Thermodesulfobacterium, Thermodesulfobium, Thermodesulforhabdus, Thermodesulfovibrio, Thermoflavimicrobium, Thermohydrogenium, Thermolithobacter, Thermomicrobium, Thermomonas, Thermomonospora, Thermonema, Thermonospora, Thermopolyspora, Thermosediminibacter, Thermosiculum, Thermosinus, Thermosipho, Thermosyntropha, Thermotoga, Thermovenabulum, Thermovibrio, Thermovirga, Thermus, Thetysia, Thialkalimicrobium, Thialkalivibrio, Thioalkalimicrobium, Thioalkalivibrio, Thiobaca, Thiobacillus, Thiobacter, Thiocapsa, Thiococcus, Thiocystis

*Thiodictyon, Thiohalocapsa, Thiolamprovum, Thiomicrospira, Thiomonas, Thiopedia, Thioreductor, Thiorhodoccocus, Thiorhodococcus, Thiorhodovibrio, Thiosphaera, Thiothrix, Thorsellia, Tindallia, Tissierella, Tolumonas, Trabulsiella, Treponema, Trichococcus, Trichotomospora, Truepera, Tsukamurella, Tuberibacillus, Turicella, Turicibacter, Unclassified, Ureibacillus, Uruburuella, Vagococcus, Varibaculum, Variovorax, Veillonella, Verrucomicrobium, Verrucosispora, Vibrio, Victivallis, Virgibacillus, Virgisporangium, Vitreoscilla, Vogesella, Volcaniella, Volucribacter, Vulcanibacillus, Vulcanithermus, Waksmania, Wautersia, Weeksella, Weissella, Williamsia, Wolinella, Woodsholea, Xanthobacter, Xanthomonas, Xenophilus, Xenorhabdus, Xylanibacter, Xylanibacterium, Xylanimicrobium, Xylanimonas, Xylella, Xylophilus, Yania, Yersinia, Yokenella, Zavarzinia, Zimmermannella, Zobellia, Zoogloea, Zooshikella, Zymobacter, Zymobacterium, Zymomonas* and *Zymophilus*.

Plants Comprising Polypeptides According to the Present Invention

The use of the polynucleotides and polypeptides according to the present invention in plant host cells and other transgenic organisms can prevent the loss of valuable crops when the climatic conditions are not optimal for the production of the crops. In particular, the present invention provides novel and innovative, transgenic plants and crops capable of sustaining climatic conditions which cannot be withstood by state-of-the-art plants and crops. Examples of crops in the form of plant host cells according to the present invention comprising polynucleotides and producing polypeptides according to the present invention are: grapes, oilseed plants, such as canola, grains (oats, barley, rye etc.), citrus fruits, and sugar cane.

The invention is also directed to trans-genic fruits and vegetables comprising the polypeptides according to the present invention. The trans-genic fruits and vegetables comprising the polypeptides according to the present invention are capable of withstanding cooler temperatures e.g. during storage and/or transport. Examples include strawberries, blueberries, raspberries, citrus fruits, bananas, grapes, kiwis, peaches, pineapples, plums, cherries, tomatoes and mangoes.

Flowers Comprising Polypeptides According to the Present Invention

Frozen flowers comtemplated in accordance with the present invention includes e.g. tulips, roses, lilies.

Fish

Examples of fish suitable for the invention are Albacore Tuna (*Thunnus alalunga*), Arrowtooth Flounder (*Atheresthes stomias*), Atlantic Cod (*Gadus morhua*), Atlantic Cutlassfish (*Trichiurus lepturus*), Atlantic Salmon (*Salmo salar*), Atlantic Wolffish (*Anarhichas lupus*), Black Drum (*Pogonias cromis*), Black Pomfret (*Parastromateus niger*), Blackback Flounder (Sole, *Pleuronectes americanus*), Blacktip Shark (*Carcharhinus limbatus*), Catfish (*Ictalurus furcatus*), Crab, Blue (*Callinectes sapidus*), Marlin (*Makaira nigricans*), Rockfish (*Sebastes auriculatus*), Puffer (*Sphoeroides annulatus*), Scorpionfish (*Scorpaena guttata*), Sheephead (*Semicossyphus pulcher*), Rockfish (*Sebastes pinniger*), Snapper (*Lutjanus purpureus*), Catfish (*Ictalurus punctatus*), Rockfish (*Sebastes goodei, Sebastes nebulosus*), Chinook (*Oncorhynchus tshawytscha*), Chub Mackerel (*Scomberjaponicus*), Coho Salmon (Silver, Medium Red) (*Oncorhynchus kisutch*), Thresher Shark (*Alopias vulpinus*), Grouper (*Epinephelus fulva*), Cusk (*Brosme brosme*), Mahi-mahi (*Coryphaena hippurus*), Sole (*Microstomus pacificus*), Sole (*Pleuronectes vetulus*), Escolar (*Lepidocybium flavobrunneum*), Dory (*Zeus faber*), Ocean Perch (*Sebastes norvegicus*), Snapper (*Lutjanus griseus*), Sole (Flounder) (*Glyptocephalus cynoglossus*), Barracuda (*Sphyraena barracuda*), Haddock (*Melanogrammus aeglefinus*), Tuna (*Euthynnus affinis*), Snapper (*Lutjanus synagris*), Lingcod (*Ophiodon elongatus*), Milkfish (*Chanos chanos*), Tilapia (*Tilapia mossambica*), Nile Tilapia (*Tilapia nilotica*), Puffer (*Sphoeroides maculatus*), Tilefish (*Caulolatilus princeps*), Oilfish (*Ruvettus pretiosus*), Orange Roughy (*Hoplostethus atlanticus*), Barracuda (*Sphyraena argentea*), (Bonito (*Sarda chiliensis*), Cod (Alaska Cod, *Gadus macrocephalus*), Jack (*Caranx caninus*), Jack (*Selene peruviana*), Ocean Perch (*Sebastes alutus*), Mackerel (*Scomber scombrus*), Spanish (*Scomberomorus sierra*), Snapper (*Lutjanus peru*), Patagonian Toothfish (*Dissostichus eleginoides*), Sole (Flounder, *Eopsetta jordan*), Pink Salmon (Humpback) (*Oncorhynchus gorbuscha*), Pollock (*Pollachius virens*), Rockfish (*Sebastes maliger*), Trout, Rainbow (Steelhead) (*Oncorhynchus mykiss*), Drum (Redfish) (*Sciaenops ocellatus*), Porgy (*Chrysophrys auratus*), Snapper (*Lutjanus campechanus*), Rockfish (*Sebastes proriger*), Sole (Flounder, *Errexachirus*), Rockfish (*Sebastes aleutianus*), Schoolmaster (*Lutjanus apodus*), Sheepshead (*Archosargus probatocephalus*), Shark, Mako (*Isurus oxyrinchus*), Snapper (*Lutjanus vivanus*), Butterfish (*Pampus argenteus*), Rockfish (*Sebastes brevispinis*), Skipjack Tuna (*Katsuwonus pelamis*), Spinefoot (*Siganus javus*), Croaker or Corvina (*Roncador stearnsi*), Flounder (*Platichthys stellatus*), Marlin (*Tetrapturus audax*), Bass (*Morone chrysops× saxatilis*), Swordfish (*Xiphias gladius*), Carp (*Barbodes schwanefeldi*), Pollock (Alaska Pollock, *Theragra chalcogramma*), Hake (*Urophycis tenuis*), Rockfish (*Sebastes entomelas*), Flounder (*Scophthalmus aquosus*), Croaker (Yellowfish, *Pseudosciaena manchurica*), Rockfish (*Sebastes ruberrimus*), Tuna (*Thunnus albacares*), Yellowstripe Scad (*Selaroides leptolepis*), Yellowtail (*Seriola lalandel*), Flounder (*Limanda ferruginea*), Rockfish (*Sebastes flavidus*) and Snapper (*Ocyurus chrysurus*) Arctic char (*Salvelinus alpinus*), Turbot, Greenland halibut (*Reinhartdius hippoglossoides*) Halibut (*Hippoglossus hippoglossus*).

Frozen Foods and Edible Products

Recrystallisation of frozen food products, including frozen vegetables, leads to a deteriorating taste and texture of such foods. Anti-freeze polypeptides according to the present invention can be used to treat frozen foods or foods to be frozen in order to prevent re-crystallization. Examples of foods for treatment with the invention include, but is not limited to: Ice cream, frozen yoghurt, soups, puddings, sorbets, ice cream bars, frozen desserts e.g. custards, puddings etc and other liquids or semi-liquids for freezing. Frozen vegetables such as celery, potatoes, asparagus, peas, carots, beans, broccoli, sweet corn, spinach, haricots verts etc. is also encompassed by the present invention.

The polypeptides according to the present invention may also affect the formation of lactose crystals. Hence, without being bound by any specific theory, it is believed that the polypeptides according to the present invention inhibit the crystallisation and/or growth of lactose crystals. It is well known that during freezing of ice creams the content of all ingredients (including lactose) is increasingly concentrated except for the content of liquid water, which is decreasing. When the content of lactose reaches a certain level, lactose crystals start to crystallize. This crystallisation is a slow process, which takes place at −20° C. Typically, ice creams are stored at about −20° C. However, in many cases the ice creams are not stored at a stabile and constant temperature, but temperatures fluctuating around −20° C. Hence, during periods where the temperature is higher than −20° C. crystals of lactose will grow and new crystals will be formed. Consequently, the mouth feel of the ice cream will become more coarse, and most people find this mouth feel unpleasant. It has now surprisingly been found that when the polypeptides according to the present invention is added to the ice cream prior to freezing of the ice cream markedly reduces the formation of lactose crystals and markedly prevent that new crystals are formed during storage at about −20° C. Consequently, the quality of the stored ice cream product is markedly improved.

Examples of frozen edible products according to the present invention are disclosed in more detail herein below.

Frozen Fermented Products Comprising the Polypeptide According to the Present Invention Frozen or refrigerated foods are now a mainstay of the human diet in developed nations. Thus extensive research has and is being carried out by food scientists to ensure high quality products for the consumers. This is particularly true with regard to frozen vegetables and frozen deserts such as ice cream and yogurt.

Frozen deserts such as ice cream or yogurt are generally eaten in the frozen state. Thus, the texture of the frozen product as well as its flavor is important to consumers. Texture is to a large extent governed by the size of the ice crystals. Producers of these frozen deserts have gone to considerable effort and expense to ensure smooth textured products. However, during frozen storage the ice crystals can grow and thus roughen and spoil this texture. The growth of ice crystals during frozen storage is known as recrystallization. This problem is particularly common when the frozen storage conditions are less than ideal, such as during transportation or storage in modern frost-free home freezers. After a relatively short period of time at above-zero temperatures (i.e., above 0° C.), or even at sustained freezing temperatures, frozen foods can become less desirable or even unsuitable for human consumption due to the ice recrystallization process.

An ideal method of incorporating anti-freeze polypeptides into frozen fermented food products is to have the organism responsible for the fermentation process produce the anti-freeze polypeptides while fermenting the food.

Hence, the present invention embraces methods for preparing a frozen fermented food product. This method comprises the steps of (a) contacting a food product with a microorganism that is capable of secreting a polypeptide according to the present invention, wherein the microorganism is capable of fermenting the food product to produce the fermented food product, (b) incubating the food product with the microorganism under conditions in which fermentation takes place so that a fermented food product is produced having the anti-freeze polypeptide present in an amount effective at inhibiting recrystallization of the product; and (c) freezing the fermented food product at a temperature below −5° C., so as to produce a frozen fermented food product.

In one embodiment the food product may be a dairy product (e.g., milk) which can be fermented to produce yogurt, buttermilk or cheese.

The microorganism of the invention is usually a bacterium (e.g., *Lactobacillus bulgaricus; Streptococcus cremoris, Streptococcus lactis; Bifidobacterium bifidum, Bifidobacterium longum*) but may also be a fungus such as a yeast (e.g., *Saccharomyces fragilis, Saccharomyces cerevisiae, Saccharomyces lactis*, and others). According to the invention these microorganisms are genetically engineered so that they are capable of secreting a polypeptide according to the present invention.

In a most preferred embodiment the invention comprises incubating milk with bacterial species *Lactobacillus balgaricus* and *Streptococcus lactis* that are capable of fermenting milk to produce yogurt and capable of secreting anti-freeze polypeptides; incubating the bacteria and milk under conditions that produce yogurt; and freezing the yogurt at a temperature below −5° C., so as to produce frozen yogurt.

The invention also provides a composition comprising yogurt and a microorganism wherein the microorganism comprises a gene encoding a polypeptide according to the present invention.

As used herein, "fermentation" refers to the chemical conversion of carbohydrates or polypeptides in food products through the use of microorganisms. In this process carbohydrates are often convened to lactic acid.

As used herein "fermented food product;" refers to an edible food product prepared by a process that includes fermentation by a microorganism.

As used herein "yogurt" refers to a dairy product produced by the lactic acid fermentation of milk by the action of microorganisms.

As used herein, "recombinantly produced polypeptides" refers to a polypeptide produced using recombinant DNA techniques. Recombinant DNA techniques are well known and are characterized by the joining of at least two segments of DNA that are not naturally joined in nature (e.g., a bacterial promoter and a polypeptide coding sequence).

The reference sequence may be shorter than the full-length naturally occurring polypeptide or polynucleotide sequence but will be at least 12 residues long for the case of a polypeptide and at least 36 bases long for the case of a polynucleotide.

The present invention also provides methods for preparing a frozen fermented food product by adding a microorganism that is capable of fermenting the food product to produce the fermented food product and also is able to secrete the polypeptide according to the present invention. The use of a microorganism that both secretes the polypeptide according to the present invention and ferments the food product has several advantages over other methods for affecting ice crystal formation and freezing temperature. For example, the claimed method avoids the costly necessity for purifying the polypeptide according to the present invention prior to addition to a food product. In addition, this will eliminate any possible contamination from the purification protocol and the pyrogenicity associated with foreign microorganisms. Furthermore, because the polypeptide according to the present invention is secret by the fermenting microorganism of the claimed invention, this process requires fewer steps than other methods.

The food product of the invention is usually milk but other foods that are fermented to produce an edible fermented food may also be used. Examples include cabbage (which can be fermented to produce sauerkraut), cucumbers (which can be fermented to produce pickles) and soybeans (which can be fermented to produce miso and other products).

In one step of the method, the food product is contacted or mixed with a microorganism capable of fermenting the food product. Examples of microorganisms useful in food fermentation are well known (see, e.g., van de Guchte, 1992, FEMS Microbiology Reviews, 88:73-92).

In a preferred embodiment the food product is milk (e.g., from a cow [i.e. bovine], ewe, mare, or goat). The action of fermenting microorganisms, typically bacteria, on the milk produces yogurt, buttermilk, or certain cheeses, according to the choice of the bacteria and the conditions of incubation. In a most preferred embodiment the method of the invention will be used to produce yogurt from milk. Yogurt is referred to by a variety of names around the world. The names and country of origin of the common varieties of yogurt are listed below:

| Product Name | Country of Origin |
| --- | --- |
| Jugurt/Eyran/Ayran | Turkey, etc. |
| Busa | Turkestan |
| Kissel Mleka | Balkans |
| Urgotnic | Balkan Mountains |
| Leban/Laban | Lebanon/Arab countries |
| Zabady (Zabbady) | Egypt/Sudan |
| Mast/Dough | Iran/Afghanistan |
| Roba | Iraq |
| Dahi/Dadhi/Dahee | India |
| Mazun/Matzoon/Matsun/Matsoni | Armenia |
| Katyk | Transcaucasia |
| Tiaourti | Greece |
| Cieddu | Italy |
| Mezzoradu | Sicily |
| Gioddu | Sardinia |
| Biokys | Czechoslovakia |
| Karmdinka | Poland |
| Tarho | Hungary |
| Tykmaelk/Ymer | Hungary |
| Villi (Fiili) | Finland |
| Filmjolk/Fillbunke/Surmelk/ Taettemjolk/Tettemelk | Scandinavia |
| Iogurte | Brazil/Portugal |
| Proghurt | Chile |
| Skyr | Iceland |
| Gruzovina | Yugoslavia |
| Kefir/Donskaya/Varentes | Soviet Union |
| Kurunga/Koumiss/Ryazhenka/ Guslyanka Tarag | Mongolia |
| Shosim/Sho/Thara | Nepal |

Methods for yogurt production can be found in Functions of Fermented Milk edited by Nakazawa and Hosono, 1992, published by Elsevier Applied Science, London-New York, p. 32, which is incorporated herein by reference. In the United States yogurt is produced from either whole or skim milk from cows. The milk is standardized to 10.5 to 11.5% solids, heated to above 90° C. (30 to 60 minutes) to destroy any contaminating microorganisms, and then cooled. The material is then inoculated with a mixed culture of *Streptococcus thermophilus* and *Lactobacillus bulgaricus* in a 1:1 ratio. The combined action of these two organisms is usually needed to obtain the desired flavor and acid in the products. In other instances, other high fermenting bacteria including bulgarian bacteria, *L. jugarti, L. acidophilus, Bifido bacterium,* spp. Yeast and lactic fungi have also been used. Examples of bacteria and other organisms used for the fermentation of milk to produce yogurt are listed below:

| Genus | Habit | Fermentation | Main Species |
| --- | --- | --- | --- |
| Streptococcus[a] | Coccal chains | Homo | S. cremoris, lactis, thermophilus |
| Leuconostoc[b] | Coccal pairs | Hetero | L. citrovorum, mesenteroides |
| Lactobacillus[c] | Rods | Homo | L. acidophilus, bulgaricus, casei, jugurti, lactis |
| Bifidobacterium | Rods | Hetero | B. bifidum, breve, longum |

Others:
Yeasts (*Torulopsis holmii; Saccharomyces fragilis, cerevisiae, lactis; Candida pseudotropicalis*, etc.)
Fungi (*Geotrichum candidum*)
Acetic acid bacteria (*Acetobacter aceti, rasens*)
[a] Now *Lactococcus lactis* subsp. *cremoris*, *Lac, lactis* subsp. *lactis* and *S. thermophilus*.
[b] Now *L. mesenteroides* subsp. *cremoris* and *L. mesenteroides* subsp. *mesenteroides*.
[c] Now *L. acidophilus, L. delbrueckii* subsp. *bulgaricus, L. casei* subsp. *casei, L. helveticus* biovar. *jugurti* and *L. delbrueckii* subsp. *lactis*.

The microorganisms may be genetically engineered (i.e., employing the techniques of recombinant DNA technology) so that they are able to secrete the polypeptide according to the present invention.

The methods for engineering bacteria and fungi capable of expressing and secreting a heterologous polypeptide are well established (see, e.g., Maniatis et al. (1982), Molecular Cloning, A Laboratory Manual, Cold Spring Harbor Press, Cold Spring Harbor, N.Y.; Berger and Kimmel, Guide to Molecular Cloning Techniques, Methods in Enzymology 152 (Academic Press, Inc., San Diego, Calif.); Simon et al., 1986, Appl. Environ. Microbiol. 52:394-395; and von Wright et a., 1985, Appl. Environ. Microbiol. 50:1100-1102, all of which are incorporated herein by reference)

The production of microorganisms capable of expressing and secreting an AFP can be carried out in a variety of ways that will be apparent to one of ordinary skill. The DNA sequence encoding the AFP will preferably be operably linked (i.e., positioned to ensure the functioning of) to an operon which allows the DNA to be transcribed (into an RNA transcript) and translated into a polypeptide in the microorganism. Promoters for both bacteria and fungi are well known in the art. Preferred operons for expression in lactic acid bacteria include the lactose operon of *S. thermophilus* or lac ABCDFEGX operon of *L. lactic* because they have been used successfully to drive foreign gene expression in the hosts (see, e.g., Simons et al., 1993, J. Bact. 175:5186-5175; Mollet et al., 1993, J. Bact. 175:4315-4324).

The polypeptide according to the present invention may be expressed as a fusion polypeptide for increased stability or other beneficial properties. Furthermore the polypeptide according to the present invention may be modified via a modification of the gene encoding the polypeptide. In general, modifications of the genes may be readily accomplished by a variety of well-known techniques, such as site-directed mutagenesis (see, e.g., Gillman and Smith, 1979, Gene 8:81-97 and Roberts et al., 1987, Nature 328:731-734).

The microorganisms of the invention are capable of secreting the polypeptide according to the present invention. Accordingly, the polypeptide according to the present invention will preferably be linked to a signal peptide sequence. Examples of suitable signal peptide sequences include those from the usp45 gene of *L. lactis* ssp *lactis* MG 1363 and the *L. lactis* ssp *cremoris* SK11 cell envelop associated protease gene (van Asseldonk et al., 1990, Gene 95:155-160; De vos et al., 1989, J. Dairy Sci. 72:3398-3405). For bacteria such as *L. lactis* the usp45 signal peptide is preferred since it derives from the same host. In one preferred embodiment the polypeptide gene according to the present invention is linked to a transcription termination sequence to ensure correct termination of transcription of the polypeptide according to the present invention in the host system.

A gene construct including elements described above is constructed using plasmids such as pUC19, pNZ18 and pDBN183 as vectors (Solaiman et al., 1992, Plasmid, 28:25-36). The gene construct is incorporated into the genome of a lactic acid bacterial species using homologous recombination techniques (Mollet et al., 1993, J. Bact., 175:4315-4324). The lactic acid bacteria and *E. coli* strains can be maintained as recommended by Maniatis et al. in Molecular Cloning, A Laboratory Manual, supra; and Chagnand et al., 1992, Can. J. Microbiol. 38:67-74.

Microorganisms comprising the polypeptide according to the present invention may be applied to food products in any conventional way. In the case of products such as milk, the bacteria or fungus can be mixed intimately with the food product that is to be fermented and frozen. It will be known by those of skill that mixtures of different microorganisms are sometimes used to produce the desired product. For example, in preparation of yogurt, *S. thermophilus* and *L. bulgaricus* are often used together.

The number of FAE microorganisms added to the food product will depend on the properties of the microorganisms and of the food. Generally, lactic acid FAE starter bacteria ($10^{10}$-$10^{11}$ per ml) are incubated at 1-5% into pasteurized and cooled milk such that the proportion results in an appropriate amount of polypeptide according to the present invention in the product. The amount of AFP in the product should be an amount effective at preventing or inhibiting ice recrystallization (1-100 mg/liter milk). This can be determined using the splat-cooling assay described by Knight et al. (1988) Cryobiology, vol. 25, pp. 55-60.

In another step of the method, the fermented food product is frozen using conventional freezer operations, such as blast freezers (−20 to 40° C.) or contact plate freezers (−300 to 40° C.) or vacuum freeze driers. It will be apparent to one of ordinary skill that numerous variations of the aforementioned embodiments are possible.

Ice Cream Comprising the Polypeptide According to the Present Invention

In another aspect, the present invention provides an ice cream product comprising a polypeptide according to the present invention. The ice cream product can also comprise an emulsifier system together with a polypeptide according to the present invention. This emulsifier system may be any system known by the skilled person. However, systems comprising mono esters of propane-1,2-diol and fatty acids, such as the ones described in US 2005/0163902 or WO 2008/064675, are particular preferred.

In the ice cream manufactured as described herein below, the polypeptide according to the present invention may be added as a purified polypeptide, mixed with other ingredients during manufacture of the ice cream or the polypeptide according to the present invention may be present as a result of secretion from the microorganism used for fermenting the milk.

One way of manufacturing the ice cream according to the present invention is as follows.

In a first step a food intermediate is contacted with the above mentioned emulsifier system.

By the term "food intermediate" as used herein is meant a mixture of ingredients suitable for preparing the ice cream. Ingredients suitable for preparing ice cream may include water, fat such as milkfat or vegetable fat, milk solids not fat (MSNF), sweeteners, stabilisers, flavourings and colurings. Furthermore, the polypeptide according to the present invention may already be present in the milk solid, or it may be added to the mixture as a separate ingredient.

Preferably, the food intermediate comprises fat. Preferably the fat is a high lauric fat or milk fat. By the term "high lauric fat" is meant a fat in which the predominant fatty acid is lauric acid. High lauric fats, such as hardened palm kernel oil and hardened coconut oil, are β' stable. Hence, preferably the food intermediate comprises β' stable fats.

After the first contact step, the selected ingredients are mixed together. Typically the liquid ingredients are mixed together first and the dry ingredients are added subsequently. The liquid ingredients may be cold or may be heated to approximately 60° C. Blending requires rapid agitation to incorporate powders and often high speed blenders are used.

If butter/butter oil or vegetable fat is used, it should ideally be melted separately and added to the mix at 40° C. or via a static mixer at the entrance of the homogeniser by means of a dosing pump.

The mix is subsequently pasteurised. Pasteurisation is carried out to destroy pathogenic bacteria and spoilage organisms such as psychrotrophs. There are three distinct stages in pasteurization: pasteurization, homogenisation and cooling Homogenisation of the mix is carried out in order to form the fat emulsion by breaking down or reducing the size of the fat globules found to less than 1 μm.

Pasteurisation may be carried out by continuous pasteurisation or batch pasteurisation.

Today the most common pasteurisation principle applied is continuous pasteurisation where the ice cream mix is typically heated for a minimum of 16 seconds at a temperature ranging from 80-90° C. in a plate heat exchanger. Continuous pasteurisation is usually performed in a high temperature short time (HTST) heat exchanger following blending of ingredients in a large, insulated feed tank. Some preheating, to 30° C. to 40° C., may be necessary for solubilisation of the components. The HTST system is equipped with heating sections, cooling sections, and regenerative sections.

Batch pasteurisation is the old method where all mix ingredients are slowly heated in a vat equipped with a hot water jacket. In order to avoid fouling on the bottom and sides of the vat, the heating process has to be gentle with a low differential temperature (delta T) between the mix and the heating medium. As the delta T has to be low and the ratio of mix volume/vat surface is typically high, it will inevitably take several minutes just to heat the mix to a temperature of 60° C. Effective agitation of the mix is needed in order to improve the transfer of heat from the vat surface to the mix. Energy consumption for batch pasteurisation is very high and, unlike continuous pasteurisation, there is no heat recovery.

Following pasteurisation, the mix is homogenised by means of high pressures. Homogenisation typically takes place at a temperature of about 80° C. and the homogenisation pressure can be in the region of 90 bar (1300 psi) to 250 bar (3600 psi) at a temperature of 65-75° C. Batch tanks are usually operated in tandem so that one is holding while the other is being prepared. Automatic timers and valves ensure the proper holding time has been met.

Homogenisation can be carried out either before or after pasteurisation.

Subsequently the mix is cooled to refrigerated temperatures (4° C.) by passing it across a heat exchanger (plate or double or triple tube).

The mixture is cooled to the aging temperature which is about 4° C. The mix is then aged for a minimum of four hours but preferably overnight. This allows time for the fat to crystallize and for the polypeptides and polysaccharides to fully hydrate.

Following aging, the mix may be drawn into a flavour tank where any liquid flavours, fruit purees, or colours are added. The mix then enters the dynamic freezing process which both freezes a portion of the water and whips air into the frozen mix. Freezing may be carried out by a continuous freezing process or by batch freezing/whipping. Continuous freezing may be carried out in a barrel freezer. The barrel freezer is a scraped-surface, tubular heat exchanger, which is jacketed with a boiling refrigerant such as ammonia or freon. The mix is pumped through the barrel freezer and is drawn off the other end in about 30 seconds to 3 minutes. In the case of batch freezers the process takes 10 to 15 minutes. When the mix is drawn off the other end about 50% of its water is frozen. There are rotating blades inside the barrel freezer that keep the ice scraped off the surface of the freezer. There are also dashers inside the machine which help to whip the mix and incorporate air.

Ice cream contains a considerable quantity of air, typically up to half of its volume. This gives the product its characteristic lightness. The air content is termed its overrun.

As the ice cream is drawn with about half of its water frozen, particulate matter such as fruit pieces, nuts or cookies, may be added to the semi-frozen slurry. The ice cream is then packaged and is placed into a blast freezer at −30° to −40° C. where most of the remainder of the water is frozen.

Hardening involves static (still, quiescent) freezing of the packaged products in blast freezers. The freezing rate should ideally be rapid, so freezing techniques involve low temperature (−40° C.) with either enhanced convection (freezing tunnels with forced air fans) or enhanced conduction (plate freezers).

Instead of a traditional hardening process the ice cream may be pumped from the ice cream freezer into a low temperature extruder (single or double screw extruder) which brings the temperature of the ice cream down to −12° C. to −18° C. After filling or extrusion the ice cream may be taken directly into cold storage.

The hardened ice cream should be stored below −25° C. Below about −25° C., ice cream is quite stable for long time without danger of fast ice crystal growth.

As previously mentioned, the process of the present invention comprises the step of contacting a food intermediate with an emulsifier system.

In one preferred embodiment, the process comprises the step of dissolving the emulsifier system in water. In this embodiment the emulsifier system may be dissolved in water and the food intermediate may then be contacted with water.

In one preferred embodiment, the process comprises the step of dissolving the emulsifier system in fat. In this embodiment the emulsifier system may be dissolved in fat and the food intermediate may then be contacted with fat.

In one preferred embodiment the process comprises a dynamic freezing step.

The term "dynamic freezing step" as defined herein means subjecting the food intermediate to freezing conditions whilst agitating the food intermediate. This is in contrast to a quiescent freezing step in which the food intermediate is subjected to freezing conditions whilst static.

In one preferred embodiment the process comprises a freezing step.

In one preferred embodiment the process comprises a freezing step with a drawing temperature from the freezer lower than −4° C. Preferably the drawing temperature from the freezer is about −4° C. to −7° C., preferably about −5° C. to −7° C., more preferably about −5° C. to −6° C., more preferably about −6° C. The drawing temperature is the temperature of the ice cream as it exits the ice cream freezer.

Aerated Food Products Comprising the Polypeptide According to the Invention

The present invention also provides an aerated food product comprising a polypeptide according to the invention. Ice cream, sherbet, sorbet and frozen yoghurt can be mentioned as examples of food products, which may be characterized as aerated products.

The term "aerated" means that gas has been intentionally incorporated into a mix, for example by mechanical means. The gas can be any gas, but is preferably, in the context of food products, a food-grade gas such as air, nitrogen, nitrous oxide, or carbon dioxide. The aerated food products of the invention comprise a population of gas bubbles, wherein at least 65% of the gas bubbles have a diameter of less than 20 µm. Preferably at least 75%, more preferably at least 80% of the gas bubbles have a diameter of less than 20 µm. Preferably at least 50%, more preferably at least 60%, most preferably at least 75% of the gas bubbles have a diameter of less than 10 µm.

The extent of aeration is typically defined in terms of "overrun". In the context of the present invention, % overrun is defined in terms of the volume of the aerated product and the volume of the unaerated mix from which it was formed:

$$\text{Overrun} = \frac{\left(\begin{array}{c}\text{Volume of final aerated product} - \\ \text{volume of unaerated mixture}\end{array}\right) \times 100}{\text{Volume of unaerated mixture}}$$

Overrun is measured at atmospheric pressure. The amount of overrun present in the product will vary depending on the desired product characteristics Preferably the food product has an overrun of at least 20%, more preferably at least 50%, most preferably at least 80%. Preferably the food product has an overrun of at most 400%, more preferably at most 200%, most preferably at most 120%.

The aerated food product may be manufactured by use of any process known in the art, such as for example by use of the pre-aeration route, which is a process for producing aerated food products comprising a large proportion of small gas bubbles starting from an unaerated mix.

In the pre-aeration route, a mix (i.e. an aqueous solution and/or suspension) comprising the polypeptide according to the present invention and optionally other ingredients, is subjected to an aeration step. The aeration step must be of a sufficiently high "intensity" so that a large number of very small gas bubbles (less than 20 µm in diameter) are created. The intensity of the aeration process depends on a number of factors, the most important of which are the rate of energy dissipation in the aeration step, the nature of the flow experienced by the mix and the gas bubbles in the aeration step, and the viscosity and temperature of the mix. In addition, the aeration step should be long enough to achieve the desired degree of aeration (i.e. overrun).

Mechanical aerating devices are often based on a rotor which shears the mix. The rate of energy dissipation is a function of the speed of rotation of the device. Generally speaking, a high rate of energy dissipation (and hence a high rotational speed) is required to produce small gas bubbles (see for example "Chemical Engineering for the Food Industry", Fryer, Pyle and Rielly, Blackie, London, 1997).

The effectiveness of the aeration step also depends on the nature of the flow in the aerating device. Aeration is normally achieved by initially incorporating relatively large gas bubbles which are subsequently broken up into smaller ones. Elongational flow or extensional flow is known to be particularly effective at breaking up large gas bubbles, compared to simple shear flow (see e.g. Rallinson, J. M. *Ann. Rev. Fluid Mech.* 16, pp 45-66, 1984). Suitable high shear aeration processes and devices that can provide at least a component of elongational flow include: continuous whipping in a rotor-stator device such as an Oakes mixer (E.T. Oakes Corp), a Megatron mixer (Kinematica AG), a Mondo mixer (Haas-Mondomix BV) or a Silverson mixer (Silverson Machines Inc.); gas injection followed by mixing and dispersion in a continuous flow device such as a scraped surface heat exchanger; and batch whipping involving surface entrainment of gas, using e.g. a Hobart whisk mixer (Hobart UK), Kenwood Chef mixer (Kenwood Ltd), Ultra-Turrax mixer (IKA Werke GmbH & Co. KG) or an electrical hand-held mixer, for example a Breville kitchen hand blender.

The effectiveness of the aeration step also depends on the viscosity and/or the temperature of the mix. By increasing the viscosity and/or lowering the temperature of the mix, the size reducing effect of the aeration device on the gas bubbles is increased. Furthermore, the effectiveness of the aeration step also depends on the formulation of the mix.

Although the effectiveness of the aeration step depends on the specific details of the process and apparatus used and the mix being aerated, it is within the compass of one skilled in the art to determine the appropriate process conditions in any particular situation, by considering the factors described above. In particular, the proportion of very small gas bubbles can be increased by increasing the energy dissipated and/or by increasing the elongational flow component and/or by increasing the viscosity of the mix and/or by lowering the temperature of the mix.

The aerated mixture may optionally be subjected to freezing during and/or after aeration, for example if the final product is to be a frozen aerated product such as an ice cream or a sorbet. Freezing may take place simultaneously with aeration, for example in a scraped surface heat exchanger. Simultaneous freezing and aeration can aid the formation of small gas bubbles because of the increase in the mix viscosity as ice forms. When freezing takes place after aeration, it is preferably carried out so that little or no further gas is incorporated.

The ice content may be increased further by subsequent freezing operations, such as low-temperature extrusion, placing the aerated mixture in a mould immersed in a bath of cold liquid such as brine or glycol, dropping portions of the aerated mixture directly into a bath of cryogenic fluid such as liquid nitrogen or placing a container comprising the aerated mixture into a cold environment such as a freezer, blast freezer or cold store. The subsequent freezing step is preferably carried out at low or zero shear so that little or no further gas is incorporated.

In addition to a polypeptide according to the invention, the aerated food products of the invention (and the mixtures from which they are made) may comprise other ingredients conventionally found in food products, such as fats, milk or cream; oil or fat, notably in the form of an emulsified phase; sugars, salt, fruit and/or vegetable material, extract, juice, thickeners, such as polysaccharides, stabilisers, colours, flavours, chemical emulsifiers, such as monoglycerides; acids and preservatives. Preferred food products include ice cream, sorbet, mousse, whipped cream, aerated beverages such as milk shakes and smoothies, low-fat spreads (e.g. having a fat content of 0-60 wt %), dressings and sauces. Preferably the food product is a frozen or chilled aerated confection such as ice cream, sorbet or mousse.

Frozen aerated confections of the invention comprise the polypeptide according to the present invention and optionally one or more anti-freeze polypeptides other than the polypeptide according to the invention. In aerated products the amount of the total of anti-freeze polypeptides is typically at least about 0.0001 wt %, more preferably at least 0.0005 wt %, most preferably at least 0.001 wt %. Anti-freeze polypeptides can be used at very low concentrations and therefore preferably the confections comprise less than 0.05 wt % Anti-freeze polypeptides. A preferred range is from about 0.001 to 0.01 wt %. Anti freeze polypeptides can be used individually or in combination with other anti freeze polypeptides known in the area.

Frozen aerated products may optionally comprise coatings, such as a layer of chocolate or couverture and/or inclusions, such as nuts, fruit, toffee or chocolate pieces. In this case, the fat content of the frozen aerated confection does not include fat present in the coating or inclusion.

In one embodiment, the frozen aerated confection comprises 3 wt % or less fat, preferably 2 wt % or less, more preferably 1 wt % or less. In a preferred embodiment, the confection is fat-free, which means that the confection comprises substantially no fat (i.e. less than 0.1 wt %).

Aerated Food Products Comprising the Polypeptide According to the Invention Together with Hydrophobin and a Surfactant The present invention also provides a frozen aerated food product, such as a confection, comprising a polypeptide according to the invention together with hydrophobin and a surfactant. Preferably the aerated food product comprises a population of gas bubbles, wherein at least 65% of the gas bubbles have a diameter of less than 20 μm.

The amount of hydrophobin present in the frozen aerated confection will generally vary depending on the confection formulation and volume of the air phase. Typically, the confection will comprise at least 0.001 wt %, hydrophobin, more preferably at least 0.005 or 0.01 wt %. Typically the confection will comprise less than 1 wt % hydrophobin. The hydrophobin can be from a single source or a plurality of sources e.g. the hydrophobin can be a mixture of two or more different hydrophobin polypeptides.

The hydrophobin is added in a form and in an amount such that it is available to stabilise the air phase. By the term "added", is meant that the hydrophobin is deliberately introduced into the confection for the purpose of taking advantage of its foam stabilising properties. Consequently, where ingredients are present or added that comprise fungal contaminants, which may comprise hydrophobin polypeptides, this does not constitute adding hydrophobin within the context of the present invention. Typically, the hydrophobin is added to the confection in a form such that it is capable of self-assembly at an air-liquid surface.

Typically, the hydrophobin is added to the confections of the invention in an isolated form, typically at least partially purified, such as at least 10% pure, based on weight of solids. By "added in isolated form", is meant that the hydrophobin is not added as part of a naturally-occurring organism, such as a mushroom, which naturally expresses hydrophobins. Instead, the hydrophobin will typically either have been extracted from a naturally-occurring source or obtained by recombinant expression in a host organism.

In one embodiment, the hydrophobin is added to the confection in monomeric, dimeric and/or oligomeric (i.e. consisting of 10 monomeric units or fewer) form. Preferably at least 50 wt % of the added hydrophobin is in at least one of these forms, more preferably at least 75, 80, 85 or 90 wt %. Once added, the hydrophobin will typically undergo assembly at the air, liquid interface and therefore the amount of monomer, dimer and oligomer would be expected to decrease.

The term "surfactant" (or "surface active agent") as used herein means a substance which lowers the surface tension of the medium in which it is dissolved and, accordingly, positively adsorbs at the liquid/vapour interfaces.

The term includes sparingly soluble substances which lower the surface tension of a liquid by spreading spontaneously over its surface. In the context of the present invention, the term "surfactant" does not include hydrophobins.

The term "surfactant" does not include trace quantities of surface active components that may be present in very small amounts in another (non-surface active) ingredient, for example stabilisers such as pectins, locust bean gum, and guar gum. In such cases, the amount of surfactant would normally be less than 0.05% by weight of the food product.

The surfactant is typically an ingredient which is used in aerated food products because of its beneficial effect on taste and/or texture. Such surfactants include (but are not limited to):

- milk polypeptides such as caseins, whey (and their polypeptide fractions), sodium caseinate, calcium caseinate, and hydrolysed whey polypeptides;
- other polypeptides such as gelatine, egg polypeptides, and soy polypeptide;
- mono- and di-glycerides of saturated or unsaturated fatty acids, e.g. monoglyceryl palmitate;
- polyoxyethylene derivatives of hexahydric alcohols (usually sorbitol), glycols, glycol esters, polyglycerol esters, sorbitan esters, stearoyl lactylate, acetic acid esters, lactic acid esters, citric acid esters, acetylated monoglyceride, diacetyl tartaric acid esters, polyoxyethylene sorbitan esters (such as polysorbate 80);
- non-ionic surfactants such as alkyl poly(ethylene oxide), fatty alcohols, and sucrose esters;
- phospholipids and mixtures of phospholipids (e.g. lecithin); and mixtures of any the above.

Preferably the surfactant is present in an amount of at least 0.05% by weight of the product, more preferably at least 0.1%. Preferably the surfactant is a polypeptide, more preferably milk polypeptide, and is present in an amount of at least 0.5% by weight of the food product, more preferably at least 1%. Preferably the surfactant is present in an amount of at most 20% by weight of the food product, more preferably at most 10%, most preferably at most 5%.

The aerated food products according to the present invention may be produced by use of the "pre-aeration" route (disclosed above in further detail), which is a process for producing aerated food products comprising a large proportion of small gas bubbles starting from an unaerated mix comprising hydrophobin and surfactant. Another route, termed "post-addition" provides a process whereby the surfactant is added after aeration.

The post-addition route provides a way in which the amount of hydrophobin can be increased in relation to the amount of surfactant at the point at which the bubbles are formed whilst it remains unchanged in the final product, by adding the surfactant after aeration has taken place. Thus a mix comprising hydrophobin but not surfactant is aerated; subsequently a second mix comprising the surfactant is combined with the aerated mix. The second mix is formulated so that the combined mixes give the desired final product formulation. A mixing step may be used to improve the homogeneity of the combined mixes. The mixing step is preferably carried out at relatively low shear and for short times so that little or no further gas is incorporated (i.e. the overrun does not increase by more than 10% during the mixing step). Suitable mixing devices include: static mixers; in-line dynamic mixers such as an auger, blender or fruit-feeder; and batch mixing devices, such as a stirred vessel. In a batch process, the second (surfactant-comprising) mix would typically be injected near the end of the processing period. The mixing step could also take place in a continuous process, for example in a scraped surface heat exchanger or screw extruder by injecting the second mix into the barrel of the scraped surface heat exchanger or screw extruder close to the point at which the product exits.

The aerated mixture may optionally be subjected to freezing during and/or after aeration, for example if the final product is to be a frozen aerated product such as an ice cream or a sorbet. Freezing may take place simultaneously with aeration, for example in a scraped surface heat exchanger. Simultaneous freezing and aeration can aid the formation of small gas bubbles because of the increase in the mix viscosity as ice forms. When freezing takes place after aeration, it is preferably carried out so that little or no further gas is incorporated. When the surfactant is added after aeration (i.e. the post-addition route) freezing may take place before and/or during the mixing step. The surfactant stream may be chilled or partially frozen before mixing.

Frozen Water Confections Comprising the Polypeptide According to the Present Invention Typically, frozen water confections are relatively small, for example having an average volume of less than 1 ml, more preferably less than 0.5 ml. By way of example, beads having a diameter of from 5 mm to 10 mm would have a volume of from about 0.065 ml to about 0.5 ml. Typically the discrete frozen confections have a minimum average volume such that each confection can be readily distinguished by a consumer. For example, the discrete frozen confection preferably has a minimum average volume of at least about 0.02 ml.

The discrete frozen water confections may be made to any shape, such as in the form of cubes or spheres. Preferably, the frozen confections are substantially spherical. The frozen water confections may be in the form of a composite product where at least one portion or region of the product, such as a core or layer, does not contain the polypeptide according to the present invention. An example of this would be a product containing a core of ice cream which lacks the polypeptide according to the present invention, coated in a layer of water ice that does contain the polypeptide according to the present invention. Preferably, substantially the outer layer of the composition confection comprises the polypeptide according to the present invention, i.e. the region which will come into contact with other discrete frozen confections. It will be appreciated that in the case of a composite product, the wt % amount of the polypeptide according to the present invention added to the confection is calculated solely in relation to those components of the confection that contain the polypeptide according to the present invention and not in relation to the complete product.

Frozen water confections may be aerated or unaerated. By unaerated is meant a frozen confection having an overrun of less then 20%, preferably less than 10%. An unaerated frozen confection is not subjected to deliberate steps such as whipping to increase the gas content. Nonetheless, it will be appreciated that during the preparation of unaerated frozen confections, low levels of gas, such as air, may be incorporated in the product.

Water ice confections typically contain sugar, water, colour, fruit acid or other acidifying agent, fruit or fruit flavouring and stabiliser. Preferably, the total solids content is at least 6 wt %, more preferably at least 8 wt % or at least 10, 12, 15 or 20 wt % and may be as high as about 35 wt %. Preferably the total solids content is less then 35 wt %, more preferably less than 25 wt %. Water ices may be aerated or unaerated. If aerated, the overrun is typically less than about 50%, for example from about 25% to 30%. In one embodiment, the water ice confections of the invention are unaerated.

Preferably the water ice confections comprise less than 2 wt % artificial sweeteners, more preferably less than 1 wt %. In a highly preferred embodiment, no artificial sweeteners, such as aspartame or acesulfame are present in the water ice confections.

Frozen water confections of the invention typically comprise one or more stabiliser, such as one or more stabilisers selected from gums, agar, alginates and derivatives thereof, gelatin, pectin, lecithin, sodium carboxymethylcellulose, carrageenan and furcelleran. Preferably a blend of stabilisers is used, such as blend of a gum and carrageenan. In a preferred embodiment, the frozen confection comprises from 0.1 to 1 wt % stabiliser.

Frozen water confections of the invention typically comprise at least about 0.0005 wt % of the polypeptide according to the present invention. The polypeptides according to the present invention can be used at very low concentrations and therefore preferably the confections comprise less than 0.05 wt % of the polypeptide according to the present invention. A preferred range is from about 0.001 to 0.01 wt %.

Frozen water confections of the invention can be manufactured using a number of techniques known in the art. For example, free-flowing beads can be manufactured by dispensing drops of the liquid mix into a freezing chamber of liquid nitrogen (see WO96/29896). Other shapes can be manufactured by moulding techniques, for example by introducing a liquid premix into a cooled mould. Moulded products may contain complex shapes and have a high degree of surface definition.

Ice cream-containing products and the like need not be subjected to a cold hardening step of below from −20° C. to −25° C., although this may be used if desired, especially if the product is a composite product with a layer or core that does not contain the polypeptide according to the present invention.

The frozen water confectionery product of the invention may be packaged in containers for sale to consumers as an individual unit. The volume of such containers is typically from 100 ml to 1000 ml, such as from 200 ml to 500 ml.

However, the product can also be packaged in larger containers for retail purposes where the product is dispensed into smaller containers at the retail premises, e.g. in fast food outlets or as a pick 'n' mix format where consumers can choose from frozen confections of the invention having different shapes, flavours and/or colours. These larger containers may, for example, have a volume greater than about 1000 ml, for example at least 2000 ml or 5000 ml.

Discrete Frozen Dairy Confection Comprising the Polypeptide According to the Present Invention The present invention also provides a frozen confectionary product comprising a plurality of discrete unaerated dairy frozen confection being able to contact directly other discrete frozen confections in the product.

Ice confections are sweet-tasting fabricated foodstuffs intended for consumption in the frozen state (i.e. under conditions wherein the temperature of the foodstuff is less than 0° C., and preferably under conditions wherein the foodstuff comprises significant amounts of ice). Ice confections of the present invention comprise from 1 to 8 wt % fat and have a total solids content of from 10 to 25 wt %. These amounts of fat and total solids, in combination with a water-soluble aerating gas and the polypeptide according to the present invention, result in products having both the desired texture and appearance. Typical water ice formulations (which do not contain fat) and standard ice cream formulations (which have a total solids content of at least about 30 wt %) do not fall within the definition of discrete frozen dairy confection.

The ice confections of the present invention preferably comprise from 2 to 6 wt %, more preferably from 2.5 to 5 wt % fat. The fat may come from any suitable source, such as for example butterfat, coconut oil, palm oil, cocoa butter, sunflower oil, olive oil or rapeseed oil, and mixtures or fractions thereof.

The total solids content of an ice confection is the dry weight of the confection, i.e. the sum of the weights of all the ingredients other than water, expressed as a percentage of the total weight. It is measured as described in Ice Cream, 6th Edition, p 296. The ice confections of the present invention have a total solids content of from 10 to 25 wt % of the ice confection. Preferably the total solids content is at least 12%, more preferably at least 15%, most preferably at least 18%. Preferably the total solids content is at most 24% more preferably at most 22%.

Ice confections according to the present invention contain ice. Since the total solids content is from 10 to 25 wt %, the water content is correspondingly from 90 to 75 wt %. At a temperature of −18° C. most, but not all, of the water is frozen.

Ice confections of the invention typically comprise at least about 0.0001 wt % of the polypeptide according to the present invention, more preferably at least 0.0005 wt %. The polypeptides according to the present invention can be used at very low concentrations and therefore preferably the confections comprise less than 0.05 wt % of the polypeptide according to the present invention. A preferred range is from about 0.001 to 0.01 wt %, more preferably from 0.005 to 0.01 wt %.

An aerating agent refers to any component which because of its surface activity and/or the viscosity it imparts, aids the formation of small gas bubbles and resists their coalescence or separation. The aerating agent is to be understood not to include the aerating gas. Preferably the aerating agent is a polypeptide-based aerating agent, for example a hydrolysed milk polypeptide such as Hygel™ and Hyfoama™ (available from Kerry Biosciences); or a hydrolysed soya polypeptide such as Versawhip (available from Kerry Biosciences) and D-100™ (available from Gunter Industries). Alternatively, the aerating agent may be non-protein-based, for example a monoglyceride, such as Myverol 18-04K (a distilled 95% monoglyceride prepared from vegetable oils, available from Quest International), or a polyglycerol ester, such as PGE 55 (a polyglycerol ester of fatty acids, available from Danisco). The amount of aerating agent in the confection is at least 0.1 wt %, preferably at least 0.15 wt %.

Preferably the amount of aerating agent is less than 0.5 wt %, preferably less than 0.4 wt %, more preferably less than 0.25 wt %.

Ice confections of the invention may comprise stabiliser. Stabilisers include polypeptides such as gelatin; plant extrudates such as gum arabic, gum ghatti, gum karaya, gum tragacanth; seed gums such as locust bean gum, guar gum, tara gum, psyyllium seed gum, quince seed gum or tamarind seed gum; konjac mannan; seaweed extracts such as agar, alganates, carrageenan or furcelleran; pectins such as low methoxyl or high methoxyl-type pectins; cellulose derivatives such as sodium carboxymethyl cellulose, microcrystalline cellulose, methyl and methylethyl celluloses, or hydroxylpropyl and hydroxypropylmethyl celluloses; and microbial gums such as dextran, xanthan or β-1,3-glucan. The stabiliser may be a single stabiliser, or a mixture of two or more stabilisers. Preferably, the stabiliser is locust bean gum. The amount of stabiliser is preferably at most 0.3 wt %, more preferably at most 0.25 wt %. For example, the amount of stabiliser is typically from 0 to 0.2 wt %.

Ice confections of the invention may contain polypeptide (in addition to any polypeptide based aerating agent), preferably in an amount of at least 1 wt %, more preferably at least 1.5 wt %. Ice confections containing at least this amount of polypeptide are perceived as milk ice-type products and are more attractive to many consumers than substantially polypeptide-free ice confections. Preferably the polypeptide content is less than 8 wt %, more preferably less than 6 wt %, most preferably less than 3 wt %. Suitable polypeptides for use in the present invention include milk polypeptides, egg polypeptides and gelatine as well as vegetable polypeptides such as soya polypeptides. Particularly preferred are milk polypeptides owing to their superior flavour and heat stability. Suitable sources of milk polypeptide include milk, concentrated milk, milk powders, whey, whey powders and whey polypeptide concentrates isolates.

Ice confections of the invention typically comprise sugars e.g. sucrose, fructose, dextrose, lactose, corn syrups, sugar alcohols; they may also contain other ingredients, for example colours and flavours.

The ice confection preferably has an overrun of at least 20%, more preferably at least 40%, most preferably at least 60%. Preferably the overrun is at most 150%, more preferably at most 120%, most preferably at most 120%.

"Mix" refers to the unaerated mix prior to aeration (or following de-aeration of the melted ice confection). Overrun is measured at atmospheric pressure.

The ice confection containing of the invention may constitute an entire product or may be a component of a composite product. In a composite product the ice confection of the invention provides contrast in texture and appearance to the other component(s) of the product. Preferably such composite products contain the ice confection as a discrete element in their structure. For example, a relatively soft ice cream core can be coated with a layer of the ice confection to provide a hard, crispy layer surrounding the ice cream core. Another example is the incorporation of the ice confection as inclusions. Alternatively the ice confection may be provided with a continuous or partial coating of, for example, a water glaze, a non-aerated water ice or chocolate on at least one surface. In a composite product the determination of the total solids and the fat, aerating agent, ice structuring polypeptide, stabiliser, and polypeptides contents takes into account only the ice confection, and not other components of the composite product.

Discrete frozen dairy confection comprising the polypeptide according to the present invention may be prepared by any suitable method known in the art. Preferably, however, the discrete frozen dairy confection is manufactured by the method comprising the steps of:
(a) preparing a mix of ingredients; then
(b) pasteurising and homogenising the mix; then
(c) adding the polypeptide according to the present invention
(d) simultaneously freezing and aerating the mix with an aerating gas which contains at least 50% by volume of a carbon dioxide, nitrous oxide or mixtures thereof to produce the ice confection (for example in an ice cream freezer);
(e) cold hardening the ice confection, wherein step (c) may take place before, during or after step (b).

The mix is aerated with a gas containing at least about 50% by volume of carbon dioxide, nitrous oxide or mixtures thereof, preferably at least about 70%, more preferably 100%. The remainder of the aerating gas will typically be a nitrogen-containing gas such as air. Most preferably the aerating gas is 100% carbon dioxide.

After freezing, the resulting ice confection may be shaped e.g. by extrusion followed by cutting or by moulding, prior to the cold hardening step. Preferably the ice confection is extruded at a temperature of from 4° to −1.5° C., more preferably from −2.5 to −1.5° C.

Relatively high extrusion temperatures result in a particularly good foam-like appearance.

Preferably the cold hardening step takes place at a temperature of about −25° C. or below, for example by blast freezing. After cold hardening, the ice confections are preferably stored at a temperature in the range of −25 to −10° C., typically about −18° C.

Low Fat Dairy Products Comprising the Polypeptide According to the Invention

The present invention also provides a frozen, low fat dairy product. Frozen dairy confections are confections that typically contain milk or milk solids, such as ice cream, milk ice, frozen yogurt and sherbet. The term "milk" includes milk substitutes such as soya milk, although mammalian milk is preferred. Preferably the frozen dairy confection is an ice cream or milk ice.

The low fat product of the present invention preferably comprises 3 wt % or less fat, preferably 2 wt % or less, more preferably less than 2 wt %, or 1 wt % or less. In one embodiment, the product is fat-free, which means that the product comprises substantially no fat (i.e. less than 0.1 wt %). Where the product is coated with a non-dairy composition such as a chocolate or couverture layer, the determination of fat content for the product should disregard the coating.

Frozen confections containing milk preferably contain at least about 3 wt % milk solid non-fat (MSNF), more preferably from about 5 wt % to about 25 wt % MSNF.

Stabilisers may be present in the frozen products of the invention although it should be noted that the stabilising effects of the polypeptides according to the present invention can allow for stabiliser replacement in some cases. However, significant levels of stabilisers may still be required, in addition to polypeptides according to the present invention, in some product formulations, such as very low fat products with less than 1 wt % fat, to produce the desired product stability. Nonetheless, the resulting products are improved over previous products because the polypeptide according to the present invention reduces or ameliorates the deleterious effects of the stabilisers on texture and taste.

Suitable stabilisers include alginates, gelatin, gum acacia, guar gum, gum karaya, locust bean gum, carageenan and salts thereof, xanthan gum, microcrystalline cellulose, cellulose ethers or mixtures thereof. The amount of stabiliser is preferably 1.5% or less by weight, more preferably 1% or less by weight such as from 0.1 to 0.8 wt %.

In one embodiment, the product comprises at least 0.5 wt % stabilisers, such as at least 0.7 wt % stabilisers. Preferably the level of fat in such a product is less than 2 or 1 wt %. In another embodiment the product comprises less than 0.5 wt % stabilisers. Preferably the level of fat in such as product is at least 1 wt % or more, more preferably at least 2 wt %.

Frozen confections of the invention typically comprise at least about 0.0001 wt % of the polypeptide according to the present invention, more preferably at least 0.0005 wt %. The polypeptides according to the present invention can be used at very low concentrations and therefore preferably the confections comprise less than 0.05 wt % polypeptide according to the present invention. A preferred range is from about 0.001 to 0.01 wt %, more preferably from 0.005 to 0.01 wt %.

The frozen confections may be aerated or unaerated, preferably aerated. By unaerated is meant a frozen confection having an overrun of less then 20%, preferably less than 10%. An unaerated frozen confection is not subjected to deliberate steps such as whipping to increase the gas content. Nonetheless, it will be appreciated that during the preparation of unaerated frozen confections, low levels of gas, such as air, may be incorporated in the product. The amount of overrun present in an aerated product will vary depending on the desired product characteristics. For example, the level of overrun in ice cream is typically from about 70 to 100%, and in confectionery such as mousses the overrun can be as high as 200 to 250 wt %, whereas the overrun in milk ices is from 25 to 30%. Aerated frozen confections preferably have an overrun of from 30% to 200%, more preferably from 50% to 150%.

Frozen confections of the invention can be manufactured using a variety of techniques known in the art. Products are typically frozen quiescently or using agitation, such as in a surface-scraped heat exchanger. Products may be moulded. Products may contain complex shapes and have a high degree of surface definition since the addition of the polypeptide according to the present invention preserves the stability of such shapes and structures.

The polypeptides according to the present invention can be added prior to, during or after freezing of the product. If added after freezing, this will take place whilst the product is still plastic so that the polypeptide according to the present invention can be mixed e.g. after extrusion from a surface-scraped heat exchanger and prior to hardening.

Ice cream products and the like can be subjected to an optional cold hardening step of below from −20° C. to −25° C.

The present invention also encompasses compositions for producing a low fat frozen confectionery product of the invention, which composition comprises the polypeptide according to the present invention, preferably at least 0.005 wt % of the polypeptide according to the present invention. Such compositions include liquid premixes and dry mixes, for example powders, to which an aqueous liquid, such as milk or water, is added.

Frozen Food Products Designed for Thawing in a Microwave, Said Products Comprising the Polypeptide According to the Present Invention Freezing is a very common technique for preserving food. With certain notable exceptions, frozen food is usually thawed prior to use or further processing (e.g., cooking). Thawing is accomplished satisfactorily by leaving the frozen food product to stand at ambient temperature. However, even on a domestic scale, the length of time taken to accomplish satisfactory thawing is considerable. Thawing is also accomplished on an industrial scale by the application of conductive or convective heat to the frozen food product. However, the apparatus needed to accomplish such thawing is not readily available to the consumer.

Microwave ovens are increasingly widespread in both an industrial and domestic context. One of their uses is in the thawing of frozen food. Microwave thawing is more rapid than thawing at ambient temperature. It still suffers from a number of disadvantages:
  the low thermal diffusivity of frozen food necessitates the use of pulsed microwaves to allow temperature equilibrium to be established;
  liquid water absorbs microwave energy much more readily than ice, tending to result in "hotspots" and uneven thawing;
  the geometry of the food item with regard to size and shape must be suitable;
  because of the necessity of using only intermittent microwave pulses, the time to thaw a food item completely is considerable.

It has been found that if a composition comprising a mesophase of water, emulsifier and the polypeptide according to the present invention is incorporated into a food product and if at least an amount of the water is present as unfrozen water in the frozen food product, an improved product is obtained.

The word mesophases herein includes both layered structures and traditional mesophases i.e. lamellar, cubic, hexagonal (1 and 2), L2 and L1 and also dispersed mesophases i.e. liposomes, cubosomes and hexosomes. Additionally, it includes the formation of micelles, which will also form such surfaces.

It has been found that the above described frozen food product may be thawed uniformly and rapidly by the application of direct microwave energy, without the necessity of using intermittent or pulsed microwaves.

It is believed that the ability of the systems of the present invention to maintain a proportion of unfrozen water when present in a frozen food product is due to the ability of the compositions to form mesophases. Mesophases are structures where the polar emulsifier and water are organised in a well-defined structure according to their polarity. The polar end group of the emulsifier is in contact with the water phase or phases. A number of different mesophase structures are believed to exist. The water close to the polar end group of the emulsifier is organised in such a way that it is protected from freezing.

The ratio of water to emulsifier in the composition of the invention will depend on the emulsifier used, and the particular application of the composition. It has been found that for any particular emulsifier/water system, the amount of liquid water present below 0° C. ("unfrozen water") tends to increase with the proportion of water up to a maximum. Up to this maximum point, it is thought that substantially all the water in the system is unfrozen. Beyond this point, a fixed amount of the water present is unfrozen, with the balance frozen.

Preferably, the compositions of the invention comprise at least an amount of unfrozen water when present in a frozen food product at a temperature of −15° C. or below. Preferably, the compositions of the invention comprise at least an amount of unfrozen water when present in a frozen food product at a temperature of −20° C. or below. Preferably, the compositions of the invention comprise at least an amount of unfrozen water when present in a frozen food product at a temperature of about −25° C. Preferably, the compositions of the invention comprise at least an amount of unfrozen water when present in a frozen food product at a temperature of about −40° C.

When present in a frozen food product, the compositions of the present invention preferably comprise an amount of unfrozen water that is thermodynamically stable at temperatures below 0° C.

Preferably, the water component is present in an amount of at least 0.1% based on the total weight of the composition. Preferably, the water component is present in an amount of at least 1% based on the total weight of the composition. Preferably, the water component is present in an amount of at least 2% based on the total weight of the composition. Preferably, the water component is present in an amount of at least 3% based on the total weight of the composition. Preferably, the water component is present in an amount of at least 5% based on the total weight of the composition. Preferably, the water component is present in an amount of at least 10% based on the total weight of the composition.

Preferably, the water component is present in an amount of at most 99.9% based on the total weight of the composition. Preferably, the water component is present in an amount of at most 50% based on the total weight of the composition. Preferably, the water component is present in an amount of at most 40% based on the total weight of the composition. Preferably, the water component is present in an amount of at most 30% based on the total weight of the composition. Preferably, the water component is present in an amount of at most 25% based on the total weight of the composition.

Preferably, the water component is present in an amount of between 0.1 and 99.9% based on the total weight of the composition. More preferably, the water component is present in an amount of between 1 and 25% based on the total weight of the composition.

Preferably, the emulsifier is present in an amount of at least 0.1% based on the total weight of the composition. Preferably, the emulsifier is present in an amount of at least 50% based on the total weight of the composition. Preferably, the emulsifier is present in an amount of at least 60% based on the total weight of the composition. Preferably, the emulsifier is present in an amount of at least 70% based on the total weight of the composition. Preferably, the emulsifier is present in an amount of at least 80% based on the total weight of the composition. Preferably, the emulsifier is present in an amount of at least 99.0% based on the total weight of the composition. Preferably, the emulsifier is present in an amount of at least 99.9% based on the total weight of the composition.

Preferably, the emulsifier is present in an amount up to 99.9% based on the total weight of the composition. Preferably, the emulsifier is present in an amount up to 99% based on the total weight of the composition. Preferably, the emulsifier is present in an amount up to 97% based on the total weight of the composition. Preferably, the emulsifier is present in an amount up to 95% based on the total weight of the composition. Preferably, the emulsifier is present in an amount up to 90% based on the total weight of the composition.

Preferably, the emulsifier is present in an amount of between 0.1 and 99.9% based on the total weight of the composition. More preferably, the emulsifier is present in an amount of between 75 and 90% based on the total weight of the composition.

Preferably, the polypeptide according to the invention is present in an amount of at least 0.001% based on the total weight of the composition. Preferably, the polypeptide according to the invention is present in an amount of at least 0.01% based on the total weight of the composition. Preferably, the polypeptide according to the invention is present in an amount of at least 0.1% based on the total weight of the composition. Preferably, the polypeptide according to the invention is present in an amount of at least 1% based on the total weight of the composition. Preferably, the polypeptide according to the invention is present in an amount of at least 5% based on the total weight of the composition. Preferably, the polypeptide according to the invention is present in an amount of at least 10% based on the total weight of the composition.

Preferably, the polypeptide according to the invention is present in an amount of at most 90% based on the total weight of the composition. Preferably, the polypeptide according to the invention is present in an amount of at most 50% based on the total weight of the composition. Preferably, the polypeptide according to the invention is present in an amount of at most 25% based on the total weight of the composition. Preferably, the polypeptide according to the invention is present in an amount of at most 15% based on the total weight of the composition. Preferably, the polypeptide according to the invention is present in an amount of at most 10% based on the total weight of the composition.

Preferably, the polypeptide according to the invention is present in an amount of between 0.001 and 90% based on the total weight of the composition. More preferably, the polypeptide according to the invention is present in an amount of between 0.01 and 10% based on the total weight of the composition.

In a preferred aspect, the composition comprises less than 25% w/w of oil. More preferably, the composition comprises less than 10% w/w of oil. More preferably, the composition comprises less than 5% w/w of oil. More preferably, the composition comprises less than 1% w/w of oil. Still more preferably the composition comprises less than 0.1% w/w of oil. Most preferably, the composition comprises substantially no oil.

Other components may also be present in the compositions of the invention, provided that they do not affect the ability to retain at least an amount of unfrozen water when present in a frozen food product.

An example of a technique of bringing into association is mixing. Mixing of water with the polypeptide according to the invention and an emulsifier may be achieved by any one of a number of means that will be apparent to one skilled in the art. Mixing in an electric mixer is one example.

If ingredients additional to polypeptide according to the invention, an emulsifier and water are present in the composition, then these may be incorporated at any appropriate stage.

Preferably, the food product comprises an amount of the composition sufficient that the amount of unfrozen water present in the food product as a whole enables uniform and rapid microwave thawing. In practice, this equates to an amount of at least 0.1% w/w of unfrozen water present in the food product as a whole.

The usage level will depend on the specific food product, the application and how much water that will be needed to preserve the food texture after freezing.

An amount of non frozen water as low as around 0.1% of the total product gives a product that rapidly and uniformly thaws when heated in a microwave oven. This even thawing results in food products with improved textural properties. To obtain 0.1% of unfrozen water according to this invention takes approximately 0.20% of PGE. The exact amount of emulsifier will depend on the nature of the emulsifier, and may readily be determined by one skilled in the art. For example, 0.14% of Dimodan® MO90 or 0.14% of Grindsted® PGE 070 (Danisco, Denmark) will produce the same effects.

Preferably, the food product comprises the composition of the invention in an amount of at least 0.1% w/w. Preferably, the food product comprises the composition of the invention in an amount of at least 0.2% w/w. Preferably, the food product comprises the composition of the invention in an amount of at least 0.3% w/w. Preferably, the food product comprises the composition of the invention in an amount of at least 0.4% w/w. Preferably, the food product comprises the composition of the invention in an amount of at least 0.5% w/w.

Preferably, the food product comprises the composition of the invention in an amount of less than 10% w/w. Preferably, the food product comprises the composition of the invention in an amount of less than 5% w/w. Preferably, the food product comprises the composition of the invention in an amount of less than 4% w/w. Preferably, the food product comprises the composition of the invention in an amount of less than 3% w/w.

Preferably, the food product comprises the composition of the invention in an amount of between 0.1 and 5% w/w, more preferably between 0.5 and 3% w/w.

The mode of application of the composition of the invention to the food product will depend on the nature of the food product in question. For instance, if the food product is liquid or semiliquid at ambient temperature, the composition may be incorporated simply by mixing it with the food product.

In some embodiments of the invention, the water, the polypeptide according to the invention and emulsifier may be added to the food product separately. Water may be added followed by the polypeptide according to the invention and emulsifier; alternatively the polypeptide according to the invention and emulsifier may be added, followed by water.

It is preferred that the polypeptide according to the invention, the emulsifier and water are combined before addition to the food product.

Alternatively, the composition may be incorporated at any point during the food preparation process. For example, the composition may be sprayed on to the surface of the food product. The composition may be injected in to the food product (e.g. in the case of poultry, meat or fish).

The skilled person will be able to judge when to best achieve this incorporation.

Preferably, the food product is selected from low fat spread, mayonnaise, yoghurt, bakery fillings, margarine, reconstituted fruits, jams, fruit preparations, fruit fillings, ripples, fruit sauces, stewed fruit, coffee whitener, instant fruit dessert, confectionery (such as marsh mallow), potato based foods (such as chips, french fries and croquettes), prepared meals (such as casseroles and stews) and fine foods (such as dressings including salad dressings; ketchup, vinaigrette dressings and soups). The food product may be a beverage, raw, processed or pasteurised foods including raw meat, cooked meat, raw poultry products, cooked poultry products, raw seafood products, cooked seafood products, [raw or cooked meat, poultry and seafood products], sausages, frankfurters, ready to eat meals, pasta sauces, pasteurised soups, marinades, oil-in-water emulsions, water-in-oil emulsions, cheese spreads, processed cheese, dairy desserts, flavoured milks, cream, fermented milk products, cheese, butter, condensed milk products, cheese spreads, pasteurised liquid egg, ice cream mixes, soya products, pasteurised liquid egg, confectionery products, fruit products, and foods with fat-based or water-containing fillings. The food product may be a bakery product such as bread, cakes, fine bakery and dough.

Cosmetic and Dermatological Compositions According to the Present Invention

The present invention also provides a cosmetic or dermatological preparation which comprises the polypeptide according to the present invention—optionally in combination with one or more additional polypeptides which are selected from anti-freezing polypeptides and anti-freezing glycoproteins.

The preparation may comprise only the polypeptide according to the present invention or the preparation may comprise at least one additional anti-freezing polypeptide. Furthermore the composition may comprise at least one anti-freezing glycoprotein together with the polypeptide according to the present invention.

In the preparation the polypeptide according to the present invention in the preparation may be present in a concentration of from 0.0001% to 50% by weight, based on the total weight of the preparation, e.g., in a concentration of from 0.001% to 50% by weight, of from 0.1% to 10% by weight, or from 0.1% to 1% by weight.

In cases where one or more additional polypeptides selected from anti-freezing polypeptides and anti-freezing glycoproteins are also present in the preparation together the polypeptide according to the present invention total amount of polypeptide may amount to from 0.0001% to 50% by weight, based on the total weight of the preparation, e.g., in a concentration of from 0.001% to 50% by weight, of from 0.1% to 10% by weight, or from 0.1% to 1% by weight.

Preferably, the at least one additional anti-freezing polypeptide may comprise at least one polypeptide selected from types AFP 1, AFP 2, AFP 3 and AFP 4, for example, at least one polypeptide of type AFP 1 that is synthesized by *pseudopluronectes americanus, myoxocephalus scorpius, myoxocephalus aenaeus* and/or *myoxocephalus scorpiodes*, at least one polypeptide of type AFP 2 that is synthesized by *hemitripterus americanus, osmerus mordax* and/or *clupea harengus harengus*, at least one polypeptide of type AFP 3 that is synthesized by *macrozoarces americanus, rhigophila dearbomi lycodes polaris* and/or the "wolf fish" *anarhichas lupus*, and/or at least one polypeptide of type AFP 4 that is synthesized by *myoxocephalus octodecimspinosis*.

Preferably, the at least one anti-freezing glycoprotein may comprise at least one polypeptide that is synthesized by *trematomas borgrevinki, dissostichus mawsoni, boreogadus saida* and/or *gadus morhua*.

In one aspect of the present invention, at least a part of the one or more polypeptides in the preparation may be encapsulated.

The present invention also provides a cosmetic or dermatological preparation which comprises the polypeptide according to the present invention and one or more polypeptides which are selected from anti-freezing polypeptides and anti-freezing glycoproteins that are synthesized by at least one of *pseudopluronectes americanus, myoxocephalus scorpius, myoxocephalus aenaeus, myoxocephalus scorpiodes, hemitripterus americanus, osmerus mordax, clupea harengus harengus, macrozoarces americanus, rhigophila dearborni, lycodes polaris, anarhichas lupus, myoxocephalus octodecimspinosis, trematomas borgrevinki, dissostichus mawsoni, boreogadus saida* and *gadus morhua*.

Preferably, the total amount of polypeptide according to the present invention in the cosmetic or dermatological preparation amounts to from 0.001% to 50% by weight, based on the total weight of the preparation, e.g., in a concentration of from 0.1% to 10% by weight. Preferably, the total amount of polypeptide in the cosmetic or dermatological preparation may amount to from 0.001% to 50% by weight, based on the total weight of the preparation, e.g., in a concentration of from 0.1% to 10% by weight.

The present invention also provides a cosmetic or dermatological product which is an o/w cream, a w/o cream, a w/o/w cream, an o cream, a w/o emulsion, a hydrodispersion, a gel cream, a w/o stick or an o stick, and which comprises the preparation of the present invention, including the various aspects thereof.

The present invention also provides a method for the treatment or prevention of undesirable skin conditions. The method comprises applying the polypeptide according to the present invention and optionally one or more polypeptides to at least parts of the skin, which polypeptides are selected from anti-freezing polypeptides and anti-freezing glycoproteins.

In one aspect, the undesirable skin conditions may include skin inflammation, pigmentation disorders, symptoms of extrinsic and intrinsic skin aging and/or skin damage caused by UV radiation.

In the technical filed of cosmetic and dermatologic preparations, the term "anti-freezing polypeptides" is used to describe polypeptides that enable an organism, even under extreme temperature conditions, to keep important cell structures functionally active. In view of their function, "anti-freezing polypeptides" in this sense also represent "frost-protection compounds" on a cellular level.

It was not foreseeable for those of skill in the art that the preparations according to the present invention protect better against structural and cellular damage in the skin due to cold better maintain or restore the barrier properties of the skin better combat drying out of the skin act better against dyschromia act better against inflammatory skin conditions act better against skin aging, and better protect the skin against environmental influences than the preparations of the prior art.

The use of a polypeptide according to the present invention optionally together with additional anti-freezing polypeptides (AFP) and/or anti-freezing glycoproteins (AFGP) or cosmetic or topical dermatological preparations with an effective content of the polypeptide according to the present invention optionally together with additional AFP and/or AFGP renders possible an effective treatment, but also a prophylaxis of structural and cellular damage in the skin due to cold, which damage with distinct climate- and weather-induced drops in temperature cause changes in the cell physiology in the cell and in the extracellular space through loss of the temperature optima of cellular enzymes, skin damage, skin redness and tight feeling of the skin and increased sensory sensitivities, induced, e.g., by cold, wind and/or UV light, temperature-sensitive skin, negative changes in the skin, the lips and the mucous membranes in the nose and mouth area and the integumentary appendage caused by environmental stress (caused by temperature changes and UV light, smoking, smog, reactive oxygen species, free radicals).

The use of the polypeptide according to the present invention optionally together with additional AFP and/or AFGP or the use of cosmetic or topical dermatological preparations with an effective content of the polypeptide according to the present invention optionally together with additional AFP and/or AFGP is an effective treatment as well as a prophylaxis of deficient, sensitive or hypoactive skin conditions or deficient, sensitive or hypoactive conditions of integumentary appendages of signs of premature aging of the skin (e.g., wrinkles, senile keratoses, telangiectases) and/or of the integumentary appendages, of environmentally induced (smoking, smog, reactive oxygen species, free radicals) and in particular light-induced negative changes in the skin and the integumentary appendages, of light-induced skin damage, of pigmentation disorders, of sensitive, irritated and itchy skin, of dry skin conditions and disorders of the horny layer barrier, of hair loss and for improved hair growth, signs of skin aging, such as, e.g., wrinkles and reduced skin regeneration, of inflammatory skin conditions, and atopic eczema, seborrhoeic eczema, polymorphous photodermatosis, psoriasis, vitiligo, to sooth sensitive or irritated skin, to stimulate the synthesis of collagen, hyaluronic acid and elastin, changes of the normal hyaluronic acid and glycosaminoglycan content of healthy skin, to stimulate the ceramide synthesis of the skin to stimulate intracellular DNA synthesis, in particular in cases of deficient or hypoactive skin conditions, to increase cell renewal and regeneration of the skin, to increase the skin's own protective and repair mechanisms (for example, for dysfunctional enzymes, DNA, lipids, polypeptides), reduction in cell-cell communication deficient, sensitive or hypoactive skin conditions or deficient, sensitive or hypoactive conditions of skin appendages, a change in the ceramide, lipid and energy metabolism of healthy skin, changes in lipid and polypeptide peroxidation, a change in the physiological transepidermal water loss, a reduction in skin hydration, normal osmoregulation and decrease in the moisture content of the skin, change in the natural moisturizing factor content, DNA damage and reduction in endogenous DNA repair mechanisms, activation of metalloproteinases and/or other proteases or inhibition of the corresponding endogenous inhibitors of these enzymes, deviations from the normal post-translational modifications of connective tissue constituents of healthy skin, dandruff formation in the hair and hair region, brittleness of the skin, loss of elasticity and skin fatigue, increase in the normal keratinocyte proliferation, reduction of the natural regeneration and structure of the skin and hair for pre- and post-treatment in cases of topical application of laser and abrasive treatments, which serve, for example, to reduce skin wrinkles and scars, to counteract the resulting skin irritations and to promote the regeneration processes in the damaged skin.

Accordingly, the use of the polypeptide according to the present invention optionally together with additional AFPs and/or AFGPs for the prophylaxis and treatment of inflammatory skin conditions—also atopical eczema—and/or for skin protection in the case of skin predisposed to be sensitive and dry is also in accordance with the invention.

Accordingly, the use of cosmetic or dermatological preparations for the production of cosmetic or dermatological preparations for the treatment and/or prophylaxis of pigmentation disorders is also in accordance with the invention.

Accordingly, the use of preparations for the production of cosmetic or dermatological preparations for the treatment and/or prophylaxis of the symptoms of intrinsic and/or extrinsic skin aging and for the treatment and prophylaxis of harmful effects of ultraviolet radiation on the skin is also according to the invention.

Hence, the use of the polypeptide according to the present invention optionally together with additional AFPs and/or AFGPs for the production of cosmetic or dermatological preparations for increasing ceramide biosynthesis is also an aspect of the invention.

Furthermore, the use of AFPs and/or AFGPs for the production of cosmetic or dermatological preparations for strengthening the barrier function of the skin is yet another aspect of the invention.

Cosmetic or dermatological preparations according to the present invention preferably contain from 0.0001% to 50% by weight, particularly preferably from 0.01% to 10% by weight, of the cited the polypeptide according to the present invention optionally together with additional AFPs and/or AFGPs or a combination of two or more of the cited AFPs and/or AFGPs, based on the total weight of the preparations.

According to the present invention, customary antioxidants can be used in the preparations that contain the active substance combinations according to the present invention.

Advantageously, the antioxidants are selected from the group of amino acids (for example, glycine, histidine, tyrosine, tryptophan, [beta]-alanine) and derivatives thereof, imidazoles (for example urocanic acid) and derivatives thereof, peptides, such as D,L-carnosine, D-carnosine, L-carnosine and derivatives thereof (for example, anserine), carotenoids, carotenes (for example, [alpha]-carotene, [beta]-carotene, lycopene) and derivatives thereof, lipoic acid and derivatives thereof (for example, dihydrolipoic acid), aurothioglucose, propylthiouracil and other thiols (for example, thioredoxin, glutathione, cysteine, cystine, cystamine and the glycosyl, N-acetyl, methyl, ethyl, propyl, amyl, butyl and lauryl, palmitoyl, oleyl, [gamma]-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (for example, buthionine sulfoximines, homocysteine sulfoximine, buthionine sulfones, penta-, hexa- and heptathionine sulfoximine) in very low tolerated doses (for example pmol to μmol/kg), and furthermore (metal) chelating agents (for example, [alpha]-hydroxy fatty acids, palmitic acid, phytic acid, lactoferrin), [alpha]-hydroxy acids (for example, citric acid, lactic acid, malic acid), humic acid, bile acid, bile extracts, bilirubin, biliverdin, EDTA, EGTA and derivatives thereof, unsaturated fatty acids and derivatives thereof (for example [gamma]-linolenic acid, linoleic acid, oleic acid), folic acid and derivatives thereof, alanine diacetic acid, flavonoids, polyphenols, catechols, vitamin C and derivatives thereof (e.g., ascorbyl palmitate, Mg-ascorbyl phosphate, ascorbyl acetate), tocopherols and derivatives thereof (for example, vitamin E acetate), and coniferyl benzoate of benzoin resin, rutinic acid and derivatives thereof, ferulic acid and derivatives thereof, butylated hydroxytoluene, butylated hydroxyanisole, nordihydroguaiacic acid, nordihydroguaiaretic acid, trihydroxybutyrophenone, uric acid and derivatives thereof, mannose and derivatives thereof, zinc and derivatives thereof (for example, $ZnO$, $ZnSO_4$), selenium and derivatives thereof (for example selenomethionine), stilbenes and derivatives thereof (for example stilbene oxide, trans-stilbene oxide) and the derivatives of these active ingredients mentioned which are suitable according to the invention (salts, esters, ethers, sugars, nucleotides, nucleosides, peptides and lipids).

The amount of the antioxidants (one or more compounds) in the preparations is preferably from 0.001% to 30% by weight, particularly preferably from 0.05% to 20% by weight, particularly preferred from 1% to 10% by weight, based on the total weight of the preparation.

In addition, it may be advantageous to encapsulate the active ingredients according to the invention, as so-called solid lipid nanoparts using molten waxes, which may be chosen, inter alia, but not exclusively, from ester waxes, triglyceride waxes or hydrocarbon waxes. In addition, it may be advantageous to encapsulate the active ingredients according to the invention in polymers, e.g., in particles based on highly crosslinked polymethacrylates and/or cellulose triacetates and/or as core/shell particles with a shell made of poly(oxymethylurea), nylon, polyamides, polyurethane, polyester, gelatin and polyolefins.

The prophylaxis or the cosmetic or dermatological treatment with the active ingredient used according to the invention or with the cosmetic or topical dermatological preparations having an effective content of active ingredient used according to the invention may be carried out in the usual manner, by applying the active ingredient used according to the invention or the cosmetic or topical dermatological preparations having an effective content of active ingredient used according to the invention to the affected areas of the skin.

The active ingredient used according to the invention can advantageously be incorporated into customary cosmetic and dermatological preparations which may assume various forms. Thus, they may, for example, be a solution, an emulsion of the water-in-oil (W/O) type or of the oil-in-water (O/W) type, or a multiple emulsion, for example of the water-in-oil-in-water (W/O/W) type or oil-in-water-in-oil (O/W/O) type, a hydrodispersion or lipodispersion, a gel, a Pickering emulsion, a solid stick or an aerosol.

Emulsions according to the invention for the purposes of the present invention, e.g., in the form of a cream, a lotion, a cosmetic milk, and a stick, are advantageous and may comprise, for example, fats, oils, waxes and/or other fatty substances, and water and one or more emulsifiers as are customarily used for this type of formulation.

It is also possible and advantageous for the purposes of the present invention to incorporate the active ingredient used in accordance with the present invention into aqueous systems or surfactant preparations for cleansing and treating the skin and the hair.

One of skill in the art is, of course, aware that demanding cosmetic compositions are almost inconceivable without the customary auxiliaries and additives. Examples thereof include builders, fillers, perfume, dyes, emulsifiers, additional active ingredients, such as vitamins or polypeptides, light protection agents, stabilizers, insect repellents, alcohol, water, salts, and antimicrobially, proteolytically or keratolytically active substances, etc.

Corresponding requirements apply mutatis mutandis to the formulation of medicinal preparations.

Medicinal topical compositions for the purposes of the present invention generally comprise one or more medicaments in an effective concentration. For the sake of simplicity, for a clear distinction between cosmetic and medicinal application and corresponding products, reference is made to the legal provisions of the Federal Republic of Germany (e.g., Cosmetics Directive, Foods and Drugs Act).

In this connection, it is likewise advantageous to add the active ingredient used according to the invention as an additive to preparations which already comprise other active ingredients for other purposes.

Accordingly, for the purposes of the present invention, cosmetic or topical dermatological compositions can, depending on their formulation, be used, for example, as skin protection cream, cleansing milk, sunscreen lotion, nourishing cream, day or night cream, lip care stick, nasal spray, etc. In some instances it is possible and advantageous to use the compositions according to the invention as bases for pharmaceutical formulations.

It is also advantageous for the purposes of the present invention to provide cosmetic and dermatological preparations whose main purpose is not protection against sunlight, but which nevertheless have a content of UV protection substances. Thus, for example, UVA and/or UVB filter substances are usually incorporated into day creams or makeup products. Also UV protection substances, likewise antioxidants and, if desired, preservatives, provide an effective protection of the preparations against deterioration. Furthermore, cosmetic and dermatological preparations are favorable which are in the form of a sunscreen.

Accordingly, the preparations according to the present invention, in addition to one or more active ingredient combinations according to the invention, preferably additionally comprise at least one further UVA filter substance and/or UVB filter substance. The formulations can, although this is not necessary, optionally also comprise one or more organic and/or inorganic pigments as UV filter substances, which can be present in the aqueous phase and/or the oil phase.

Preferred inorganic pigments are metal oxides and/or other metal compounds which are insoluble or sparingly soluble in water, in particular the oxides of titanium ($TiO_2$), zinc ($ZnO$), iron (e.g., $Fe_2O_3$), zirconium ($ZrO_2$), silicon ($SiO_2$), manganese (e.g. $MnO$), aluminum ($Al_2O_3$), cerium (e.g., $Ce_2O_3$), mixed oxides of the corresponding metals, and mixtures of such oxides.

According to the invention such pigments can advantageously be surface-treated ("coated") whereby, e.g., an amphiphilic or hydrophobic character of these pigments is to be formed or retained. This surface treatment can comprise providing the pigments with a thin hydrophobic layer by methods known per se.

According to the invention, e.g., titanium dioxide pigments are advantageous that are coated with octylsilanol. Suitable titanium dioxide particles are available under the trade name T805 from Degussa. Furthermore, $TiO_2$ pigments coated with aluminum stearate are particularly advantageous, e.g., those available under the trade name MT 100 T from TAYCA.

A further advantageous coating of the inorganic pigments comprises dimethylpolysiloxane (also: dimethicone), a mixture of completely methylated, linear siloxane polymers which are terminally blocked with trimethylsiloxy units. For the purposes of the present invention, particularly advantageous pigments are zinc oxide pigments which are coated in this way.

Also advantageous is a coating of the inorganic pigments with a mixture of dimethylpolysiloxane, in particular dimethylpolysiloxane having an average chain length of from 200 to 350 dimethylsiloxane units, and silica gel, which is also referred to as simethicone. It is particularly advantageous if the inorganic pigments have been additionally coated with aluminium hydroxide or hydrated aluminium oxide (also alumina, CAS No.: 1333-84-2). Particularly advantageous are titanium dioxides which have been coated with simethicone and alumina, it being possible for the coating to also comprise water. One example thereof is the titanium dioxide available under the trade name Eusolex T2000 from Merck.

An advantageous organic pigment for the purposes of the present invention includes 2,2'-methylenebis-(6-(2H-benzotriazol-2-yl)-4-(1,1,3,3-tetramethylbutyl)phenol) [INCI: Bisoctyltriazole], which is obtainable from CIBA Chemikalien GmbH under the trade name Tinosorb® M.

Advantageously, preparations according to the invention contain substances that absorb UV radiation in the UVA and/or the UVB range, whereby the total amount of the filter substances is, e.g., from 0.1% by weight to 30% by weight, preferably 0.5 to 20% by weight, in particular from 1.0 to 15% by weight, based on the total weight of the preparations, in order to provide cosmetic preparations that protect the hair or the skin against the entire range of ultraviolet radiation. They can also be used as sunscreen for the hair or the skin.

Further advantageous UVA filter substances for the purposes of the present invention include dibenzoylmethane derivatives, in particular 4-(tert-butyl)-4'-methoxydibenzoylmethane (CAS No. 70356-09-1), which is sold by Givaudan under the trademark Parsol® 1789 and by Merck under the trade name Eusolex® 9020.

Advantageous further UVA filter substances include phenylene-1,4-bis-(2-benzimidazyl)-3,3',5,5'-tetrasulfonic acid and its salts, particularly the corresponding sodium, potassium or triethanolammonium salts, in particular the phenylene-1,4-bis-(2-benzimidazyl)-3,3',5,5'-tetrasulfonic acid bis-sodium salt with the INCI name Bisimidazylate, which is available, for example, under the trade name Neo Heliopan AP from Haarmann & Reimer.

Also advantageous are 1,4-di(2-oxo-10-sulfo-3-bornylidenemethyl)benzene and salts thereof (particularly the corresponding 10-sulfato compounds, in particular the corresponding sodium, potassium or triethanolammonium salt), which is also referred to as benzene-1,4-di(2-oxo-3-bornylidenemethyl-10-sulfonic acid).

Advantageous UV filter substances for the purposes of the present invention are also so-called broadband filters, i.e., filter substances which absorb both UVA and UVB radiation.

Advantageous broadband filters or UVB filter substances include, for example, bis-resorcinyltriazine derivatives. Particularly preferred are 2,4-bis{[4-(2-ethylhexyloxy)-2-hydroxylphenyl}-6-(4-methoxyphenyl)-1,3,5-triazine (INCI: Aniso Triazine), which is available under the trade name Tinosorb® S from CIBA-Chemikalien GmbH.

Particularly advantageous preparations for the purposes of the present invention that are characterized by a high or very high UVA protection preferably contain several UVA and/or broadband filters, in particular dibenzoylmethane derivatives [e.g., 4-(tert.butyl)-4'-methoxydibenzoylmethane], benzotriazole derivatives [e.g., 2,2'methylene-bis-(6-(2H-benzotriazol-2-yl)-4-(1,1,3,3-tetramethylbutyl)-phenol], phenylene-1,4-bis-(2-benzimidazyl)-3,3',5,5'-tetrasulfonic acid and/or salts thereof, 1,4-di(2-oxo-10-sulfo-3-bornylidenemethyl)-benzene and/or salts thereof and/or 2,4-bis-{[4-(2-ethylhexyloxy)-2-hydroxy]-phenyl}-6-(4-methoxyphenyl)-1,3, 5-triazine, individually or in any combinations with one another.

A further light protection filter substance which can be used advantageously according to the invention is ethylhexyl 2-cyano-3,3-diphenylacrylate (octocrylene), which is available from BASF under the designation Uvinul® N 539.

It may also be considerably advantageous to use polymer-bound or polymeric UV filter substances in preparations according to the present invention, in particular those described in WO-A-92/20690.

In addition, it may optionally be advantageous to incorporate further UVA and/or UVB filters into cosmetic or dermatological preparations according to the invention, for example, certain salicylic acid derivatives, such as 4-isopropylbenzyl salicylate, 2-ethylhexyl salicylate (-Octyl salicylate), and homomenthyl salicylate.

Of course, the list of cited UV filters which can be used for the purposes of the present invention is not intended to be limiting.

Preparations according to the invention advantageously contain substances which absorb UV radiation in the UVA and/or UVB range, in a total amount of, e.g., from 0.1% by weight to 30% by weight, preferably from 0.5% to 20% by weight, in particular from 1.0% to 15.0% by weight, based on the total weight of the preparations, in order to make available cosmetic preparations which protect the hair or the skin from the entire range of ultraviolet radiation. They can also be used as sunscreen compositions for the hair or the skin.

The cosmetic and dermatological preparations according to the invention may comprise cosmetic active agents, auxiliaries and additives, as are customarily used in such preparations, e.g., antioxidants, preservatives, bactericides, perfumes, antifoams, dyes, coloring pigments, thickeners, surfactants, emulsifiers, emollients, moisturizers and/or humectants, fats, oils, waxes and other customary constituents of a cosmetic or dermatological formulation, such as alcohols, polyols, polymers, foam stabilizers, electrolytes, organic solvents or silicone derivatives.

If the cosmetic or dermatological preparation according to the present invention is present in the form of a solution or emulsion or dispersion, the following may be used as solvents: water or aqueous solutions; oils such as triglycerides of capric or caprylic acid, preferably castor oil; fats, waxes and other natural and synthetic lipids, preferably esters of fatty acids with alcohols of low C number, for example with isopropanol, propylene glycol or glycerol, or esters of fatty alcohols with alkanoic acids of low C number or with fatty acids; alcohols, diols or polyols of low C number and their ethers, preferably ethanol, isopropanol, propylene glycol, glycerol, ethylene glycol, ethylene glycol monoethyl ether or monobutyl ether, propylene glycol monomethyl ether, monoethyl ether or monobutyl ether, diethylene glycol monomethyl ether or monoethyl ether, and analogous products.

In particular, mixtures of the above-mentioned solvents may be used. In the case of alcoholic solvents, water may be a further constituent.

The oil phase of the emulsions, oleogels or hydro- or lipodispersions in accordance with the present invention may advantageously be selected from esters of saturated and/or unsaturated, branched and/or unbranched alkanecarboxylic acids with a chain length of from 3 to 30° C. atoms and saturated and/or unsaturated, branched and/or unbranched alcohols with a chain length of from 3 to 30° C. atoms, from esters of aromatic carboxylic acids and saturated and/or unsaturated, branched and/or unbranched alcohols with a chain length of from 3 to 30° C. atoms. In this case, such ester oils may be selected advantageously from isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, for example jojoba oil.

Furthermore, the oil phase may advantageously be selected from branched and unbranched hydrocarbons and hydrocarbon waxes, silicone oils, dialkyl ethers, saturated or unsaturated, branched or unbranched alcohols and fatty acid triglycerides, viz. the triglycerol esters of saturated and/or unsaturated, branched and/or unbranched alkanecarboxylic acids with a chain length of from 8 to 24, in particular from 12 to 18° C. atoms. For example, the fatty acid triglycerides may advantageously be selected from synthetic, semisynthetic and natural oils, for example olive oil, sunflower oil, soya oil, peanut oil, rapeseed oil, almond oil, palm oil, coconut oil, palm kernel oil and the like.

Any mixtures of such oil and wax components may also advantageously be employed in accordance with the present invention. If appropriate, it may also be advantageous to employ waxes, for example cetyl palmitate, as the only lipid component of the oil phase.

The oil phase may advantageously be selected from 2-ethylhexyl isostearate, octyldodecanol, isotridecyl isononanoate, isoeicosane, 2-ethylhexyl cocoate, $C_{12-15}$ alkyl benzoate, caprylic/capric acid triglyceride, dicaprylyl ether.

Especially advantageous mixtures are those of $C_{12-15}$ alkyl benzoate and 2-ethylhexyl isostearate, those of $C_{12-15}$ alkyl benzoate and isotridecyl isononanoate and those of $C_{12-15}$ alkyl benzoate, 2-ethylhexyl isostearate and isotridecyl isononanoate.

Amongst the hydrocarbons, liquid paraffin, squalane and squalene may advantageously be used according to the present invention.

The oil phase may furthermore advantageously comprise cyclic or linear silicone oils, or consist entirely of such oils, but it is preferred to use an additional content of other oil phase components, apart from the silicone oil(s).

Cyclomethicone (octamethylcyclotetrasiloxane) is advantageously employed as silicone oil to be used according to the invention. However, other silicone oils may also be used advantageously in accordance with the present invention, for example, hexamethylcyclotrisiloxane, polydimethylsiloxane, and poly(methylphenylsiloxane).

Especially advantageous mixtures are furthermore those of cyclomethicone and isotridecyl isononanoate and of cyclomethicone and 2-ethylhexyl isostearate.

If appropriate, the aqueous phase of the preparations according to the invention may advantageously comprise alcohols, diols or polyols of low C number, and their ethers, preferably ethanol, isopropanol, propylene glycol, glycerol, ethylene glycol, ethylene glycol monoethyl ether or monobutyl ether, propylene glycol monomethyl ether, monoethyl ether or monobutyl ether, diethylene glycol monomethyl ether or monoethyl ether and analogous products, furthermore alcohols of low C number, for example ethanol, isopropanol, 1,2-propanediol, glycerol, and, in particular, one or more thickeners which may advantageously be selected from silicon dioxide, aluminum silicates, polysaccharides and their derivatives, for example hyaluronic acid, xanthan gum, hydroxypropyl methylcellulose, especially advantageously from polyacrylates, preferably a polyacrylate from the group of the so-called Carbopols, for example type 980, 981, 1382, 2984 and 5984 Carbopols, in each case individually or in combination.

Gels which may be used according to the present invention usually comprise alcohols of low C number, for example ethanol, isopropanol, 1,2-propanediol, glycerol and water, or an above-mentioned oil in the presence of a thickener, which is preferably silicon dioxide or an aluminum silicate in the case of oily-alcoholic gels, and preferably a polyacrylate in the case of aqueous-alcoholic or alcoholic gels.

Solid sticks may comprise, for example, natural or synthetic waxes, fatty alcohols or fatty acid esters.

Customary basic materials which are suitable for use as cosmetic sticks in accordance with the present invention include liquid oils (for example liquid paraffin, castor oil, isopropyl myristate), semi-solid constituents (for example petrolatum, lanolin), solid constituents (for example beeswax, ceresine and micro-crystalline waxes, or ozocerite) and waxes of high melting point (for example carnauba wax and candelilla wax). Suitable propellants for cosmetic and/or dermatological preparations in accordance with the present invention which can be sprayed from aerosol containers are the customary known volatile, liquefied propellants, for example hydrocarbons (propane, butane, isobutane), which may be employed individually or as a mixture with each other. Pressurized air may also be used advantageously.

Those of skill in the art will, of course, be familiar with the fact that there are non-toxic propellants, which would be suitable in principle for putting into practice the present invention in the form of aerosol preparations; however, it is recommended to dispense with the use of these-in particular fluorohydrocarbons and fluorochlorohydrocarbons (FCHCs)-due to their unacceptable effect on the environment or other accompanying circumstances.

Cosmetic preparations in accordance with the present invention may also take the form of gels which comprise not only an effective amount of active ingredient according to the invention and conventionally used solvents therefor, preferably water, but also organic thickeners, for example gum arabic, xanthan gum, sodium alginate, cellulose derivatives, preferably methylcellulose, hydroxymethylcellulose, hydroxyethylcellulose, hydroxypropylcellulose, hydroxypropyl methylcellulose, or inorganic thickeners, for example, aluminum silicates such as, for example, bentonites, or a mixture of polyethylene glycol and polyethylene glycol stearate or polyethylene glycol distearate. The gel comprises the thickener for example in an amount of between 0.1 and 30% by weight, preferably between 0.5 and 15% by weight.

It is particularly advantageous for the purposes of the present invention if the cosmetic or dermatological preparations according to the present invention contain further active substances, in particular natural active substances and/or derivatives thereof, such as, e.g., alpha-lipoic acid, phytoene, D-biotin, coenzyme Q10, alpha-glucosyl rutin, carnitine, carnosine, osmolytes, clover extract, hop extract or hop-malt extract.

The concentration of the active ingredients (one or more substances) is advantageously from 0.0001% to 30% by weight, based on the total weight of the preparations. The cosmetic or dermatological preparation according to the present invention may be prepared by any method known within the art.

Treatment of Organs and Tissue Samples

Perfusing organs or tissue samples with a composition comprising an anti-freeze polypeptide according to the present invention makes it possible the store such organs and tissue samples, or other biological materials, at a lower temperature, thereby preventing deterioration or degradation of the sample, but without the risk of generating a freeze damage to said tissues, organs, cells or other biological materials. In many instances, damage to organs and biological tissues is caused not so much by the generation of a frozen state of the organ or tissue in question, but by the recrystallization which may occur.

Examples of biological materials, organs and tissue samples include, but is not limited to, e.g. samples comprising one or more polypeptides, samples comprising one or more microsomes or micelles comprising one or more polypeptides, samples comprising whole blood, samples comprising blood plasma, samples comprising blood platelets, samples comprising red blood cells, samples comprising semen, samples comprising gametes.

Tissue culture samples can comprise any form of biological cells, including mammalian cells, such as animal cells and human cells, rodent cells and insect cells. The organ to be treated can be e.g. a kidney, a lung, a heart, a spleen or a liver. Accordingly, there is provided a method for inhibiting recrystallization of an organ or a biological sample, said method comprising the step of contacting the organ or biological sample with the polypeptide according to the present invention under conditions allowing the polypeptide to prevent recrystallization of the organ or the biological sample.

There is also provided a method for improving the preservation of an organ or a biological sample, said method comprising the step of contacting the organ or biological sample with the polypeptide according to the present invention under conditions allowing the polypeptide to contact the organ or biological sample in question, thereby allowing the organ or biological sample to be stored at a sub-freezing temperature as compared to the storage temperature of an untreated organ or biological sample.

A new method has recently been developed which is based on vitrification. This method suffers, however, from the fact that during de-freezing of the gameter, embryos or stem cells relaxation occurs, which means that ice crystals are formed. During the de-freezing process these ice crystals grow due to re-crystallisation. It is believed that if one or more of the polypeptides according to the present invention is present in the solvents in which the gameter, embryos or stem cells are present during this vitrification process, then the crystal formation as well as the crystal growth will be markedly reduced or may be even prevented.

Further cryo-protective uses of the polypeptides according to the present invention are disclosed in more detail in the following.

In a separate aspect the present invention relates to methods for protecting cells and their membranes from damage which they would otherwise suffer upon exposure to non-physiological conditions such as temperature abnormalities, including both hyperthermic, hypothermic and subfreezing temperatures. Improved rates of cell viability are observed over a wide range of conditions which do not involve ice formation, including temperatures above the freezing range as well as temperatures below the freezing range but in vitrification conditions. Heretofore the only known property of these polypeptides was their ability to interact with ice crystals. In conditions in which ice crystals are formed, it is further discovered that use of the polypeptides with human cells at the concentrations in which they naturally occur in the source organisms results in aggravating the injury to the cells rather than reducing it, but that the injury is lessened, and the survival rate improved, by using low concentrations. The polypeptides thus offer benefits in the preservation and improved viability of cell suspensions, tissues and whole organs. The polypeptides are further discovered to have the ability to block ion channels in mammalian cell membranes, thereby providing a further utility in the treatment of disease conditions.

The present invention makes use of the recognized but unutilized quality of anti-freeze polypeptides and their ability to interact with cells and cell membranes. The interaction occurs with cell membranes in a wide range of structures, including individual cells in cell suspensions, connected cell masses in tissues and organs, and cell structures which are pervaded with a vascular system. The interaction is a favorable one, imparting to the cell membranes and the structures which incorporate these membranes a variety of benefits, including improvements in cell viability and survival rate, prolongation of the functionality, stability and structural integrity of the cells and cell tissues, reduction of the occurrence of structural damage to membranes and cells under adverse conditions, and control of the transport of ions across the cell membranes.

The various types of interaction are unrelated to the known effects of these polypeptides on ice crystal propagation, since the beneficial effects of these interactions are observed under conditions where ice crystals do not form at all, in addition to their occurrence in the presence of ice crystals. For example, benefits are observed at temperatures ranging from cryogenic temperatures to temperatures well above physiological temperatures. The invention thus extends to situations involving physiological conditions as well as nonphysiological conditions, and to situations that involve the presence of ice crystals as well as those in which ice crystals are completely absent. Nonphysiological conditions in which beneficial effects on viable cells and cell membranes are observed therefore include: (i) hypothermal conditions defined by temperatures above the normal freezing point of water (0° C.), and therefore with no possibility of ice formation, and below the physiological temperature of the cells; (ii) vitrification conditions defined by temperatures at or below the glass formation (or glass transition) temperature, such as for example from 150K down to about 4K, and by the presence of vitrifying agents which promote vitrification and inhibit crystallization; (iii) freezing conditions, such as temperatures from the normal freezing point of water down to about 4K, which permit the formation of ice crystals; (iv) hyperthermal conditions defined by temperatures above the physiological temperature of the cells, for example temperatures within the range of the physiological temperature up to about 10° C. above the physiological temperature; and (v) conditions defined by chemical environments which differ from the physiological chemical environment of the cells, such as conditions of nonphysiological pH and other variations from the physiological chemical composition, as well as such conditions in combination with conditions of nonphysiological temperature.

Applicability of the invention aim extends to abnormal physiological conditions such as diseases associated with the instability of cell membranes and diseases associated with imbalances of ions between intracellular and extracellular spaces giving rise to abnormal ion transport across the cell membranes. The unexpected nature of this behavior is heightened by the discovery that the blockage of ion channels, such as for example those of calcium and potassium ion in epithelial cells, is achieved without interference with other metabolic functions of the cells, including ATP ion pumps and interactions with carbachol. Still further, the invention offers benefits to cells in normal physiological conditions, such as through the use of cosmetics or medications designed to restore, preserve or repair epidermal tissue.

The invention finds applicability to a wide range of living cells, including both animal cells and plant cells. A particularly unusual and interesting discovery in connection with the present invention, however, is the utility of the anti-freeze polypeptides in the treatment and preservation of mammalian cells, tissues and organs. In their natural form, these polypeptides exist in non-mammalian species only, and the differences in cell and membrane structure as well as in blood and cytoplasm composition between these species and mammalian species renders the presently discovered benefits surprising and unexpected. The invention is thus of particular interest and utility as applied to mammalian cells, tissues, organs and organisms which are exposed to conditions which differ from the normal physiological condition of the mammal. Examples of cells to which the invention is applicable are mammalian oocytes, hepatocytes, erythrocytes and leukocytes, and various types of plant cells. Examples of tissues and organs are tissue of livers, hearts, and kidneys, and the organs themselves. Examples of organisms are embryos, self-sustaining whole animals, plant seeds and whole plants.

Additional benefits arising from the invention are many and varied. Included among these are the elimination of the need to maintain a fast cooling rate during freezing to cryogenic temperatures, the ability of the polypeptides to raise the viscosity of solutions at considerably lower concentrations than known cryoprotectants, and the ability of the polypeptides to preserve foods upon freezing. Other advantages, benefits, and applications of the present invention will be apparent from the description which follows.

Within the technical field of cryopreservation, the following terms are used with the following definitions:

"Abnormal" or "non-physiological conditions" for cells, tissues, organs or organisms refer to conditions which differ from the normal physiological conditions. Abnormal or non-physiological conditions include, but are not limited to, a temperature which is significantly higher or lower than the normal physiological temperature of the healthy organism of which the cell, tissue or organ is native, or the organism itself; an excess or subnormal amount of carbon dioxide, oxygen, inorganic salts, or organic compounds, a pH value significantly higher or lower than that of the healthy organism, and combinations of these conditions.

"Anti-freeze polypeptides," "anti-freeze polypeptides" ("AFPs"), "anti-freeze glycoproteins" and "anti-freeze glycopeptides" ("AFGPs") refer to macromolecules found in the body fluids of some animals, which have the commonly known property that they reduce non-colligatively the freezing point of water. Anti-freeze polypeptides, polypeptides, glycoproteins and glycopeptides are also known as "thermal hysteresis polypeptides" because the temperature at which freezing occurs is depressed to a greater degree than one could attribute to any colligative character of the polypeptides, whereas the temperature at which ice melts during melting is depressed is significantly less, in accordance solely with colligative behavior.

"Cryogenic temperatures" refers to temperatures below 0° C.

"Freezing" refers to the transition from the liquid phase of water to the solid phase of water.

"Hyperthermic" refers to temperatures higher than the normal physiological temperature of a cell, tissue, organ or organism, such as for example from slightly above the physiological temperature up to about 20° C. above, preferably to about 10° C. above, and more preferably to about 5° C. above the physiological temperature.

"Hypothermic" refers to temperatures lower than the normal physiological temperature of a cell, tissue, organ or organism, but not low enough to cause a phase transition to the solid phase.

"Isolated and purified" refers to molecular species which are extracted from the organism in which they naturally occur, and concentrated by conventional laboratory techniques such as chromatography, preferably to a concentration of at least about 85%, more preferably to at least about 95%. This invention further extends to molecules which have a molecular structure which is either the same, highly similar, or homologous to naturally occurring forms of the molecules, and which may have been synthesized either by chemical means or by recombinant DNA techniques.

"Mammal" refers to any warm blooded mammal as the term is generally used in biology, including, for example, pig, cow, rabbit, horse and human being.

"Polar fish species" refers to cold-blooded aquatic animals, particularly vertebrates, which reside in waters of the polar regions of the earth, including the regions within the Arctic and Antarctic Circles. Polar fish species of particular interest in connection with this invention are those which remain in waters which become or remain ice-laden.

"Spicule" and "spicular" refer to ice crystals and ice crystal growth in which the dominant direction of crystal propagation is along the c-axis, i.e., perpendicular to the basal plane, to form crystals having a needle-like shape.

"Viable" means capable of living, capable of surviving and developing under, or upon a return to, normal physiological conditions, or capable of germinating under conditions normally favorable to germination.

"Vitrification" refers to solidification at cryogenic temperatures in such a manner that a glass phase, i.e., a non-crystalline solid, is formed, as opposed to crystalline ice. "Apparent vitrification" refers to vitrification as determined by visual observation under a microscope. Vitrification of a biological material is generally achieved by introducing any of a variety of cryoprotective or "vitrifying" agents, including polyhydric alcohols such as glycerol and propylene glycol, or other compounds such as dimethylsulfoxide into the material. The introduction of vitrifying agents is often accompanied by relatively high rates of cooling. The optimal rates in each case vary with the composition and thermodynamics of the system. Typical cooling rates in most cases for small unorganized cells such as ova, sperm, and embryos, and for organs, generally fall within the ranges of about 100° C./min to about 2,000° C./min, preferably about 200° C./min to about 1,750° C./min, and more preferably about 700° C./min to about 1,750° C./min. Rates on the order of 1500° C./min are commonly used.

In the practice of the present invention, the anti-freeze polypeptides according to the present invention are generally used in the form of a liquid solution, and preferably an aqueous solution. The anti-freeze polypeptides according to the present invention may be used individually or in combination with other polypeptides. When the polypeptides are used in combination, it will often be most convenient to use the polypeptides in the physiological combinations in which they naturally occur in the source species, i.e., the same mixture and proportions of the polypeptide species as they are found in the fluid of the fish, insect or other organism from which they are extracted, although isolated from other components of the fluid and redissolved in a different solvent or solution, perhaps at a total concentration which differs from that in which the mixture is present in its natural environment. In certain cases, however, activity and effectiveness may be improved by fractionating the polypeptides in the source mixture and selecting and recombining fractions in an optimal manner.

The concentration of the anti-freeze polypeptides according to the represent invention in the liquid solution as used in the present invention may vary widely, although in certain cases, improved results will be obtained within certain concentration ranges, and in certain cases, the concentration must be restricted to certain ranges to avoid injury caused by the polypeptides themselves. In general, however, the polypeptides will be used in concentrations of from about 0.01 mg/mL to about 80 mg/mL, preferably from about 0.1 mg/mL to about 60 mg/mL, more preferably from about 1 mg/mL to about 40 mg/mL, and most preferably from about 1 mg/mL to about 20 mg/mL. When used with human cells, particularly under temperatures below the physiological temperature of the cells, preferred concentrations are from about 0.1 mg/mL to about 40 mg/mL, more preferably from about 0.1 mg/mL to about 3 mg/mL. In applications where the polypeptides are used to protect tissue at temperatures below the physiological temperature of the tissue, preferred concentrations are within the range of about 0.1 mg/mL to about 50 mg/mL, and when the tissue is human tissue, preferred concentrations are within the range of about 0.1 mg/mL to about 3 mg/mL. In applications where the polypeptides are used to protect cells in general at temperatures below the physiological temperature of the cells but above the freezing temperature of the cells, or below the freezing temperature of the cells but in the presence of a vitrifying agent or other non-peptide cryoprotectant, preferred concentrations are within the range of about 0.01 mg/mL to about 60 mg/mL, and more preferred concentrations are within the range of about 1 mg/mL to about 40 mg/mL. In applications where the polypeptides are used to block ion channels across cell membranes, preferred concentrations are at least about 0.01 mg/mL, more preferably at least about 0.1 mg/mL, and most preferably from about 0.5 mg/mL to about 40 mg/mL. All concentrations of anti-freeze polypeptides are expressed as totals of the concentrations of individual anti-freeze polypeptides when a solution contains a mixture of different anti-freeze polypeptides.

Aqueous solutions of the anti-freeze polypeptides for use in the present invention may further contain any of the wide variety of mixtures of salts, sugars, ions and other nutrients which are included in electrolyte solutions known in the art to be useful for preserving biological agents. These include tissue culture media, organ perfusion fluids, and the like. Electrolyte solutions are particularly useful for enhancing the biological compatibility of the polypeptides. Examples of the many electrolyte solutions known in the art are: Physiological Saline, in which the NaCl concentration is either 0.9% or 0.95% Ringer's Injection Solution (U.S.), listed in Facts and Comparisons, p. 50, Lippincott Publishing Co., St. Louis, Mo. (October 1981) Mammalian Ringer's Solution (U.K. and Canada), listed by Best and Taylor, Basis of Medical Practice, 6th ed., Baltimore (1950) Lactated Ringer's Solution (U.S.), listed in Facts and Comparisons, p. 50, Lippincott Publishing Co., St. Louis, Mo. (October 1981) Lactated Ringer's Solution (Hartmann), listed by Hartmann, A. F., J. Am. Med. Assoc. 103:1349-1354 (1934) Acetated Ringer's Solution, listed by Fox, C. L., et al., J. Am. Med. Assoc. 148:825-833 (1952) Locke's Solution, listed by Locke, F. S., Zbl. Physiol. 8:166 (1894); 14:670 (1900); 15:490 (1901) Tyrode's Solution, listed by Tyrode, M. J., Arch. Int. Pharmacodyn. 20:205 (1910) Krebs Henseleit Solution, listed by Krebs, H. A., et al., Hoppe-Seyle's Z. Physiol. Chem. 210:33-66 (1932) Krebs Ringer Phosphate Solution, listed by Krebs, H. A., Hoppe-Seyle's Z. Physiol. Chem. 217:193 (1933) Krebs Serum Substitute Solution, listed by Krebs, H. A., Biochem. Biophys. Acta 4:249-269 (1950) Krebs Improved Ringer II Solution, listed by Krebs, H. A., Biochem. Biophys. Acta 4:249-269 (1950) Krebs Improved Ringer III Solution, listed by Krebs, H. A., Biochem. Biophys. Acta 4:249-269 (1950) Krebs Liver Perfusion Solution with Bovine Serum Albumin and Red Cells, listed by Hem, R., et al., Biochem. J. 101:284 (1966) Schimassek Liver Perfusion Solution, listed by Schimassek, H., et al., Biochem. Z. 336,440 (1963) Krebs Kidney Perfusion Solution, listed by Nishiitsutsuji-Uwo, J., et al., Biochem. J. 103:852-862 (1967) Hepatocyte Incubation Solution, listed by Crow, K. E., et al., Biochem. J. 172:29-36 (1978) Bahlman Kidney Perfusion Solution, listed by Bahlman, J., et al., Am. J. Physiol. 212:77 (1967) Fulgraff Kidney Perfusion Solution, listed by Fulgraff, et al., Arch. Int. Pharmacodyn. 172:49 (1972)

The optimal choice of electrolyte solution for any particular application will vary with the application, such as, for example, the form of the cells (whether the cells are present as cell suspensions, tissues, or organs) to be treated or protected by the anti-freeze polypeptides, the animal from which the cells are derived, and the conditions to which the cells have been, or are expected to be, exposed.

In embodiments of the invention involving vitrification conditions, the anti-freeze polypeptides are used in combination with vitrifying agents which prevent or inhibit ice crystal formation during solidification of the intracellular and extracellular fluids upon cooling to sub-freezing temperatures. Various vitrifying agents are known in the art, and may be used either individually or in combination with other vitrifying agents or biologically compatible solutes. Examples of vitrifying agents are glycerol, dimethyl sulfoxide, ethylene glycol, polyvinylpyrrolidone, glucose, sucrose, propanediol, butanediol, and carboxymethyl cellulose. Polyhydric alcohols as a class are useful as vitrifying agents. Prominent examples are glycerol, ethylene glycol, propanediol, butanediol, and butanetriol. Concentrations of vitrifying agents may vary widely, depending on the concentrations of other components in the system, the cooling rate and the lowest temperature reached. In general, best results will be obtained with concentrations of from about 5% to about 35% by weight. Vitrification is usually practiced with a rapid cooling rate, such as for example a rate exceeding 100° C./min, and preferably exceeding 1,000° C./min.

In embodiments which involve the use of non-peptide cryoprotectants, without necessarily avoiding the formation of ice crystals, many of the same considerations apply. The agents listed above as examples of vitrifying agents serve as well as cryoprotectants, within similar concentration ranges.

The beneficial effect of the anti-freeze polypeptides on cells and/or cell membranes is achieved by placing the polypeptides in contact with the cells and maintaining such contact throughout, or for a substantial portion of, the period of exposure to otherwise injurious conditions. When the cells are in the form of cell suspensions, contact of this type is achieved by simply adding the polypeptides to the suspension fluid. When the cells are in the form of tissues or organs, contact is achieved by immersing the tissues or organs in a solution of the polypeptides. When the cells are in the form of tissues or organs which contain a vascular system, contact is achieved by perfusing the vascular system with a solution of the polypeptides, and once perfused, holding the polypeptide solution in the vascular system throughout the period of storage, preservation or exposure to the injurious conditions. Methods of perfusion are well known among those skilled in physiology and surgical procedures.

Cells which can benefit from treatment with the anti-freeze polypeptides in accordance with this invention include cells of a wide variety of types. Examples are oocytes, embryos, leukocytes, erythrocytes, platelets, pancreatic islets, and hepatocytes. Organs which can benefit from the present invention are also widely varied. Examples include the liver, kidney, heart, brain, lung, pancreas, spleen, ovary, and stomach. Tissues which can benefit from the invention include tissues of any of these organs, as well as skin tissue, bone marrow tissue, cornea tissue, and a wide range of others. The invention finds applicability to mammals in general, and will be of particular interest and utility when used in connection with human cells, tissues and organs.

The effect of the anti-freeze polypeptides according to the present invention in inhibiting ion transport across cell membranes extends to a variety of ions, with particular interest to $Ca^{++}$, $K^+$ and $Na^+$ ions, as well as two or more of these ions in combination.

Since excessive ion transport is one physiological effect which accompanies hypothermia, the ability of the anti-freeze polypeptides according to the present invention to inhibit ion transport may be related to the ability of the polypeptides to enhance cell viability under hypothermic conditions. Accordingly, the amounts and concentrations of polypeptide administered to achieve the effect of inhibition of ion transport are generally the same or similar to the amounts used in enhancing viability under hypothermic exposure.

The ability of the polypeptides to inhibit ion transport across cell membranes also renders the polypeptides useful in treating diseases and abnormal physiological conditions in which excessive trans-membrane ion transport is present. Examples of such diseases and conditions are cystic fibrosis, Kartagener's Syndrome, diabetes insipidus, diabetes mellitus, and antidiuretic hormone abnormalities. Administration of the polypeptides for this effect may be achieved by ingestion, vascular injection, localized application, and various means in general by which other drugs or treatment agents are administered when used in the treatment or management of these diseases and conditions. Again, the concentrations for useful results are generally the same as those referred to above, and the dosage or frequency of administration will be determined by the degree to which the condition being treated has progressed as well as the observed response to the treatment.

Application of the anti-freeze polypeptides comprising the polypeptide of the present invention also extend to the use of the polypeptides in the preservation of foods which have a cellular structure. Foods of particular interest for this application are meats and meat products, but other types of foods will benefit as well. For purposes of this invention, meats and meat products include fresh meat and poultry, as well as frozen, canned and dried meats and poultry. Many such foods when cooled to avoid spoilage during transport or storage tend to lose turgor, freshness and other qualities which contribute to their taste, mouthfeel and general appeal. These qualities can be preserved by treatment of the foods with solutions of the polypeptides in accordance with the present invention. The mode of treatment will vary from one type of food to the next, but will generally involve equilibration of the food with the polypeptide in solution, either by immersion, perfusion, or any other kind of absorption or other means of achieving prolonged contact. The types of solutions and the methods of immersion and perfusion described above in connection with other applications of the invention will be applicable here as well.

Fluids Comprising Polypeptides According to the Present Invention

The use of the anti-freeze polypeptides according to the present invention as an additive e.g. to fluids and liquids, such as refridgerants and many different types of aqueous solutions is provided in accordance with the present invention in order to prevent freezing of the refridgerant or the aqueous solutions. The feature of preventing freezing of a solution is beneficial in many different technical areas.

Carriers and Solid Supports Linked to the Polypeptides According to the Present Invention A polypeptide according to the present invention can be linked to a carrier, such as a solid support or a semi-solid support. The polypeptide can be covalently or non-covalently linked to any such carrier, for example a surface of a material desirably displaying the polypeptides according to the invention. Surfaces and solid supports according to the invention can comprising one or more polypeptides according to the invention, or functional fragments thereof displaying anti-freeze activity, which are either directly or indirectly attached to the surface, such as a solid or semi-solid support.

Attachment includes in principle all state-of-the-art technologies for covalently or non-covalently attaching a polypeptides to a surface e.g. directly, through a linker residue, through entrapment of the polypeptides in a caged structure, which retains the polypeptides in reactive contact with the surface, or any other way of attaching the polypeptide(s) according to the present invention to a solid support or semi-solid support.

A number of techniques are available for attaching polypeptides to solid or semi-solid supports. The attachment of a polypeptide to a solid surface has e.g. been disclosed by Cordek et al. 1999, Anal. Chem., 71: 1529-1533; Blasi et al. 2005, Enzyme and Microbial Tech., 36: 818-823; Parrado et al. (1995), Proc. Chem., 30(8): 735-741; Yakovleva et al. (2003), Biosensors and Bioelectronics, 19: 21-34; Cao, L., Carrier-bound Immobilized Enzymes. Principles, Applications and Design, Wiley-VCH, 2005; and Immobilization of Enzymes and Cells (Methods in Biotechnology), Birkerstaff, G. F., eds., Humana Press, 1997. Other techniques are also available and well known to the skilled person.

In one aspect of the present invention there is provided a coating composition comprising one or more polypeptides according to the present invention. The coating composition can further comprise one or more further ingredients, including pigments and resins, as disclosed herein below in more detail.

Much attention has been focused on immobilization of biomolecules, including polypeptides, in silicate glass formed by the sol-gel method (Eggers et al., Protein Sci. 2001, 10, 250-261). The process involves hydrolyzing an alkoxide to produce a sol, which then undergoes polycondensation to form a gel. Biomolecules are immobilized by being entrapped in the gel during the sol-to-gel transition. The sol-gel materials offer advantages over more traditional organic polymers for biomolecule entrapment in that these materials have increased mechanical strength, chemical stability, biocompatibility, and resistance to microbial attack.

The sol-gel encapsulation of polypeptides according to the present invention can be performed by using precursors, based around polyol silicates and polyol siloxanes, especially those derived from glycerol. Poly(glyceryl silicate) (PGS) can be prepared and employed for sol-gel bioentrapment of the polypeptides, in an approach distinguished by a high degree of biocompatibility and mild encapsulation conditions, and which enables the reproducible and efficient confinement of the polypeptides inside silica.

The above-disclosed methodology can be extended to metallosilicate, alkylsiloxane, functionalized siloxane, and various composite sol-gels, thereby allowing the fabrication of a physicochemically diverse range of bio-doped polymers comprising the anti-freeze polypeptides according to the present invention.

The hybrid materials according to the present invention preferably display activities approaching those of the free anti-freeze polypeptides, together with high stabilities and robustness that characterize sol-gel bioceramics.

In one aspect of the present invention, a sol-gel process well know to those of ordinary skill in the art is used for attaching the polypeptides according to the invention to the solid or semi-solid support. The sol-gel process is conventional and typically produces a sol-gel glass, which results from an optically transparent amorphous silica or silicate material produced by forming interconnections in a network of colloidal sub-micrometer particles under increasing viscosity until the network becomes completely rigid, with about one-half the density of glass. Accordingly, a sol-gel glass comprising one or more polypeptides according to the invention is also claimed. Reference is made—among others—to Gill and Ballesteros, J. Am. Chem. Soc. 1998, 120, 8587-8598. Solution polymerization to form sol of cross-linked particles is disclosed e.g. in U.S. Pat. No. 5,863,996 and can be used in conjunction with the present invention.

The coating compositions according to another aspect of the present invention preferably comprises a resin which is compatible with the polypeptide(s) according to the present invention—i.e. allows said polypeptides to exert an anti-freeze activity when forming part of the coating composition. Resins are well-known in the art and polypeptide compatible resins are also disclosed in the prior art. See e.g. WO 01/72911 and U.S. Pat. No. 5,998,200.

There is also provided in accordance with the present invention a composition comprising a mesoporous aerogel having a three-dimensional nanoarchitecture comprising the polypeptides according to the present invention. The three-dimensional nanoarchitecture preferably comprises a colloidal metal encapsulating anti-freeze polypeptide bio-composite superstructure which is nano-glued therein. Accordingly, there is also provided a method for making a mesoporous aerogel having a three-dimensional nanostructure with a colloidal metal encapsulating anti-freeze polypeptide biocomposite nanoglued therein, said method comprising the steps of: Forming a metal encapsulating anti-freeze polypeptide biocomposite by mixing together said one or more anti-freeze polypeptides according to the present invention and said colloidal metal; forming a sol, such as a silica sol, by mixing together a catalyst and an alkoxide, such as a silicon alkoxide; forming a gel by mixing together said sol, such as a silica sol, and said biocomposite and allowing said sol to gel; and extracting and supercritically drying said gel with carbon dioxide to form said aerogel with said metal encapsulating anti-freeze polypeptide bio-composite superstructure nano-glued therein. In one embodiment, the mesoporous aerogel is a silica mesoporous aerogel. Reference is made to US 2004/0209338.

Use of the Polypeptides According to the Present Invention in the Inhibition of the Formation of Gas Hydrates.

The polypeptides according to the present invention may also find use in the inhibition of the formation of gas hydrates in the oceans. It is well known that gas hydrates are ice-like crystalline molecular complexes formed from mixtures of water and suitably sized "guest" gas molecules. The water (host) molecules, upon hydrogen bonding, form lattice structures with several interstitial cavities. The guest gas molecules can occupy the lattice cavities, and when a minimum number of cavities are filled, the crystalline structure will become stable and solid gas hydrates will form, even at temperatures well above the melting point of water ice. When gas hydrates dissociate (melt), the crystalline lattice breaks down into liquid water (or converts to ice if conditions are below the freezing point of water) and the gas is released. Commercially, the gas may be utilized for energy production. However, the phenomenon does represent an environmental risk in cases where the gas escapes in a non-controlled manner. This could be in areas where earth crakes appear from time to time.

It is well known that the problem with regard to gas hydrate formation also occurs in pipeline on the bottom of the oceans. However, due to the ice crystal formation inhibiting properties of the polypeptides according to the present invention, it is believed that the presence of said polypeptides may prevent the formation of gas hydrates, due to the fact that the structure of these hydrates are very similar to the structure of ice crystals.

Selected items of the present invention are disclosed herein below.

1. A polypeptide comprising a plurality of consecutively linked amino acid residues, said polypeptide comprising the sequence:

$X_1-X_2-X_3-X_4-X_5-X_6-X_7-X_8-X_9$, (SEQ ID NO: 90)

wherein $X_1$ is selected from the group of amino acid residues consisting of S, A, G and D;

$X_2$ is selected from the group of amino acid residues consisting of A, V, I, T and S;

$X_3$ is selected from the group of amino acid residues consisting of non-bulky amino acid residues;

$X_4$ is selected from the group of amino acid residues consisting of S, I, T and V;

$X_5$ is selected from the group of amino acid residues consisting of S, A, I and T;

$X_6$ is selected from the group of amino acid residues consisting of S, T and V;

$X_7$ is selected from the group of amino acid residues consisting of non-bulky amino acid residues;

$X_8$ is selected from the group of amino acid residues consisting of S, T and V;

$X_9$ is selected from the group of amino acid residues consisting of S, A and G;

wherein at least one of the residues $X_2$, $X_4$, $X_6$ and $X_8$ of SEQ ID NO:90 is T or V;

wherein the total number of amino acid residues of the polypeptide is less than 250; and wherein the polypeptide possesses an ice-binding capability.

2. The polypeptide according to item 1, wherein $X_1$ is S.
3. The polypeptide according to item 1, wherein $X_1$ is A.
4. The polypeptide according to item 1, wherein $X_1$ is G.
5. The polypeptide according to item 1, wherein $X_1$ is D.
6. The polypeptide according to item 1, wherein $X_2$ is A.
7. The polypeptide according to item 1, wherein $X_2$ is V.
8. The polypeptide according to item 1, wherein $X_2$ is I.
9. The polypeptide according to item 1, wherein $X_2$ is T.
10. The polypeptide according to item 1, wherein $X_2$ is S.
11. The polypeptide according to item 1, wherein $X_3$ does not contain a cyclic aliphatic side chain or an aromatic side chain.
12. The polypeptide according to item 1, wherein $X_4$ is S.
13. The polypeptide according to item 1, wherein $X_4$ is I.

14. The polypeptide according to item 1, wherein $X_4$ is T.
15. The polypeptide according to item 1, wherein $X_4$ is V.
16. The polypeptide according to item 1, wherein $X_5$ is S.
17. The polypeptide according to item 1, wherein $X_5$ A.
18. The polypeptide according to item 1, wherein $X_5$ I.
19. The polypeptide according to item 1, wherein $X_5$ T.
20. The polypeptide according to item 1, wherein $X_6$ is S
21. The polypeptide according to item 1, wherein $X_6$ is T.
22. The polypeptide according to item 1, wherein $X_6$ is V.
23. The polypeptide according to item 1, wherein $X_7$ does not contain a cyclic aliphatic side chain or an aromatic side chain.
24. The polypeptide according to item 1, wherein $X_8$ is S.
25. The polypeptide according to item 1, wherein $X_8$ is T.
26. The polypeptide according to item 1, wherein $X_8$ is V.
27. The polypeptide according to item 1, wherein $X_9$ is S.
28. The polypeptide according to item 1, wherein $X_9$ is A.
29. The polypeptide according to item 1, wherein $X_9$ is G.
30. The polypeptide according to item 1, wherein at least one of the residues $X_2$, $X_4$, $X_6$ and $X_8$ of SEQ ID NO:90 is T.
31. The polypeptide according to item 1, wherein at least two of the residues $X_2$, $X_4$, $X_6$ and $X_8$ of SEQ ID NO:90 are T.
32. The polypeptide according to item 1, wherein at least three of the residues $X_2$, $X_4$, $X_6$ and $X_8$ of SEQ ID NO:90 are T.
33. The polypeptide according to item 1, wherein all four of the residues $X_2$, $X_4$, $X_6$ and $X_8$ of SEQ ID NO:90 are T.
34. The polypeptide according to item 1, wherein at least one of the residues $X_2$, $X_4$, $X_6$ and $X_8$ of SEQ ID NO:90 is V.
35. The polypeptide according to item 1, wherein at least two of the residues $X_2$, $X_4$, $X_6$ and $X_8$ of SEQ ID NO:90 are V.
36. The polypeptide according to item 1, wherein at least three of the residues $X_2$, $X_4$, $X_6$ and $X_8$ of SEQ ID NO:90 are V.
37. The polypeptide according to item 1, wherein all four of the residues $X_2$, $X_4$, $X_6$ and $X_8$ of SEQ ID NO:90 are V.
38. The polypeptide according to item 1, wherein the maximum number of amino acid residues of the polypeptide is less than 240, such as less than 230, for example less than 220, such as less than 210, for example less than 200, such as less than 190, for example less than 180, such as less than 150, for example less than 140, such as less than 130, for example less than 120, such as less than 110, for example less than 100, such as less than 95, for example less than 90, such as less than 85, for example less than 80, such as less than 75, for example less than 70, such as less than 65, for example less than 60, such as less than 55, for example less than 50, such as less than 45, for example less than 40, such as less than 30, for example less than 20, such as less than 15.
39. The polypeptide according to item 1, wherein the minimum number of amino acid residues of the polypeptide is 10 or more, such as 12 or more, for example 14 or more, such as 16 or more, for example 18 or more, such as 20 or more, for example 22 or more, such as 24 or more, for example 26 or more, such as 28 or more, for example 30 or more, such as 32 or more, for example 34 or more, such as 36 or more, for example 38 or more, such as 40 or more, for example 42 or more, such as 44 or more, for example 46 or more, such as 48 or more, for example 50 or more, such as 55 or more, for example 60 or more, such as 65 or more, for example 70 or more, such as 75 or more, for example 80 or more, such as 85 or more, for example 90 or more, such as 95 or more, for example 100 or more.
40. The polypeptide according to item 1 further comprising a second copy of SEQ ID NO:90, which does not overlap with the first copy of SEQ ID NO:90, wherein the second copy of SEQ ID NO:90 comprises the sequence:

$X_a$-$X_b$-$X_c$-$X_d$-$X_e$-$X_f$-$X_g$-$X_h$-$X_i$,     (SEQ ID NO: 90)

wherein
   $X_a$ is selected from the group of amino acid residues consisting of S, A, G and D;
   $X_b$ is selected from the group of amino acid residues consisting of A, V, I, T and S;
   $X_c$ is selected from the group of amino acid residues consisting of non-bulky amino acid residues;
   $X_d$ is selected from the group of amino acid residues consisting of S, I, T and V;
   $X_e$ is selected from the group of amino acid residues consisting of S, A, I and T;
   $X_f$ is selected from the group of amino acid residues consisting of S, T and V;
   $X_g$ is selected from the group of amino acid residues consisting of non-bulky amino acid residues;
   $X_h$ is selected from the group of amino acid residues consisting of S, T and V;
   $X_i$ is selected from the group of amino acid residues consisting of S, A and G; wherein at least one of the residues $X_b$, $X_d$, $X_f$ and $X_h$ of SEQ ID NO:90 is T or V.
41. The polypeptide according to item 40, wherein $X_a$ is S.
42. The polypeptide according to item 40, wherein $X_a$ is A.
43. The polypeptide according to item 40, wherein $X_a$ is G.
44. The polypeptide according to item 40, wherein $X_a$ is D.
45. The polypeptide according to item 40, wherein $X_b$ is A.
46. The polypeptide according to item 40, wherein $X_b$ is V.
47. The polypeptide according to item 40, wherein $X_b$ is I.
48. The polypeptide according to item 40, wherein $X_b$ is T.
49. The polypeptide according to item 40, wherein $X_b$ is S.
50. The polypeptide according to item 40, wherein $X_c$ does not contain a cyclic aliphatic side chain or an aromatic side chain.
51. The polypeptide according to item 40, wherein $X_d$ is S.
52. The polypeptide according to item 40, wherein $X_d$ is I.
53. The polypeptide according to item 40, wherein $X_d$ is T.
54. The polypeptide according to item 40, wherein $X_d$ is V.
55. The polypeptide according to item 40, wherein $X_e$ is S.
56. The polypeptide according to item 40, wherein $X_e$ A.
57. The polypeptide according to item 40, wherein $X_e$ I.
58. The polypeptide according to item 40, wherein $X_e$ T.
59. The polypeptide according to item 40, wherein $X_f$ is S
60. The polypeptide according to item 40, wherein $X_f$ is T.
61. The polypeptide according to item 40, wherein $X_f$ is V.
62. The polypeptide according to item 40, wherein $X_g$ does not contain a cyclic aliphatic side chain or an aromatic side chain.
63. The polypeptide according to item 40, wherein $X_h$ is S.
64. The polypeptide according to item 40, wherein $X_h$ is T.
65. The polypeptide according to item 40, wherein $X_h$ is V.
66. The polypeptide according to item 40, wherein $X_i$ is S.
67. The polypeptide according to item 40, wherein $X_i$ is A.
68. The polypeptide according to item 40, wherein $X_i$ is G.
69. The polypeptide according to item 40, wherein at least one of the residues $X_b$, $X_d$, $X_f$ and $X_h$ of SEQ ID NO:90 is T.

70. The polypeptide according to item 40, wherein at least two of the residues $X_b$, $X_d$, $X_f$ and $X_h$ of SEQ ID NO:90 are T.
71. The polypeptide according to item 40, wherein at least three of the residues $X_b$, $X_d$, $X_f$ and $X_h$ of SEQ ID NO:90 are T.
72. The polypeptide according to item 40, wherein all four of the residues $X_b$, $X_d$, $X_f$ and $X_h$ of SEQ ID NO:90 are T.
73. The polypeptide according to item 40, wherein at least one of the residues $X_b$, $X_d$, $X_f$ and $X_h$ of SEQ ID NO:90 is V.
74. The polypeptide according to item 40, wherein at least two of the residues $X_b$, $X_d$, $X_f$ and $X_h$ of SEQ ID NO:90 are V.
75. The polypeptide according to item 40, wherein at least three of the residues $X_b$, $X_d$, $X_f$ and $X_h$ of SEQ ID NO:90 are V.
76. The polypeptide according to item 40, wherein all four of the residues $X_b$, $X_d$, $X_f$ and $X_h$ of SEQ ID NO:90 are V.
77. The polypeptide according to item 40, wherein the first and second copy of SEQ ID NO:90 are separated by one or more amino acid residues.
78. The polypeptide according to item 40, wherein the first and second copies of SEQ ID NO:90 are separated by 2 amino acid residues, such as 3 amino acid residues, for example 4 amino acid residues, such as 5 amino acid residues, for example 6 amino acid residues, such as 7 amino acid residues, for example 8 amino acid residues, such as 9 amino acid residues, for example 10 amino acid residues, such as 11 amino acid residues, for example 12 amino acid residues, such as 13 amino acid residues, for example 14 amino acid residues, such as 15 amino acid residues, for example 16 amino acid residues, such as 17 amino acid residues, for example 18 amino acid residues, such as 19 amino acid residues, for example 20 amino acid residues, such as 21 amino acid residues, for example 22 amino acid residues, such as 23 amino acid residues, for example 24 amino acid residues, such as 25 amino acid residues, for example 26 amino acid residues, such as 27 amino acid residues, for example 28 amino acid residues, such as 29 amino acid residues, for example 30 amino acid residues.
79. The polypeptide according to item 40, wherein the first and second copies of SEQ ID NO:90 are separated by at least 2 amino acid residues, such as at least 3 amino acid residues, for example at least 4 amino acid residues, such as at least 5 amino acid residues, for example at least 6 amino acid residues, such as at least 7 amino acid residues, for example at least 8 amino acid residues, such as at least 9 amino acid residues, for example at least 10 amino acid residues, such as at least 11 amino acid residues, for example at least 12 amino acid residues, such as at least 13 amino acid residues, for example at least 14 amino acid residues, such as at least 15 amino acid residues, for example at least 16 amino acid residues, such as at least 17 amino acid residues, for example at least 18 amino acid residues, such as at least 19 amino acid residues, for example at least 20 amino acid residues, such as at least 21 amino acid residues, for example at least 22 amino acid residues, such as at least 23 amino acid residues, for example at least 24 amino acid residues, such as at least 25 amino acid residues, for example at least 26 amino acid residues, such as at least 27 amino acid residues, for example at least 28 amino acid residues, such as at least 29 amino acid residues, for example at least 30 amino acid residues.
80. The polypeptide according to item 40, wherein the first and second copies of SEQ ID NO:90 are separated by less than 100 amino acid residues, such as less than 95 amino acid residues, for example less than 90 amino acid residues, such as less than 85 amino acid residues, for example less than 80 amino acid residues, such as less than 75 amino acid residues, for example less than 70 amino acid residues, such as less than 65 amino acid residues, for example less than 60 amino acid residues, such as less than 55 amino acid residues, for example less than 50 amino acid residues, such as less than 45 amino acid residues, for example less than 40 amino acid residues, such as less than 35 amino acid residues, for example less than 30 amino acid residues, such as less than 25 amino acid residues, for example less than 24 amino acid residues, such as less than 23 amino acid residues, for example less than 22 amino acid residues, such as less than 21 amino acid residues, for example less than 20 amino acid residues, such as less than 19 amino acid residues, for example less than 18 amino acid residues, such as less than 17 amino acid residues, for example less than 16 amino acid residues, such as less than 15 amino acid residues, for example less than 14 amino acid residues, such as less than 13 amino acid residues, for example less than 12 amino acid residues, such as less than 11 amino acid residues, for example less than 10 amino acid residues, such as less than 9 amino acid residues, for example less than 8 amino acid residues, such as less than 7 amino acid residues, for example less than 6 amino acid residues, such as less than 5 amino acid residues.
81. The polypeptide according to item 40, wherein the first copy of SEQ ID NO:90 is located N-terminally to the second copy of SEQ ID NO:90.
82. The polypeptide according to item 40, wherein the second copy of SEQ ID NO:90 is located N-terminally to the first copy of SEQ ID NO:90.
83. The polypeptide according to item 40 further comprising a third copy of SEQ ID NO:90, which does not overlap with the first and second copy of SEQ ID NO:90, wherein the third copy of SEQ ID NO:90 comprises the sequence:

$X_{aa}-X_{ba}-X_{ca}-X_{da}-X_{ea}-X_{fa}-X_{ga}-X_{ha}-X_{ia}$, (SEQ ID NO: 90)

wherein $X_{aa}$ is selected from the group of amino acid residues consisting of S, A, G and D;

$X_{ba}$ is selected from the group of amino acid residues consisting of A, V, I, T and S;

$X_{ca}$ is selected from the group of amino acid residues consisting of non-bulky amino acid residues;

$X_{da}$ is selected from the group of amino acid residues consisting of S, I, T and V;

$X_{ea}$ is selected from the group of amino acid residues consisting of S, A, I and T;

$X_{fa}$ is selected from the group of amino acid residues consisting of S, T and V; $X_{ga}$ is selected from the group of amino acid residues consisting of non-bulky amino acid residues;

$X_{ha}$ is selected from the group of amino acid residues consisting of S, T and V;

$X_{ia}$ is selected from the group of amino acid residues consisting of S, A and G; wherein at least one of the residues $X_{ba}$, $X_{da}$, $X_{fa}$ and $X_{ha}$ of SEQ ID NO:90 is T or V.

84. The polypeptide according to item 83, wherein $X_{aa}$ is S.
85. The polypeptide according to item 83, wherein $X_{aa}$ is A.
86. The polypeptide according to item 83, wherein $X_{aa}$ is G.
87. The polypeptide according to item 83, wherein $X_{aa}$ is D.
88. The polypeptide according to item 83, wherein $X_{ba}$ is A.
89. The polypeptide according to item 83, wherein $X_{ba}$ is V.
90. The polypeptide according to item 83, wherein $X_{ba}$ is I.
91. The polypeptide according to item 83, wherein $X_{ba}$ is T.
92. The polypeptide according to item 83, wherein $X_{ba}$ is S.
93. The polypeptide according to item 83, wherein $X_{ca}$ does not contain a cyclic aliphatic side chain or an aromatic side chain.
94. The polypeptide according to item 83, wherein $X_{da}$ is S.
95. The polypeptide according to item 83, wherein $X_{da}$ is I.
96. The polypeptide according to item 83, wherein $X_{da}$ is T.
97. The polypeptide according to item 83, wherein $X_{da}$ is V.
98. The polypeptide according to item 83, wherein $X_{ea}$ is S.
99. The polypeptide according to item 83, wherein $X_{ea}$ A.
100. The polypeptide according to item 83, wherein $X_{ea}$ I.
101. The polypeptide according to item 83, wherein $X_{ea}$ T.
102. The polypeptide according to item 83, wherein $X_{fa}$ is S
103. The polypeptide according to item 83, wherein $X_{fa}$ is T.
104. The polypeptide according to item 83, wherein $X_{fa}$ is V.
105. The polypeptide according to item 83, wherein $X_{ga}$ does not contain a cyclic aliphatic side chain or an aromatic side chain.
106. The polypeptide according to item 83, wherein $X_{ha}$ is S.
107. The polypeptide according to item 83, wherein $X_{ha}$ is T.
108. The polypeptide according to item 83, wherein $X_{ha}$ is V.
109. The polypeptide according to item 83, wherein $X_{ia}$ is S.
110. The polypeptide according to item 83, wherein $X_{ia}$ is A.
111. The polypeptide according to item 83, wherein $X_{ia}$ is G.
112. The polypeptide according to item 83, wherein at least one of the residues $X_{ba}$, $X_{da}$, $X_{fa}$ and $X_{ha}$ of SEQ ID NO:90 is T.
113. The polypeptide according to item 83, wherein at least two of the residues $X_{ba}$, $X_{da}$, $X_{fa}$ and $X_{ha}$ of SEQ ID NO:90 are T.
114. The polypeptide according to item 83, wherein at least three of the residues $X_{ba}$, $X_{da}$, $X_{fa}$ and $X_{ha}$ of SEQ ID NO:90 are T.
115. The polypeptide according to item 83, wherein all four of the residues $X_{ba}$, $X_{da}$, $X_{fa}$ and $X_{ha}$ of SEQ ID NO:90 are T.
116. The polypeptide according to item 83, wherein at least one of the residues $X_{ba}$, $X_{da}$, $X_{fa}$ and $X_{ha}$ of SEQ ID NO:90 is V.
117. The polypeptide according to item 83, wherein at least two of the residues $X_{ba}$, $X_{da}$, $X_{fa}$ and $X_{ha}$ of SEQ ID NO:90 are V.
118. The polypeptide according to item 83, wherein at least three of the residues $X_{ba}$, $X_{da}$, $X_{fa}$ and $X_{ha}$ of SEQ ID NO:90 are V.
119. The polypeptide according to item 83, wherein all four of the residues $X_{ba}$, $X_{da}$, $X_{fa}$ and $X_{ha}$ of SEQ ID NO:90 are V.
120. The polypeptide according to item 83, wherein the different copies of SEQ ID NO:90 are separated by one or more amino acid residues.
121. The polypeptide according to item 83, wherein the second and the third copy of SEQ ID NO:90 are separated by one or more amino acid residues.
122. The polypeptide according to item 83, wherein the first copy of SEQ ID NO:90 and the third copy of SEQ ID NO:90 are separated by 2 amino acid residues, such as 3 amino acid residues, for example 4 amino acid residues, such as 5 amino acid residues, for example 6 amino acid residues, such as 7 amino acid residues, for example 8 amino acid residues, such as 9 amino acid residues, for example 10 amino acid residues, such as 11 amino acid residues, for example 12 amino acid residues, such as 13 amino acid residues, for example 14 amino acid residues, such as 15 amino acid residues, for example 16 amino acid residues, such as 17 amino acid residues, for example 18 amino acid residues, such as 19 amino acid residues, for example 20 amino acid residues, such as 21 amino acid residues, for example 22 amino acid residues, such as 23 amino acid residues, for example 24 amino acid residues, such as 25 amino acid residues, for example 26 amino acid residues, such as 27 amino acid residues, for example 28 amino acid residues, such as 29 amino acid residues, for example 30 amino acid residues.
123. The polypeptide according to item 83, wherein the first copy of SEQ ID NO:90 and the third copy of SEQ ID NO:90 are separated by at least 2 amino acid residues, such as at least 3 amino acid residues, for example at least 4 amino acid residues, such as at least 5 amino acid residues, for example at least 6 amino acid residues, such as at least 7 amino acid residues, for example at least 8 amino acid residues, such as at least 9 amino acid residues, for example at least 10 amino acid residues, such as at least 11 amino acid residues, for example at least 12 amino acid residues, such as at least 13 amino acid residues, for example at least 14 amino acid residues, such as at least 15 amino acid residues, for example at least 16 amino acid residues, such as at least 17 amino acid residues, for example at least 18 amino acid residues, such as at least 19 amino acid residues, for example at least 20 amino acid residues, such as at least 21 amino acid residues, for example at least 22 amino acid residues, such as at least 23 amino acid residues, for example at least 24 amino acid residues, such as at least 25 amino acid residues, for example at least 26 amino acid residues, such as at least 27 amino acid residues, for example at least 28 amino acid residues, such as at least 29 amino acid residues, for example at least 30 amino acid residues.
124. The polypeptide according to item 83, wherein the second copy of SEQ ID NO:90 and the third copy of SEQ ID NO:90 are separated by 2 amino acid residues, such as 3 amino acid residues, for example 4 amino acid residues, such as 5 amino acid residues, for example 6 amino acid residues, such as 7 amino acid residues, for example 8 amino acid residues, such as 9 amino acid residues, for example 10 amino acid residues, such as 11 amino acid residues, for example 12 amino acid residues, such as 13 amino acid residues, for example 14 amino acid residues, such as 15 amino acid residues, for example 16 amino acid residues, such as 17 amino acid residues, for example 18 amino acid residues, such as 19 amino acid residues, for example 20 amino acid residues, such as 21 amino acid residues, for example 22 amino acid residues, such as 23 amino acid residues, for example 24 amino acid residues, such as 25 amino acid residues, for example 26 amino acid residues, such as 27 amino acid residues, for example 28 amino acid residues, such as 29 amino acid residues, for example 30 amino acid residues.

125. The polypeptide according to item 83, wherein the second copy of SEQ ID NO:90 and the third copy of SEQ ID NO:90 are separated by at least 2 amino acid residues, such as at least 3 amino acid residues, for example at least 4 amino acid residues, such as at least 5 amino acid residues, for example at least 6 amino acid residues, such as at least 7 amino acid residues, for example at least 8 amino acid residues, such as at least 9 amino acid residues, for example at least 10 amino acid residues, such as at least 11 amino acid residues, for example at least 12 amino acid residues, such as at least 13 amino acid residues, for example at least 14 amino acid residues, such as at least 15 amino acid residues, for example at least 16 amino acid residues, such as at least 17 amino acid residues, for example at least 18 amino acid residues, such as at least 19 amino acid residues, for example at least 20 amino acid residues, such as at least 21 amino acid residues, for example at least 22 amino acid residues, such as at least 23 amino acid residues, for example at least 24 amino acid residues, such as at least 25 amino acid residues, for example at least 26 amino acid residues, such as at least 27 amino acid residues, for example at least 28 amino acid residues, such as at least 29 amino acid residues, for example at least 30 amino acid residues.

126. The polypeptide according to item 83, wherein the first copy of SEQ ID NO:90 and the third copy of SEQ ID NO:90 are separated by less than 100 amino acid residues, such as less than 95 amino acid residues, for example less than 90 amino acid residues, such as less than 85 amino acid residues, for example less than 80 amino acid residues, such as less than 75 amino acid residues, for example less than 70 amino acid residues, such as less than 65 amino acid residues, for example less than 60 amino acid residues, such as less than 55 amino acid residues, for example less than 50 amino acid residues, such as less than 45 amino acid residues, for example less than 40 amino acid residues, such as less than 35 amino acid residues, for example less than 30 amino acid residues, such as less than 25 amino acid residues, for example less than 24 amino acid residues, such as less than 23 amino acid residues, for example less than 22 amino acid residues, such as less than 21 amino acid residues, for example less than 20 amino acid residues, such as less than 19 amino acid residues, for example less than 18 amino acid residues, such as less than 17 amino acid residues, for example less than 16 amino acid residues, such as less than 15 amino acid residues, for example less than 14 amino acid residues, such as less than 13 amino acid residues, for example less than 12 amino acid residues, such as less than 11 amino acid residues, for example less than 10 amino acid residues, such as less than 9 amino acid residues, for example less than 8 amino acid residues, such as less than 7 amino acid residues, for example less than 6 amino acid residues, such as less than 5 amino acid residues.

127. The polypeptide according to item 83, wherein the second copy of SEQ ID NO:90 and the third copy of SEQ ID NO:90 are separated by less than 100 amino acid residues, such as less than 95 amino acid residues, for example less than 90 amino acid residues, such as less than 85 amino acid residues, for example less than 80 amino acid residues, such as less than 75 amino acid residues, for example less than 70 amino acid residues, such as less than 65 amino acid residues, for example less than 60 amino acid residues, such as less than 55 amino acid residues, for example less than 50 amino acid residues, such as less than 45 amino acid residues, for example less than 40 amino acid residues, such as less than 35 amino acid residues, for example less than 30 amino acid residues, such as less than 25 amino acid residues, for example less than 24 amino acid residues, such as less than 23 amino acid residues, for example less than 22 amino acid residues, such as less than 21 amino acid residues, for example less than 20 amino acid residues, such as less than 19 amino acid residues, for example less than 18 amino acid residues, such as less than 17 amino acid residues, for example less than 16 amino acid residues, such as less than 15 amino acid residues, for example less than 14 amino acid residues, such as less than 13 amino acid residues, for example less than 12 amino acid residues, such as less than 11 amino acid residues, for example less than 10 amino acid residues, such as less than 9 amino acid residues, for example less than 8 amino acid residues, such as less than 7 amino acid residues, for example less than 6 amino acid residues, such as less than 5 amino acid residues.

128. The polypeptide according to item 83, wherein the third copy of SEQ ID NO:90 is located N-terminally to both the first copy of SEQ ID NO:90 and the second copy of SEQ ID NO:90.

129. The polypeptide according to item 83, wherein the third copy of SEQ ID NO:90 is located N-terminally to the first copy of SEQ ID NO:90 and C-terminally to the second copy of SEQ ID NO:90.

130. The polypeptide according to item 83, wherein the third copy of SEQ ID NO:90 is located N-terminally to the second copy of SEQ ID NO:90 and C-terminally to the first copy of SEQ ID NO:90.

131. The polypeptide according to item 83, wherein the third copy of SEQ ID NO:90 is located C-terminally to both the first copy of SEQ ID NO:90 and the second copy of SEQ ID NO:90.

132. The polypeptide according to item 83 further comprising a fourth copy of SEQ ID NO:90, which does not overlap with any of the first, second and third copies of SEQ ID NO:90, wherein the fourth copy of SEQ ID NO:90 comprises the sequence:

$$X_{ab}\text{-}X_{bb}\text{-}X_{cb}\text{-}X_{db}\text{-}X_{eb}\text{-}X_{fb}\text{-}X_{gb}\text{-}X_{hb}\text{-}X_{ib},  \quad \text{(SEQ ID NO: 90)}$$

wherein $X_{ab}$ is selected from the group of amino acid residues consisting of S, A, G and D;

$X_{bb}$ is selected from the group of amino acid residues consisting of A, V, I, T and S;

$X_{cb}$ is selected from the group of amino acid residues consisting of non-bulky amino acid residues;

$X_{db}$ is selected from the group of amino acid residues consisting of S, I, T and V;

$X_{eb}$ is selected from the group of amino acid residues consisting of S, A, I and T;

$X_{fb}$ is selected from the group of amino acid residues consisting of S, T and V;

$X_{gb}$ is selected from the group of amino acid residues consisting of non-bulky amino acid residues;

$X_{hb}$ is selected from the group of amino acid residues consisting of S, T and V;

$X_{ib}$ is selected from the group of amino acid residues consisting of S, A and G;

wherein at least one of the residues $X_{bb}$, $X_{db}$, $X_{fb}$, and $X_{hb}$ of SEQ ID NO:90 is T or V.

133. The polypeptide according to item 83, wherein $X_{ab}$ is S.
134. The polypeptide according to item 83, wherein $X_{ab}$ is A.
135. The polypeptide according to item 83, wherein $X_{ab}$ is G.
136. The polypeptide according to item 83, wherein $X_{ab}$ is D.
137. The polypeptide according to item 83, wherein $X_{bb}$ is A.
138. The polypeptide according to item 83, wherein $X_{bb}$ is V.
139. The polypeptide according to item 83, wherein $X_{bb}$ is I.
140. The polypeptide according to item 83, wherein $X_{bb}$ is T.
141. The polypeptide according to item 83, wherein $X_{bb}$ is S.
142. The polypeptide according to item 83, wherein $X_{cb}$ does not contain a cyclic aliphatic side chain or an aromatic side chain.
143. The polypeptide according to item 83, wherein $X_{db}$ is S.
144. The polypeptide according to item 83, wherein $X_{db}$ is I.
145. The polypeptide according to item 83, wherein $X_{db}$ is T.
146. The polypeptide according to item 83, wherein $X_{db}$ is V.
147. The polypeptide according to item 83, wherein $X_{eb}$ is S.
148. The polypeptide according to item 83, wherein $X_{eb}$ A.
149. The polypeptide according to item 83, wherein $X_{eb}$ I.
150. The polypeptide according to item 83, wherein $X_{eb}$ T.
151. The polypeptide according to item 83, wherein $X_{fb}$ is S
152. The polypeptide according to item 83, wherein $X_{fb}$ is T.
153. The polypeptide according to item 83, wherein $X_{fb}$ is V.
154. The polypeptide according to item 83, wherein $X_{gb}$ does not contain a cyclic aliphatic side chain or an aromatic side chain.
155. The polypeptide according to item 83, wherein $X_{hb}$ is S.
156. The polypeptide according to item 83, wherein $X_{hb}$ is T.
157. The polypeptide according to item 83, wherein $X_{hb}$ is V.
158. The polypeptide according to item 83, wherein $X_{ib}$ is S.
159. The polypeptide according to item 83, wherein $X_{ib}$ is A.
160. The polypeptide according to item 83, wherein $X_{ib}$ is G.
161. The polypeptide according to item 83, wherein at least one of the residues $X_{bb}$, $X_{db}$, $X_{fb}$, and $X_{hb}$ of SEQ ID NO:90 is T.
162. The polypeptide according to item 83, wherein at least two of the residues $X_{bb}$, $X_{db}$, $X_{fb}$, and $X_{hb}$ of SEQ ID NO:90 are T.
163. The polypeptide according to item 83, wherein at least three of the residues $X_{bb}$, $X_{db}$, $X_{fb}$, and $X_{hb}$ of SEQ ID NO:90 are T.
164. The polypeptide according to item 83, wherein all four of the residues $X_{bb}$, $X_{db}$, $X_{fb}$, and $X_{hb}$ of SEQ ID NO:90 are T.
165. The polypeptide according to item 83, wherein at least one of the residues $X_{bb}$, $X_{db}$, $X_{fb}$, and $X_{hb}$ of SEQ ID NO:90 is V.
166. The polypeptide according to item 83, wherein at least two of the residues $X_{bb}$, $X_{db}$, $X_{fb}$, and $X_{hb}$ of SEQ ID NO:90 are V.
167. The polypeptide according to item 83, wherein at least three of the residues $X_{bb}$, $X_{db}$, $X_{fb}$, and $X_{hb}$ of SEQ ID NO:90 are V.
168. The polypeptide according to item 83, wherein all four of the residues $X_{bb}$, $X_{db}$, $X_{fb}$, and $X_{hb}$ of SEQ ID NO:90 are V.
169. The polypeptide according to item 83, wherein the first copy of SEQ ID NO:90 and the fourth copy of SEQ ID NO:90 are separated by one or more amino acid residues.
170. The polypeptide according to item 83, wherein the second copy of SEQ ID NO:90 and the fourth copy of SEQ ID NO:90 are separated by one or more amino acid residues.
171. The polypeptide according to item 83, wherein the third copy of SEQ ID NO:90 and the fourth copy of SEQ ID NO:90 are separated by one or more amino acid residues.
172. The polypeptide according to item 83, wherein the first copy of SEQ ID NO:90 and the fourth copy of SEQ ID NO:90 are separated by 2 amino acid residues, such as 3 amino acid residues, for example 4 amino acid residues, such as 5 amino acid residues, for example 6 amino acid residues, such as 7 amino acid residues, for example 8 amino acid residues, such as 9 amino acid residues, for example 10 amino acid residues, such as 11 amino acid residues, for example 12 amino acid residues, such as 13 amino acid residues, for example 14 amino acid residues, such as 15 amino acid residues, for example 16 amino acid residues, such as 17 amino acid residues, for example 18 amino acid residues, such as 19 amino acid residues, for example 20 amino acid residues, such as 21 amino acid residues, for example 22 amino acid residues, such as 23 amino acid residues, for example 24 amino acid residues, such as 25 amino acid residues, for example 26 amino acid residues, such as 27 amino acid residues, for example 28 amino acid residues, such as 29 amino acid residues, for example 30 amino acid residues.
173. The polypeptide according to item 83, wherein the second copy of SEQ ID NO:90 and the fourth copy of SEQ ID NO:90 are separated by 2 amino acid residues, such as 3 amino acid residues, for example 4 amino acid residues, such as 5 amino acid residues, for example 6 amino acid residues, such as 7 amino acid residues, for example 8 amino acid residues, such as 9 amino acid residues, for example 10 amino acid residues, such as 11 amino acid residues, for example 12 amino acid residues, such as 13 amino acid residues, for example 14 amino acid residues, such as 15 amino acid residues, for example 16 amino acid residues, such as 17 amino acid residues, for example 18 amino acid residues, such as 19 amino acid residues, for example 20 amino acid residues, such as 21 amino acid residues, for example 22 amino acid residues, such as 23 amino acid residues, for example 24 amino acid residues, such as 25 amino acid residues, for example 26 amino acid residues, such as 27 amino acid residues, for example 28 amino acid residues, such as 29 amino acid residues, for example 30 amino acid residues.

174. The polypeptide according to item 83, wherein the third copy of SEQ ID NO:90 and the fourth copy of SEQ ID NO:90 are separated by 2 amino acid residues, such as 3 amino acid residues, for example 4 amino acid residues, such as 5 amino acid residues, for example 6 amino acid residues, such as 7 amino acid residues, for example 8 amino acid residues, such as 9 amino acid residues, for example 10 amino acid residues, such as 11 amino acid residues, for example 12 amino acid residues, such as 13 amino acid residues, for example 14 amino acid residues, such as 15 amino acid residues, for example 16 amino acid residues, such as 17 amino acid residues, for example 18 amino acid residues, such as 19 amino acid residues, for example 20 amino acid residues, such as 21 amino acid residues, for example 22 amino acid residues, such as 23 amino acid residues, for example 24 amino acid residues, such as 25 amino acid residues, for example 26 amino acid residues, such as 27 amino acid residues, for example 28 amino acid residues, such as 29 amino acid residues, for example 30 amino acid residues.

175. The polypeptide according to item 83, wherein the first copy of SEQ ID NO:90 and the fourth copy of SEQ ID NO:90 are separated by at least 2 amino acid residues, such as at least 3 amino acid residues, for example at least 4 amino acid residues, such as at least 5 amino acid residues, for example at least 6 amino acid residues, such as at least 7 amino acid residues, for example at least 8 amino acid residues, such as at least 9 amino acid residues, for example at least 10 amino acid residues, such as at least 11 amino acid residues, for example at least 12 amino acid residues, such as at least 13 amino acid residues, for example at least 14 amino acid residues, such as at least 15 amino acid residues, for example at least 16 amino acid residues, such as at least 17 amino acid residues, for example at least 18 amino acid residues, such as at least 19 amino acid residues, for example at least 20 amino acid residues, such as at least 21 amino acid residues, for example at least 22 amino acid residues, such as at least 23 amino acid residues, for example at least 24 amino acid residues, such as at least 25 amino acid residues, for example at least 26 amino acid residues, such as at least 27 amino acid residues, for example at least 28 amino acid residues, such as at least 29 amino acid residues, for example at least 30 amino acid residues.

176. The polypeptide according to item 83, wherein the second copy of SEQ ID NO:90 and the fourth copy of SEQ ID NO:90 are separated by at least 2 amino acid residues, such as at least 3 amino acid residues, for example at least 4 amino acid residues, such as at least 5 amino acid residues, for example at least 6 amino acid residues, such as at least 7 amino acid residues, for example at least 8 amino acid residues, such as at least 9 amino acid residues, for example at least 10 amino acid residues, such as at least 11 amino acid residues, for example at least 12 amino acid residues, such as at least 13 amino acid residues, for example at least 14 amino acid residues, such as at least 15 amino acid residues, for example at least 16 amino acid residues, such as at least 17 amino acid residues, for example at least 18 amino acid residues, such as at least 19 amino acid residues, for example at least 20 amino acid residues, such as at least 21 amino acid residues, for example at least 22 amino acid residues, such as at least 23 amino acid residues, for example at least 24 amino acid residues, such as at least 25 amino acid residues, for example at least 26 amino acid residues, such as at least 27 amino acid residues, for example at least 28 amino acid residues, such as at least 29 amino acid residues, for example at least 30 amino acid residues.

177. The polypeptide according to item 83, wherein the third copy of SEQ ID NO:90 and the fourth copy of SEQ ID NO:90 are separated by at least 2 amino acid residues, such as at least 3 amino acid residues, for example at least 4 amino acid residues, such as at least 5 amino acid residues, for example at least 6 amino acid residues, such as at least 7 amino acid residues, for example at least 8 amino acid residues, such as at least 9 amino acid residues, for example at least 10 amino acid residues, such as at least 11 amino acid residues, for example at least 12 amino acid residues, such as at least 13 amino acid residues, for example at least 14 amino acid residues, such as at least 15 amino acid residues, for example at least 16 amino acid residues, such as at least 17 amino acid residues, for example at least 18 amino acid residues, such as at least 19 amino acid residues, for example at least 20 amino acid residues, such as at least 21 amino acid residues, for example at least 22 amino acid residues, such as at least 23 amino acid residues, for example at least 24 amino acid residues, such as at least 25 amino acid residues, for example at least 26 amino acid residues, such as at least 27 amino acid residues, for example at least 28 amino acid residues, such as at least 29 amino acid residues, for example at least 30 amino acid residues.

178. The polypeptide according to item 83, wherein the first copy of SEQ ID NO:90 and the fourth copy of SEQ ID NO:90 are separated by less than 100 amino acid residues, such as less than 95 amino acid residues, for example less than 90 amino acid residues, such as less than 85 amino acid residues, for example less than 80 amino acid residues, such as less than 75 amino acid residues, for example less than 70 amino acid residues, such as less than 65 amino acid residues, for example less than 60 amino acid residues, such as less than 55 amino acid residues, for example less than 50 amino acid residues, such as less than 45 amino acid residues, for example less than 40 amino acid residues, such as less than 35 amino acid residues, for example less than 30 amino acid residues, such as less than 25 amino acid residues, for example less than 24 amino acid residues, such as less than 23 amino acid residues, for example less than 22 amino acid residues, such as less than 21 amino acid residues, for example less than 20 amino acid residues, such as less than 19 amino acid residues, for example less than 18 amino acid residues, such as less than 17 amino acid residues, for example less than 16 amino acid residues, such as less than 15 amino acid residues, for example less than 14 amino acid residues, such as less than 13 amino acid residues, for example less than 12 amino acid residues, such as less than 11 amino acid residues, for example less than 10 amino acid residues, such as less than 9 amino acid residues, for example less than 8 amino acid residues, such as less than 7 amino acid residues, for example less than 6 amino acid residues, such as less than 5 amino acid residues.

179. The polypeptide according to item 83, wherein the second copy of SEQ ID NO:90 and the fourth copy of SEQ ID NO:90 are separated by less than 100 amino acid residues, such as less than 95 amino acid residues, for example less than 90 amino acid residues, such as less than 85 amino acid residues, for example less than 80 amino acid residues, such as less than 75 amino acid residues, for example less than 70 amino acid residues, such as less than 65 amino acid residues, for example less than 60 amino acid residues, such as less than 55 amino acid residues, for example less than 50 amino acid residues, such as less than 45 amino acid residues, for example less than 40 amino acid residues, such as less than 35 amino acid residues, for example less than 30 amino acid residues, such as less than 25 amino acid residues, for example less than 24 amino acid residues, such as less than 23 amino acid residues, for example less than 22 amino acid residues, such as less than 21 amino acid residues, for example less than 20 amino acid residues, such as less than 19 amino acid residues, for example less than 18 amino acid residues, such as less than 17 amino acid residues, for example less than 16 amino acid residues, such as less than 15 amino acid residues, for example less than 14 amino acid residues, such as less than 13 amino acid residues, for example less than 12 amino acid residues, such as less than 11 amino acid residues, for example less than 10 amino acid residues, such as less than 9 amino acid residues, for example less than 8 amino acid residues, such as less than 7 amino acid residues, for example less than 6 amino acid residues, such as less than 5 amino acid residues.

180. The polypeptide according to item 83, wherein the third copy of SEQ ID NO:90 and the fourth copy of SEQ ID NO:90 are separated by less than 100 amino acid residues, such as less than 95 amino acid residues, for example less than 90 amino acid residues, such as less than 85 amino acid residues, for example less than 80 amino acid residues, such as less than 75 amino acid residues, for example less than 70 amino acid residues, such as less than 65 amino acid residues, for example less than 60 amino acid residues, such as less than 55 amino acid residues, for example less than 50 amino acid residues, such as less than 45 amino acid residues, for example less than 40 amino acid residues, such as less than 35 amino acid residues, for example less than 30 amino acid residues, such as less than 25 amino acid residues, for example less than 24 amino acid residues, such as less than 23 amino acid residues, for example less than 22 amino acid residues, such as less than 21 amino acid residues, for example less than 20 amino acid residues, such as less than 19 amino acid residues, for example less than 18 amino acid residues, such as less than 17 amino acid residues, for example less than 16 amino acid residues, such as less than 15 amino acid residues, for example less than 14 amino acid residues, such as less than 13 amino acid residues, for example less than 12 amino acid residues, such as less than 11 amino acid residues, for example less than 10 amino acid residues, such as less than 9 amino acid residues, for example less than 8 amino acid residues, such as less than 7 amino acid residues, for example less than 6 amino acid residues, such as less than 5 amino acid residues.

181. The polypeptide according to item 83, wherein the fourth copy of SEQ ID NO:90 is located N-terminally to the first copy of SEQ ID NO:90.

182. The polypeptide according to item 83, wherein the fourth copy of SEQ ID NO:90 is located C-terminally to the first copy of SEQ ID NO:90.

183. The polypeptide according to item 83, wherein the fourth copy of SEQ ID NO:90 is located N-terminally to the second copy of SEQ ID NO:90.

184. The polypeptide according to item 83, wherein the fourth copy of SEQ ID NO:90 is located C-terminally to the second copy of SEQ ID NO:90.

185. The polypeptide according to item 83, wherein the fourth copy of SEQ ID NO:90 is located N-terminally to the third copy of SEQ ID NO:90.

186. The polypeptide according to item 83, wherein the fourth copy of SEQ ID NO:90 is located C-terminally to the third copy of SEQ ID NO:90.

187. The polypeptide according to any of items 1 to 186 attached to a carrier.

188. The polypeptide according to item 187 wherein the carrier comprises an avidin moiety, such as streptavidin, which is optionally biotinylated.

189. The polypeptide according to any of items 1 to 186 attached, such as covalently bound, to a solid support or a semi-solid support.

190. The polypeptide according to any of items 1 to 186 operably fused to an affinity tag, such as a His-tag.

191. A fusion polypeptide comprising the polypeptide according to any of items 1 to 186 operably fused to an N-terminal flanking sequence.

192. A fusion polypeptide comprising the polypeptide according to any of items 1 to 186 operably fused to an C-terminal flanking sequence.

193. The polypeptide according to any of items 1 to 186 operably fused to a signal peptide.

194. The polypeptide according to any of items 1 to 186 operably fused to a pro-region.

195. The polypeptide according to any of items 1 to 186 operably fused to a pre-pro-region.

196. The polypeptide according to any of items 1 to 186, wherein one or more amino acid residues are modified, said modification(s) preferably being selected from the group consisting of in vivo or in vitro chemical derivatization, such as acetylation or carboxylation, glycosylation, such as glycosylation resulting from exposing the polypeptide to enzymes which affect glycosylation, for example mammalian glycosylating or deglycosylating enzymes, phosphorylation, such as modification of amino acid residues which results in phosphorylated amino acid residues, for example phosphotyrosine, phosphoserine and phosphothreonine.

197. The polypeptide according to any of items 1 to 186, wherein one or more amino acid residues are modified so as to preferably improve the resistance to proteolytic degradation and stability or to optimize solubility properties or to render the polypeptide more suitable as a therapeutic agent.

198. The polypeptide according to item 197 comprising amino acid residues other than naturally occurring L-amino acid residues.

199. The polypeptide according to item 198 comprising D-amino acid residues.

200. The polypeptide according to item 198 comprising non-naturally occurring, synthetic amino acids.
201. The polypeptide according to item 197 comprising one or more blocking groups preferably in the form of chemical substituents suitable to protect and/or stabilize the N- and C-termini of the polypeptide from undesirable degradation.
202. The polypeptide according to item 201, wherein the one or more blocking groups include protecting groups which do not adversely affect in vivo activities of the polypeptide.
203. The polypeptide according to item 201, wherein the one or more blocking groups are introduced by alkylation or acylation of the N-terminus.
204. The polypeptide according to item 201, wherein the one or more blocking groups are selected from N-terminal blocking groups comprising $C_1$ to $C_5$ branched or non-branched alkyl groups and acyl groups, such as formyl and acetyl groups, as well as substituted forms thereof, such as the acetamidomethyl (Acm) group.
205. The polypeptide according to item 201, wherein the one or more blocking groups are selected from N-terminal blocking groups comprising desamino analogs of amino acids, which are either coupled to the N-terminus of the peptide or used in place of the N-terminal amino acid residue.
206. The polypeptide according to item 201, wherein the one or more blocking groups are selected from C-terminal blocking groups wherein the carboxyl group of the C-terminus is either incorporated or not, such as esters, ketones, and amides, as well as descarboxylated amino acid analogues.
207. The polypeptide according to item 201, wherein the one or more blocking groups are selected from C-terminal blocking groups comprising ester or ketone-forming alkyl groups, such as lower ($C_1$ to $C_6$) alkyl groups, for example methyl, ethyl and propyl, and amide-forming amino groups, such as primary amines ($-NH_2$), and mono- and di-alkylamino groups, such as methylamino, ethylamino, dimethylamino, diethylamino, methylethylamino, and the like.
208. The polypeptide according to item 201, wherein free amino group(s) at the N-terminal end and free carboxyl group(s) at the termini can be removed altogether from the polypeptide to yield desamino and descarboxylated forms thereof without significantly affecting the biological activity of the polypeptide.
209. An acid addition salt of the polypeptide according to any of items 1 to 208, said salt being obtainable by treating the polypeptide with an inorganic acid, such as hydrochloric acid, hydrobromic acid, sulfuric acid, nitric acid, phosphoric acid, and the like, or an organic acid such as an acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, or salicylic acid, to provide a water soluble salt of the polypeptide.
210. A method for producing the polypeptide according to any of items 1 to 208, said method comprising the steps of providing a polynucleotide encoding said polypeptide and expressing said polynucleotide either in vitro, or in vivo in a suitable host organism, thereby producing the polypeptide according to any of items 1 to 208.
211. A polynucleotide encoding at polypeptide part of the polypeptide according to any of items 1 to 208.
212. An expression vector comprising the polynucleotide according to item 211, said polynucleotide being optionally operably linked to regulatory sequence controlling the expression of said polynucleotide in a suitable host cell.
213. A recombinant or transgenic host cell comprising the polypeptide according to any of items 1 to 208 and/or the polynucleotide according to item 211 and/or the expression vector according to item 212.
214. A method for generating a recombinant or transgenic host cell, said method comprising the steps of providing a polynucleotide encoding a polypeptide according to any of items 1 to 208, introducing said polynucleotide into said recombinant or transgenic host cell and optionally also expressing said polynucleotide in said recombinant or transgenic host cell, thereby generating a recombinant or transgenic host cell producing said polypeptide.
215. A transgenic, mammalian organism comprising the host cell according to item 213.
216. The transgenic, mammalian organism according to item 215, wherein said mammalian host cell is an animal cell selected from the monophyletic group Bilateria, including a mammalian cell belonging to any of the four major lineages Deuterostomes, Ecdysozoa, Platyzoa and Lophotrochozoa.
217. The transgenic, mammalian organism according to item 215, wherein said mammalian host cell is an animal cell selected from the group consisting of a Blastomere cell, an Egg cell, an Embryonic stem cell, an Erythrocyte, a Fibroblast, a Hepatocyte, a Myoblast, a Myotube, a Neuron, an Oocyte, an Osteoblast, an Osteoclast, a Sperm cell, a T-Cell and a Zygote.
218. A method for generating a transgenic, mammalian host cell, said method comprising the steps of providing a polynucleotide encoding a polypeptide according to any of items 1 to 208, introducing said polynucleotide into said recombinant or transgenic host cell and optionally also expressing said polynucleotide in said transgenic, mammalian host cell, thereby generating a transgenic, mammalian host cell producing said polypeptide.
219. A transgenic fish comprising the polypeptide according to any of items 1 to 208 and/or the polynucleotide according to item 211 and/or the expression vector according to item 212.
220. The transgenic fish according to item 219, wherein said fish is a salmon
221. The transgenic fish according to item 219, wherein said fish is a flounder
222. The transgenic fish according to item 219, wherein said fish is a cod
223. The transgenic fish according to item 219, wherein said fish is a herring.
224. A transgenic plant comprising the host cell according to item 213.
225. The transgenic, plant host cell according to item 224, wherein said host cell is a plant cell of the taxon Embryophyta or Viridiplantae or Chlorobionta, preferably selected from the group consisting of Aleurone cells, Collenchyma cells, Endodermis cells, Endosperm cells, Epidermis cells, Mesophyll cells, Meristematic cells, Palisade cells, Parenchyma cells, Phloem sieve tube cells, Pollen generative cells, Pollen vegetative cells, Sclerenchyma cells, Tracheids cells, Xylem vessel cells and Zygote cells.
226. The transgenic plant according to item 224, wherein said plant is a potato plant.

227. The transgenic plant according to item 224, wherein said plant is a tomato plant.
228. The transgenic plant according to item 224, wherein said plant is a grape vine.
229. The transgenic plant according to item 224, wherein said plant is a cucumber plant.
230. The transgenic plant according to item 224, wherein said plant is wheat.
231. The transgenic plant according to item 224, wherein said plant is a barley.
232. The transgenic plant according to item 224, wherein said plant is rye.
233. The transgenic plant according to item 224, wherein said plant is oats.
234. The transgenic plant according to item 224, wherein said plant is a tobacco plant.
235. The transgenic plant according to item 224, wherein said plant is a citrus plant.
236. The transgenic plant according to item 224, wherein said plant is an apple plant.
237. The transgenic plant according to item 224, wherein said plant is a strawberry plant.
238. The transgenic plant according to item 224, wherein said plant is a raspberry plant.
239. A method for generating a transgenic plant, said method comprising the steps of providing a polynucleotide encoding a polypeptide according to any of items 1 to 208, introducing said polynucleotide into said plant and optionally also expressing said polynucleotide in said plant, thereby generating a transgenic plant producing said polypeptide.
240. A recombinant bacterial host cell comprising the polypeptide according to any of items 1 to 208 and/or the polynucleotide according to item 211 and/or the vector according to item 212.
241. The bacterial host cell according to item 240, wherein said bacterial host cell is selected from a Gram-positive bacterial host cell and a Gram-negative bacterial host cell.
242. The bacterial host cell according to item 240, wherein said bacterial cell is a strain of *Lactobacillus*.
243. The bacterial host cell according to item 240, wherein said bacterial cell is a strain of *Streptococcus*.
244. The bacterial host cell according to item 240, wherein said bacterial cell is a strain of *Bifidobacterium*.
245. A method for generating a recombinant bacterial cell, said method comprising the steps of providing a polynucleotide encoding a polypeptide according to any of items 1 to 208, introducing said polynucleotide into said bacterial cell and optionally also expressing said polynucleotide in said bacterial cell, thereby generating a recombint bacterial cell producing said polypeptide.
246. A recombinant yeast cell comprising the polypeptide according to any of items 1 to 208 and/or the polynucleotide according to item 211 and/or the vector according to item 212.
247. The yeast host cell according to item 246, wherein said yeast host cell belongs to the genera of *Saccharomyces, Scizosacchomyces* or *Pichia*.
248. The yeast host cell according to item 246, wherein said yeast is a *Saccharomyces cerevisiae*.
249. The yeast host cell according to item 246, wherein said yeast is a *Scizosacchomyces pompe*.
250. The yeast host cell according to item 246, wherein said yeast is a *Pichia pastoris*.
251. A method for generating a recombinant yeast cell, said method comprising the steps of providing a polynucleotide encoding a polypeptide according to any of items 1 to 208, introducing said polynucleotide into said yeast cell and optionally also expressing said polynucleotide in said yeast cell, thereby generating a recombint yeast cell producing said polypeptide.
252. A recombinant fungal host cell comprising the polypeptide according to any of items 1 to 208 and/or the polynucleotide according to item 211 and/or the vector according to item 212.
253. The fungal host cell according to item 252, wherein said fungal cell belongs to the genus of *Aspergillus*.
254. A method for generating a recombinant fungal cell, said method comprising the steps of providing a polynucleotide encoding a polypeptide according to any of items 1 to 208, introducing said polynucleotide into said fungal cell and optionally also expressing said polynucleotide in said fungal cell, thereby generating a recombint bacterial cell producing said polypeptide.
255. An antibody, or a binding fragment thereof, specific for the polypeptide according to any of items 1 to 208.
256. The antibody according to item 255, wherein said antibody is polyclonal.
257. The antibody according to item 255, wherein said antibody is monoclonal.
258. The antibody fragment according to item 255, wherein said antibody fragment comprises a portion of an antibody selected from the group consisting of F(ab')$_2$, F(ab)$_2$, Fab' and Fab.
259. The antibody fragment according to item 255, wherein said antibody fragment is synthetic or a genetically engineered polypeptide that binds to a specific antigen.
260. The antibody fragment according to item 255, wherein said antibody fragment is selected from the group consisting of antibody fragments comprising or consisting of the light chain variable region, antibody fragments comprising or consisting of a "Fv" fragment consisting of the variable regions of the heavy and light chains, antibody fragments comprising or consisting of recombinant single chain polypeptide molecules in which light and heavy variable regions are connected by a peptide linker ("scFv polypeptides") and antibody fragments comprising or consisting of minimal recognition units consisting of the amino acid residues that mimic the hypervariable region.
261. The antibody according to item 255, wherein said antibody is a chimeric antibody in the form of a recombinant polypeptide that contains the variable domains and complementary determining regions derived from a rodent antibody, while the remainder of the antibody molecule is derived from a human antibody.
262. The antibody according to item 255, wherein said antibody is a humanized antibody in the form of a recombinant polypeptide in which murine complementarity determining regions of a monoclonal antibody have been transferred from heavy and light variable chains of the murine immunoglobulin into a human variable domain.
263. The antibody according to any of items 255 to 262 further comprising or being associated with a detectable label in the form of a molecule or atom which can be conjugated to an antibody moiety to produce a moiety which can be more easily detected.
264. The antibody according to item 263, wherein the label is selected from the group consisting of chelators, photoactive agents, radioisotopes, fluorescent agents and paramagnetic ions.

265. A method for generating a polyclonal antibody, or a binding fragment thereof specific for the polypeptide according to any of items 1 to 208, said method comprising the steps of immunizing a mammalian subject with the polypeptide according to any of items 1 to 208 under conditions eliciting an antibody response, identifying an antibody which bind specifically to the polypeptide, and optionally isolating said antibody or binding fragment thereof from said mammalian subject.
266. A method for generating a monoclonal antibody specific for the polypeptide according to any of items 1 to 208, said method comprising the steps of immunizing a mammalian subject with the polypeptide according to any of items 1 to 208 under conditions eliciting an antibody response, preparing a hybridoma producing a monoclonal antibody specific for the polypeptide according to any of items 1 to 208, and identifying an antibody which bind specifically to the polypeptide.
267. A composition comprising the polypeptide according to any of items 1 to 208 and a carrier.
268. An ice repelling surface comprising the polypeptide according to any of items 1 to 208 or the composition according to item 267.
269. A refrigerator comprising the ice repelling surface according to item 268.
270. A freezer comprising the ice repelling surface according to item 268.
271. A window comprising the ice repelling surface according to item 268.
272. A windmill wing comprising the ice repelling surface according to item 268.
273. A radio detection and ranging device (radar) comprising the ice repelling surface according to item 268.
274. An automobile comprising the ice repelling surface according to item 268.
275. A heat pump comprising the ice repelling surface according to item 268.
276. A sailing vessel comprising the ice repelling surface according to item 268.
277. A road surface comprising the ice repelling surface according to item 268.
278. A pipe for diverting a liquid source, such as water, said pipe comprising the ice repelling surface according to item 268.
279. The pipe according to item 278 made of plastic.
280. The pipe according to item 278 made of metal.
281. A roof construction comprising the ice repelling surface according to item 268.
282. A bottle comprising the ice repelling surface according to item 268.
283. A can comprising the ice repelling surface according to item 268.
284. An antenna device comprising the ice repelling surface according to item 268.
285. A windshield wiper comprising the ice repelling surface according to item 268.
286. A rubber tire comprising the ice repelling surface according to item 268.
287. An air-conditioning installation comprising the ice repelling surface according to item 268.
288. A railroad track comprising the ice repelling surface according to item 268.
289. A train wheel comprising the ice repelling surface according to item 268.
290. A power cable comprising the ice repelling surface according to item 268.
291. An ice nucleating surface comprising the polypeptide according to any of items 1 to 208 or the composition according to item 267.
292. A refrigerator comprising the ice nucleating surface according to item 291.
293. A freezer comprising the ice nucleating surface according to item 291.
294. A window comprising the ice nucleating surface according to item 291.
295. A windmill wing comprising the ice nucleating surface according to item 291.
296. A radio detection and ranging device (radar) comprising the ice nucleating surface according to item 291.
297. An automobile comprising the ice nucleating surface according to item 291.
298. A heat pump comprising the ice nucleating surface according to item 291.
299. A sailing vessel comprising the ice nucleating surface according to item 291.
300. A road surface comprising the ice nucleating surface according to item 291.
301. A pipe for diverting a liquid source, such as water, said pipe comprising the ice nucleating surface according to item 291.
302. The pipe according to item 301 made of plastic.
303. The pipe according to item 301 made of metal.
304. A roof construction comprising the ice nucleating surface according to item 291.
305. A bottle comprising the ice nucleating surface according to item 291.
306. A can comprising the ice nucleating surface according to item 291.
307. An antenna device comprising the ice nucleating surface according to item 291.
308. A windshield wiper comprising the ice nucleating surface according to item 291.
309. A rubber tire comprising the ice nucleating surface according to item 291.
310. An air-conditioning installation comprising the ice nucleating surface according to item 291.
311. A railroad track comprising the ice nucleating surface according to item 291.
312. A train wheel comprising the ice nucleating surface according to item 291.
313. A power cable comprising the ice nucleating surface according to item 291.
314. A method for lowering the freezing point of an aqueous, liquid composition, said method comprising the steps of contacting the polypeptide according to any of items 1 to 209 and said aqueous, liquid composition, wherein said contacting results in lowering the freezing point of said aqueous, liquid composition.
315. The method of item 314, wherein said liquid composition comprises a paint composition.
316. The method of item 314, wherein said liquid composition comprises an anti-freeze for use in freezers.
317. The method of item 314, wherein said liquid composition comprises an anti-freeze for use in refrigerators.
318. The method of item 314, wherein said liquid composition comprises an anti-freeze for use in engines.
319. The method of item 314, wherein said liquid composition comprises a windshield wash.
320. The method of item 314, wherein said liquid composition comprises a silicone.
321. The method of item 314, wherein said liquid composition comprises a coating composition, such as a paint, a lacquer or a varnish.

322. The method of item 314, wherein said liquid composition comprises a vax.
323. The method of item 314, wherein said liquid composition comprises an oil.
324. The method of item 314, wherein said liquid composition comprises cement.
325. The method of item 314, wherein said liquid composition comprises concrete.
326. The method of item 314, wherein said liquid composition comprises a soap.
327. The method of item 314, wherein said liquid composition comprises an anti-freeze composition for use in a lock.
328. A method for reducing or eliminating recrystallisation of an aqueous, liquid composition, said method comprising the step of contacting the polypeptide according to any of items 1 to 209 and the aqueous liquid composition prior to freezing, thereby reducing or eliminating recrystallisation of the aqueous, liquid composition.
329. The method of item 328, wherein said liquid composition comprises a paint composition.
330. The method of item 328, wherein said liquid composition comprises an anti-freeze for use in freezers.
331. The method of item 328, wherein said liquid composition comprises an anti-freeze for use in refrigerators.
332. The method of item 328, wherein said liquid composition comprises an anti-freeze for use in engines.
333. The method of item 328, wherein said liquid composition comprises a windshield wash.
334. The method of item 328, wherein said liquid composition comprises a silicone.
335. The method of item 328, wherein said liquid composition comprises a lacquer.
336. The method of item 328, wherein said liquid composition comprises a vax.
337. The method of item 328, wherein said liquid composition comprises an oil.
338. The method of item 328, wherein said liquid composition comprises cement.
339. The method of item 328, wherein said liquid composition comprises concrete.
340. The method of item 328, wherein said liquid composition comprises a soap.
341. The method of item 328, wherein said liquid composition comprises an anti-freeze composition for use in a lock.
342. A method for preserving and/or lowering the freezing point of a biological sample or an organ by contacting the polypeptide according to items 1 to 209 and the biological sample or the organ, thereby allowing storage of the biological sample or the organ in a super cooled condition or a frozen condition.
343. The method of item 342, wherein the biological sample comprises polypeptide
344. The method of item 342, wherein the biological sample comprises microsomes or micelles.
345. The method of item 342, wherein the biological sample comprises whole blood.
346. The method of item 342, wherein the biological sample comprises blood plasma.
347. The method of item 342, wherein the biological sample comprises blood platelets.
348. The method of item 342, wherein the biological sample comprises red blood cells.
349. The method of item 342, wherein the biological sample comprises semen.
350. The method of item 342, wherein the biological sample comprises gametes.
351. The method of item 342, wherein said sample comprises a cell culture of insect cells.
352. The method of item 342, wherein said sample comprises a cell culture of mammalian cells.
353. The method of item 352, wherein the mammalian cells are rodent cells.
354. The method of item 352, wherein the mammalian cells are human cells.
355. The method of item 352, wherein said biological sample comprises or consists of an organ.
356. The method of items 355, wherein the organ is selected from the group consisting of kidney, a lung, a heart, a spleen, and a liver.
357. A method for inhibiting recrystallization of a biological sample or an organ during storage thereof, said method comprising the step of contacting the polypeptide according to items 1 to 209 to said biological sample or organ, thereby inhibiting recrystallization and allowing storage of the biological sample or organ in a super cooled condition or a frozen condition.
358. The method of item 357, wherein the biological sample comprises polypeptide
359. The method of item 357, wherein the biological sample comprises microsomes or micelles.
360. The method of item 357, wherein the biological sample comprises whole blood.
361. The method of item 357, wherein the biological sample comprises blood plasma.
362. The method of item 357, wherein the biological sample comprises blood platelets.
363. The method of item 357, wherein the biological sample comprises red blood cells.
364. The method of item 357, wherein the biological sample comprises semen.
365. The method of item 357, wherein the biological sample comprises gametes.
366. The method of item 357, wherein said sample comprises a cell culture of insect cells.
367. The method of item 357, wherein said sample comprises a cell culture of mammalian cells.
368. The method of item 367, wherein the mammalian cells are rodent cells.
369. The method of item 367, wherein the mammalian cells are human cells.
370. The method of item 357, wherein said biological sample comprises or consists of an organ.
371. The method of items 370, wherein the organ is selected from the group consisting of kidney, a lung, a heart, a spleen, and a liver.
372. A method for preserving an edible or drinkable composition, such as a food, by contacting the food with the polypeptide according to any of items 1 to 209, thereby allowing improved or prolonged storage of the edible or drinkable composition in a non-frozen state at a temperature at which the food would otherwise be in a frozen state.
373. The method of item 372, wherein the composition is selected from the group consisting of milk, a fermented milk product, cheese, minced meat, minced fish, yoghurt, sorbet, sherbet, pudding, a vegetable puree, a fruit puree, a dough, ice milk, custard, water-ices, slush ice, smoothies, ice cream, granitas, paste and meat.
374. A method for reducing or inhibiting recrystallisation of ice crystals on an edible or drinkable composition, such as a food, by contacting the food with the polypeptide according to any of items 1 to 209, thereby reducing or inhibiting recrystallisation of ice crystals formed on the composition during storage at a temperature at which ice crystals would otherwise have been formed.

375. The method of item 374, wherein the composition is selected from the group consisting of milk, a fermented milk product, cheese, minced meat, minced fish, yoghurt, sorbet, sherbet, pudding, a vegetable puree, a fruit puree, a dough, ice milk, custard, water-ices, slush ice, smoothies, ice cream, granitas, paste and meat.

376. A method for increasing the cold resistance of a cosmetic product capable of being applied to the skin of an individual, said method comprising the step of contacting the polypeptide according to any of items 1 to 209 to a cosmetic product, thereby increasing the cold resistance of the cosmetic product while being applied on the skin.

377. A method for increasing the moisture content of a product capable of absorbing water, said method comprising the step of contacting the polypeptide according to any of items 1 to 209, thereby increasing the moisture content of the product.

378. A method for liminating a tumour by surgery, said method comprising the step of injecting the polypeptide according to any of items 1 to 209 into the tumour prior to subjecting said tumour to a freezing step, thereby enhancing the killing of the tumour.

379. A method for controlled removal of adipose tissue by surgery, said method comprising the step of injecting the polypeptide according to any of items 1 to 209 into the adipose tissue prior to removing the adipose tissue.

380. A method for inhibiting clathrate formation in a crude oil product, said method comprising the step of adding the polypeptide according to any of items 1 to 209 to the crude oil product, thereby inhibiting clathrate formation.

381. A method for stabilising a biological sample during drying or during subjection to high or low osmolalities, said method comprising the step of contacting the polypeptide according to any of items 1 to 209, thereby stabilizing the biological sample during drying or during subjection to high or low osmolalities.

382. The method of item 381, wherein the biological sample comprises one or more of a polypeptide, microsomes, micelles, whole blood, blood plasma, blood platelets, red blood cells, semen, gametes.

383. The method of item 381, wherein the biological sample comprises a cell culture.

384. The method of item 383, wherein the cell culture comprises one or more of insect cells, mammalian cells, rodent cells and human cells.

385. A method for purifying one or more molecules from a composition comprising different molecules, said method comprising the step of performing said purification in the presence of a composition comprising the polypeptide according to any of items 1 to 209, thereby allowing the purification to take place at temperatures below the freezing point of the composition comprising the different molecules.

386. The method of item 385, wherein the molecules of the composition comprising different molecules are selected from the group consisting of polypeptides, peptides, amino acids, sugars, fatty acids, DNA molecules, RNA molecules, phospholipids, organels, such as e.g. mithocondria, ribosomes etc., adenosine triphosphate.

387. A method for improved dehydration of a composition to be dehydrated, said method comprising the step of contacting said composition with the polypeptide according to any of items 1 to 209, and dehydrating said composition.

388. A composition comprising the polypeptide according to items 1 to 209.

389. A composition comprising the polypeptide according to items 1 to 209, wherein the polypeptide is distributed superficially, either homogenously or heterogeneously.

390. A composition comprising the polypeptide the polypeptide according to items 1 to 209, wherein the polypeptide is distributed throughout said composition, either homogenously or heterogeneously.

391. A composition intended for freezing comprising the polypeptide according to items 1 to 209, wherein the polypeptide is added prior to freezing.

392. A composition intended for freezing comprising the polypeptide according to items 1 to 209, wherein the polypeptide is added after freezing.

393. A pharmaceutical composition comprising the polypeptide according to items 1 to 209.

394. A surface comprising the polypeptide according to items 1 to 209, wherein said surface is ice-repelling.

395. A surface comprising the polypeptide according to items 1 to 209, wherein said surface is ice-binding.

396. A biological sample comprising the polypeptide according to items 1 to 209.

397. An edible composition comprising the polypeptide according to items 1 to 209

398. A liquid composition comprising the polypeptide according to items 1 to 209.

399. A solid composition comprising the polypeptide according to items 1 to 209.

400. A solid composition comprising the polypeptide according to items 1 to 209, wherein the polypeptide is distributed superficially.

401. A solid composition comprising the polypeptide according to items 1 to 209, wherein the polypeptide is distributed throughout the sample, either homogenously or heterogeneously.

The invention will now be described in more detail by describing the recombinant expression, purification and characterization of antifreeze proteins from *Rhagium mordax*

EXAMPLES

Two different strategies were used for the identification and purification of anti-freeze polypeptides from *R. mordax*.
1) The method published in Kristiansen et al. (2005) was used for purifying the anti-freeze polypeptides.
2) Two degenerated primers were designed to match regions in the N- and C-terminal region of the *R. Inquisitor* AFP (FIG. 1). These were used to amplify cDNA regions from *R. mordax* RNA isolated from winter-collected animals in a conventional RT-PCR reaction. Such cDNA encodes the central region of putative AFP's from *R. mordax*. By this approach, the sequence of central portions (99-108 aa) of two types (families) of polypeptides were obtained.
3) Full length AFP sequences were subsequently obtained for 9 isozymes. Primers specific for each of the central portions of the cDNA encoding putative AFP's were employed in combination with amplification of the pertinent 5' ends (5'RACE) using the Clontech Smart RACE cDNA amplification kit. Once the 5' ends of each cDNA is obtained, this sequence will be used for obtaining full length clones. This is done using a primer matching the extreme 5-end of each cDNA in combination with a primer matching the mRNA poly-A tail in a RT-PCR reaction of *R. mordax* RNA.

In total, 9 full length cDNAs encoding various isoforms of the group I AFP's were obtained and the encoded polypeptides deduced.

Expression and Purification

Figure 5:
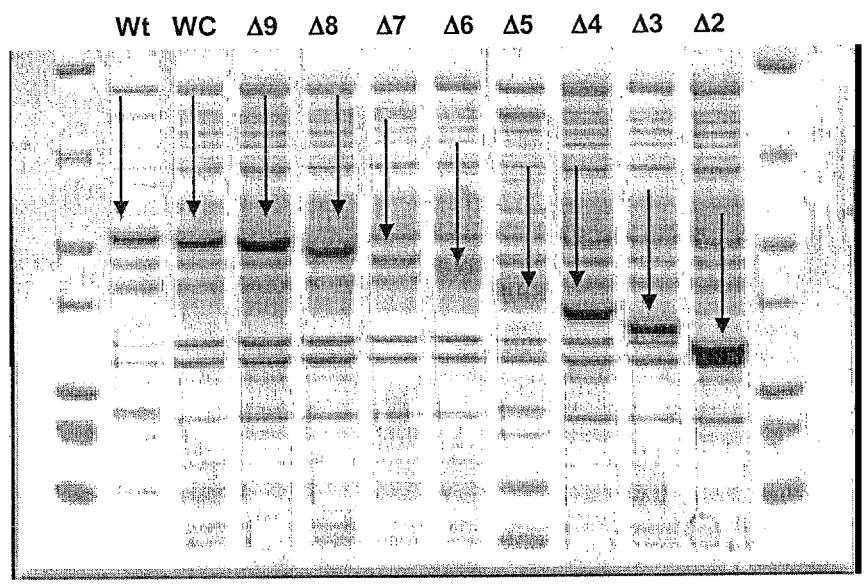
FIG. 5. Illustrates an SDS-PAGE gel of wild type (wt) soform RmAFP1 and deletion variants (Δ2-9, WC (Trp-Cys)). The RmAFP variants were constructed as deletions of the ice binding domains one at a time from the C-terminal of RmAFP1 (Δ2-Δ9) (for example Δ4 indicates that putative ice binding domain 4-9 (see FIG. 2) has been deleted) and a variant containing a Trp and Cys residue in the C-terminal (WC). These were cloned into pGEX vector system (GE Healthcare) and transformed in E. coli (strains: Origami, BL21). The proteins were expressed as a fusion protein to Glutathione-S-transferase (GST) containing a thrombin cleavage site between GST and RmAFP.

Six isoforms of antifreeze proteins (AFPs) from *Rhagium mordax* RmAFP has been cloned. FIG. 5 shows an SDS-PAGE gel of wild type (wt) soform RmAFP1 and deletion variants (Δ2-9, WC (Trp-Cys)). The RmAFP variants were constructed as deletions of the ice binding domains one at a time from the C-terminal of RmAFP1 (Δ2-Δ9) (for example Δ4 indicates that putative ice binding domain 4-9 has been deleted) and a variant containing a Trp and Cys residue in the C-terminal (WC). These were cloned into pGEX vector system (GE Healthcare) and transformed in *E. coli* (strains: Origami, BL21). The proteins were expressed as a fusion protein to Glutathione-S-transferase (GST) containing a thrombin cleavage site between GST and RmAFP. The cells were lysed by French press and the purification was based on affinity chromatography using reduced glutathione covalently attached to sepharose beads and size exclusion chromatography. The arrows in FIG. 5 indicate the positions of the deletion derivatives of AFP1.

Activity Measurements

Wild type isoforms of *Rhagium mordax* antifreeze proteins and variants of these were tested for activity using a nano-litre osmometer. The results are shown in the table 4 below. The RmAFP variants were constructed as deletions of the ice binding domains one at a time from the C-terminal of RmAFP1 and a variant containing a Trp and Cys residue in the C-terminal. $TH_{app}$ is the thermal hysteresis estimated directly from the assay without considering concentration of AFP, purified or as fusion protein or ice fractionation in the individual measurement; except for the asterisk marked TH which was estimated by extrapolation of a straight line through the points in a plot of TH versus the ice fraction. n is the number of measurements. Not determined, but in progress (N.D.) The fact that we find detectable activity in Δ5-9 and Δ4-9 demonstrates that truncated versions of AFP1 containing 4 and 3 putative ice-binding motifs, respectively, retains the ability to prevent growth of ice crystals. The specific activity of deletion derivatives has not been determined and their activity relative to wt protein is at present unknown.

TABLE 4

| AFP Variant # | Purification step | TH app (° C.) | n |
|---|---|---|---|
| 1 | Purified; fusion protein | 8.0*; 2-6 | 4 |
| 2 | Cell lysate/fusion protein | 1.0 | 3 |
| 3 | Cell lysate/fusion protein | 1.4 | 4 |
| 4 | Cell lysate/fusion protein | 1.1 | 3 |
| 5 | Cell lysate/fusion protein | 1.4 | 3 |
| 8 | Purified fusion protein | 2.0 | 3 |
| Δ2-9 | Cell lysate/fusion protein | <0.1 | 2 |
| Δ3-9 | Cell lysate/fusion protein | N.D. | — |
| Δ4-9 | Cell lysate/fusion protein | 0.79 | 3 |
| Δ5-9 | Cell lysate/fusion protein | 0.39 | 2 |
| Δ6-9 | Cell lysate/fusion protein | N.D. | — |
| Δ7-9 | Cell lysate/fusion protein | N.D. | — |
| Δ8-9 | Cell lysate/fusion protein | N.D. | — |
| Δ9 | Cell lysate/fusion protein | <0.1 | 1 |
| WC | Cell lysate/fusion protein | >1 | 2 |

Visual Inspection of RmAFP Activity

Figure 6:
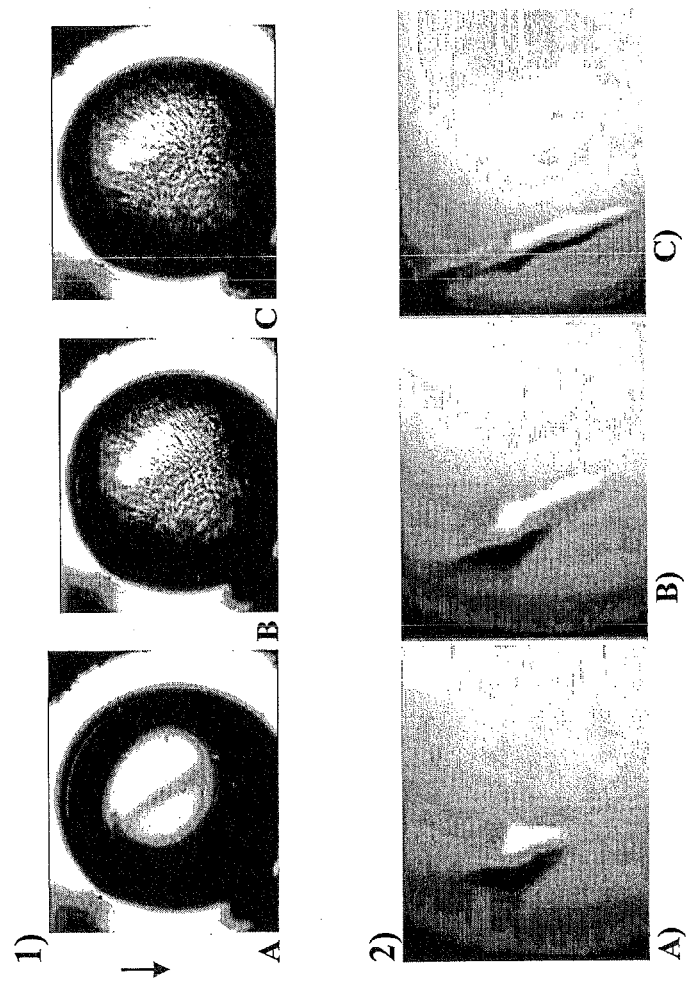
FIG. 6. Shows the progression of the "ice growth-explosion" which occurs at the hysteresis freezing point in 1) a solution of RmAFP1 and 2) in serum of the eel pout Zoarces viviparus (a danish fish with type 3 AFP). In both cases a small ice crystal was allowed to anneal in the solution before the temperature was lowered. When decreasing the temperature in the RmAFP solution the initial ice crystal (at the arrow in 1A) does not grow or change shape before the hysteresis freezing point is reached. At the hysteresis freezing point (1B) the ice crystal bursts and due to the super cooled surroundings the solution freezes. Note that in this case the ice growth pattern at the hysteresis freezing point is cauliflower like (1B, 1C). This is in contrast to the events seen in 2) (the Z. viviparus serum) where, upon cooling, the ice crystal slowly changes shape and become a bipyramid with a hexagonal base plane (2A). At the hysteresis freezing point the ice growth is spicular (2B) and all ice in the solution is growing as spicules (2C).

FIG. 6 illustrates the progression of the "ice growth-explosion" which occurs at the hysteresis freezing point in 1) a solution of RmAFP1 and 2) in serum of the eel pout *Zoarces viviparus* (a danish fish with type 3 AFP). In both cases a small ice crystal was allowed to anneal in the solution before the temperature was lowered. When decreasing the temperature in the RmAFP solution the initial ice crystal (at the arrow in 1A) does not grow or change shape before the hysteresis freezing point is reached. At the hysteresis freezing point (1B) the ice crystal bursts and due to the super cooled surroundings the solution freezes. Note that in this case the ice growth pattern at the hysteresis freezing point is cauliflower like (1B, 1C). This is in contrast to the events seen in 2) (the *Z. viviparus* serum) where, upon cooling, the ice crystal slowly changes shape and become a bipyramid with a hexagonal base plane (2A). At the hysteresis freezing point the ice growth is spicular (2B) and all ice in the solution is growing as spicules (2C). In conclusion the RmAFP is able to inhibit all ice growth or change of ice crystal shape (1). This is significantly different from fish antifreeze protein solutions which in general follow the pattern seen in (2).

Physico-Chemical Characterization of RmAFP1—Mass Spectrometry (MALDI-ToF)

Figure 7:
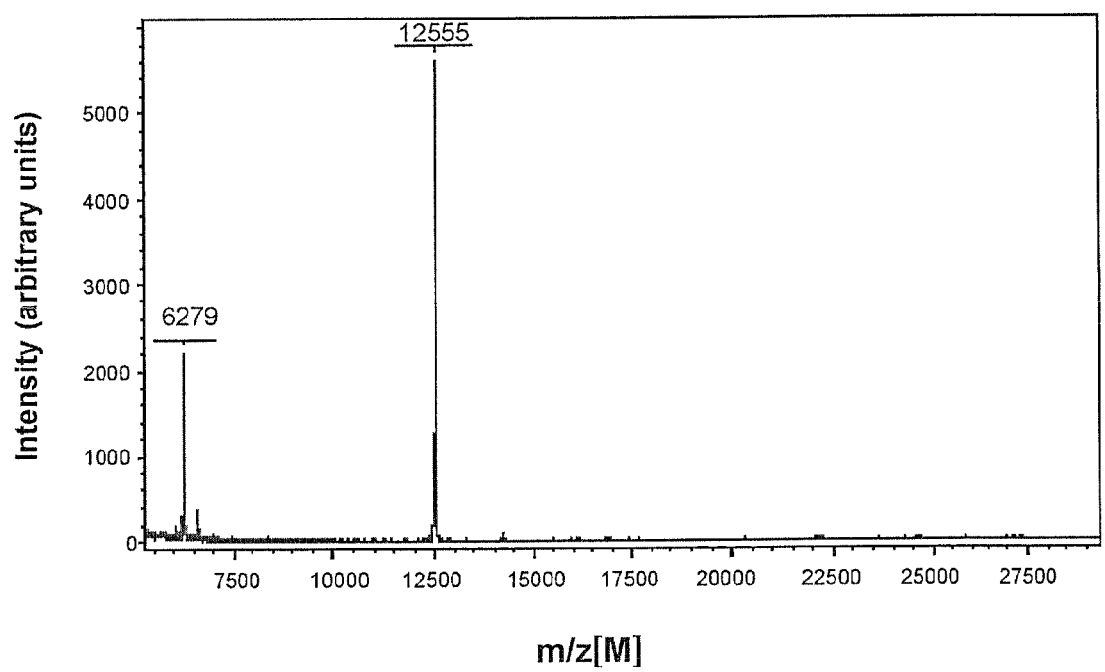
FIG. 7. Shows the molecular weight determination of cloned and purified Rhagium mordax AFP1.

Molecular weight determination of cloned and purified *Rhagium mordax* AFP1 is shown in FIG. 7. The analysis by mass spectrometry of the purified recombinant rRmAFP1 was performed by MALDI-ToF analysis by Alphalyse (Odense, Denmark). Molecular weight determination of rRmAFP1 gave an average value of 12555 Da. This discrepancy may be due to the use of external references when calibrating the apparatus.

Size-Exclusion Chromatography

Figure 8:
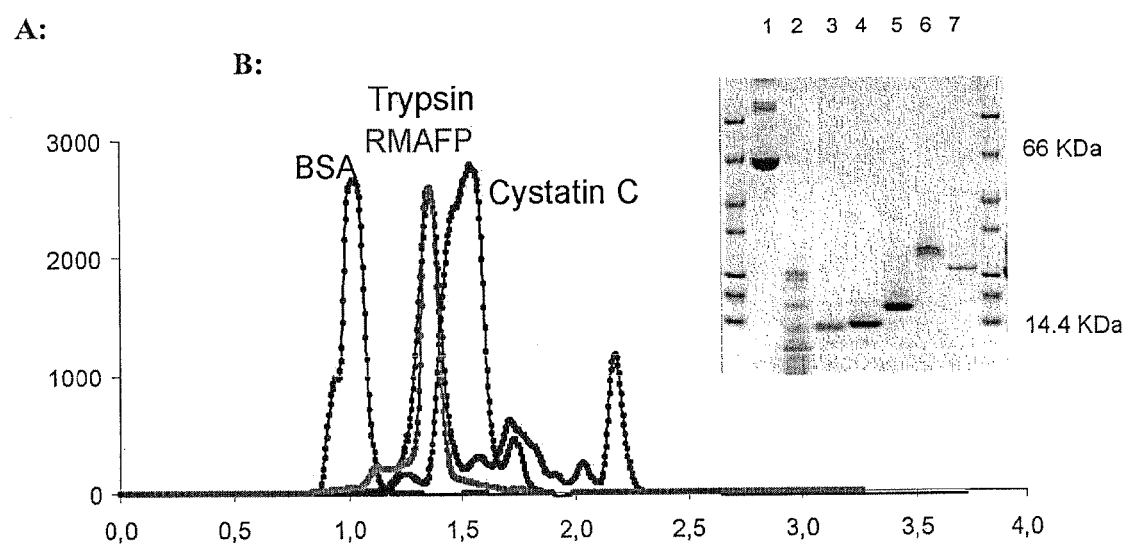
FIG. 8. Shows dimerization of rRmAFP1. A: Under native conditions rRmAFP behaves as a dimer, since when it is passed over a size exclusion column (Superdex 75, 10/30, GE Healthcare) it has shorter retention times than other proteins in the same Mw range. Mw estimation from SEC of rRmAFP1 gave 28 KDa when the Superdex 75 was calibrated with bovine serum albumin (68 KDa, BSA), trypsin (25 KDa), and human cystatin C (13 KDa). B: Likewise RmAFP behaves as a dimer when run in an SDS PAGE giving an estimated Mw of 28 KDa. Lane 1: Bovine serum albumin (BSA); 2: Trypsin; 3: RNAse A; 4 Cystatin C; 5: Lysozyme; 6 RmAFP1; 7: Glutathione S transferase (GST).

Dimerization of rRmAFP1 has also been investigated and the result is shown in FIG. 8. Under native conditions rRmAFP behaves as a dimer, since when it is passed over a size exclusion column (Superdex 75, 10/30, GE Healthcare) it has shorter retention times than other proteins in the same Mw range. Mw estimation from SEC of rRmAFP1 gave 28 KDa when the Superdex 75 was calibrated with bovine serum albumin (68 KDa, BSA), trypsin (25 KDa), and human cystatin C (13 KDa). This is shown in FIG. 8 A. Likewise RmAFP behaves as a dimer when run in an SDS PAGE giving an estimated Mw of 28 KDa. Lane 1: Bovine serum albumin (BSA); 2: Trypsin; 3: RNAse A; 4 Cystatin C; 5: Lysozyme; 6 RmAFP1; 7: Glutathione S transferase (GST). This is shown in FIG. 8 B.

Circular Dichroism Spectroscopy

Figure 9:
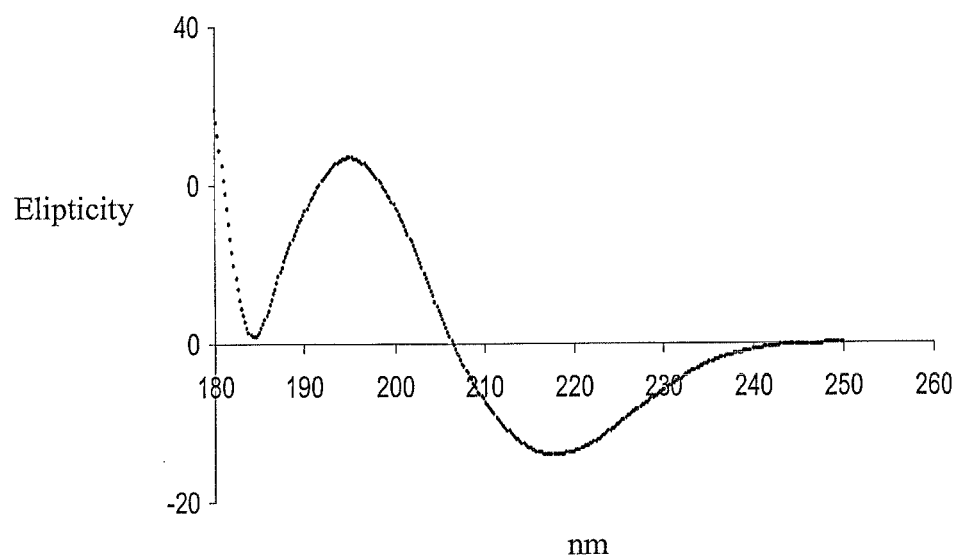
FIGS. 9A-B. Show circular dichroism spectroscopy (CD) of a polypeptide according to the invention.
Figure 9:
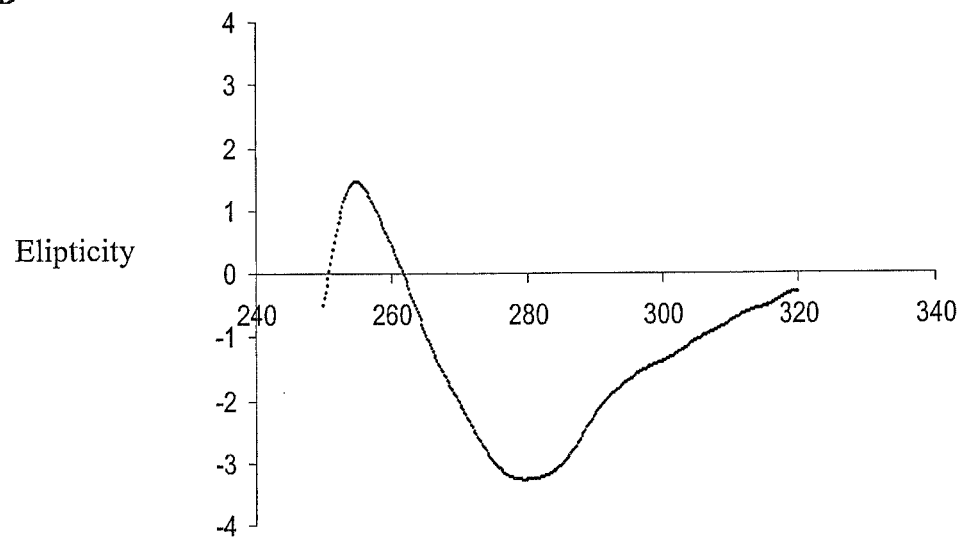

Circular dichroism spectroscopy (CD) was performed at University of Copenhagen. The results can be seen in FIG. 9. According to FIG. 9 A the far UV CD spectrum indicates that the recombinant protein has a defined structure. The near UV CD spectrum, which is shown in FIG. 9 B suggests that rRmAFP has a high content of beta-sheet structure.

Differential Scanning Calorimetry

Figure 10:
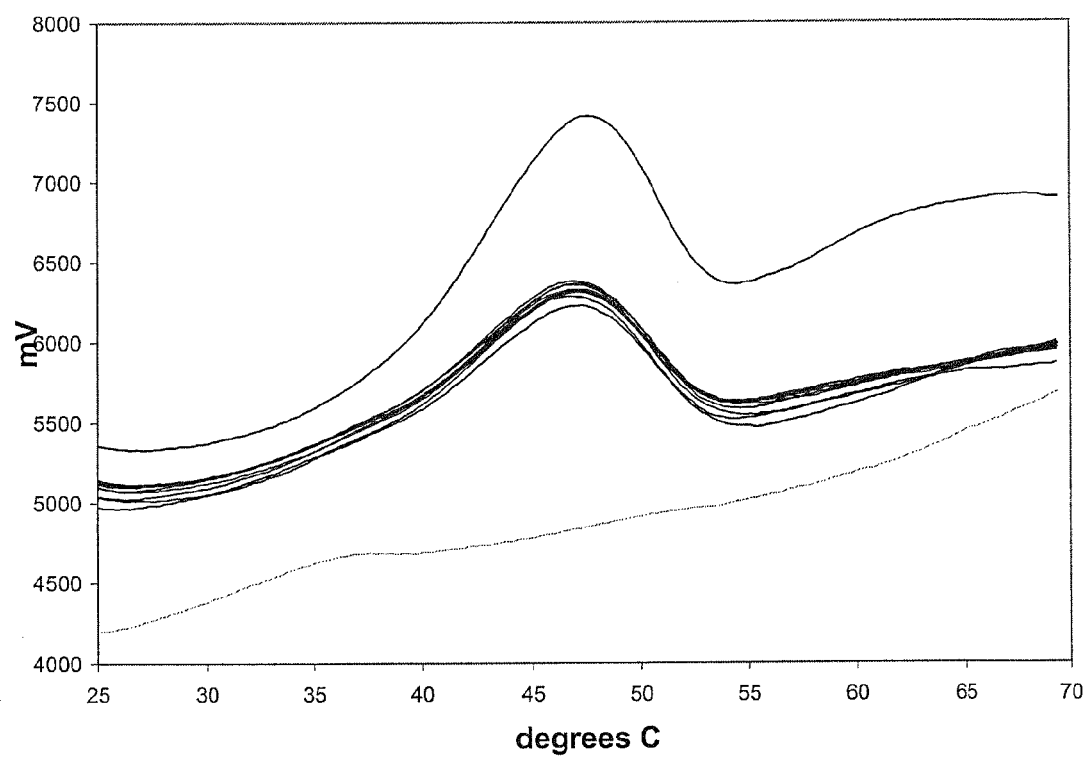
FIG. 10. Shows the temperature stability of RmAFP1 within the temperature range 6-100° C. and succeeding 11 scans were performed within the temperature range 6-70° C.

Temperature stability was investigated by differential scanning calorimetry (DSC; Scal, Moscow, Russia). The results are shown in FIG. 10. The transition temperature, Tm, of RmAFP1 was estimated to 47.7° C. The first scan was performed within the temperature range 6-100° C. and the succeeding 11 scans were performed within the temperature range 6-70° C. The asymmetric shape of the curve suggests a dissociation of the protein dimer followed by the unfolding of the monomers. The overall similarity of the curves resulting from 11 scans indicate that the RmAFP is capable of denaturing and renaturing multiple times upon successive heating/cooling cycles without any loss of material. The lower line gives the result of a similar heating cycle performed on a buffer control. Subsequently a sample that had undergone 12 heating-cooling cycles was analyzed for activity and gave a thermal hysteresis, $TH_{app}$ at 0.94° C. which did not differ from the activity of the staring material. These studies suggest a moderately, stable protein, however, with the noticeable feature of renaturation into a biologically active molecule after denaturation.

Influence of pH on Activity and Stability

Figure 11:
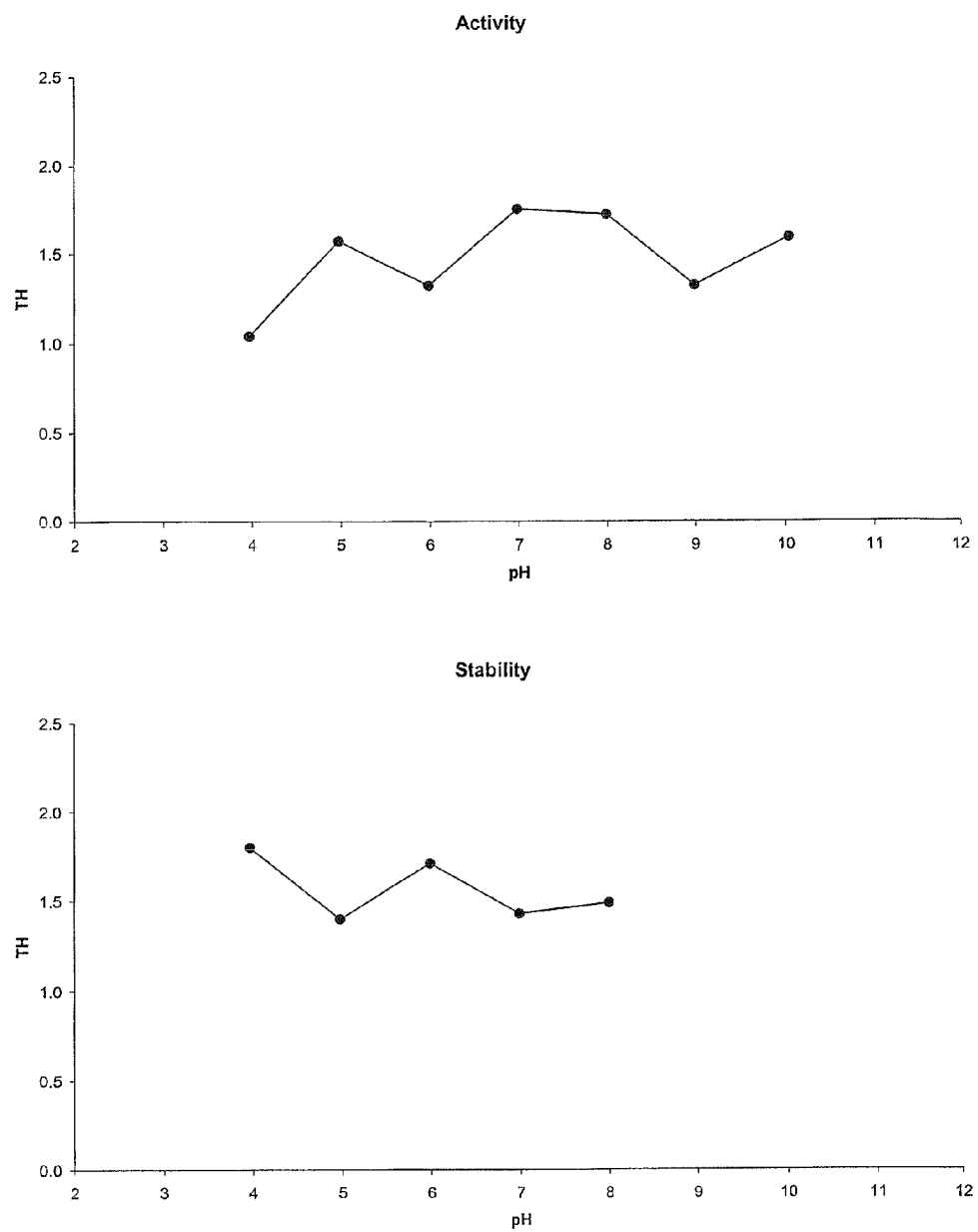
FIG. 11. Show the influence of pH on activity and stability of RmAFP1.

The influence of pH on activity and stability has also been investigated. The effect of pH on stability of RmAFP shown as TH at pH 7.2 when pre-incubated 1 h at the indicated pH values are shown in FIG. 11.

---

What is claimed is:

1. An edible product comprising a polypeptide comprising a sequence of amino acid residues selected from the group consisting of SEQ ID NO:1, SEQ ID NO:2, SEQ ID NO:3, SEQ ID NO:4, SEQ ID NO:5, SEQ ID NO:6, SEQ ID NO:7, and SEQ ID NO:8, or a polypeptide comprising a sequence of amino acid residues which is at least 85% identical to any of SEQ ID NO:1, SEQ ID NO:2, SEQ ID NO:3, SEQ ID NO:4, SEQ ID NO:5, SEQ ID NO:6, SEQ ID NO:7, and SEQ ID NO:8, wherein said polypeptide is capable of reducing or inhibiting the formation and/or growth of ice crystals.

2. The edible product according to claim 1, wherein the polypeptide comprises SEQ ID NO:1 or a sequence of amino acid residues at least 85% identical to SEQ ID NO:1.

3. The edible product according to claim 1, wherein the polypeptide comprises SEQ ID NO:2 or a sequence of amino acid residues at least 85% identical to SEQ ID NO:2.

4. The edible product according to claim 1, wherein the polypeptide comprises SEQ ID NO:3 or a sequence of amino acid residues at least 85% identical to SEQ ID NO:3.

5. The edible product according to claim 1, wherein the polypeptide comprises SEQ ID NO:4 or a sequence of amino acid residues at least 85% identical to SEQ ID NO:4.

6. The edible product according to claim 1, wherein the polypeptide comprises SEQ ID NO:5 or a sequence of amino acid residues at least 85% identical to SEQ ID NO:5.

7. The edible product according to claim 1, wherein the polypeptide comprises SEQ ID NO:6 or a sequence of amino acid residues at least 85% identical to SEQ ID NO:6.

8. The edible product according to claim 1, wherein the polypeptide comprises SEQ ID NO:7 or a sequence of amino acid residues at least 85% identical to SEQ ID NO:7.

9. The edible product according to claim 1, wherein the polypeptide comprises SEQ ID NO:8 or a sequence of amino acid residues at least 85% identical to SEQ ID NO:8.

10. The edible product according to claim 1, wherein the edible product is frozen.

11. The edible product according to claim 10, wherein the edible product is a confectionary product.

12. The edible product according to claim 10, wherein the edible product is an ice cream product or a bread.

13. An isolated polypeptide comprising a sequence of amino acid residues selected from the group consisting of SEQ ID NO:1, SEQ ID NO:2, SEQ ID NO:3, SEQ ID NO:4, SEQ ID NO:5, SEQ ID NO:6, SEQ ID NO:7, and SEQ ID NO:8, or a polypeptide comprising a sequence of amino acid residues which is at least 85% identical to any of SEQ ID NO:1, SEQ ID NO:2, SEQ ID NO:3, SEQ ID NO:4, SEQ ID NO:5, SEQ ID NO:6, SEQ ID NO:7, and SEQ ID NO:8, wherein said polypeptide is capable of reducing or inhibiting the formation and/or growth of ice crystals.

14. The isolated polypeptide according to claim 13 fused to an affinity tag.

* * * * *